US006900053B2

(12) United States Patent
Freier

(10) Patent No.: US 6,900,053 B2
(45) Date of Patent: May 31, 2005

(54) ANTISENSE MODULATION OF FIBROBLAST GROWTH FACTOR RECEPTOR 2 EXPRESSION

(75) Inventor: Susan M. Freier, San Diego, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 257 days.

(21) Appl. No.: 09/954,556

(22) Filed: Sep. 14, 2001

(65) Prior Publication Data

US 2003/0078219 A1 Apr. 24, 2003

(51) Int. Cl.[7] .......................... C12Q 1/68; C07H 21/04; C12N 15/85

(52) U.S. Cl. .......................... 435/375; 435/6; 435/91.1; 435/325; 435/366; 536/23.1; 536/24.31; 536/24.33; 536/24.5

(58) Field of Search ................................ 435/325, 375, 435/6; 536/24.1, 24.5, 23.1, 24.3; 514/44

(56) References Cited

U.S. PATENT DOCUMENTS 5,578,566 A 11/1996 Bottaro et al.
5,801,154 A * 9/1998 Baracchini et al. ........... 514/44
6,008,048 A * 12/1999 Monia et al. ............... 435/375
6,054,312 A 4/2000 Larocca et al.

FOREIGN PATENT DOCUMENTS

WO WO 98/13521 * 9/1997

OTHER PUBLICATIONS

Jen et al. Suppression of Gene Expression by Targeted Disruption of Messenger RNA: Available Options and Current Strategies. Stem Cells,2000; 18:307–319.*

Branch, A. A good antisense molecule is hard to find. TIBS, 1998 pp. 45–50.*

Fritz et al. Cationic Polystyrene Nonoparticles: Preparation and Characterization of a Model Drug Carrier System for Antisense Oligonucleotides. Journal of Colloid and Interface Science, 1997; 195:272–288.*

Wilson, S. (1997) Accession No.: 132954 (GenEmbl Database).*

Wilson, S. (1998) Accession No.: 187104 (GenEmbl Database).*

Chenchik et al (2000) Accession No.: AR090312 (GenEmbl Database).*

Powers et al. Fibroblast growth factors, their receptors and signaling. Endocrine–Related Cancer (2000). vol. 7:165–197.*

Yamada et al. Suppression of Glioblastoma Cell Growth Following Antisense Oligonucleotide–Mediated inhibition of Fibroblast Growth Factor Receptor Expression, Glia, 1999 vol. 28:66–76.*

Danilenko, *Preclinical and early clinical development of keratinocyte growth factor, an epithelial–specific tissue growth factor, Toxicol. Pathol.*, 1999, 27:64–71.

Dionne et al., *Cloning and expression of two distinct high–affinity receptors cross–reacting with acidic and basic fibroblast growth factors, Embo J.*, 1990, 9:2685–2692.

Dionne et al., *BEK, a receptor for multiple members of the fibroblast growth factor (FGF) family, maps to human chromosome 10q25.3–q26, Cytogenet. Cell. Genet.*, 1992, 60:34–36.

Hajihosseini et al., *A splicing switch and gain–of–function mutation in FgfR2–IIIc hemizygotes causes Apert/Pfeiffer–syndrome–like phenotypes, Proc. Natl. Acad. Sci. U. S. A.*, 2001, 98:3855–3860.

Houssaint et al., *Related fibroblast growth factor receptor genes exist in the human genome, Proc. Natl. Acad. Sci. U. S. A.*, 1990, 87:8180–8184.

Ishiwata et al., *Characterization of keratinocyte growth factor and receptor expression in human pancreatic cancer, Am. J. Pathol.*, 1998, 153:213–222.

Lemonnier et al., *Role of N–cadherin and protein kinase C in osteoblast gene activation induced by the S252W fibroblast growth factor receptor 2 mutation in Apert craniosynostosis, J. Bone Miner. Res.*, 2001, 16:832–845.

Lorenzi et al., *FRAG1, a gene that potently activates fibroblast growth factor receptor by C–terminal fusion through chromosomal rearrangement, Proc. Natl. Acad. Sci. U. S. A.*, 1996, 93:8956–8961.

Meyers et al., *FGFR2 exon IIIa and IIIc mutations in Crouzon, Jackson–Weiss, and Pfeiffer syndromes: evidence for missense changes, insertions, and a deletion due to alternative RNA splicing, Am. J. Hum. Genet.*, 1996, 58:491–498.

Miki et al., *Expression cDNA cloning of the KGF receptor by creation of a transforming autocrine loop, Science*, 1991, 251:72–75.

Ozawa et al., *Growth factors and their receptors in pancreatic cancer, Teratog. Carcinog. Mutagen.*, 2001, 21:27–44.

Plomp et al., *Pfeiffer syndrome type 2: further delineation and review of the literature, Am. J. Med. Genet.*, 1998, 75:245–251.

Post et al., *Keratinocyte growth factor and its receptor are involved in regulating early lung branching, Development*, 1996, 122:3107–3115.

(Continued)

*Primary Examiner*—John L. LeGuyader
*Assistant Examiner*—Terra C. Gibbs
(74) *Attorney, Agent, or Firm*—Licata & Tyrrell P.C.

(57) ABSTRACT

Antisense compounds, compositions and methods are provided for modulating the expression of fibroblast growth factor receptor 2. The compositions comprise antisense compounds, particularly antisense oligonucleotides, targeted to nucleic acids encoding fibroblast growth factor receptor 2. Methods of using these compounds for modulation of fibroblast growth factor receptor 2 expression and for treatment of diseases associated with expression of fibroblast growth factor receptor 2 are provided.

11 Claims, No Drawings

OTHER PUBLICATIONS

Powers et al., *Fibroblast growth factors, their receptors and signaling, Endocr. Relat. Cancer*, 2000, 7:165–197.

Ricol et al., *Tumour suppressive properties of fibroblast growth factor receptor 2–IIIb in human bladder cancer, Oncogene*, 1999, 18:7234–7243.

Yamada et al., *Suppression of glioblastoma cell growth following antisense oligonucleotide–mediated inhibition of fibroblast growth factor receptor expression, Glia*, 1999, 28:66–76.

Yu et al., *Loss of fibroblast growth factor receptor 2 ligand–binding specificity in Apert syndrome, Proc. Natl. Acad. Sci. U. S. A.*, 2000, 97:14536–14541.

* cited by examiner

ANTISENSE MODULATION OF FIBROBLAST GROWTH FACTOR RECEPTOR 2 EXPRESSION

FIELD OF THE INVENTION

The present invention provides compositions and methods for modulating the expression of fibroblast growth factor receptor 2. In particular, this invention relates to compounds, particularly oligonucleotides, specifically hybridizable with nucleic acids encoding fibroblast growth factor receptor 2. Such compounds have been shown to modulate the expression of fibroblast growth factor receptor 2.

BACKGROUND OF THE INVENTION

The fibroblast growth factor (FGF) family of signaling polypeptides regulates a diverse array of physiologic functions including mitogenesis, wound healing, cell differentiation and angiogenesis, and development. Both normal and malignant cell growth and proliferation are affected by changes in local concentration of these extracellular signaling molecules, which act as autocrine and paracrine factors. Autocrine FGF signaling may be particularly important in the progression of steroid hormone-dependent cancers to a hormone independent state (Powers et al., *Endocr. Relat. Cancer,* 2000, 7, 165–197). FGFs and their receptors are expressed at increased levels in several tissues and cell lines, and overexpression is believed to contribute to the malignant phenotype. Furthermore, a number of oncogenes are homologues of genes encoding growth factor receptors, and there is a potential for aberrant activation of FGF-dependent signaling in human pancreatic cancer (Ozawa et al., *Teratog. Carcinog. Mutagen.,* 2001, 21, 27–44).

The two prototypic members are acidic fibroblast growth factor (aFGF or FGF1) and basic fibroblast growth factors (bFGF or FGF2), and to date, at least twenty distinct FGF family members have been identified. The cellular response to FGFs is transmitted via four types of high affinity transmembrane tyrosine-kinase fibroblast growth factor receptors numbered 1 to 4 (FGFR-1 to FGFR-4). Upon ligand binding, the receptors dimerize and auto- or trans-phosphorylate specific cytoplasmic tyrosine residues to transmit an intracellular signal that ultimately reaches nuclear transcription factor effectors. Mitogenic signaling by these FGFRs is subsequently mediated via a number of pathways, including the ras/raf/MAP kinase cascade (Ozawa et al., *Teratog. Carcinog. Mutagen.,* 2001, 21, 27–44).

Alternative splicing of the mRNA from the FGFRs 1, 2, and 3 results in a wide range of receptor isoforms with varying ligand-binding properties and specificities. With seven different receptor possibilities and at least 20 ligands in the FGF family, there is a great deal of diversity in the FGF signaling pathway (Powers et al., *Endocr. Relat. Cancer,* 2000, 7, 165–197). Furthermore, expression and localization of the receptor isoforms is regulated in a tissue specific manner. Thus, the various FGFs may exert different influences upon different cell types by interacting with different receptor splice variants to initiate unique intracellular signaling cascades, leading to a panoply of cellular responses (Ozawa et al., *Teratog. Carcinog. Mutagen.,* 2001, 21, 27–44).

Fibroblast growth factor receptor 2 (also known as FGF receptor-2, FGFR-2, Crouzon syndrome, craniofacial dysostosis 1 (CFD1), Pfeiffer syndrome, JWS, CEK3, ECT1, TK14, TK25, BFR-1, and K-Sam) as well as its splice variant, keratinocyte growth factor receptor (KGFR or bek), have high affinity for the acidic and/or basic fibroblast growth factors, as well as the keratinocyte growth factor ligands.

The human fibroblast growth factor receptor 2 gene was originally isolated as the protein tyrosine kinase 14 (TK14) from a human tumor cDNA library. High levels of amino acid homology to the chicken bFGF receptor, to a partial sequence of the mouse bek protein, and to another human protein encoded by the fms-like tyrosine kinase gene were noted, indicating that the human genome had at least two distinct fibroblast growth factor receptors. As further evidence that this was a true cell-surface receptor, overexpression of the TK14 gene in COS-1 cells lead to the appearance of new cell-surface binding sites for acidic and basic FGFs (Houssaint et al., *Proc. Natl. Acad. Sci. U.S.A.,* 1990, 87, 8180–8184). Independently, fibroblast growth factor receptor 2 was cloned from a human brainstem cDNA library, using the murine bek gene as a probe (Dionne et al., *Embo J.,* 1990, 9, 2685–2692). The human fibroblast growth factor receptor 2 gene was mapped to the 10q25.3–q26 locus (Dionne et al., *Cytogenet. Cell. Genet.,* 1992, 60, 34–36).

The keratinocyte growth factor receptor, a splice variant related to, but distinct from, fibroblast growth factor receptor 2, was cloned from a B5/589 mammary epithelial cell cDNA library (Miki et al., *Science,* 1991, 251, 72–75). KGF is expressed only by mesenchymal cells, such as fibroblasts and hair follicular dermal papilla cells, and KGFR is expressed only by epithelial tissues, such as epidermis and intestinal epithelium, generally in close proximity to cells that express KGF. This splice variant of fibroblast growth factor 2 is an important mediator of proliferation and differentiation in a wide variety of epithelial cells including hepatocytes, gastrointestinal epithelial cells, type II pneumocytes, transitional urothelial cells, and keratinocytes in all stratified squamous epithelia (Danilenko, *Toxicol. Pathol.,* 1999, 27, 64–71).

Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signaling in intramembranous bone formation. For example, in Apert (AP) syndrome, characterized by premature cranial suture ossification, most cases are associated with point mutations engendering gain-of-function in fibroblast growth factor receptor 2 (Lemonnier et al., *J. Bone Miner. Res.,* 2001, 16, 832–845).

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene (Meyers et al., *Am. J. Hum. Genet.,* 1996, 58, 491–498; Plomp et al., *Am. J. Med. Genet.,* 1998, 75, 245–251), and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by a typical FGF ligands. This loss of ligand specificity leads to aberrant signaling and suggests that the severe phenotypes of these disease syndromes result from ectopic ligand-dependent activation of fibroblast growth factor receptor 2 (Yu et al., *Proc. Natl. Acad. Sci. U.S.A.,* 2000, 97, 14536–14541).

In keeping with the findings in humans, the heterozygous abrogation of one fibroblast growth factor receptor 2 allele in mice resulted in a splicing switch leading to a gain-of-function mutation. The consequences of this mutation are neonatal growth retardation and death, ocular proptosis, precocious ossification of the coronal sutures, zygomatic arch joints, and sternabrae, and abnormalities in secondary branching of organs that undergo branching morphogenesis in development, as well as other major defects in the kidney, lung, and lacrimal glands. This phenotype strongly parallels those of Apert and Pfeiffer syndrome patients (Hajihosseini et al., *Proc. Natl. Acad. Sci. U.S.A.,* 2001, 98, 3855–3860).

Gene rearrangements of fibroblast growth factor receptor 2 have also been shown to lead to ligand independent activation of FGFRs (Powers et al., *Endocr. Relat. Cancer,* 2000, 7, 165–197). A constitutively active form of fibroblast growth factor receptor 2 with an altered C-terminus was identified in a rat osteosarcoma cDNA library, and this isoform arose from a chromosomal rearrangement of the fibroblast growth factor receptor 2 gene with a novel gene, FGFR activating gene 1 (FRAG1). The FGFR-2/FRAG1 fusion protein seems to form constitutive dimers, resulting in autophosphorylation of the fibroblast growth factor receptor 2 kinase domains and activation of the FGF signaling pathway (Lorenzi et al., *Proc. Natl. Acad. Sci. U.S.A.,* 1996, 93, 8956–8961).

KGFR and fibroblast growth factor receptor 2 mRNAs were found to be overexpressed in both human pancreatic cancer cells and the adjacent pancreatic parenchyma (Ishiwata et al., *Am. J. Pathol.,* 1998, 153, 213–222), and expression of the FGFR2-IIIb isoform of fibroblast growth factor receptor 2 is downregulated in a subset of transitional cell carcinomas of the bladder, further indicating the involvement of this gene in tumorogenesis (Ricol et al., *Oncogene,* 1999, 18, 7234–7243).

The modulation of fibroblast growth factor receptor 2 activity and/or expression is an ideal target for therapeutic intervention aimed at regulating the FGF signaling pathway in the prevention and treatment of many cancers and hyperproliferative diseases.

Investigative strategies aimed at modulating fibroblast growth factor receptor 2 function have involved the use of antibodies directed against a peptide fragment of fibroblast growth factor receptor 2 to perturb ligand-receptor binding and functionally block signaling, and the use of antisense oligonucleotides.

A phosphorothioate antisense oligodeoxynucleotide 15 nucleotides in length which does not discriminate between any of the alternate splice forms of fibroblast growth factor receptor 2, spanning the translation start site was used to investigate the role of fibroblast growth factor receptor 2 in FGF signaling. In the same study, two additional phosphorothioate antisense oligodeoxynucleotides 19 and 16 nucleotides in length were designed to be specific for KGFR and bek exon sequences, respectively (Post et al., *Development,* 1996, 122, 3107–3115). These antisense oligonucleotides were used to show that lung branching morphogenesis is reduced in cultures of embryonic rat lung explants when expression of fibroblast growth factor receptor 2 is abrogated. KGFR-specific antisense oligonucleotides dramatically inhibited lung branching, while bek-specific antisense oligonucleotides reduced lung branching to a lesser degree (Post et al., *Development,* 1996, 122, 3107–3115).

A phosphorothioate antisense oligodeoxynucleotide of unspecified length, complementary to the translation start site of fibroblast growth factor receptor 2 was used to investigate the role of fibroblast growth factor receptor 2 signaling in human glioblastoma cells (Yamada et al., *Glia,* 1999, 28, 66–76).

Disclosed and claimed in U.S. Pat. No. 5,578,566 are KGFR peptides which inhibit binding between keratinocyte growth factor (KGF) and the FGFR-1, FGFR-2 and KGFR receptors. The sequence of the peptides is derived from regions in the receptors which specifically bind the growth factor. Also provided are pharmaceutical compositions and methods of inhibiting the interaction of KGF and the receptor in a patient to treat various carcinomas (Bottaro et al., 1996).

Disclosed and claimed in U.S. Pat. No. 6,054,312 is a composition comprising a physiologically acceptable buffer and filamentous phage particles presenting a ligand that binds to a mammalian cell surface molecule, wherein the cell surface molecule is an FGF receptor, and the phage genome encodes a therapeutic gene product which is an antisense oligonucleotide (Larocca et al., 2000).

Currently, there are no known therapeutic agents that effectively inhibit the synthesis of fibroblast growth factor receptor 2. Consequently, there remains a long felt need for additional agents capable of effectively inhibiting fibroblast growth factor receptor 2 function.

Antisense technology is emerging as an effective means for reducing the expression of specific gene products and therefore may prove to be uniquely useful in a number of therapeutic, diagnostic, and research applications for the modulation of fibroblast growth factor receptor 2 expression.

The present invention provides compositions and methods for modulating fibroblast growth factor receptor 2 expression, including modulation of the truncated mutants and alternatively spliced forms of fibroblast growth factor receptor 2 such as KGFR.

SUMMARY OF THE INVENTION

The present invention is directed to compounds, particularly antisense oligonucleotides, which are targeted to a nucleic acid encoding fibroblast growth factor receptor 2, and which modulate the expression of fibroblast growth factor receptor 2. Pharmaceutical and other compositions comprising the compounds of the invention are also provided. Further provided are methods of modulating the expression of fibroblast growth factor receptor 2 in cells or tissues comprising contacting said cells or tissues with one or more of the antisense compounds or compositions of the invention. Further provided are methods of treating an animal, particularly a human, suspected of having or being prone to a disease or condition associated with expression of fibroblast growth factor receptor 2 by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding fibroblast growth factor receptor 2, ultimately modulating the amount of fibroblast growth factor receptor 2 produced. This is accomplished by providing antisense compounds which specifically hybridize with one or more nucleic acids encoding fibroblast growth factor receptor 2. As used herein, the terms "target nucleic acid" and "nucleic acid encoding fibroblast growth factor receptor 2" encompass DNA encoding fibroblast growth factor receptor 2, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of fibroblast growth factor receptor 2. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding fibroblast growth factor receptor 2. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding fibroblast growth factor receptor 2, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.,* 2000, 480, 17–24; Celis, et al., *FEBS Lett.,* 2000, 480, 2–16), SAGE (serial analysis of gene expression) (Madden, et al., *Drug Discov. Today,* 2000, 5, 415–425), READS (restriction enzyme amplification of digested cDNAs) (Prashar and Weissman, *Methods Enzymol.,* 1999, 303, 258–72), TOGA (total gene expression analysis) (Sutcliffe, et al., *Proc. Natl. Acad. Sci. U.S.A.,* 2000, 97, 1976–81), protein arrays and proteomics (Celis, et al., *FEBS Lett.,* 2000, 480, 2–16; Jungblut, et al., *Electrophoresis,* 1999, 20, 2100–10), expressed sequence tag (EST) sequencing (Celis, et al., *FEBS Lett.,* 2000, 480, 2–16; Larsson, et al., *J. Biotechnol.,* 2000, 80, 143–57), subtractive RNA fingerprinting (SuRF) (Fuchs, et al., *Anal. Biochem.,* 2000, 286, 91–98; Larson, et al., *Cytometry,* 2000, 41, 203–208), subtractive cloning, differential display (DD) (Jurecic and Belmont, *Curr. Opin. Microbiol.,* 2000, 3, 316–21), comparative genomic hybridization (Carulli, et al., *J. Cell Biochem. Suppl.,* 1998, 31, 286–96), FISH (fluorescent in situ hybridization) techniques (Going and Gusterson, *Eur. J. Cancer,* 1999, 35, 1895–904) and mass spectrometry methods (reviewed in (To, *Comb. Chem. High Throughput Screen,* 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'–5' linkages, 2'–5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O—(2-methoxyethyl) or 2'-MOE) (Martin et al., *Helv. Chim. Acta,* 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne ($—CH_2—)_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196 (filed Oct. 23, 1992) the entire disclosure of which is incorporated herein by reference. Conjugate moieties include but are not limited to lipid moieties such as a cholesterol moiety (Letsinger et al., *Proc. Natl. Acad. Sci. USA,* 1989, 86, 6553–6556), cholic acid (Manoharan et al., *Bioorg. Med. Chem. Let.,* 1994, 4, 1053–1060), a thioether, e.g., hexyl-S-tritylthiol (Manoharan et al., *Ann. N.Y. Acad. Sci.,* 1992, 660, 306–309; Manoharan et al., *Bioorg. Med. Chem. Let.,* 1993, 3, 2765–2770), a thiocholesterol (Oberhauser et al., *Nucl. Acids Res.,* 1992, 20, 533–538), an aliphatic chain, e.g., dodecandiol or undecyl residues (Saison-Behmoaras et al., *EMBO J.,* 1991, 10, 1111–1118; Kabanov et al., *FEBS Lett.,* 1990, 259, 327–330; Svinarchuk et al., *Biochimie,* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651–3654; Shea et al., *Nucl. Acids Res.,* 1990, 18, 3777–3783), a polyamine or a polyethylene glycol chain (Manoharan et al., *Nucleosides & Nucleotides,* 1995, 14, 969–973), or adamantane acetic acid (Manoharan et al.,

*Tetrahedron Lett.,* 1995, 36, 3651–3654), a palmityl moiety (Mishra et al., *Biochim. Biophys. Acta,* 1995, 1264, 229–237), or an octadecylamine or hexylamino-carbonyl-oxycholesterol moiety (Crooke et al., *J. Pharmacol. Exp. Ther.,* 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of fibroblast growth factor receptor 2 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding fibroblast growth factor receptor 2, enabling sandwich and other assays to easily be constructed to exploit this fact. Hybridization of the antisense oligonucleotides of the invention with a nucleic acid encoding fibroblast growth factor receptor 2 can be detected by means known in the art. Such means may include conjugation of an enzyme to the oligonucleotide, radiolabelling of the oligonucleotide or any other suitable detection means. Kits using such detection means for detecting the level of fibroblast growth factor receptor 2 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain ($C_8$–$C_{12}$) mono, di, and tri-glycerides, polyoxyethylated glyceryl fatty acid esters, fatty alcohols, polyglycolized glycerides, saturated polyglycolized $C_8$–$C_{10}$ glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research,* 1994, 11, 1385–1390; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research,* 1994, 11, 1385; Ho et al., *J. Pharm. Sci.,* 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.,* 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release,* 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting,* 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research,* 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.,* 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters,* 1987, 223, 42; Wu et al., *Cancer Research,* 1993, 53, 3765).

Various liposomes comprising one or more glycolipids are known in the art. Papahadjopoulos et al. (*Ann. N.Y. Acad. Sci.,* 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.,* 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.,* 1980, 53, 2778) described liposomes comprising a nonionic detergent, $2C_{12}15G$, that contains a PEG moiety. Illum et al. (*FEBS Lett.,* 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.,* 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta,* 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al.

discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems,* 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems,* 1991, p.92); and perfluorochemical emulsions, such as FC-43. Takahashi et al., *J. Pharm. Pharmacol.,* 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems,* 1991, p.92; Muranishi, *Critical Reviews in Therapeutic Drug Carrier Systems,* 1990, 7, 1–33; El Hariri et al., *J. Pharm. Pharmacol.,* 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics,* 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 In: *Remington's Pharmaceutical Sciences,* 18th Ed., Gennaro, ed., Mack Publishing Co., Easton, Pa., 1990, pages 782–783; Muranishi, *Critical Reviews in Therapeutic Drug Carrier Systems,* 1990, 7, 1–33; Yamamoto et al., *J. Pharm. Exp. Ther.,* 1992, 263, 25; Yamashita et al., *J. Pharm. Sci.,* 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems,* 1991, page 92; Muranishi, *Critical Reviews in Therapeutic Drug Carrier Systems,* 1990, 7, 1–33; Buur et al., *J. Control Rel.,* 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems,* 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy,* 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy,* 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research,* 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.,* 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta,* 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl -5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(dimethylaminooxyethyl) Nucleoside Amidites 2'-(Dimethylaminooxyethoxy) Nucleoside Amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy) ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was strirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 Al 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O—$CH_2$—O—$CH_2$—$N(CH_2)_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl)]-5-methyl uridine

To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using $MeOH:CH_2Cl_2:Et_3N$ (20:1, v/v, with 1% triethylamine) gives the title compound.

5'-O-Dimethoxytrityl-2'-O-[2(2-N,N-dimethylamino-ethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P═O) oligonucleotides are synthesized on an automated DNA synthesizer (Applied Biosystems model 380B) using standard phosphoramidite chemistry with oxidation by iodine.

Phosphorothioates (P═S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P═O or P═S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry,* 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)]Chimeric Phosphorothioate Oligonucleotides

[2'-O-(2-methoxyethyl)]-[2'-deoxy]-[-2'-O-(methoxyethyl)]chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 6 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

A431 Cells:

The human epidermoid carcinoma cell line A431 was obtained from the American Type Culure Collection (Manassas, Va.). A431 cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analyses, cells may be seeded onto 100 mm or other standard tissue culture plates and treated similarly, using appropriate volumes of medium and oligonucleotide.

3T3-L1 Cells:

The mouse embryonic adipocyte-like cell line 3T3-L1 was obtained from the American Type Culure Collection (Manassas, Va.). 3T3-L1 cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 80% confluence. Cells were seeded into 96-well plates (Falcon-Primaria #3872) at a density of 4000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds:

When cells reached 80% confluency, they were treated with oligonucleotide. For cells grown in 96-well plates, wells were washed once with 200 μL OPTI-MEM™-1 reduced-serum medium (Gibco BRL) and then treated with 130 μL of OPTI-MEM™-1 containing 3.75 μg/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Fibroblast Growth Factor Receptor 2 Expression Antisense modulation of fibroblast growth factor receptor 2 expression can be assayed in a variety of ways known in the art. For example, fibroblast growth factor receptor 2 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of fibroblast growth factor receptor 2 can be quantitated in a variety of ways well known in the art, such as immunoprecipitation, Western blot analysis (immunoblotting), ELISA or fluorescence-activated cell sorting (FACS). Antibodies directed to fibroblast growth factor receptor 2 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+ mRNA Isolation

Poly(A)+ mRNA was isolated according to Miura et al., *Clin. Chem.,* 1996, 42, 1758–1764. Other methods for poly(A)+ mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY96™ kit and buffers purchased from Qiagen Inc. (Valencia Calif.) following the manufacturer's recommended procedures. Briefly, for cells grown on 96-well plates, growth medium was removed from the cells and each well was washed with 200 μL cold PBS. 100 μL Buffer RLT was added to each well and the plate vigorously agitated for 20 seconds. 100 μL of 70% ethanol was then added to each well and the contents mixed by pipetting three times up and down. The samples were then transferred to the RNEASY96™ well plate attached to a QIAVAC™ manifold fitted with a waste collection tray and attached to a vacuum source. Vacuum was applied for 15 seconds. 1 mL of Buffer RW1 was added to each well of the RNEASY96™ plate and the vacuum again applied for 15 seconds. 1 mL of Buffer RPE was then added to each well of the RNEASY96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of Fibroblast Growth Factor Receptor 2 mRNA Levels Quantitation of fibroblast growth factor receptor 2 mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 μL PCR cocktail (1×TAQMAN™ buffer A, 5.5 mM $MgCl_2$, 300 μM each of DATP, dCTP and dGTP, 600 μm of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 μL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry,* 1998, 265, 368–374.

In this assay, 175 μL of RiboGreen™ working reagent (RiboGreen™ reagent diluted 1:2865 in 10 mM Tris-HCl, 1 mM EDTA, pH 7.5) is pipetted into a 96-well plate containing 25 μL purified, cellular RNA. The plate is read in a CytoFluor 4000 (PE Applied Biosystems) with excitation at 480 nm and emission at 520 nm.

Probes and primers to human fibroblast growth factor receptor 2 were designed to hybridize to a human fibroblast growth factor receptor 2 sequence, using published sequence information (GenBank accession number NM_000141, incorporated herein as SEQ ID NO:3). For human fibroblast growth factor receptor 2 the PCR primers were: forward primer: AAGGACCACTCTTCTGCGTTTG (SEQ ID NO: 4) reverse primer: TGGGTCGGGATGGAGAAAG (SEQ ID NO: 5) and the PCR probe was: FAM-CCCACAACCCCGGGCTCGTC-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were: forward primer: GAAGGTGAAGGTCGGAGTC (SEQ ID NO: 7) reverse primer: GAAGATGGTGATGGGATTTC (SEQ ID NO: 8) and the PCR probe was: 5' JOE-CAAGCTTCCCGTTCTCAGCC— TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Probes and primers to mouse fibroblast growth factor receptor 2 were designed to hybridize to a mouse fibroblast growth factor receptor 2 sequence, using published sequence information (GenBank accession number M86441, incorporated herein as SEQ ID NO:10). For mouse fibroblast growth factor receptor 2 the PCR primers were: forward primer: ACCTGGATGTCGTTGAACGTT (SEQ ID NO:11) reverse primer: GACCACCGTGGAGGCATTT (SEQ ID NO: 12) and the PCR probe was: FAM-CCACACCGTCCCATCCTCCAAGCT-TAMRA (SEQ ID NO: 13) where FAM (PE-Applied Biosystems, Foster City, Calif.) is the fluorescent reporter dye) and TAMRA (PE-Applied Biosystems, Foster City, Calif.) is the quencher dye. For mouse GAPDH the PCR primers were: forward primer: GGCAAATTCAACGGCACAGT (SEQ ID NO: 14) reverse primer: GGGTCTCGCTCCTGGAAGAT (SEQ ID NO: 15) and the PCR probe was: 5' JOE-AAGGCCGAGAATGGGAAGCTTGTCATC— TAMRA 3' (SEQ ID NO: 16) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of Fibroblast Growth Factor Receptor 2 mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ U Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human fibroblast growth factor receptor 2, a human fibroblast growth factor receptor 2 specific probe was prepared by PCR using the forward primer AAGGACCACTCTTCTGCGTTTG (SEQ ID NO: 4) and the reverse primer TGGGTCGGGATGGAGAAAG (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

To detect mouse fibroblast growth factor receptor 2, a mouse fibroblast growth factor receptor 2 specific probe was prepared by PCR using the forward primer ACCTGGATGTCGTTGAACGTT (SEQ ID NO:11) and the reverse primer GACCACCGTGGAGGCATTT (SEQ ID NO: 12). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Fibroblast Growth Factor Receptor 2 Expression by Chimeric Phosphorothioate Oligonucleotides Having 2'-MOE Wings and a Deoxy Gap In accordance with the present invention, a series of oligonucleotides were designed to target different regions of the human fibroblast growth factor receptor 2 RNA, using published sequences (GenBank accession number NM_000141, incorporated herein as SEQ ID NO: 3, four ordered contiguous sequences from AC009988, corrected with sequences from AF097344 and M97193 concatenated and incorporated herein as SEQ ID NO: 17, GenBank accession number AB030073, incorporated herein as SEQ ID NO: 18, GenBank accession number AB030076, incorporated herein as SEQ ID NO: 19, GenBank accession number AB030077, incorporated herein as SEQ ID NO: 20, GenBank accession number AB030078, incorporated herein as SEQ ID NO: 21, GenBank accession number S41878, incorporated herein as SEQ ID NO: 22, GenBank accession number M35718, incorporated herein as SEQ ID NO: 23, GenBank accession number M87771, incorporated herein as SEQ ID NO: 24, GenBank accession number M97193, incorporated herein as SEQ ID NO: 25, GenBank accession number M87772, incorporated herein as SEQ ID NO: 26, GenBank accession number U11814, incorporated herein as SEQ ID NO: 27, GenBank accession number X56191, incorporated herein as SEQ ID NO: 28, residues 92947–129167 from GenBank accession number AC012690, incorporated herein as SEQ ID NO: 29, and residues 8890–11287 from GenBank accession number AC012690, the complement of which is incorporated herein as SEQ ID NO: 30). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P═S) throughout the oligonucleotide. All cytidine residues are 5-ethylcytidines. The compounds were analyzed for their effect on human fibroblast growth factor receptor 2 mRNA levels by quantitative real-time PCR as described in other examples herein. Data are averages from two experiments. If present, "N.D." indicates "no data".

TABLE 1

Inhibition of human fibroblast growth factor receptor 2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 143337 | 5'UTR | 3 | 150 | tgcggtgggctcaggaaccg | 42 | 31 |
| 143338 | 5'UTR | 3 | 228 | ttccatatctccatgtggac | 41 | 32 |
| 143339 | Start Codon | 3 | 266 | ccagctgaccatggttacgg | 13 | 33 |
| 143340 | Coding | 3 | 308 | caaggttgccatggtgacca | 21 | 34 |
| 143341 | Coding | 3 | 313 | agggacaaggttgccatggt | 18 | 35 |
| 143342 | Coding | 3 | 336 | ctaaactgaaggagggccgg | 15 | 36 |
| 143343 | Coding | 3 | 381 | ggtatttggttggtggctct | 32 | 37 |
| 143344 | Coding | 3 | 461 | cacggcggcatctttcaaca | 0 | 38 |
| 143345 | Coding | 3 | 471 | tccaactgatcacggcggca | 25 | 39 |
| 143346 | Coding | 3 | 481 | ccatccttagtccaactgat | 28 | 40 |
| 143347 | Coding | 3 | 497 | gggccccaagtgcaccccat | 25 | 41 |
| 143348 | Coding | 3 | 502 | ttgttgggccccaagtgcac | 36 | 42 |
| 143349 | Coding | 3 | 512 | cactgtcctattgttgggcc | 3 | 43 |
| 143350 | Coding | 3 | 522 | ccccaataagcactgtccta | 39 | 44 |
| 143351 | Coding | 3 | 630 | ctgtgacattcaccatgaag | 32 | 45 |
| 143352 | Coding | 3 | 635 | ggcatctgtgacattcacca | 38 | 46 |
| 143353 | Coding | 3 | 640 | gagatggcatctgtgacatt | 14 | 47 |
| 143354 | Coding | 3 | 853 | tgcttaaactccttcccgtt | 0 | 48 |
| 143355 | Coding | 3 | 858 | gctcctgcttaaactccttc | 22 | 49 |
| 143356 | Coding | 3 | 863 | gcgatgctcctgcttaaact | 0 | 50 |
| 143357 | Coding | 3 | 895 | cagtgctggtttcgtacctt | 23 | 51 |
| 143358 | Coding | 3 | 900 | ggctccagtgctggtttcgt | 9 | 52 |
| 143359 | Coding | 3 | 969 | acccgtattcattctccacc | 19 | 53 |
| 143360 | Coding | 3 | 974 | gatggacccgtattcattct | 26 | 54 |
| 143361 | Coding | 3 | 1186 | accttgaggtagggcagccc | 23 | 55 |
| 143362 | Coding | 3 | 1202 | accggcggccttgagaacct | 0 | 56 |
| 143363 | Coding | 3 | 1216 | tccgtggtgttaacaccggc | 0 | 57 |
| 143364 | Coding | 3 | 1243 | cgaatatagagaacctcaat | 38 | 58 |
| 143365 | Coding | 3 | 1248 | cattccgaatatagagaacc | 11 | 59 |
| 143366 | Coding | 3 | 1258 | tcaaaagttacattccgaat | 37 | 60 |
| 143367 | Coding | 3 | 1317 | cagagtgaaaggatatccca | 51 | 61 |
| 143368 | Coding | 3 | 1318 | gcagagtgaaaggatatccc | 0 | 62 |
| 143369 | Coding | 3 | 1411 | aagacccctatgcagtaaat | 24 | 63 |
| 143370 | Coding | 3 | 1421 | ggcgattaagaagaccccta | 15 | 64 |
| 143371 | Coding | 3 | 1479 | agtctggcttcttggtcgtg | 60 | 65 |
| 143372 | Coding | 3 | 1484 | gctgaagtctggcttcttgg | 4 | 66 |
| 143373 | Coding | 3 | 1489 | tggctgctgaagtctggctt | 39 | 67 |
| 143374 | Coding | 3 | 2023 | atgtcataggagtactccat | 33 | 68 |
| 143375 | Coding | 3 | 2028 | ggttaatgtcataggagtac | 0 | 69 |
| 143376 | Coding | 3 | 2032 | acacggttaatgtcatagga | 23 | 70 |
| 143377 | Coding | 3 | 2387 | ttcctccacgggaatccctg | 33 | 71 |
| 143378 | Coding | 3 | 2536 | agaattcgatccaagtcttc | 11 | 72 |
| 143379 | Coding | 3 | 2557 | tcctcattggttgtgagagt | 26 | 73 |
| 143380 | Coding | 3 | 2562 | agtattcctcattggttgtg | 15 | 74 |
| 143381 | Coding | 3 | 2701 | tttatgtgtggatactgagg | 17 | 75 |
| 143382 | Stop Codon | 3 | 2729 | cacagtcattcatgttttaa | 12 | 76 |
| 143383 | 3'UTR | 3 | 2982 | ccagaacgcacggcaggtga | 45 | 77 |
| 143384 | 3'UTR | 3 | 3006 | accttgagtcctactggtcc | 25 | 78 |
| 143385 | 3'UTR | 3 | 3091 | actgcatttgtgctctgtaa | 37 | 79 |
| 143386 | 3'UTR | 3 | 3551 | caatcgtctgacagcagcat | 49 | 80 |
| 143387 | 3'UTR | 3 | 3758 | cagagagaagcacattctgc | 28 | 81 |
| 143388 | 3'UTR | 3 | 3890 | tttctatgatgggacttgaa | 19 | 82 |
| 143389 | 3'UTR | 3 | 3992 | ctggatcttttggtgaggtc | 29 | 83 |
| 143390 | 3'UTR | 3 | 4040 | tagtacagaaggaacaacgg | 34 | 84 |
| 143391 | 3'UTR | 3 | 4103 | tgcattcatcttgcacggct | 0 | 85 |
| 143392 | Exon 4: Intron 4 | 17 | 34376 | gcagttacttactcttgttg | 8 | 86 |

TABLE 1-continued

Inhibition of human fibroblast growth factor receptor 2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 143393 | Intron 8: Exon 9 | 17 | 79949 | ccccgagtgctagaacagac | 40 | 87 |
| 143394 | Intron 9: Exon 10 | 17 | 81315 | accggcggcctagaaaacaa | 22 | 88 |
| 143395 | Genomic | 17 | 109858 | ccactcttgcctctcctgaa | 16 | 89 |
| 143396 | Intron: Start of exon 20a | 17 | 116607 | ctttcagatctgataggaaa | 5 | 90 |
| 143397 | Intron: Start of exon 20b | 17 | 118671 | caagtattcctgaaagaagg | 37 | 91 |
| 143398 | Coding | 18 | 2818 | cacaggaaatggcaggtgtt | 68 | 92 |
| 143399 | 3'UTR | 19 | 2780 | acttcattcttggaccacat | 13 | 93 |
| 143400 | Coding | 20 | 2781 | tgcctctgtgaggtccccac | 17 | 94 |
| 143401 | 3'UTR | 21 | 2783 | ggcacctagtggagtttcag | 20 | 95 |
| 143402 | 3'UTR | 22 | 145 | atactgttcgagaggttggc | 0 | 96 |
| 143403 | Coding | 23 | 694 | gagatggcatcttctggctc | 1 | 97 |
| 143404 | Coding | 23 | 2521 | cagtccctcatcatcatgta | 41 | 98 |
| 143405 | Coding | 24 | 1416 | agccgaaaccttgagaacct | 20 | 99 |
| 143406 | Coding | 25 | 1682 | gcgcttgctgttttggcagg | 13 | 100 |
| 143407 | 3'UTR | 26 | 1247 | gtcctcagaccttttccttt | 0 | 101 |
| 143408 | Coding | 27 | 1187 | ccccgagtgcttgagaacct | 32 | 102 |
| 143409 | Coding | 27 | 1335 | accggcggccttgctgtttt | 33 | 103 |
| 143410 | 3'UTR | 28 | 2593 | tggcatgatctcggctcact | 18 | 104 |
| 143411 | Intron: Start of exon 20c | 29 | 23615 | ttggctttactgcagaaaat | 32 | 105 |
| 143412 | Intron: Start of exon 20d | 29 | 31981 | gcagcttgtaccgctgtggg | 27 | 106 |
| 143413 | Intron: Start of Exon 20e | 30 | 1332 | ggatagaggctgtggaaaaa | 22 | 107 |
| 143423 | Intron 10: Exon 11 | 17 | 83454 | gcgctagattgcagatcaca | 2 | 108 |

As shown in Table 1, SEQ ID NOs 31, 32, 37, 39, 40, 41, 42, 44, 45, 46, 54, 58, 60, 61, 65, 67, 68, 71, 73, 77, 78, 79, 80, 81, 83, 84, 87, 91, 92, 98, 102, 103, 105 and 106 demonstrated at least 25% inhibition of human fibroblast growth factor receptor 2 expression in this assay and are therefore preferred. The target sites to which these preferred sequences are complementary are herein referred to as "active sites" and are therefore preferred sites for targeting by compounds of the present invention.

Example 16

Antisense Inhibition of Mouse Fibroblast Growth Factor Receptor 2 Expression by Chimeric Phosphorothioate Oligonucleotides Having 2'-MOE Wings and a Deoxy Gap.

In accordance with the present invention, a second series of oligonucleotides were designed to target different regions of the mouse fibroblast growth factor receptor 2 RNA, using published sequences (GenBank accession number M86441, incorporated herein as SEQ ID NO: 10). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P═S) throughout the oligonucleotide. All cytidine residues are 5-methylcytidines. The compounds were analyzed for their effect on mouse fibroblast growth factor receptor 2 mRNA levels by quantitative real-time PCR as described in other examples herein. Data are averages from two experiments. If present, "N.D." indicates "no data".

TABLE 2

Inhibition of mouse fibroblast growth factor receptor 2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 143340 | Coding | 10 | 641 | caaggttgccatggtgacca | 27 | 34 |
| 143341 | Coding | 10 | 646 | agggacaaggttgccatggt | 0 | 35 |
| 143342 | Coding | 10 | 669 | ctaaactgaaggagggccgg | 0 | 36 |
| 143343 | Coding | 10 | 714 | ggtatttggttggtggctct | 72 | 37 |
| 143344 | Coding | 10 | 794 | cacggcggcatctttcaaca | 30 | 38 |
| 143345 | Coding | 10 | 804 | tccaactgatcacggcggca | 40 | 39 |
| 143346 | Coding | 10 | 814 | ccatccttagtccaactgat | 66 | 40 |
| 143347 | Coding | 10 | 830 | gggccccaagtgcaccccat | 28 | 41 |
| 143348 | Coding | 10 | 835 | ttgttgggccccaagtgcac | 54 | 42 |
| 143349 | Coding | 10 | 845 | cactgtcctattgttgggcc | 0 | 43 |
| 143350 | Coding | 10 | 855 | ccccaataagcactgtccta | 80 | 44 |
| 143351 | Coding | 10 | 963 | ctgtgacattcaccatgaag | 25 | 45 |
| 143352 | Coding | 10 | 968 | ggcatctgtgacattcacca | 97 | 46 |
| 143353 | Coding | 10 | 973 | gagatggcatctgtgacatt | 0 | 47 |
| 143354 | Coding | 10 | 1186 | tgcttaaactccttcccgtt | 0 | 48 |
| 143355 | Coding | 10 | 1191 | gctcctgcttaaactccttc | 43 | 49 |
| 143356 | Coding | 10 | 1196 | gcgatgctcctgcttaaact | 0 | 50 |
| 143357 | Coding | 10 | 1228 | cagtgctggtttcgtacctt | 0 | 51 |
| 143358 | Coding | 10 | 1233 | ggctccagtgctggtttcgt | 12 | 52 |
| 143359 | Coding | 10 | 1302 | acccgtattcattctccacc | 73 | 53 |
| 143360 | Coding | 10 | 1307 | gatggacccgtattcattct | 0 | 54 |
| 143361 | Coding | 10 | 1519 | accttgaggtagggcagccc | 83 | 55 |
| 143363 | Coding | 10 | 1549 | tccgtggtgttaacaccggc | 0 | 57 |
| 143364 | Coding | 10 | 1576 | cgaatatagagaacctcaat | 66 | 58 |
| 143365 | Coding | 10 | 1581 | cattccgaatatagagaacc | 4 | 59 |
| 143366 | Coding | 10 | 1591 | tcaaaagttacattccgaat | 66 | 60 |
| 143368 | Coding | 10 | 1651 | gcagagtgaaaggatatccc | 25 | 62 |
| 143369 | Coding | 10 | 1744 | aagacccctatgcagtaaat | 56 | 63 |
| 143370 | Coding | 10 | 1754 | ggcgattaagaagacccta | 2 | 64 |
| 143371 | Coding | 10 | 1812 | agtctggcttcttggtcgtg | 64 | 65 |
| 143372 | Coding | 10 | 1817 | gctgaagtctggcttcttgg | 0 | 66 |
| 143373 | Coding | 10 | 1822 | tggctgctgaagtctggctt | 65 | 67 |
| 143374 | Coding | 10 | 2356 | atgtcataggagtactccat | 38 | 68 |
| 143375 | Coding | 10 | 2361 | ggttaatgtcataggagtac | 0 | 69 |
| 143376 | Coding | 10 | 2365 | acacggttaatgtcatagga | 0 | 70 |
| 143377 | Coding | 10 | 2720 | ttcctccacgggaatccctg | 89 | 71 |
| 143378 | Coding | 10 | 2869 | agaattcgatccaagtcttc | 10 | 72 |
| 143379 | Coding | 10 | 2890 | tcctcattggttgtgagagt | 38 | 73 |
| 143380 | Coding | 10 | 2895 | agtattcctcattggttgtg | 0 | 74 |
| 143381 | Coding | 10 | 3034 | tttatgtgtggatactgagg | 0 | 75 |

As shown in Table 2, SEQ ID NOs 37, 39, 40, 42, 44, 46, 49, 53, 55, 58, 60, 63, 65, 67 and 71 demonstrated at least 40% inhibition of mouse fibroblast growth factor receptor 2 expression in this experiment and are therefore preferred. The target sites to which these preferred sequences are complementary are herein referred to as "active sites" and are therefore preferred sites for targeting by compounds of the present invention.

Example 17

Western Blot Analysis of Fibroblast Growth Factor Receptor 2 Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to fibroblast growth factor receptor 2 is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. A compound 8 to 50 nucleobases in length targeted to nucleobases 1479 through 1508 of a coding region of a nucleic acid molecule encoding human fibroblast growth factor receptor 2, wherein said compound is an antisense oligonucleotide, wherein said antisense oligonucleotide comprises at least one modified internucleoside linkage, and wherein said compound specifically hybridizes with said nucleic acid molecule encoding human fibroblast growth factor receptor 2 (SEQ ID NO: 3) and inhibits the expression of human fibroblast growth factor receptor 2.

2. The compound of claim 1 wherein the modified internucleoside linkage is a phosphorothioate linkage.

3. The compound of claim 1 wherein the antisense oligonucleotide comprises at least one modified sugar moiety.

4. The compound of claim 3 wherein the modified sugar moiety is a 2'-o-methoxyethyl sugar moiety.

5. The compound of claim 1 wherein the antisense oligonucleotide comprises at least one modified nucleobase.

6. The compound of claim 5 wherein the modified nucleobase is a 5-methylcytosine.

7. The compound of claim 1 wherein the antisense oligonucleotide is a chimeric oligonucleotide.

8. A composition comprising the compound of claim 1 and a pharmaceutically acceptable carrier or diluent.

9. The composition of claim 8 further comprising a colloidal dispersion system.

10. The composition of claim 8 wherein the compound is an antisense oligonucleotide.

11. A method of inhibiting the expression of fibroblast growth factor receptor 2 in cells or tissues comprising contacting said cells or tissues in vitro with the compound of claim 1 so that expression of fibroblast growth factor receptor 2 is inhibited.

* * * * *

SEQUENCE LISTING

```
<160> NUMBER OF SEQ ID NOS: 108

<210> SEQ ID NO 1
<211> LENGTH: 20
<212> TYPE: DNA
<213> ORGANISM: Artificial Sequence
<220> FEATURE:
```

```
<223> OTHER INFORMATION: Antisense Oligonucleotide

<400> SEQUENCE: 1

tccgtcatcg ctcctcaggg                                                   20


<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2

atgcattctg cccccaagga                                                   20


<210> SEQ ID NO 3
<211> LENGTH: 4268
<212> TYPE: DNA
<213> ORGANISM: Homo sapiens
<220> FEATURE:
<221> NAME/KEY: CDS
<222> LOCATION: (274)...(2739)

<400> SEQUENCE: 3

cccaaggacc actcttctgc gtttggagtt gctccccaca accccgggct cgtcgctttc      60

tccatcccga cccacgcggg gcgcggggac aacacaggtc gcggaggagc gttgccattc     120

aagtgactgc agcagcagcg gcagcgcctc ggttcctgag cccaccgcag gctgaaggca     180

ttgcgcgtag tccatgcccg tagaggaagt gtgcagatgg gattaacgtc cacatggaga     240

tatggaagag gaccggggat tggtaccgta acc atg gtc agc tgg ggt cgt ttc      294
                                     Met Val Ser Trp Gly Arg Phe
                                       1               5

atc tgc ctg gtc gtg gtc acc atg gca acc ttg tcc ctg gcc cgg ccc      342
Ile Cys Leu Val Val Val Thr Met Ala Thr Leu Ser Leu Ala Arg Pro
         10                  15                  20

tcc ttc agt tta gtt gag gat acc aca tta gag cca gaa gag cca cca      390
Ser Phe Ser Leu Val Glu Asp Thr Thr Leu Glu Pro Glu Glu Pro Pro
     25                  30                  35

acc aaa tac caa atc tct caa cca gaa gtg tac gtg gct gcg cca ggg      438
Thr Lys Tyr Gln Ile Ser Gln Pro Glu Val Tyr Val Ala Ala Pro Gly
 40                  45                  50                  55

gag tcg cta gag gtg cgc tgc ctg ttg aaa gat gcc gcc gtg atc agt      486
Glu Ser Leu Glu Val Arg Cys Leu Leu Lys Asp Ala Ala Val Ile Ser
                 60                  65                  70

tgg act aag gat ggg gtg cac ttg ggg ccc aac aat agg aca gtg ctt      534
Trp Thr Lys Asp Gly Val His Leu Gly Pro Asn Asn Arg Thr Val Leu
             75                  80                  85

att ggg gag tac ttg cag ata aag ggc gcc acg cct aga gac tcc ggc      582
Ile Gly Glu Tyr Leu Gln Ile Lys Gly Ala Thr Pro Arg Asp Ser Gly
         90                  95                 100

ctc tat gct tgt act gcc agt agg act gta gac agt gaa act tgg tac      630
Leu Tyr Ala Cys Thr Ala Ser Arg Thr Val Asp Ser Glu Thr Trp Tyr
    105                 110                 115

ttc atg gtg aat gtc aca gat gcc atc tca tcc gga gat gat gag gat      678
Phe Met Val Asn Val Thr Asp Ala Ile Ser Ser Gly Asp Asp Glu Asp
120                 125                 130                 135

gac acc gat ggt gcg gaa gat ttt gtc agt gag aac agt aac aac aag      726
Asp Thr Asp Gly Ala Glu Asp Phe Val Ser Glu Asn Ser Asn Asn Lys
                140                 145                 150

aga gca cca tac tgg acc aac aca gaa aag atg gaa aag cgg ctc cat      774
Arg Ala Pro Tyr Trp Thr Asn Thr Glu Lys Met Glu Lys Arg Leu His
```

-continued

```
            155                 160                 165

gct gtg cct gcg gcc aac act gtc aag ttt cgc tgc cca gcc ggg ggg      822
Ala Val Pro Ala Ala Asn Thr Val Lys Phe Arg Cys Pro Ala Gly Gly
        170                 175                 180

aac cca atg cca acc atg cgg tgg ctg aaa aac ggg aag gag ttt aag      870
Asn Pro Met Pro Thr Met Arg Trp Leu Lys Asn Gly Lys Glu Phe Lys
    185                 190                 195

cag gag cat cgc att gga ggc tac aag gta cga aac cag cac tgg agc      918
Gln Glu His Arg Ile Gly Gly Tyr Lys Val Arg Asn Gln His Trp Ser
200                 205                 210                 215

ctc att atg gaa agt gtg gtc cca tct gac aag gga aat tat acc tgt      966
Leu Ile Met Glu Ser Val Val Pro Ser Asp Lys Gly Asn Tyr Thr Cys
                220                 225                 230

gtg gtg gag aat gaa tac ggg tcc atc aat cac acg tac cac ctg gat     1014
Val Val Glu Asn Glu Tyr Gly Ser Ile Asn His Thr Tyr His Leu Asp
            235                 240                 245

gtt gtg gag cga tcg cct cac cgg ccc atc ctc caa gcc gga ctg ccg     1062
Val Val Glu Arg Ser Pro His Arg Pro Ile Leu Gln Ala Gly Leu Pro
        250                 255                 260

gca aat gcc tcc aca gtg gtc gga gga gac gta gag ttt gtc tgc aag     1110
Ala Asn Ala Ser Thr Val Val Gly Gly Asp Val Glu Phe Val Cys Lys
    265                 270                 275

gtt tac agt gat gcc cag ccc cac atc cag tgg atc aag cac gtg gaa     1158
Val Tyr Ser Asp Ala Gln Pro His Ile Gln Trp Ile Lys His Val Glu
280                 285                 290                 295

aag aac ggc agt aaa tac ggg ccc gac ggg ctg ccc tac ctc aag gtt     1206
Lys Asn Gly Ser Lys Tyr Gly Pro Asp Gly Leu Pro Tyr Leu Lys Val
                300                 305                 310

ctc aag gcc gcc ggt gtt aac acc acg gac aaa gag att gag gtt ctc     1254
Leu Lys Ala Ala Gly Val Asn Thr Thr Asp Lys Glu Ile Glu Val Leu
            315                 320                 325

tat att cgg aat gta act ttt gag gac gct ggg gaa tat acg tgc ttg     1302
Tyr Ile Arg Asn Val Thr Phe Glu Asp Ala Gly Glu Tyr Thr Cys Leu
        330                 335                 340

gcg ggt aat tct att ggg ata tcc ttt cac tct gca tgg ttg aca gtt     1350
Ala Gly Asn Ser Ile Gly Ile Ser Phe His Ser Ala Trp Leu Thr Val
    345                 350                 355

ctg cca gcg cct gga aga gaa aag gag att aca gct tcc cca gac tac     1398
Leu Pro Ala Pro Gly Arg Glu Lys Glu Ile Thr Ala Ser Pro Asp Tyr
360                 365                 370                 375

ctg gag ata gcc att tac tgc ata ggg gtc ttc tta atc gcc tgt atg     1446
Leu Glu Ile Ala Ile Tyr Cys Ile Gly Val Phe Leu Ile Ala Cys Met
                380                 385                 390

gtg gta aca gtc atc ctg tgc cga atg aag aac acg acc aag aag cca     1494
Val Val Thr Val Ile Leu Cys Arg Met Lys Asn Thr Thr Lys Lys Pro
            395                 400                 405

gac ttc agc agc cag ccg gct gtg cac aag ctg acc aaa cgt atc ccc     1542
Asp Phe Ser Ser Gln Pro Ala Val His Lys Leu Thr Lys Arg Ile Pro
        410                 415                 420

ctg cgg aga cag gta aca gtt tcg gct gag tcc agc tcc tcc atg aac     1590
Leu Arg Arg Gln Val Thr Val Ser Ala Glu Ser Ser Ser Ser Met Asn
    425                 430                 435

tcc aac acc ccg ctg gtg agg ata aca aca cgc ctc tct tca acg gca     1638
Ser Asn Thr Pro Leu Val Arg Ile Thr Thr Arg Leu Ser Ser Thr Ala
440                 445                 450                 455

gac acc ccc atg ctg gca ggg gtc tcc gag tat gaa ctt cca gag gac     1686
Asp Thr Pro Met Leu Ala Gly Val Ser Glu Tyr Glu Leu Pro Glu Asp
                460                 465                 470

cca aaa tgg gag ttt cca aga gat aag ctg aca ctg ggc aag ccc ctg     1734
```

-continued

```
Pro Lys Trp Glu Phe Pro Arg Asp Lys Leu Thr Leu Gly Lys Pro Leu
            475                 480                 485

gga gaa ggt tgc ttt ggg caa gtg gtc atg gcg gaa gca gtg gga att      1782
Gly Glu Gly Cys Phe Gly Gln Val Val Met Ala Glu Ala Val Gly Ile
        490                 495                 500

gac aaa gac aag ccc aag gag gcg gtc acc gtg gcc gtg aag atg ttg      1830
Asp Lys Asp Lys Pro Lys Glu Ala Val Thr Val Ala Val Lys Met Leu
    505                 510                 515

aaa gat gat gcc aca gag aaa gac ctt tct gat ctg gtg tca gag atg      1878
Lys Asp Asp Ala Thr Glu Lys Asp Leu Ser Asp Leu Val Ser Glu Met
520                 525                 530                 535

gag atg atg aag atg att ggg aaa cac aag aat atc ata aat ctt ctt      1926
Glu Met Met Lys Met Ile Gly Lys His Lys Asn Ile Ile Asn Leu Leu
                540                 545                 550

gga gcc tgc aca cag gat ggg cct ctc tat gtc ata gtt gag tat gcc      1974
Gly Ala Cys Thr Gln Asp Gly Pro Leu Tyr Val Ile Val Glu Tyr Ala
            555                 560                 565

tct aaa ggc aac ctc cga gaa tac ctc cga gcc cgg agg cca ccc ggg      2022
Ser Lys Gly Asn Leu Arg Glu Tyr Leu Arg Ala Arg Arg Pro Pro Gly
        570                 575                 580

atg gag tac tcc tat gac att aac cgt gtt cct gag gag cag atg acc      2070
Met Glu Tyr Ser Tyr Asp Ile Asn Arg Val Pro Glu Glu Gln Met Thr
    585                 590                 595

ttc aag gac ttg gtg tca tgc acc tac cag ctg gcc aga ggc atg gag      2118
Phe Lys Asp Leu Val Ser Cys Thr Tyr Gln Leu Ala Arg Gly Met Glu
600                 605                 610                 615

tac ttg gct tcc caa aaa tgt att cat cga gat tta gca gcc aga aat      2166
Tyr Leu Ala Ser Gln Lys Cys Ile His Arg Asp Leu Ala Ala Arg Asn
                620                 625                 630

gtt ttg gta aca gaa aac aat gtg atg aaa ata gca gac ttt gga ctc      2214
Val Leu Val Thr Glu Asn Asn Val Met Lys Ile Ala Asp Phe Gly Leu
            635                 640                 645

gcc aga gat atc aac aat ata gac tat tac aaa aag acc acc aat ggg      2262
Ala Arg Asp Ile Asn Asn Ile Asp Tyr Tyr Lys Lys Thr Thr Asn Gly
        650                 655                 660

cgg ctt cca gtc aag tgg atg gct cca gaa gcc ctg ttt gat aga gta      2310
Arg Leu Pro Val Lys Trp Met Ala Pro Glu Ala Leu Phe Asp Arg Val
    665                 670                 675

tac act cat cag agt gat gtc tgg tcc ttc ggg gtg tta atg tgg gag      2358
Tyr Thr His Gln Ser Asp Val Trp Ser Phe Gly Val Leu Met Trp Glu
680                 685                 690                 695

atc ttc act tta ggg ggc tcg ccc tac cca ggg att ccc gtg gag gaa      2406
Ile Phe Thr Leu Gly Gly Ser Pro Tyr Pro Gly Ile Pro Val Glu Glu
                700                 705                 710

ctt ttt aag ctg ctg aag gaa gga cac aga atg gat aag cca gcc aac      2454
Leu Phe Lys Leu Leu Lys Glu Gly His Arg Met Asp Lys Pro Ala Asn
            715                 720                 725

tgc acc aac gaa ctg tac atg atg atg agg gac tgt tgg cat gca gtg      2502
Cys Thr Asn Glu Leu Tyr Met Met Met Arg Asp Cys Trp His Ala Val
        730                 735                 740

ccc tcc cag aga cca acg ttc aag cag ttg gta gaa gac ttg gat cga      2550
Pro Ser Gln Arg Pro Thr Phe Lys Gln Leu Val Glu Asp Leu Asp Arg
    745                 750                 755

att ctc act ctc aca acc aat gag gaa tac ttg gac ctc agc caa cct      2598
Ile Leu Thr Leu Thr Thr Asn Glu Glu Tyr Leu Asp Leu Ser Gln Pro
760                 765                 770                 775

ctc gaa cag tat tca cct agt tac cct gac aca aga agt tct tgt tct      2646
Leu Glu Gln Tyr Ser Pro Ser Tyr Pro Asp Thr Arg Ser Ser Cys Ser
                780                 785                 790
```

-continued tca gga gat gat tct gtt ttt tct cca gac ccc atg cct tac gaa cca 2694
Ser Gly Asp Asp Ser Val Phe Ser Pro Asp Pro Met Pro Tyr Glu Pro
795 800 805 tgc ctt cct cag tat cca cac ata aac ggc agt gtt aaa aca tga 2739
Cys Leu Pro Gln Tyr Pro His Ile Asn Gly Ser Val Lys Thr
810 815 820 atgactgtgt ctgcctgtcc ccaaacagga cagcactggg aacctagcta cactgagcag 2799 ggagaccatg cctcccagag cttgttgtct ccacttgtat atatggatca gaggagtaaa 2859 taattggaaa agtaatcagc atatgtgtaa agatttatac agttgaaaac ttgtaatctt 2919 ccccaggagg agaagaaggt ttctggagca gtggactgcc acaagccacc atgtaacccc 2979 tctcacctgc cgtgcgttct ggctgtggac cagtaggact caaggtggac gtgcgttctg 3039 ccttccttgt taattttgta ataattggag aagatttatg tcagcacaca cttacagagc 3099 acaaatgcag tatataggtg ctggatgtat gtaaatatat tcaaattatg tataaatata 3159 tattatatat ttacaaggag ttattttttg tattgatttt aaatggatgt cccaatgcac 3219 ctagaaaatt ggtctctctt tttttaatag ctatttgcta aatgctgttc ttacacataa 3279 tttcttaatt ttcaccgagc agaggtggaa aaatactttt gctttcaggg aaaatggtat 3339 aacgttaatt tattaataaa ttggtaatat acaaaacaat taatcattta tagttttttt 3399 tgtaatttaa gtggcatttc tatgcaggca gcacagcaga ctagttaatc tattgcttgg 3459 acttaactag ttatcagatc ctttgaaaag agaatattta caatatatga ctaatttggg 3519 gaaaatgaag ttttgattta tttgtgttta aatgctgctg tcagacgatt gttcttagac 3579 ctcctaaatg ccccatatta aaagaactca ttcataggaa ggtgtttcat tttggtgtgc 3639 aaccctgtca ttacgtcaac gcaacgtcta actggacttc ccaagataaa tggtaccagc 3699 gtcctcttaa aagatgcctt aatccattcc ttgaggacag accttagttg aaatgatagc 3759 agaatgtgct tctctctggc agctggcctt ctgcttctga gttgcacatt aatcagatta 3819 gcctgattct cttcagtgaa ttttgataat ggcttccaga ctctttgcgt tggagacgcc 3879 tgttaggatc ttcaagtccc atcatagaaa attgaaacac agagttgttc tgctgatagt 3939 tttggggata cgtccatctt tttaagggat tgctttcatc taattctggc aggacctcac 3999 caaaagatcc agcctcatac ctacatcaga caaaatatcg ccgttgttcc ttctgtacta 4059 aagtattgtg ttttgctttg gaaacaccca ctcactttgc aatagccgtg caagatgaat 4119 gcagattaca ctgatcttat gtgttacaaa attggagaaa gtatttaata aaacctgtta 4179 atttttatac tgacaataaa aatgtttcta cagatattaa tgttaacaag acaaaataaa 4239 tgtcacgcaa cttaaaaaaa aaaaaaaaa 4268

<210> SEQ ID NO 4
<211> LENGTH: 22
<212> TYPE: DNA
<213> ORGANISM: Artificial Sequence
<220> FEATURE:
<223> OTHER INFORMATION: PCR Primer

<400> SEQUENCE: 4
aaggaccact cttctgcgtt tg 22

<210> SEQ ID NO 5
<211> LENGTH: 19
<212> TYPE: DNA
<213> ORGANISM: Artificial Sequence
<220> FEATURE:
<223> OTHER INFORMATION: PCR Primer

<400> SEQUENCE: 5
tgggtcggga tggagaaag 19

<210> SEQ ID NO 6
<211> LENGTH: 20
<212> TYPE: DNA
<213> ORGANISM: Artificial Sequence
<220> FEATURE:
<223> OTHER INFORMATION: PCR Probe

<400> SEQUENCE: 6
cccacaaccc cgggctcgtc 20

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc 19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc 20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc 20

<210> SEQ ID NO 10
<211> LENGTH: 3306
<212> TYPE: DNA
<213> ORGANISM: Mus musculus
<220> FEATURE:
<221> NAME/KEY: CDS
<222> LOCATION: (607)...(3072)

<400> SEQUENCE: 10
gaattcccgc gcggccgcca gagctccggc ccgggggctg cctgtgtgtt cctggcccgg 60
cgtggcgact gctctccggg ctggcggggg ccgggcgtga gcccgggcct cagcgttcct 120
gagcgctgcg agtgttcact actcgccagc aaagtttgga gtaggcaacg caagctccag 180
tcctttcttc tgctgctgcc cagatccgag agcagctccg gtgtatgtct agctgttctg 240
cgatcccggc gcgcgtgaag cctcggaacc ttggcgccgg ctgctaccca aggaatcgtt 300
ctctttttgg agttttcctc cgagatcatc gcctgctcca tcccgatcca ctctgggctc 360
cggcgcagca ccgagcgcag aggagcgctg ccattcaagt ggcagccaca gcagcagcag 420
cagcagcagt gggagcagga acagcagtaa caacagcaac agcagcacag ccgcctcaga 480

-continued

```
gctttgctcc tgagcccctg tgggctgaag gcattgcagg tagcccatgg tctcagaaga    540

agtgtgcaga tgggattacc gtccacgtgg agatatggaa gaggaccagg gattggcact    600

gtgacc atg gtc agc tgg ggg cgc ttc atc tgc ctg gtc ttg gtc acc      648
       Met Val Ser Trp Gly Arg Phe Ile Cys Leu Val Leu Val Thr
         1               5                  10

atg gca acc ttg tcc ctg gcc cgg ccc tcc ttc agt tta gtt gag gat      696
Met Ala Thr Leu Ser Leu Ala Arg Pro Ser Phe Ser Leu Val Glu Asp
 15                  20                  25                  30

acc act tta gaa cca gaa gag cca cca acc aaa tac caa atc tcc caa      744
Thr Thr Leu Glu Pro Glu Glu Pro Pro Thr Lys Tyr Gln Ile Ser Gln
                 35                  40                  45

cca gaa gcg tac gtg gtt gcc ccc ggg gaa tcg cta gag ttg cag tgc      792
Pro Glu Ala Tyr Val Val Ala Pro Gly Glu Ser Leu Glu Leu Gln Cys
             50                  55                  60

atg ttg aaa gat gcc gcc gtg atc agt tgg act aag gat ggg gtg cac      840
Met Leu Lys Asp Ala Ala Val Ile Ser Trp Thr Lys Asp Gly Val His
         65                  70                  75

ttg ggg ccc aac aat agg aca gtg ctt att ggg gag tat ctc cag ata      888
Leu Gly Pro Asn Asn Arg Thr Val Leu Ile Gly Glu Tyr Leu Gln Ile
     80                  85                  90

aaa ggt gcc aca cct aga gac tcc ggc ctc tat gct tgt act gca gct      936
Lys Gly Ala Thr Pro Arg Asp Ser Gly Leu Tyr Ala Cys Thr Ala Ala
 95                 100                 105                 110

agg acg gta gac agt gaa act tgg atc ttc atg gtg aat gtc aca gat      984
Arg Thr Val Asp Ser Glu Thr Trp Ile Phe Met Val Asn Val Thr Asp
                115                 120                 125

gcc atc tca tct gga gat gat gag gac gac aca gat agc tcc gaa gac     1032
Ala Ile Ser Ser Gly Asp Asp Glu Asp Asp Thr Asp Ser Ser Glu Asp
            130                 135                 140

gtt gtc agt gag aac agg agc aac cag aga gca ccg tac tgg acc aac     1080
Val Val Ser Glu Asn Arg Ser Asn Gln Arg Ala Pro Tyr Trp Thr Asn
        145                 150                 155

acc gag aag atg gag aag cgg ctc cac gct tgt cct gcc gcc aac act     1128
Thr Glu Lys Met Glu Lys Arg Leu His Ala Cys Pro Ala Ala Asn Thr
    160                 165                 170

gtg aag ttc cgc tgt ccg gct ggg ggg aat cca acg tcc aca atg agg     1176
Val Lys Phe Arg Cys Pro Ala Gly Gly Asn Pro Thr Ser Thr Met Arg
175                 180                 185                 190

tgg tta aaa aac ggg aag gag ttt aag cag gag cat cgc att gga ggc     1224
Trp Leu Lys Asn Gly Lys Glu Phe Lys Gln Glu His Arg Ile Gly Gly
                195                 200                 205

tat aag gta cga aac cag cac tgg agc ctt att atg gaa agt gtg gtc     1272
Tyr Lys Val Arg Asn Gln His Trp Ser Leu Ile Met Glu Ser Val Val
            210                 215                 220

ccg tca gac aaa ggc aac tac acc tgc ctg gtg gag aat gaa tac ggg     1320
Pro Ser Asp Lys Gly Asn Tyr Thr Cys Leu Val Glu Asn Glu Tyr Gly
        225                 230                 235

tcc atc aac cac acc tac cac ctg gat gtc gtt gaa cgt tca cca cac     1368
Ser Ile Asn His Thr Tyr His Leu Asp Val Val Glu Arg Ser Pro His
    240                 245                 250

cgt ccc atc ctc caa gct gga ctg cct gca aat gcc tcc acg gtg gtc     1416
Arg Pro Ile Leu Gln Ala Gly Leu Pro Ala Asn Ala Ser Thr Val Val
255                 260                 265                 270

gga ggg gat gtg gag ttt gtc tgc aag gtt tac agc gat gcc cag ccc     1464
Gly Gly Asp Val Glu Phe Val Cys Lys Val Tyr Ser Asp Ala Gln Pro
                275                 280                 285

cac atc cag tgg atc aag cac gtg gaa aag aac ggc agt aaa aac ggg     1512
His Ile Gln Trp Ile Lys His Val Glu Lys Asn Gly Ser Lys Asn Gly
```

-continued

```
            290                 295                 300

cct gat ggg ctg ccc tac ctc aag gtt ctg aaa gct gcc ggt gtt aac     1560
Pro Asp Gly Leu Pro Tyr Leu Lys Val Leu Lys Ala Ala Gly Val Asn
        305                 310                 315

acc acg gac aaa gag att gag gtt ctc tat att cgg aat gta act ttt     1608
Thr Thr Asp Lys Glu Ile Glu Val Leu Tyr Ile Arg Asn Val Thr Phe
    320                 325                 330

gag gat gct ggg gaa tat acg tgc ttg gcg ggt aat tct atc ggg ata     1656
Glu Asp Ala Gly Glu Tyr Thr Cys Leu Ala Gly Asn Ser Ile Gly Ile
335                 340                 345                 350

tcc ttt cac tct gca tgg ttg aca gtt ctg cca gcg cct gtg aga gag     1704
Ser Phe His Ser Ala Trp Leu Thr Val Leu Pro Ala Pro Val Arg Glu
                355                 360                 365

aag gag atc acg gct tcc cca gat tat ctg gag ata gct att tac tgc     1752
Lys Glu Ile Thr Ala Ser Pro Asp Tyr Leu Glu Ile Ala Ile Tyr Cys
            370                 375                 380

ata ggg gtc ttc tta atc gcc tgc atg gtg gtg aca gtc atc ttt tgc     1800
Ile Gly Val Phe Leu Ile Ala Cys Met Val Val Thr Val Ile Phe Cys
        385                 390                 395

cga atg aag acc acg acc aag aag cca gac ttc agc agc cag cca gct     1848
Arg Met Lys Thr Thr Thr Lys Lys Pro Asp Phe Ser Ser Gln Pro Ala
    400                 405                 410

gtg cac aag ctg acc aag cgc atc ccc ctg cgg aga cag gta aca gtt     1896
Val His Lys Leu Thr Lys Arg Ile Pro Leu Arg Arg Gln Val Thr Val
415                 420                 425                 430

tcg gcc gag tcc agc tcc tcc atg aac tcc aac acc ccg ctg gtg agg     1944
Ser Ala Glu Ser Ser Ser Ser Met Asn Ser Asn Thr Pro Leu Val Arg
                435                 440                 445

ata aca acg cgt ctg tcc tca aca gcg gac acc ccg atg cta gca ggg     1992
Ile Thr Thr Arg Leu Ser Ser Thr Ala Asp Thr Pro Met Leu Ala Gly
            450                 455                 460

gtc tcc gag tat gag ttg cca gag gat cca aag tgg gaa ttc ccc aga     2040
Val Ser Glu Tyr Glu Leu Pro Glu Asp Pro Lys Trp Glu Phe Pro Arg
        465                 470                 475

gat aag ctg acg ctg ggc aaa ccc ctg ggg gaa ggt tgc ttc ggg caa     2088
Asp Lys Leu Thr Leu Gly Lys Pro Leu Gly Glu Gly Cys Phe Gly Gln
    480                 485                 490

gta gtc atg gct gaa gca gtg gga atc gat aaa gac aaa ccc aag gag     2136
Val Val Met Ala Glu Ala Val Gly Ile Asp Lys Asp Lys Pro Lys Glu
495                 500                 505                 510

gcg gtc acc gtg gca gtg aag atg ttg aaa gat gat gcc aca gag aag     2184
Ala Val Thr Val Ala Val Lys Met Leu Lys Asp Asp Ala Thr Glu Lys
                515                 520                 525

gac ctg tct gat ctg gta tca gag atg gag atg atg aag atg att ggg     2232
Asp Leu Ser Asp Leu Val Ser Glu Met Glu Met Met Lys Met Ile Gly
            530                 535                 540

aaa cat aag aac att atc aac ctc ctg ggg gcc tgc acg cag gat gga     2280
Lys His Lys Asn Ile Ile Asn Leu Leu Gly Ala Cys Thr Gln Asp Gly
        545                 550                 555

cct ctc tac gtc ata gtt gaa tat gca tcg aaa ggc aac ctc cgg gaa     2328
Pro Leu Tyr Val Ile Val Glu Tyr Ala Ser Lys Gly Asn Leu Arg Glu
    560                 565                 570

tac ctc cga gcc cgg agg cca cct ggc atg gag tac tcc tat gac att     2376
Tyr Leu Arg Ala Arg Arg Pro Pro Gly Met Glu Tyr Ser Tyr Asp Ile
575                 580                 585                 590

aac cgt gtc ccc gag gag cag atg acc ttc aag gac ttg gtg tcc tgc     2424
Asn Arg Val Pro Glu Glu Gln Met Thr Phe Lys Asp Leu Val Ser Cys
                595                 600                 605

acc tac cag ctg gct aga ggc atg gag tac ttg gct tcc caa aaa tgt     2472
```

-continued

```
Thr Tyr Gln Leu Ala Arg Gly Met Glu Tyr Leu Ala Ser Gln Lys Cys
            610                 615                 620

atc cat cga gat ttg gct gcc aga aac gtg ttg gta aca gaa aac aat      2520
Ile His Arg Asp Leu Ala Ala Arg Asn Val Leu Val Thr Glu Asn Asn
        625                 630                 635

gtg atg aag ata gca gac ttt ggc ctg gcc agg gat atc aac aac ata      2568
Val Met Lys Ile Ala Asp Phe Gly Leu Ala Arg Asp Ile Asn Asn Ile
    640                 645                 650

gac tac tat aaa aag acc aca aat ggg cga ctt cca gtc aag tgg atg      2616
Asp Tyr Tyr Lys Lys Thr Thr Asn Gly Arg Leu Pro Val Lys Trp Met
655                 660                 665                 670

gct cct gaa gcc ctt ttt gat aga gtt tac act cat cag agc gat gtc      2664
Ala Pro Glu Ala Leu Phe Asp Arg Val Tyr Thr His Gln Ser Asp Val
                675                 680                 685

tgg tcc ttc ggg gtg tta atg tgg gag atc ttt act tta ggg ggc tca      2712
Trp Ser Phe Gly Val Leu Met Trp Glu Ile Phe Thr Leu Gly Gly Ser
            690                 695                 700

ccc tac cca ggg att ccc gtg gag gaa ctt ttt aag ctg ctc aaa gag      2760
Pro Tyr Pro Gly Ile Pro Val Glu Glu Leu Phe Lys Leu Leu Lys Glu
        705                 710                 715

gga cac agg atg gac aag ccc acc aac tgc acc aat gaa ctg tac atg      2808
Gly His Arg Met Asp Lys Pro Thr Asn Cys Thr Asn Glu Leu Tyr Met
    720                 725                 730

atg atg agg gat tgc tgg cat gct gta ccc tca cag aga ccc aca ttc      2856
Met Met Arg Asp Cys Trp His Ala Val Pro Ser Gln Arg Pro Thr Phe
735                 740                 745                 750

aag cag ttg gtc gaa gac ttg gat cga att ctg act ctc aca acc aat      2904
Lys Gln Leu Val Glu Asp Leu Asp Arg Ile Leu Thr Leu Thr Thr Asn
                755                 760                 765

gag gaa tac ttg gat ctc acc cag cct ctc gaa cag tat tct cct agt      2952
Glu Glu Tyr Leu Asp Leu Thr Gln Pro Leu Glu Gln Tyr Ser Pro Ser
            770                 775                 780

tac ccc gac aca agt agc tct tgt tct tca ggg gac gat tct gtg ttt      3000
Tyr Pro Asp Thr Ser Ser Ser Cys Ser Ser Gly Asp Asp Ser Val Phe
        785                 790                 795

tct cca gac ccc atg cct tat gaa ccc tgt ctg cct cag tat cca cac      3048
Ser Pro Asp Pro Met Pro Tyr Glu Pro Cys Leu Pro Gln Tyr Pro His
    800                 805                 810

ata aac ggc agt gtt aaa aca tga gtgaatgtgt cttcctgtcc ccaaacagga     3102
Ile Asn Gly Ser Val Lys Thr
815                 820

cagcaccagg aacctactta cactgagcag agaggctgtg ctccagagcc tgtgacacgc    3162

ctccacttgt atatatggat cagaggagta aatagtggga agcatatttg tcacgtgtgt    3222

aaagatttat acagttggaa catgtactac aggaaggaga ctgttctgat agtgacagcc    3282

gccaccatgc cacctttgac caca                                           3306


<210> SEQ ID NO 11
<211> LENGTH: 21
<212> TYPE: DNA
<213> ORGANISM: Artificial Sequence
<220> FEATURE:
<223> OTHER INFORMATION: PCR Primer

<400> SEQUENCE: 11

acctggatgt cgttgaacgt t                                                21


<210> SEQ ID NO 12
<211> LENGTH: 19
<212> TYPE: DNA
```

<213> ORGANISM: Artificial Sequence
<220> FEATURE:
<223> OTHER INFORMATION: PCR Primer

<400> SEQUENCE: 12
gaccaccgtg gaggcattt 19

<210> SEQ ID NO 13
<211> LENGTH: 24
<212> TYPE: DNA
<213> ORGANISM: Artificial Sequence
<220> FEATURE:
<223> OTHER INFORMATION: PCR Probe

<400> SEQUENCE: 13
ccacaccgtc ccatcctcca agct 24

<210> SEQ ID NO 14
<211> LENGTH: 20
<212> TYPE: DNA
<213> ORGANISM: Artificial Sequence
<220> FEATURE:
<223> OTHER INFORMATION: PCR Primer

<400> SEQUENCE: 14
ggcaaattca acggcacagt 20

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
gggtctcgct cctggaagat 20

<210> SEQ ID NO 16
<211> LENGTH: 27
<212> TYPE: DNA
<213> ORGANISM: Artificial Sequence
<220> FEATURE:
<223> OTHER INFORMATION: PCR Probe

<400> SEQUENCE: 16
aaggccgaga atgggaagct tgtcatc 27

<210> SEQ ID NO 17
<211> LENGTH: 132762
<212> TYPE: DNA
<213> ORGANISM: Homo sapiens
<220> FEATURE:
<221> NAME/KEY: misc_feature
<222> LOCATION: (1)...(132762)
<223> OTHER INFORMATION: n = A,T,C or G

<400> SEQUENCE: 17
catctgtgga ctgctaccga gcgggcgagg gagcgcgcgc ggccgccaca aagctcgggc 60
gccgcggggc tgcatgcggc gtacctggcc cggcgcggcg actgctctcc gggctggcgg 120
gggccggccg cgagccccgg gggccccgag gccgcagctt gcctgcgcgc tctgagcctt 180
cgcaactcgc gagcaaagtt tggtggaggc aacgccaagc ctgagtcctt tcttcctctc 240
gttccccaaa tccgaggcag cccgcgggcg tcatgcccgc gctcctccgc agcctggggt 300
acgcgtgaag cccgggaggc ttggcgccgg cgaagaccca aggaccactc ttctgcgttt 360

-continued

```
ggagttgctc cccgcaaccc cgggctcgtc gctttctcca tcccgaccca cgcggggcgc     420
ggggacaaca caggtcgcgg aggagcgttg ccattcaagg taatcgccgc gcaagacgcc     480
tcggggagct tcgccagccg gggacgtggg cgccacggga gcccgggacg ccgggtgcac     540
cgtcctccgg gcggggggcg cggaaggact agcattgtgg aggacgctcc gtgtcctccc     600
tctgtggctg cataggtgat gggggaggtg ggtgcgtgct gacggccggc gttctggaag     660
ttctgcctct gctacccccca tccagatgct gacatctgct tctggcgttg acgcccccct     720
ccctgtcaaa ccctggcggg cgcattcccg ctgactgggc gcgtttctcc gaccccagag     780
cagacgggcg gaaggttcgc ctgcccgtgg cacagccccg caggccggtt cccggggtca     840
tctccgaggt gccccatccg tgtgtcctgg gaacttccgt accatccagg ccctgcggag     900
acccctttttt cgggaggggg ccgctggggt ggggccggtg acatcccgta ggggtggcga     960
tggccagggg tggcactgct ggggaggcga cggctccggt gcctgggcgc ccctcgcccg    1020
cagccgccgt cggcgctgga gggagcgcag tgcgcctggg gctagggggc gaactggacc    1080
gactttttct agttcgcctg cctgctctgc cgcagcggct gggagatgtc gaaagcgcag    1140
gcgagttcta acttgcgcgc tcatttttttt cggccacggg gccgcgctgg ggaaaaaagc    1200
cgagggccct gcgtggcgct ggctccgacc ctcgcggacc acggacctgg cgcaggaggc    1260
ccgctcgggg accaccagcc tccgtcgctc tcctcgcacc ccgctccctt gcagaccgtt    1320
ctccagaccc tccttccttt ctcccaattc aataaaacct acccttaaag gcaaacctgc    1380
tttcaaactc agggcaccca ttatgtgttt ggtgtgaaac gctatcaaca tttaaaactc    1440
cattgtctcc ctggtcccaa atccctgtaa atcttccacc gggctcgact cattttcatc    1500
tgaaaagcct gtttagtttg aatagaaaag caatcaggcg cccctctctc tttccctgga    1560
atgtcaatta aaatgcagat ttctctgagc tctttagcgc cccgagaagg gggagaaaaa    1620
caggatattt caggcaaaca aatgaaagaa gtgctgccct gaaagggggt ggtggtgggg    1680
agcacccccca agctgctcgc aagttctgat tggacgcaag cattaaaccg ggagggcttt    1740
gtggtcctgg gtcagtgtgt gttttttgag atttcaattt gttgaggaat ttcccccctag    1800
ccttgacccc ttgacagctc ccgctcctac tcagtgctgg ggagaagtag ggaggcctta    1860
agcgaagaga tgggtctgca ctttggagga gccggacact gttgactttc ctgatgtgaa    1920
atctacccag gaacaaaaca ccaggtgatc ccagtggccg agccagcagt ggacagatca    1980
ccccttaggt ggaagcccaa agcggaggc actgtattgg tctgccttct tggagggcgg    2040
gggttttggg aatgtcatgg taaattgaag agcccagcac aggcctggca tggggaccgc    2100
tccgcagcca agcccttcct gcttgtcact ctgcctgtct ttgggggcag gcttgtgccg    2160
aggtgaaaat ggaccggggg gcgggcggcc gagaagagcc atccatcaga gggagggtga    2220
caactcctcc cgcgtgcagg ctgagaagag agttcccttt caaggggaaa aataaacacg    2280
ctggggcttt cactggggct cagactccag gaaggattat ggtattgaag gcaggaagcc    2340
gggattgtgg ccgccagcgg catgctgggc ctgtattccc aacaccgagc ctggggacct    2400
aattatcctg cctaggaggt cgcaccatac ttttgtccac tggtgtgagg aactgtgcag    2460
acctgtcgcc ttaggtctcc gccttccaga gttttgggga gggggctgcc gtggggtttg    2520
gacctggaaa tggctgaaat gcaaatttct agtgccagct agcgggatga tggaacggct    2580
tgagattcag cggagcgccc tgtccacctt tctctgcctg gagccaagga ggctcctctg    2640
ggcagggaca ggtgggcgag caggccgggg aaggagcctg ggtgaaaccc tctgcgagga    2700
```

-continued

```
cttaggattg ttcctgaagt cgtgttagag gtagaaaatt cccctgcatt ctgcaaatgc   2760
ttagtaaatc aatgagaatg tttgtgtact ttcctcccac atgtatgtag aaatagatcc   2820
gaaattatct tctgaggctc ttgactaaga ggaaagaaaa gttaagagga aaaatctttc   2880
aagctatctg aaagcacatg cacacaccgt gcacgcacac accatgtaca cacacacacc   2940
gtgcatacac acacaccatg cacgcacaca caccgtgtac acacacacac actgcacaca   3000
tacttttctt gcttttgctg tgaatcacac cgtttcacct gtgctatctt tgaagcagag   3060
gttttcttta ttcctccttt ggaaatgatg tggcatattc ttttccctcc tccatttttg   3120
tcctcagtca aagctaaaag gagcagtttt tatgatgaga tttggggagg ctccagcagt   3180
gttgaaatcc tatgacataa cttgaaacat cgagtgggta cataaaaaat gtagagttta   3240
gagatttttg tattaaaggc ctccctgcca cccccagtct tagaaaatgt ggttcattcc   3300
tgtggttcac agaatctgaa gcctgagatt gatgagcccc ttcttgtgat tgttttaatc   3360
attctctaaa gtttgtgcat tttactgtac ccttagtcac agagagtact gagtgaattt   3420
aaagttgctt ggaatatatt aagctttctt ggaaaattct ctttcccttg gatcaaatgg   3480
gtgaacagaa tattaagttg agtgtcctct tctaacttat actctgaaaa tttagccagt   3540
aggtttgcat atggaaagtt attggtccaa tcacatacca tgactataat ttacataatt   3600
tacatcatca ttattaataa attcctgcat tattcatcag aatttgcatc tgctcagttt   3660
cctcaccctt ctacagaggt tgaagacatt tagcagccct ggactgccat ttagtcacag   3720
gggaagggaa ttcaggcttc gaagtccttt ttggatcagc tgcgttgaat gcgctgcagt   3780
tgtgttcact cttcgtaagt ggctgcttgg cggaagactg aaagacactt ctccatttga   3840
aaatgaatcc tgacaagtgt aaactggtgg gaattttctg tagccttcct gggattcttt   3900
tgattttgct ggtctccttt cttcccaaga gcgacagtga gggtgggaga ctgctcacct   3960
ccagcccagc agaaatacgg agctgtgagc agactcctcc aacagtttag ctttctaaag   4020
cccagttgga ctaagagaag ggaacgaggt tggttatgcc aacccgagca tttttaactt   4080
gcttttgtag ttgcccttga aactaaggtc acgttgcttc tgctcattga gggcggtgga   4140
ggcgatagtg gatagtagaa gagagcacac attgcctcac tgaagtggct gcacgtatct   4200
gagtcctgta gctactgttt tatctctgtt tcttaaaagt atgcttttaa aaagattagc   4260
ctcacacatt tctgtggacc ggtctggtgg tatcacctgg gactctgagg tgaggatgga   4320
aggatttagc agataatgaa aaagaactct gtttgcgcac atttgagagg ctgaaaaatg   4380
gttttatccc acttgggctg gagtgatttg gcattgggga agattccctg actcgccaat   4440
ctctttcctt tagtgactgc agcagcagcg gcagcgcctc ggttcctgag cccaccgcag   4500
gctgaaggca ttgcgcgtag tccatgcccg tagaggaagt gtgcagatgg gattaacgtc   4560
cacatggaga tatggaagag gaccggggat tggtaccgta accatggtca gctggggtcg   4620
tttcatctgc ctggtcgtgg tcaccatggc aaccttgtcc ctggcccggc cctccttcag   4680
tttagttgag gataccacat tagagccaga aggtaagtca tttaatttca cttttcaggt   4740
ttgttttggg atttgtctgg gggcagattg ttaaggcctg ttttagaatc agctaccctt   4800
gcattgtaaa tggggcttct aagagcacca gatcgtggtc tcttggctcc cggcaaggca   4860
gagctgatga gagaaggtcc tttgccgcag cactgcaggc aggatggtat agtttggtgg   4920
tttcttgctg tgtgtgtttc tctgtgctgg gtgagggaga cagctgggag ttggccttta   4980
tccagtgccc gagagagctg tggaagggat gaaccttggg aggatgaatg tcatctctag   5040
tctcccccag catcattcct actgcttaca atgtaaagaa ttgctatttt cggacaagat   5100
```

-continued

```
gaaccactaa aagaaattgc caacatctga aatgctgaca tcttattttc attgtttaag   5160
gagaaaagaa gtttctgaag tttagcacag agagagaggc ttgacatctc agaatttttt   5220
tttagccatt gtaattcata atacttaagc aatgcatcat cacagagtgg cagattctag   5280
tttaggtaaa cttgaaagtg aatgtgccag gggatctcct ccagctccga gaacctccaa   5340
gtatcacagg gcatgcgccg gtgtcacagc tttggaaatt taattttcaa ggtgtaagtc   5400
caattacgag gactacatga ggctgaatta ttcagcttag cagatttgga acctctctcc   5460
cagccctttg gagacaacgt gagccaagcc tctacttggt gctgcactga aatctgtcat   5520
cagtagggaa tattggtagc tgagttattt ttcgagtggt aatccgagaa taaaacggca   5580
gatcccagca ctcatcgcca cttaatgaac ctgtttgtgg agagtccacc tggtgcctgc   5640
ctggctttag gaacccgcag cagtccgagt ggtgtctggg gtaagctgag ctgctctggg   5700
aacacatctc gtgcgtgggg tgaatgaaca gcacacttac ccagtggggt aggctgggag   5760
aggacagaga gcccagcctc cttagctgga tcaggacagt ttaggaagga gggttgcgtc   5820
catctgagat gagagttctg agagacatgg gctccccagg aagaccccag gcacttgtca   5880
ttgaaggatg aggaccgaag cacttatcac ctgaagcaat cgtgtgagac tggggaactt   5940
ttcgttacac agagggatgg cagctctata attaacaggt gtggtgacat ctccctgcgt   6000
ctctgggaag ggaatctggt aggagtttgt gtctgaggct tgtatagcta cagctacagg   6060
ccgattatgg aactgcctct tggtgatttg tgctgggaca ccaggatgag tgtaatttgc   6120
agtggtgatg catttttaca gggctttcat gtaagaggga aaaagttcct ggtttctgaa   6180
agtcatgcct gtacgtcttt aattttgcta ataattaaaa tggatgtttc cgtgattgct   6240
ggttttccct tgagtgcgtg gctcggcaaa aactgaggaa gctgagctgg gatttcctac   6300
ggtgtgggct ttaggagcaa cccaggttag ggaaaaactg tcatttttca ttttggcttt   6360
tcagggcagc gttattgtga gtttatttca acataaagtg taaaatggtc ccagaggatt   6420
tgttttactg tatttaattc ttgaaggaag tttaaaattg tgtatacatg cagggaggga   6480
caggtgaggc agagggaaga aatcgtggaa agggacgaag ttccccgagt gagtctttgt   6540
gtaagaattt acatccaaca atgtgggtat tgttggaagc aggcctgctc aacctgggat   6600
ctgtggatgc acttatggat caggaaggag gtcgatgaag ttctggaaat tttaggtaat   6660
attttgttaa tgtccttttg tgcattttta tgggtttata gtttccatga gctatgagtt   6720
catttgcatc cagaattatg agatggaaaa gaaaagatgt cttagaggaa ggtgcaaaac   6780
ctggcaaaga agaggctttg gaaaagtata caagtcccag gcctcagttt ccctttctgt   6840
cgtctgaggg cttaagaaga tgatctttag ggtctcttca ttaatagtca ttgaatatta   6900
atgtcctcag aagtcttctg actcttccac caaaaggttg ttaggagatt tccatttgac   6960
ctggacataa agagcaatta gcacaggggc tggcatccag taagcaccgg gtgcatggcc   7020
ttgtcgccgt tgtcgccagg gagctgggaa catgggtctt cccagtcccg tgggctggct   7080
gtgccaggtg ccacaatgtc aaaaaacatc taggcttttg gagacagttg agaagaaagt   7140
tgtttttgga tggaggaggc ccttggtgtt tccaggaagc tgtgtttgct ttctgtaggg   7200
tccccacttc ccctcatctg ttagtctaat actggccact gatttgagcc ctaagaccag   7260
ttcttctgtt gcaggagttc gctttggtgt cagaggtgat taggaaggtc attgaattat   7320
agatgagaaa ggagttttta acagctgaaa atgggctcag gtttaggctc tgtgctggtg   7380
aattggaaga gagagagaga gagagagagt gtgcgtgtgt gtgtgtgtgt gcgcgagtgc   7440
```

-continued

```
gcgtgcgtgc gtgcgtgcct gtgcccctgt ccatcagttc tccatgatta gaactactat   7500
agctttggtt agcagtaagt tccaccttga ccttctgtgc accaaggtct tatcttgtaa   7560
gactttttgg tttgctaatt tatttggaag ctcagtttag ataatgtcta ttggatagga   7620
gaaaaatgtg actgagaagt tccaggaaga agcctgggcc ctaacactag agggtccttt   7680
tcttttggcc cctcagggaa aggttatgtt tagtcatctt ggctttgtgc aatatcgtat   7740
catatcatat gtcatatcat atatcatata tatcatttgt cttctggaca cgttctgaaa   7800
tagtagcagt ggggttgggc ccactcaatt gacttaagaa aataatctct agaagatttt   7860
agtttttaat atttcagatt aaatatgagt tttccagttg gtcattcatt gttaatttcc   7920
ttttggtcat tcattgttat agggcaccag cagaggagtg aaaacatggt tattgactcg   7980
aagggggggca gtcctcaatg ccaagtacta ttctgttgat taacattata aatatttgaa   8040
gtctagtcaa gcttgattac cctgagaggg ggcaactctt actttcaagt tcttcctgac   8100
attgtcacct actctggtta attaagtcat tgttgacatt aatggcatct ttgtttacac   8160
caacccagta ggagctaaaa tgaaagggct tttcaaccct acacccttaa ttactttccc   8220
accctccaca gagtgtgact ctgaaaagta acaacctgaa aaaaaatgta gtttgtgtag   8280
caatttttttg tcaatcttct gagaggtgat gctctcctgg accaacgtga gttggtccag   8340
agttcagtag cagaaacgtc gaggacagga tctacacaga gacctcccta agtcagattt   8400
ttccagtatg gtttaagtcc tttgttagaa gtattgtaaa tgccataata ttaaccatac   8460
gcatttaatt gcaagttaaa agaaaggaag aaagaatata tccgcatacc aagagtgaat   8520
gatttaaaat aatcttctgt ttcgtattat ctgcatcttt gtttttcaat atgagtgtta   8580
atatttaaga gttgactgta acttgatagt tagctttgga acaaggactt attcttggtc   8640
aattaaacca aatacaggct tacgcagtta aatacacaat gaagtacaca ttctttatta   8700
gtatataaag tgtttcacaa ttcatagacc aagagccatg tttaatatta cttatagagc   8760
agaaatctgg caagcccaga gaactggtac ttgtatcatt tttatactggc tctctctgat   8820
tcaaatttgg ggtatatgtg tgtgtttctg ttttgtctgt ttatttcaac cagttaaaag   8880
acagagcact tactatgcca atggccccgc atcaagccat aagtaaagac tttattcctt   8940
tcaagtcttt ctgacccagt tgagggtgag aattcacaaa accacagcaa tccaatatga   9000
gatgttttta atatcagact taacaaataa ttacatggct atgaaataac tggggtcgtg   9060
tttaaactgg aagtgttttg tttaatgttc gtagtttcaa taaaatgtat ccactagtct   9120
tccagtttgc agactgttgt ttaggtgttt gtttagccag ggtaattgtt aaaaactccc   9180
tctaatctag cttaccctta catttccatg gaagcgaatt ttagtcatta aaggaaaaca   9240
tgggaaattg atttttgggt gcctggctgt taagctaggt aggaaatata gctggtgtgc   9300
tactctccac tgtactggtc cgattctcgc caggggggaca tctctgtagg cagttcagaa   9360
attatttttt ggaagttttt taggctattc cacagataat tctgatccag taggttttat   9420
gcaactgtgc aaaatgctta tggtctctat ttttttttcc ttgagagatg attttagcct   9480
ttggtttttt gtttgttttt gttttttgag acagagtctt gatctgccac ccaggctgga   9540
gtacaatggt gcaattgtac cctcactgca ttgtcaaacg tggctcactg taccctcgga   9600
ctcctgggct gaaggggtcc tccaacctcc tgagtagctg ggactacagg cctggataat   9660
ttttaaaaat atttcgtaga tatggggttt cgccatgttg ctcaggctgg tctccaactc   9720
ctggcagcct tggcctccca aagtgctggg attacaagtg tgagccacca cacctgtcct   9780
agccttaagt tttgcatttt tttccatctt tttgctgtat cccatatgat ttagagattt   9840
```

-continued

```
ttgctgtatc ccatgagatt tagagatggc tctacttttt ttagctttcc tagcattgaa   9900
atgcttggtg ttgctaatca taccccatct ttaccacacc atcttcctcc ctgacttgcc   9960
ttcttagtgt agtttggtca agaacttgag gccaagttct tttttttttt aaatttagct  10020
tttattttag gtttgggggt acatgtgaag gtttgttatg taggtaaact cgtgtcatgg  10080
gggttcgttg tacagattgt ttcatcaccc aggtattaag cccagtaccc aatagctatt  10140
ttttctgctc ctctctctcc tcccacccac cctccaccct caagtagacc tcagtgtctg  10200
ttgttctttt ctttgtgttc atgagttttc atcatttagc tcccacttat aaatgagaat  10260
atgcagtatt tggttttctg tatttggttt attgctaagg ataatggcct ctagctccat  10320
ccatgttctt gcaaaagaca tgatcttgct ctttttttatg gctgcatagt attctatgtt  10380
gtatatgtac tacattttct ttatccaatc tgttactgat gagcatttag gtagattcca  10440
tgtctttgct attgtgaata gtgctgcaat gaacatttgt gtgcatgtgt ctttatggta  10500
gaatgattta tattcctctg ggtatatacc cagtaatggg attgctgggt cgaatggtag  10560
ttctgctttt acctctttga gtaatcgcca cacggctttc cacaattatt gggctaattt  10620
gcactcctac taacagtata taagtgtttc cttttctctg caatctcacc agcatctatt  10680
attttttgac gttttattaa tagccattct gacttgtgtg agatggtatc tcatcgtggt  10740
tttgatttgc atttctctag tgatgagctt ttttttttcat atgctggtgg gacgtatata  10800
tgtcttcttt tgaaaagtgt ctatgtcctt tgtctacttt ttatgtggtt atttgttttt  10860
ctcttgtaaa tttaagttcc ttatagatgc tggacattag atctttgtta gatgcatagt  10920
ttacaaatat tttatcccat tacgtaggtt gtctatttac tctgttgata gtttcttttg  10980
ctgtgcagaa gctcttaagt ttaattagat cccatttgtc aatttttgct tttgttgcaa  11040
ttgcttttga tgtctttgtc atgaaatctt tgcccattcc tatgtccagg atggtatatt  11100
gcctaagttg tcttccgggg ttttatagtt ttggatttga catttaagtc tttcttccat  11160
cttgaggtga ttttttgtat atggtataag gaaggggtca gcttcaatct tctgcatgtg  11220
gctagccagt tatcccagca ccatttattg aatagggagt cttttcccca ttgcttgttt  11280
tcatcagttt tgtcgaagat cagatggtcg taggtgtgcg gtaggtgtgt ggccttattt  11340
ctgggctctc tattctgttc cattggtcta cgtgcctgtt tttataccag taccatgctg  11400
ttttggttac cgtagcccca cagtatagtt tgaagtcagg taatgtgatg cccccagctt  11460
tgttattttt gcttaggatt gccttggcta ttcagaggct aagttctttt aaggagaggt  11520
ctgattgaac aagatgctgg acaggtcatt gtggtgatcc ttcacgtctt gaagatgtct  11580
ccttctgtaa tagacaaaag tcacactttt tacaagtttc tctttcctca ctgtgatttg  11640
tatgtggtag ctgacttcta tttatataac ttcaagctct taccatttaa atatttatac  11700
acaagtatga atcattggga caagccatgg ccatccttga agagtgtgtg tcaagtaaaa  11760
taggcgtgct ttagattttc agtaattttg gttttgggaa accggtacca tggaagagct  11820
ttcagatgct gaatgtgtaa tttactccac tttggaatac tgtaagtaat tctgcgccat  11880
tgtggacttt ggccacatca tgccactctc aaaaacttct gattcttttt gacagtacca  11940
agtcaggggg ctaagctgtt gtatattctt tcctttaacc ccttgtctaa ctaaagaatg  12000
gtaaattcca attcatttca gaatggaatg cacacatata gagtttcagg ttatgctgaa  12060
tgtgttttat gaggaggcta aaaatagctt ataaggaaaa tgctgataga ttcaagaacg  12120
agaacaaggg atgtatttat ttgtatgatt tatgtagcgc ctttcttgga gaggactcaa  12180
```

-continued

```
ttctgagctc taacgttaat aaactctata tcaattatcg tgattatttt cgaacccttg  12240
agctcctata ttactatatg tgacccattt gtatacctga cagtttactg ttaaattttc  12300
catagtgacc agttgtaata ttttaaaagt atccagacat tgaaaaggcc aactgtgtgt  12360
atctatggtg tgtgtatgtg ctcagggggg tgtactataa aatgaatgtc aagatcattg  12420
caatggttaa gtttaggttt taaactcttt gaacaccctt aaagttcaga ttttcagttg  12480
acagtgggat tgcccccaaa gatgtgtggc tgccttaagg agccttcttg tcctgctaag  12540
cctcctggat ttccaccaat gcatgttgca tttctacctg gctgcaatag acgcacaact  12600
gaatatatat cgtggacatt tataaatgtt tcaaatttaa aaccactcaa atttttaaaa  12660
gaacaagaat cttctgtgca tttaatctaa attctgtatc agccattctt aaaaatagaa  12720
ttgaataaaa tcattttgga tggcatgtgg tatgctttct ggagacataa actaacagag  12780
ggaacttgac cttgggaggt aggtttgaat ctctctacta tctactgatg ctgtgatttc  12840
agaaaagtta gataacctct ctgagcctca gagatagtat ctatcttgaa gggtgaatgt  12900
gcagattaaa tgcaaatgaa atgtaaagcc cctactgaat ttcctggccc agagtaggtg  12960
ttcattaaat gctgatttct tccctgtccc acttcctgtc aacatttcct ggaccaacaa  13020
gatgtttact ctacaatatt accaatattt cctggaccaa taagatgttt actctacagt  13080
gtatagtgat aattgtctga tgagaagcat ttacattaat taaaatgtaa aactggctct  13140
aggccctgga tttgtccaac cctttttatt atcttgggct tttgcaagtc ccatggattt  13200
tagaaatggg atcatcctgc tgcttgcagt ccaaatggtt caaggttgaa atttttttc  13260
ccctctgttg aaaaaagtca gttgcagctc tgtaataata acagcagaca catacttcat  13320
gaggaacaat gtattttggc aaaagagttt tctgtttgaa gcttcaaaat acaaaatact  13380
ctgccacatt gccattaggc ccggcgaaga acattggaga ggggttatgg aatcggttgg  13440
ggtggggtgc gggatggaga ggggttatgg gatcggttgg ggtggtgcgg gatggagagg  13500
ggttatggga tcgtttgggg tggggtgcgg gatggagagg gttatgggat cggttggggt  13560
ggggtgcggg atggagaggg gttatgggat cggttggggt ggtgcgggat ggagagggtt  13620
atgggatcgt ttggggtggg gtgcgggatg gagaggggtt atgggatcag ttggggtggg  13680
gtgtgggatg gagaggggtt atgggattgg ttggggtggg gtgcgggatg gagaggggtt  13740
atgggatcgg ttggggtggg gtgtgggatg gagaggggtt atgggatcgg ttggggtggg  13800
gtgcgggatg gagaggggtt atgggatcgg ttggggtggt gcgggatgga gaggggttat  13860
gggatcgttt ggggtggggt gtgggatgga gaggggttat gggatctctt cgggtggggt  13920
gcgggatgga gaggggttat ggcatcggtt ggggtggggt gcgggatgga gaggggttat  13980
gggatcggtt ggggtggggt gtgggatgga gaggggttat gggataggtt ggggtggggt  14040
gcgggatgga gaggggttat gggattggtt ggggtggggt gcggtgtggt gtgttctgct  14100
tttggccagg ctggagaggt gagctccata acatggtatg gtcatccttg ccatgtttgc  14160
ctgtagtgac ctcccctgaa cactcctaga tgagattttt gtctgcatgg aagggagctc  14220
aaggaaattg tgatgggacc cacagtactg aagtggacag gagctgaaca agcatttgca  14280
catgataccc ctatggaggt tacttggtag gacaggctat gaagtagggg cagtatggat  14340
gaggtcacgt ttctttagcc cattccttga gatgatgatg atgatgatgg tgatgatgat  14400
aactggctac catttattga gtgcctgtca tggttggact ctgtgctagg tactttaaca  14460
tatattatct ctcatcttaa taacccagaa catcttgggt tttcctgttc ttattttatg  14520
gacaaggtaa ctgaaattct tggggatcaa gtgactcctc caggacctca tcattagtga  14580
```

-continued

```
gtgtgggccc aggtctttgg gtgaatgtgt tggtgtaaga aaaatttccc ttcttcctga  14640
gcaggaggat tttttttttt tgctggagaa tgtggtgacc cctcattctt tcctaaatct  14700
gtcgtttgac tattaaacct gttagggaca ctgctggttg attctgtttc tttctcacac  14760
atccataccg aattctccta aagacatttg aagaaaaatt ccagacaata aaaatgttta  14820
atgattatac tttgtgattc ttctagaatg gcttctggtg gcatgtgact tattggaaag  14880
aggctaaccc tgactgctgc caaggagacc aatgggagac tgggtcccag ttggtggtcc  14940
aggctgcgcc acaccgtagg agtccataac aagaagggct ggcctctgtt gcccgttgat  15000
gcatgagcca tctcagcaga gcaggccgtc cccagttatt ccttgtccca gatgcctctg  15060
ctggtttgtc ctagtgcctg ctaaccctca gctgttgcca cttggatatt atgtcaagct  15120
tttcttccca gaatttctga tttacgactg ggtatgaagt caaggcctac ctgcatagac  15180
agacccctgt acttgggact cccacgaact gtggtcatgg aaacaagcac caaggactac  15240
ctgacccttc taatgtcact tttctgcaga gattaggagg agagactaag aaagccaaaa  15300
aagaaaaaat tccaagaatg aaaaggccaa aagcagaaac acctactctt cttccagtct  15360
tggccagaaa gggtgtcctt aggggaaaaa aagaggccag ggaatggagc ccatttttaa  15420
agcaagcaaa gatcagtttg gtatttaaaa ataaaaagtg aactccagta ccagctaatg  15480
tgtaggtgaa tcgaggctgg tttaggcagc tgaactttgt tcttggctac ctgtacagca  15540
gttgcagaac actcaggggt tccaggcatt tccaagtggg agttgagttt tggaggaaag  15600
ttgtagaatt cctttttctt ttttttcttt ttttgtgaga cagagtctct tgctctgtca  15660
cccaggctgg agtgcagtgg tgcgatcttg gatcactgca acctctgcct cgcgggttca  15720
agcgattctc ctgcctcagc gtctagagta gctgggatta cagatgtgca ccaccacgcc  15780
cggctaattg tatttttagt agagctgggg tttcaccatg ttggtctcga actcttgacc  15840
tcgggtgatc cacccacctc agcctcccaa agtgctggga ttacaggtgt gaaccaccgc  15900
acctggccgt agagttcttg actaggagat gctgcaaatt tccctcttaa atttgcagct  15960
ccccgtgcga tgacaacttt cagagcttgg cagaggcaag atggtataaa catgattttt  16020
agattgcagg gtaattgctg tggtttcttt gagtttttttc atccatttgc tccccaaata  16080
atttttgaga cctactatgt gccaggttct gtggggatgg aatagcaagc aatgaacagt  16140
tgagtggggg agacaggctc ttgtcaaata attgcaaaaa tgaagggcta ggactgggtg  16200
cagtggctca cgcctgtaat cccagcactt tgaggggccg aggtgggcgg atcatgaggt  16260
gaggagtttg agactagcct ggccaacatg gtgaaacgtg gtctctacta aaaatacaaa  16320
aattagccgg gggtggtggc aggcacctgt agtcccaggt acttgggggg cggaggcagg  16380
agaatctttg aacctgggag gcagaggttt cagtaagctg agatcacgcc attgcattcc  16440
agcctgggcg acagggtgag actctgtctc aaaaataaaa aaaaaaatca aaataaataa  16500
acaaaaataa aaaatgaagg gctaggtcca gtcaaaggtg aagattctgt gaaggaaaag  16560
catgggccgg aggcatgtgc cccatgttta ggagttccca gggactggga ctatgaagct  16620
gctgctgctg ctgctttttt tttttttttt ttttttttta aatgcagggt ctctctctgt  16680
tcactgtgtc acccaggctg gagtgcagtg gtgcaatcac agctcattgc atcctggacc  16740
tcctgggctc aagcggtctt cccaccttag ccttctgagt agctgcgact ataggcgcag  16800
gctgattttt ctttttcttt tcttttttttc tttttttttt tttttggtag agatgggttc  16860
tcacttgttg cccagcctgg tctcaaactc ctgggctcaa gcgatcctcc caccttggcc  16920
```

-continued

```
tcccagagtg ctgggatcac aggtgttagc caccacacct gaggctggtc ttccccttaa  16980
ggaggtggca cccacctgga ttccccagca aacccacctg cattgcaagg ttgaccctca  17040
tcagtaccag ccaccttgcc tgctaggttg acccttgtcc agtgaggtga ttttccaggg  17100
cctagcctct ctgctgtccc ttgctggctt cacctgttga tgttgatgga ggtggagcag  17160
aggccgttga gtgaatgcgt gcagctgggc tcagaggccc ctcttctccc ctcctgtgag  17220
gtgcttgccc ttgaaggtgt ggcgagtgag gaggccggtc aagggcatcc cggcggcctc  17280
caggccgtat ttgagtgggt catttcagcc tgcttcctat ctcttttctg ttactacctc  17340
taattggcag agtttcttgc caggtcaatg tggaggcaga gagatggccg gagggcggcc  17400
aggggagtca ggccaggtgt gggcaggatg ggattctgcc tcctcccagg tgcctcgcct  17460
gggggatgcc ctgtcccaga aagcctacat tcgtgggagc cggcgcacag cccttctgag  17520
atctaaagct tccctctgaa tgctgctttg gaggattgtg agaggtagtg actcttcaaa  17580
gtttgtttgt tttcttgaag cttttacctc tatgcaaata tgcggtttgg agcagggaag  17640
aaaggttaac tgtgatggcg ccggctctta acgtggaatg tcctgaatta atgtgggttt  17700
cagtcctctg gctcaggatc ccctgaggga gagtttttct ttcctctgca aaacacagga  17760
gaaaagtgat ccctgtggct ccgacctgcc ttccttgggt cctgcggtgc aaaaccagct  17820
gggaccgtgt cccgcccacc cgaaggcagt gtggggaacc tttcctccag gtcattccca  17880
ttcagctgat tgctgccggc tccccaggcc acaactctgt gccttcaggc gtctgcacgg  17940
gtttcgagat gctggccagg cctgaacttg gtgagcctca agcagaccgt tcaaacccat  18000
tcaaatgagg aagaccatct gtttcccagt ctccagctgc tgctgcttca tttgcaaatg  18060
gctgggatgc tgctgagggg atcaggcggg gacacatctg cagactctga aggagtgttg  18120
gaaccgagat cctgctgaga gaagaaaggc cgagcccttt aaatcaactt gccaaacagt  18180
acccccagaa ggtcctgagt tgagaaagca ggaggcagcc ttgccctcct ggaataactc  18240
ttaaccttcc cttttctttt gtagccttgg ccactttaaa agtatttctt tattcagaaa  18300
gtgcgcagtg tgggagggcc tgctctatgg gcttggggga aaatgtcaaa cgggatctgg  18360
acatctatct gacctttcag ggccatacag ggcaaacgta tccgctggag tatgcaccat  18420
ttattgaatg tttacatcaa tatcagggag gtgagcttgt cccagcagca gcttctagga  18480
gccacaggta acagtaagtg tggcaaggtg actgtccctg aaaacctgct tctggaatga  18540
gtcaggcttt agggtatgct ctctggaatg caggccagcc gccccaactc gcagtaacgc  18600
aggcccttag ctctgtggac tgcgtgaggc acagctgtgg ggactcttgc ccatggtttg  18660
gtgtttgcag ggttattctc ggcatgctgt ggggctaggg taagttatcc ggctcctgag  18720
ccctgctggg gttctcatct caagggaatt ctgtggtgtg ttactgtgcc ccacatgcaa  18780
atatcagcta ctctcaaatg tgttggatgg atgaatagta gaaggtattt taagaagcca  18840
caggcctctt tgtaaattaa acaggcatca tacatgggtg ttgataatga tgaatctcac  18900
aaaatcttca gatgtttagt ctctgggaac attccaggaa tcctcattta ggtaacttat  18960
atgtgatgag acctatttgt tcacttgaaa gaaaacctgt tttgaagtca gaggaatgcg  19020
aatagaggct ctcacatggt tggaaaaagc aatctgcagg ccagttacgc cccgtaaaca  19080
ggaacccagg actgccctcc tggccagggc tgagttgcag gatggggacc ccccactacc  19140
tccaaccgcc cgccaggatg aggagtgctt gctctcagac gtgcccctca ctttaaatat  19200
acagaggcct tcctaggcag cctttgattg tgtccttgtg gtgaccttgc cctgcagcag  19260
gcagcactgg agatgttttt ctcttctcta aagcatgact ctgaggctca gcggtgtgag  19320
```

-continued

```
gctgtccaag ctgacacgtt cactactggc agaggcgggt ctcaaagtct catccttgga  19380
cactggagct gaacttcttg tagtgtgggt cttggaccag cagcatcagg cctcacctgt  19440
gggaaataaa gaatgtcagc ccgcacctgc aggcctactg acccagaatc tttttttgtt  19500
ttttcctttt gagacagact tttgctcttg ttgtccaggc tggagtgcaa tggcacaatc  19560
ttggctcact gcaacctctg cctccgaagt tcaagtgatt ctcttgcctc agcctcccga  19620
gtagctggga ttataggctc ctgccaccag acctggctaa tttttgcatt tttagtagag  19680
acagggtttc actgtgttgg ccaggctgtt ctctacctcc tggcctcaag tgacccacct  19740
gtcttggcct cccaaagtgc tgggattaca ggcgtaagcc acagcgccca gctgacccag  19800
catctttgga agtgggagca aggaagctgt cttaaactga ccacgtggtt ttacgcacag  19860
taaagtctga gaaacattgc attgatccct actccagtcc ctctccgtac accttttggg  19920
tggagtgggc tggggacgca gactgtcttt ggctgtgcat gtcctagagg ctgaacagga  19980
cgagatggga gcagtgcagt gtcttaatgg gaatcgggat tttcacggag gagctgttgg  20040
aactgggctg aataggagcc tgccaggcag cagagctggg tgggcttgta ggtagaggga  20100
acagtgccca tgtggacagg taagccagag tgtcagagag agggatgtgg ggcttggagc  20160
aaccaagcct caatgcgcca tgatgttctt tgggttttat tctctctgac tttggagtgg  20220
tctgtgcctt tttaaaagag tagagatcat gtgcttttca gaagattcct ctgggggtct  20280
gcggtggcta caagaggcgc accatgggtg atgggttagg cgcattgcag aggtcttgtg  20340
gaggactgga ggagacctgt gggatgcagt tttgcctgta ctttctttca gagctaagct  20400
ttctatcagg gataggccta ataggtgaag ggtgtgtggg actgatcaga ggaagggcca  20460
gaggaaaaga ggggcttcag ggccgacttg gagcttgggc ggcagttcag tggtgtgact  20520
cccttcatcg tgtaagagaa gaggctggtg gaggaggagg aggttgaagg tcacttgctt  20580
gttttggata cgacctctgt agacatccag gttatgtatt tcctccccccc gggcaggtgg  20640
aaatatgaac ctacaagcag ggacttgagt ggcatctgcg gggaggaggt gggaaaagcc  20700
acacgtgccc aggagactgg aatgcaggga aaggaccaga agagccagag gtagaattct  20760
gggtatatcc atggatacag gaggggtggc agggaaggag aaatttccta gaaaggcgag  20820
aagtcctcct tgacatgttc ctgtccataa gaacacatac gcacatgtac gcaccagcag  20880
gaagcagaat gctaaccgaa gataattaac ccccaattct gtgttaggga ttgagaaata  20940
gaccaggagc cctgcccccct cctctctcat ttcctgacct tccacactga gaagacctgg  21000
ctaggcagcc ttgctttttt tcctgtttag cggaggagtg aggatttcag ccggaaggtc  21060
tttctgatgg cagatgtgta agtgccagac attgtgctgg gtgccttctg tgtcctatct  21120
catttattat tgttcctgct ccgaggactt gcctcaaggt catacgattt gtaagtggca  21180
tagtctcggt gtcagtgaca ggtctgtttg gtgtctctct ctctctctct ctctctctct  21240
ctatatatat atatatatat attttttttt tttttttttt ttttttgaga tggagtctcg  21300
ctctgtcatc caggctggag cacagtggcg tgatcttggc tcactgcaac ttccgcctcc  21360
caggttcaag cgattctcct gcctcagcct cccgagtagc tgggactata ggcgcctgcc  21420
accatgccca gctaactttt gtatttttaa tagagatggg gtctccccat gttggccagg  21480
ctggtctcga actcctgacc ttgaatgatc cacctgcctc agcttcccaa agttctggga  21540
ttacaggcat gagccaccat gcccggcctt ggtctgtacc tttaacaccc ccagcctttt  21600
ctgaagagtc accagagaag ggacaaaaat gaggccatag ccttactgct aagggaccat  21660
```

-continued

```
gagaggcttg gggtatagct gtctgttgag acaggtgctt tactactttg taagatgaag 21720
agagctgcct ctggctgagc actgtcatta ggactcaggg aatggaagtg ttttgagacc 21780
agagggttca gtttcaggac tggagatcac aatgcattca ttttacagag tgacaactct 21840
gtagggccac tcttcaccct aagattgggt cattaaaggc caggcacatc ctattcactc 21900
cttcacctcc ttgtgagccc cccacatgcc ttttgatgaa aggggttttcc ccagaacagt 21960
gtgtcccaag aagccctgaa gggctggaga tgtaccagct ttctctgcta tgtccagcaa 22020
gtgtattttc agaaggtagg aggctcgggc tgggctggcc aggcagccag gcacacagac 22080
tcctcattgt acatccaagc cggggcgtgc aggacttcaa catagcttgt aacgtaagta 22140
tctatttcct gggcgctaca tgatctaatg gcctgtcgct ttgggaaatg ctttctgaac 22200
aaaagactcg atttatttat ttatttattt tttgagacgg agtttcgctc ttgttgccca 22260
ggttggaggg cagtggcgtg atctcggctc acggcaacct ccaccgccca ggttcaagcg 22320
attctcctgc ctcaccctcc ttagtagctg ggattacagg cgtgtgccac cacgcccggc 22380
taattttgta tttttagtag agacggggtt tctccatgtt ggtcaggctg gtcttgaact 22440
ctcctgacct caggtgatcc accctccttg gcctcccaaa gtgctgggat tacagatgtg 22500
agccactgcg cccggccttt tattttttta aattattatt atttttattt atttatttat 22560
ttttttgaga tgaagtctcg ctctgtcacc cggctggagt gcagtggcac gatctcggct 22620
cactgcaacc tctgcctccc tggtttaagc gattctcctg cctcagcctc ccgagtagct 22680
gggattacag gggtgcacca ccatgcctgg cttaattttt gtatttttag tagagatggg 22740
gtttcaccat gttggccagg ctgctcttga actcctgacc tcaggtgatc cacccgcctc 22800
ggcctgccaa agtgctggga ttacaggcat gagccaccgc actcggccag gactcaattt 22860
tgaagttctt atgcaagcaa agctgcccat atctaggagt ttatgcacac agtactgatt 22920
caatacctgc gtcttagtgg tccatcagga atttttcact catgaaatat gactttaata 22980
cacgtgttgg gaccagagag aaaaccttcc ctctgtgcat cttttttttgg agaacactgt 23040
catgaacagc cgaaaacatc agatcaaaag caagagggat actgacaaaa cagggagtgc 23100
ggatttccac tgtgggtggg gacattggga gacacggtga ctcactcctc agtaagtgca 23160
ttcttaggct ctttactctg tgtgcatttt tattttctca tgggcaacaa tataatttct 23220
ttcaaacatg aagagccatc cagcatgttt ctcaaaggca gacttaaatg atatgagggg 23280
tgtgcctaaa tatataattt ttaatggtta ccatattgga aacattagcc atgatcccat 23340
ctgatgacta ggaacatgag ccagtctgga gtttctggag aaatccagct accgctgcag 23400
aggcggctgt tagctgttgt taccggcatc cttgttagcg accagggagg tttcagtccc 23460
gacttgtgtc taccagacac cctgacaact ggttagaaag agaggactgc accctttcat 23520
cctgcgtact tatctgttgt ttgttgcttt gacttctttt tgttctccgt ttttatgttg 23580
gcagtatttc tcgaggtaga gaactttcac ctttatattg tgcggagtat ttgtcccttc 23640
ctcgccccct taaagaacac gtagtaccta tgccttataa ggtctctgtt tgatgtgagg 23700
aatttggtct tcttgcaagt cggctcttgc agaggggagg ctttgaggat gtctgggctg 23760
cagcaggctg tcttcgttgc tgtgtacaca gccctcatgg cagggcatgc aaaggtggtt 23820
ggttctgact tcaatggcgg gactccattg cctttatttt ttaatttaat tattattatt 23880
attattattt ttgagatgga gtttagttct gtcacccagg ctggagtgca gtggtgcgat 23940
ctgggctcac tgcaaccccc gcctcccgga ttcaagcaat tctcctgcct cagcttcccg 24000
tgtagctggg actacaggca cacaccacca tgcccatcta atttttgtgt ttttagtaga 24060
```

-continued

```
gacggggttt cgtcttgttg gccaggccgg tctcgaactc ctgacctcaa gtgatccacc  24120
tgcctgggcc tcccaaagtg ctggtattac agacatgagc caccgcacct ggcctccatt  24180
gcctttattt ctttctgctg ataagttctg atgccagtga tacccagatt gtgccatagg  24240
aaagaggggg ctgggctctt ccagaaaccc tatcttgcag aaatctctct tctgttccta  24300
cggacagaga attgggtatt gaccagtgag gacttcttac tgggactggg cgtggccact  24360
acaggacatc ttccagacta agagggccag ttggggggtta ctggaccagg gaggacagtg  24420
gcggccactt acttgccatg tgctttgtgt gcagtgacta tgtagcgaca tttgcagccg  24480
gactgtgttt ctcctgtaga gacactggca gccctacagc cctacagccg tgacatttac  24540
tctgtacaag gtggcaggag gtgtgggagg gcaccgggaa ccgaaggcca ttttactacc  24600
cttcccgcag cgctcctgtt acagtgcttg tgggagtccc agctgtgcct ccaggtacaa  24660
acgggtttct tcctgcaacc cacaaccctg acaggacatg cctcccgggt gtgctcctaa  24720
cctgcctctt ctctctgccc ctccctcttt ctcctctccc cttcccctct ctttcttcct  24780
cttgccttcc tcttctttcc tctccctccc tctgtttctc tcccttcctt ttccttgtct  24840
ccgtctctcc tctcctttt cccctctcc ctctctttca tccttctgtc tcttccagag  24900
gagtctgttc agggatttct ttctctcttt cttcttcctg gaggaatgtg tttagggatt  24960
ggacacctct gactttggag gagggagaaa cctcagtggg atgggttcca ggacgacccc  25020
accgcatcct tggaactagg atgatctaga cgttggaaaa gacaccatcc ctgggaaacc  25080
ccagaaaagg cttaatttgt gaaaagtaat ggagggagct gtgccgttgg tagaaactgc  25140
tttttcttc cttaacagtt taaatctgtc gtccattctc cgtgaagtga ttggacgggg  25200
caagactcag gtttcccatc tgttctctgt ttgcatttgg gcgccatttc aaaaaccaca  25260
cgggaaaagt ttataggcaa acattataaa aagtgacagt ctgaagtgct gctatcgctg  25320
gtttggcaac gtaaagtgtt acctgaaata gcttaccgtt tccaaaccct tttgctgttt  25380
caactgtctc aagacaaccc tcccgctgag atgggtgaga agtccagctg gatgtgtgca  25440
gtgaagtcac ataagtcaca gcctttttg acttttacaa gatttccccc tcctggggct  25500
atcttcacac acagcgagga tttttttctc tctgtttact tatagagagg taaattcatg  25560
cagcttgtgg ctagtggcac tctgtgtgat gtcaaatggt ctgctgaggg gctcggagag  25620
tcaggcagcc cctgcctcag tttctctctc tccccagtca gaggtcctat gagctcccaa  25680
ggaataacag gatggttttc ttagggaagg aaggccaggt caaggcagga attactcaca  25740
gctcatgtgc agatgcctgt tgttattcat actatttatt tatttgtgtt tttttttgt  25800
ttgagacagt ttcactcatg tcgcccaggc tggagtgcaa tggcatggtc tcggctcact  25860
gcaacctcca ccttctgggt taaacgattc tcctctgcct cagcctccca aatagctggg  25920
attacaggca catgccacca cgcccagcta attttttata tttaatagag atgggtttca  25980
ccatgttggt gaggctggtc tcgaacttct gatctcaggt gatccactcg ctttggtctc  26040
ccaaagtgct gaaattacag gcatgagcca ctgtgcctgg gctacttatt tatttttgga  26100
gacaggttct cgtctcgctg tgtcacccag gcaggaatgc agtggcgcga tcatagctca  26160
gtgcagcctc tggggctcaa gcgatcttcc tacctcagcc ccctgtgtag ctgggactac  26220
aggtgtttat catcattccc ggcttttttt tttttttttt ttcatttttt ggggagagag  26280
gatcttacta tgttccctag gctggtcttg aactcctgac ctcaagtgat tctcccacct  26340
cgacctccca aagtgctggg attgtaggca tgacctgctg tgcctggccc atttattttt  26400
```

-continued

```
tgattagctg tacaagtacc tgtctctctc atttttaaag tatcaaaaca gtcaattttt  26460
tttttattt ttttttgag atggagtttt gctcttgttg ccccggctgg agtgcaatgg  26520
cgtgagctca actcaccaca acctccagct tttgggttca agcgattctc ctgcctcagc  26580
ctcccgagta gctgggacta taggcatgcc ccaccatgcc cagctaattt tgcattctca  26640
gtagagacgg ggtttctccc tgttggccag gctgggatcg aactcctgac ctaaggtgat  26700
ccgcccgctt tggcctccca aagtgctggg attacaagcc ctaaccaccg tgcccggcca  26760
accactttgg gtcgttggtt ggttgttagg tagatttaaa aaaagctttt tgtggccaag  26820
ttcggttgct acagctcttg gttattacca cttttggatt actgacgcaa ttcgccctac  26880
cccgaagttt tatacaattt tggattggct ctgcaccacc ctgaaatgca acccccctga  26940
gttagcctgg aacttgcgga tcacaaaacc cccatttgtt tcccggggcc tcctgtatcg  27000
cgaattttac ctacttatga caacaatatt gtatatccac aaacccttct ttaaggactt  27060
ggttcaaaca agtgttttcg aacatccatt ggatagagcc agagatacac tttcgtcgtt  27120
ggttaaactt atggcaatga gatatgcgag tcagctcttc cccataacta ttaggcctaa  27180
ccacaagggg atatatggct cctcttaaac ttttctagaa aacataaaac agattttgta  27240
aaaattatct ctcccccgta gagcctattg ctcaatcttn nnnnnnnnnn nnnnnnnnnn  27300
nnnnnnnnnn nnnnnnnnnn nnnnnnnnnn nnnnnnnnnn nnnnnnnnnn nnnnnnnnnn  27360
nnnnnnnnnn nnnnnnnnng aagacaccct gtctctacta aaatacaaca acaacaagag  27420
aattcccagg cgtgatggca tgcacctgta atcccattac tccagaggct gaggcaggag  27480
aatcacttga acccaggagg tggagcttgc agtgagccga gatcgcacca ctgcactcca  27540
gcctgggaga gagcgagact ccgtctcaaa aaaaaaaaaa aaaaaaaaaa aggccaggca  27600
cggtggctca cgcctgtaat cccagcactt tgggaggctg aggtgggcgt atcacgaggt  27660
gaggagatca agatcatcct ggccaacatg gtgaaaccca ccccgtctct actaaaaaaa  27720
ataccaaaaa ttagccaggt gtggtggcag gctcctgtag tcccagctac tcaggaggct  27780
gaggcaggtg aatagcgtga acccgggagg tggagcttgc agtgagccaa gatcgcgcca  27840
ctgcactcca gcctgggcga caaagccaga ctccgtctca aaaaaaaaaa gaaaaaaaag  27900
gctgcttgct aacacgctgc tggtacttcc caagtatttg aaacttctgg gagaaaattc  27960
acgtggatgc aactgagctt tatgcagcag ggctgcagta gtgtggccac ggcagtagaa  28020
acgagtgttg agctgtgtcc caggaaggag acttggtgcc ttgtttgttt accagtttta  28080
ggaaacagtg acaaagattg gccaatacta ctgtgaagct tgcttgcttc ttttcgactt  28140
ttaattcata ttgcgaaaaa tacatggaaa catattctct gtctgtggaa gcctctgaaa  28200
gagcatttgt gcatagcaag gcggcttctg gaaccttctc cccattgcgt tttggcagga  28260
gatgaggaga tgttgggctg tgcacccctg gtggattcgc acaggaaagg tgaaaagtat  28320
gccacagcaa tgggaaaaag taaatccagg aagtgctcac atgactataa aaggagttat  28380
gtacatttcc tggggaattc tttgctcttt cacagagcag gctgtgcagc ctggtggagt  28440
cagggagagg ttgtccatcc atggggggtg accagagtta gggaggcccc tttgcacatg  28500
caggcacagg ggattctctg attgtcctgg ctccgcgcag cctggggcca ggtcagtaca  28560
actgtgggga tgaacatgga gggctcaggg agtgcatgtt tgcagggagt gggcagcggg  28620
tcaggtcacc tgcagcattc aaacccagaa gagaagctaa gccctgtgga cggcaaatgg  28680
acccaaggac acgggcaggg acagagctgc ttccactgag ccagctgtta ggtgcttgtg  28740
ttcttggccc cctggccggg gttgtctttg atatgtgtcg tgtgtgctgg gccctgcagg  28800
```

-continued

```
ctgggcttgg ggggccactg ggtggcctgg gaggctacca gtgtggcatt tggcccctcc  28860
ccagcgtatg gccccacccc atccctgcct ctcttcttac ttacatcctc ctctttttat  28920
tctccccaac ctctttctct cttgtgtgtt tattcatgca ttctccctaa catgtgcttg  28980
cagagtcttc tgggataccc aggggtatta ctggcatgtt tactaaaggc accgctgatc  29040
cccaaaatgg gccctttgtg aaatgaccac tgaaggggtg gagggaggag tccttgcttt  29100
ctcagtttac caagacagca gttactggtt tgagactttg aagacaggat ggcttgattt  29160
ttatggataa acatcattat ctcattggtg tattttaggg ggtgatattt tactatcctt  29220
gaagcttgga tatctagatg acagttttga tctggtttta ctgggatcaa aagcagtttt  29280
agtacgtcaa gtcatcttaa ctgtccattg agatgggact cctgtaaaat cactttgtat  29340
ctggagatag caatccaagt gttctggctg ggcgcagtgg ctcacgccta taatcccagc  29400
actttgggag gccgaggcgg gcagatcacg aggtcaggag ttcaagacca gcatggccaa  29460
tatggtaaac gctgtctctc ataaaaatac aaaaaagtta gctgggtgtg gtggtgcacg  29520
cctgtaatcc caactacttg ggaggctgag gcaggagaat cacttgaacc tgggaggcgg  29580
aggttgcggt gagccgagat cgtgccactg gattccagcc tgggtgacag agcaagactc  29640
tgtctcaaaa aaaaaaaaaa gaaaagaaaa gaaaagaaaa gaaaaagaaa cccagatgtt  29700
ctgtgattat cctctgaaaa tcgtggtgct taaaaaatca cggcaagcat cttccgcctt  29760
gaagagtaac agtaatagtg acagtcatta gcccgacatg ttgtagttga tgatcaggtt  29820
catcttcgtt ggctcattgg aatcttacca ataataaacc agtatttggg tactcttacc  29880
ctgcaacaga tggggaacac caggccaaaa ggttaagcag gaatggagag gcgtgggaac  29940
tcagggcttc atcctcttct cgtccagggc agcacccttc accaggcatc tcccatgtcc  30000
agctccaaat aagacacagg tcctcgctgt cccctgtact tccttctaga acagcacgtg  30060
gtagtccagc agctcagata cccccagttt cagcaagatt ttggggttta ctgattttag  30120
gtgaaggaaa ggattctcaa tgaaaacact ttcatttaaa aacaggaaat catacatcat  30180
aactcctcct ttgccgggag agagattttt ttctgcatca caattgcaaa tgccttgctt  30240
atcttttttt tttcttttttt tccccctaat ggagtcttag agcattcctc tgcgtgacat  30300
agggacatgg ttgcacctta tctgagggtc aggatggagc agattggtgt gtgggtccca  30360
ggtgccttcc ctgtgaggga gggaagcttt gctgcttctg ctcagcggct gccctggtga  30420
tcaattctgg ctaagaggaa agtacattcc ataacatttc tggtgacttg ctgatcatgt  30480
gatgttgtca taatagacat tgatcatttt atgacccaga ctgatccaat gtaaattcat  30540
tctaacatgg tgggtgctgt ttcagcaatg agttgttgga gacctgggac tcaaaggaca  30600
tctggtcctt gccttagcca gctgtcaaag gggttggacc aatagcgttt ggggcccctt  30660
cagctctcat gttgagtgaa tctgtgactc taggatgttg ggagtgggag atgggccaag  30720
atttgggacc agactgaatc cctgccgtct tctcctcctt ctcatatttc tcttcctttc  30780
tttttctgt ttggtctcca tagtttaaag tatttctatt agtcactcaa ttcagccgca  30840
ttttgactta accagccttg agagacctgc tctaagagcc ttcaaactaa gttcccaaca  30900
tcttttaaac ttcgctttgt ccttcacttc tcagctcaaa tgcctgttct ttggagaagt  30960
ctctctgatt gtcttataca acagggattg aaacactttt tgcaaaggca agactgcaaa  31020
tattgtaggg cttgcaggcc acagggtttc tgttgcaatg actgaactct gcccttgtaa  31080
cacacaaaag cagcgccaga caataaggaa tgggcatggc cgtgttctaa taaagctttg  31140
```

-continued

```
tttacaaaaa caagctgcgg ctggcttggc ccgcgggcca tcatccgcca cctcctgcca  31200
agggaccagc cctcctctgc cactgctgtg tgtgcccgta ccttgccatg tccttcttcc  31260
taatgcttaa gcaagaacac tgtatttttt gtagattttg tatctatcgt ctgtcacccc  31320
caccataatg gacgctccac aagtgcaggg tctttatctt gtctcctctt gctgcggagc  31380
ttccagaata ggcttgttgt atagtagaca tgcagtaaat aattactgag tgagaaaaca  31440
aatgttagaa acataacctg cccgtcagct gggctttcct tgctttgggg tgcatttgtc  31500
catgttacat ttagcttcta ttttcctcct tttgttgtga ttctctcttt gtgttcacgt  31560
gctagttggc atctggggct tggcatgcat gcctttggtg atgccccctt gagaagcccc  31620
gggcctcctg tgtggctgtt gatggtggtg gtgaggggga tttcttgtcc ccaatgcatg  31680
tggcccttgc tcctttcaca gtgggactga aacacagatt gacttgattt cagtctcctg  31740
tgggagattt gttcttctga ggggtgtcta ggcaaaacag ttgcctttga tcctgccctg  31800
atttggtgct gtctcagtgc tgggaagctt tgcattttct aggcctggaa ctctgggtcc  31860
cattcacact tctcactgga gggatgaaag cctccttctt gggccctcgt ggccatccca  31920
gctggccgct ccagctgttg ttattaataa atgccagtgg tgtcctctca actccagtgg  31980
agaggttgtg tgggttggat ccttgtgggt ccaatcccgt gctgcatatc tgggaactgt  32040
gaccttgttt gacatggcca tgtgtctgcc aagcaggatg gggtcggtgg cgggaagcac  32100
agagaaccat gagacccacg ccttttctct agggtcttgg tgtctccgtg gggagatggg  32160
atgcattcat gagaatatgg tgcatcccat gagctggcaa agtgggcagg tgtatggtgg  32220
agggggaggg agccagtgct cttccgccca gggggactga tgcaaggtga ctcccatcac  32280
ggaggaccct gcttgatttg ggtcttggag ggtggatgac agggaagaga gggaggaagg  32340
actgtcccta cagaagaagc ctgggacatg tgtggtgggt gttggtgagc agggtgggac  32400
tcagctttgt cgtgtggagt cgggggcaca cagcacccag cggcttcatt tcaggacccc  32460
tgtaagtgca acggagactg ccttgcagct gtctgggcat tttgctcttt ttgtttttgg  32520
tgttaaggcc tctaggcttt tatcattttg ggaaaacagc aggtctcagc tcacccagca  32580
cagaattagg tctctaaacc ggcaaagtac tgatctgaac atgagagctc atgaaaactc  32640
tggatggcaa aaaatcttgt agagggatcc cttagttttc cttgagtttg agacatttca  32700
ttttaagaag cttggccttg gggcaacaga ccaagtctag cacaaataat aaagagtgta  32760
tgtgtgtgtg gcgcacagtc acgtttcacg tacaaatgtg taaaactcgg cattcttaca  32820
aataaaacat accacaataa cagatttttg caggtattac agtgcaagca cgctttggca  32880
atcaatttaa acattttctt gtggaatatt cttccatgct atggtttggt ttgtttctaa  32940
agccccatag gatgtggaaa ctaagtcagg acagattttc tgggggtatc ctctggttgc  33000
tcttccagat acttcctgac ttcctggggc ttggggagag gtggatgcct gctggggcca  33060
tttgcagagc aagaacagct tctcctggga ataagcaggc ctccactgac ctttgttgga  33120
cgttctctcc tctccctcct tcccatctgt ctccgtcttc tctctcccac ctttctgcag  33180
agccaccaac caaataccaa atctctcaac cagaagtgta cgtggctgcg ccaggggagt  33240
cgctagaggt gcgctgcctg ttgaaagatg ccgccgtgat cagttggact aaggatgggg  33300
tgcacttggg gcccaacaat aggacagtgc ttattgggga gtacttgcag ataaagggcg  33360
ccacgcctag agactccggc ctctatgctt gtactgccag taggactgta gacagtgaaa  33420
cttggtactt catggtgaat gtcacaggtg agttggcccg ccagcactat gctctctctt  33480
ctctgtagcc attacatttt tttggccaag tgaaaaggta gtgagatctc taattgtaat  33540
```

-continued

```
tggatgccag gcatacagct tcatagtttt tgaaattctt ctttgggacc tggtgcacca 33600
gaaaggccga tcattaagaa tgatagaatt cttgtgcaca aagtaacatt tttcttaaga 33660
tagtacgctt ttatttaagt aaatacatgc tttttttttt tttttttgt accactgaca 33720
tctctggcat ttagaatata gggttgaaat ttggatactc aagatttctg attcatttat 33780
tagagtttga gtttctctcc atgatttcct tctatgcagt gagcgggaca gaacaggccc 33840
cctttgtggc cgagtttaaa gttctgcttt cagaatgtta gttgacgatg agaagggcca 33900
cacagggact gagttttgtt agggatcaat ttctctcttc aaggagaccc cgcatactga 33960
aaggttaatg ttggaaaaag agtctttggg tgctacacaa ttggtaaatt tgtcaggggc 34020
ttgaatactg tttgaagctt gaaatccagt tctcatatat ccaattttat agcctgttta 34080
aatagcgtga aagcagaaaa cattgagaat cataacatag accaactgtc atcatggagg 34140
gaaaatttaa gccattaaaa ctatcttaac tgaaaacaat cccaggctct ttgcgagggt 34200
tcctgggttg ttgactttgc tatggagaag gtctcagttg tagataattg caaccttttt 34260
gctttgcaaa aaacacatcc atggaatatg ttcttttgca tacagatgcc atctcatccg 34320
gagatgatga ggatgacacc gatggtgcgg aagattttgt cagtgagaac agtaacaaca 34380
agagtaagta actgcccggc tccgatggtc cccgagagag gagcatggag ggaagttctg 34440
cctgtcacct gtcttcttgt cgactcttct gcgccatgct gtgtcccgcg gcccttgcct 34500
ttccccgctg tgtctacttt cctgactttc aaacctgaga ataaaccagt gttgctgcac 34560
agccttctct atcgtttgtc ctttcttctc gtgtcactgg tcattcgttt ttcaaagcag 34620
ttactacttt tctttccttg attttccctt ttccctttga cttctcccta ttcagagaca 34680
taagaatagt agaaccatgt aacatcttgg ttttccttgt aatcagtgat tgtgcttggt 34740
ttaatccagt ggtgtgtgac tggggcaatt gcctattctt gctctcccgg cacattgggc 34800
aatatttggt tgtcacaaca gagggagggg gtgctggtgg cctttagctg gggaggggcc 34860
agggatgcag agcacagccc cataacaaag aattatctgg tccaagatgt caatcatccc 34920
tagggtgaga aacccggcct cctacaacac acacctcatg ctgagtgaaa atgaaggacg 34980
tgtgccttac tttgtagacc acgattgaaa agggagccaa gggtggcttg cttaatgagg 35040
gccatgaaca ctgagcgcta acatgggaga ggccatttac ttgcgaggaa gaacatggcg 35100
tagcctcttg gagctgggca acctgggttt gaatcttgct ccacaacttc tgagttgctc 35160
atttcacttc tgtgccttag tttctttata aaatgggagt aataataata atactatttt 35220
ctggggttgt tatgaggatt acatgagttc ctagttgtat agtgctcaga agagtggttg 35280
cttgcaaatg tttattcaat acacaaaata caatatagca ttacttgcat tttccaatga 35340
cttggctaga atgttcctaa agtgtttgta catagggtat tgggattctc tgcttacatg 35400
gtatattcta catttttctt aaaaggattt tagtcaattt ggtacattta aacaaggcct 35460
aagtaatata ccacacccgg ctaatttatg tatatatata tattttttcc cgagatgcag 35520
tcttgttctg tcacccaggc tggagtgcag tggcgccatc ttggctcact gcaacctgca 35580
cctcccaggt tcaagcaatt ctcctgcctc agcctcccga gtaactagga ctacaggggc 35640
ctgccactac acctggctaa tttttgtatt tttagtagag atggggtttc accatgttgg 35700
ctaggctggt ctcgaactct tgaccttgtg attcacctgc ctcggcctcc caaagtgctg 35760
agactacagg cgtcagccac cgtgcccagc ctaatttatg tatttttagt agagacaggg 35820
ttttaccatg ttggccaggc tggtcttgaa ctcctgacct caagtgatcc acccgcctca 35880
```

-continued

```
gcctcctgaa gtgctgggat tacaggtgtg agccactgcg cctggcaata ctttattttt  35940
tcgagcagtt tcaggtccac agcaaaataa agaggaagga acaaagattt cccatataat  36000
cttccccaac acatgcatag cctgtcctgt tatcaacatc cccaccagaa tggtacatct  36060
gttccagttg atgaacctgc actgccatca ttatcaccca aagtgtgtgg ttgactttag  36120
ggtatgtaat catacagtgt gtagccttta cagattggct tctttgactt agtaagatgc  36180
atgtaagttt ctctcatgtc ttttcatggc ttgatgggtc atttgtttgt agcactgagt  36240
attccattgt ttgtatgtat caaagtttat ttacccgttt acctactaaa agatatctcg  36300
gctgggcacc gttgctcacg cctgtaatcc tagcactttg tgaggccgag gcgggtggat  36360
cacttgggaa caaaagttcg agaccagctt ggccaacatg gcaaaatccc tgtctctgct  36420
aaaaatacat aggttagcca agtgtagtgg tgcatgcctg taatcccagc tactcgggag  36480
gctgaggcat gagaatcact tgaacccagg atgcggaggt tgcagtgagt cgagatcaca  36540
ccactgcact ccctcctgcc tgggtgacag agtgagactc catctcaaaa aaaaaaaaaa  36600
caaactctgt tgcttccaag ttttgacagt tgcaaataaa gctgctacag acatctttgt  36660
gcgggttttt gtggggacat agttttcaat tactttgggt aaatgttaag gagtgtgatt  36720
gctggattat gtgagaagag tatgtttaga tttgtaggaa accacctagc tgccttgcaa  36780
agtggctgca ccattttgta ttcccaccag caatgaatga gagttcctgt tgctccacat  36840
cattcgatgt gcttggtgtt ctggattttg gccattctga taggtgtgta atggtatttt  36900
gttgttttaa tttaaatttc tctgatgaca gatgatgtga agcatctttt catatgatta  36960
attgccatcc atgtatcttc tttggtgaga tgtctgttaa ggccgttggc ccatttttta  37020
attaggttgt ttgttttctt actgtcgagt tataagagtt ctttgtatat tttggataac  37080
agtcctttat tacatctctt ttgcaaatag tttctcccct cacctgtggc ttgccttttc  37140
attctcttga cagtgtctct tgcagagcag aaatttttaa gtttcatgta gtctggtttt  37200
tcttttatgg atggtgcctt tggtgttata cctaaaatgt catcacccaa cccaaggtca  37260
tctagatttt ctcctatgtt acctcctagg agtattattg ttttgtattt tgtatttatg  37320
tgtgtaatct attttaagtt aatttttgta aaggatgtaa ggtgtgtgtg tggattcact  37380
ttttagcctg tggatgtcca gtggttctgg gactatttgt tgaaaagact gtcctttagg  37440
tttttttttt tttttttttg agatgggagt ttcgctcttg ttgcccaggc tggagcgcaa  37500
tggtgcgatc tcagctcacc gcagcccctg cctcccgggt tcaagcaatt ctcctgcctc  37560
agcctcctga gtagctggga ttacaggtac atgctaccac accccgctaa ttttgtattt  37620
ttagtagaga cggggtttct ccatgttggt caggctggtc tggaactccc gacctcaggt  37680
gatctgcctg cctcggcctc ccaaagtgct gggattacag gtgtgagcca ctgcgcccgg  37740
cctgtcttct taaaggaaaa agataaaata gatattggta ggtgcctcgg ataaatgagt  37800
tacttaagtg aagacttaga tttgtccctg agtctcctag cagctggggc aaaagagaaa  37860
tattttggtt ggtgcagttt ttactttttg tcaagaggaa gcttagggca gtggttctca  37920
aagtaaagtt cctggaccag cagcatcagc atcacctgag aactccctcg aaatgcagat  37980
tctcaggttc ctcctcagac ccactgcctc agaaactctg ggctgattc tgattcacac  38040
tgaaatgcga gaaccactgg cttagaattt gcacgtggag gtctgccctg aatgggagct  38100
tactgttagt ggtcttgttc gtaaaacagt ggataataag gtgagtggaa gtatcttctg  38160
tgatttgtac cagccttcta aagaggttat cattattgtt atttaataaa aagcactgat  38220
aagtggagca tgtcactcgc ctcttttttt tttttttttt tttttttttg gggacggagt  38280
```

-continued

```
cttgctctgt tgcccaggct ggagtgcagt ggtgctatct cggctcactg caagctccgc  38340
ctcccgggtt cacgccattc tcctgcctca gcctcccgag tagctgggac tacaggtgcc  38400
caccaccaca cccggctaat tttttgtatt ttttagtaga gatggggttc caccatgtta  38460
gccagaatgg tctcgatctc ctgacctcgt gatctgctcg cctcggcctc ccaaagtgct  38520
gggattacag gcgtgagcca cggcacctgg cccactcact tcttttggcc agtggctctg  38580
gcatgaagct ggaggcaaag atgctgaggg cctgcactag acaggctctg tgctggctgc  38640
tggttccgtc catgccacca ataacccgat caggtggaga gagtatttat tcttgcttta  38700
ttgaatggaa aattgtggct tagcaagcaa aagaagggct gcgtttcagt tgtaggcctg  38760
ttgcctgaga gcatcctagg gtcacgatgg gggtggagtg agaatgcttg tacaggtgtt  38820
tacagctctc cagttttact gtatgtgggt gccctcgcta tggattgaga catcagattc  38880
tgtcagcttg gtttttggat gcctggggaa ctgcgttgtc ctggttgtcg gctacctgcc  38940
taatagcagg ttaccgtgaa accatgtgaa gcaatagaat gcaacagcaa ggtatggatt  39000
acatgacagg caggctgagt ggttcagaag gattatatgc tgtggacctt atgctttgca  39060
ttgtgaacag tgttcctaac tgcccagcgc ccatgcagaa gggccagggg gtagagcacc  39120
catgtgatga atgccaacca acagtgtact tgccatgcct tcaccttgca agcagggttc  39180
ttttgtaatt agctctcgaa tgacagcaac tctgcccctg aaatgggtgc tctgcagtga  39240
ttaagggcta gtgttagctg taccagggag atactgctgt gaggaggtgc ctctgtttgg  39300
tgtctgtgaa acattagatg ctatttaaag tgatagcggt tcttagctgg ctacttggcc  39360
tctgccatct gttagtgtga ttaggctggt ctgattcaca ggtgcagcct ggggcggctg  39420
agattaagca gctgtggtct gtgtggacag aggaatgcca cggccggggt aattggcaag  39480
gcaggaaagg ggacgttgcc attaaaacaa ttttttgcca cctcaagtgt caaatgcctg  39540
acccgattaa tagggaaaat tgcagaagca ccaaattctt tgtattttca gccacctgga  39600
aaacactcat gtgtccagat tgatttcttt ggtgccttct gattgtctga aaatgccact  39660
ggggtgtgtt tgtatgttct tctttaggaa ctttgacaaa tgatgctcca gtgaccctgt  39720
gttgatggtg acgtttttgg gctttttga gtttttttt tttttttt tttctccttt  39780
tggattgaga cattgaaaat ttagttctgt atcttccagt tggaaaaata tattgcaggt  39840
tattccctct gctgatttgc tagattattg atctaatttt gttggttaac ataagaaggc  39900
aagctcagct gcctgctaga gtgtttttta gattctgtac agagtacgaa aagcttgggt  39960
gccaaataca atggcaaaaa taacaatgaa gaattaaaga tcgggcgcgg tggctcatgg  40020
atgtaatccc agtactttgg gaggccgagg caggcggatc acaaggtcag gagttcgaga  40080
ccagcctggc caatatggtg aaactccatc tctactaaaa tataaaaatt agccgggctt  40140
ggtggcgggc gcctgaggct gaggcaggag aatcacttga acccgggaag tggaggttgc  40200
agtgagccga aattgtgcca ctgcacccca gcctgggcga cagagtgaga ctccgtctca  40260
aaaaaaaaaa aaaacaaaaa actgtatcta ttaacatcat gttgtacatg cattgaaaaa  40320
cccagccatg ggctgatttg attgatcttt ttaagttggt ttcttcatca cagatgtgca  40380
gggcattctc tggtcatatt ttagcagctg actagctgat gacctcacat ggtaccagca  40440
ctagatgttt ccaagtggaa cagtcctgtg atgtcattac aagcctggtt gccaggaaat  40500
aatgctgtta catatgcccc tcggtgcaac acattttctc cagaaagaaa gttgcagttt  40560
catatgctaa tttttgaaat gcatccaggt tgagggtttt gaagggttga gaatttatcc  40620
```

-continued

```
tttcgcatag aaaagtataa gttaactagt tcttgccttc cctaggtact aggtatgtta  40680
atgggttatc tggcagcaac taggtagatg catataccca tttgttcgag ggatttttat  40740
tgtttccagc ttgtttcggt gattaatgtt tctgaagagc ttgagactta gtttttgaga  40800
agatcatgat ggacgaaaag ttcaggtcca ttgcttaact cgagggaagt gatggagaga  40860
cagttgcatc aagactcttg ctgctaaagt ggttctttct ctcgagtgat gagagaaaaa  40920
gtaattttct attttggttt cattcctgtt gagacctgca gatgcccaca ctccatgtca  40980
gggagaaagg ctattttttt tggaagtacc tagggaaaat gaaggtagtt agcctgagat  41040
tccaaactca tttcattgat taacctgccg ataacagttc aaagtcacct ttgttctaat  41100
tgggattttt acttggtaga gatcctaagt tggtaacagc aggcttctta gttgtgttga  41160
agtttctagg aattgaaaag aacaatatca gtaataaaaa caacaaaaaa cccacacagg  41220
ctttgcaaat ttttagaaat tccctttgta atgaaaacat catcaataag ttggtttggg  41280
ccagcatagc agctcgcacc tgtaattcca gctagttggg aggccgaagc aggaggatcg  41340
tgtataccca ggagtttgag actagcctcg ggagcatagc aagaccgcat ctctacaaaa  41400
aataaaagat tagccaggtg tggtagctca tgcctgcagt cccagttact tgggaggctc  41460
aggtgggagg atcacctgag cccaggaggt caaggctgca gtgagctgtg gttgtaccac  41520
tgcagtgcag cctgggcaac ggagcaagac cctgtctctt aaaaagaaga aaaagctgct  41580
tttggtattt tatcacaaat actgttgatg gtgttccatc caatggttgg actgaatatc  41640
tttctcagtc tcctccttgg tcaaacagca tagccaatga ttggagaagt ttcctttgaa  41700
ggcagatctt gggaattccc atgggctaac tggtctgcta gtgggctcag ttctttcact  41760
tgtggttaac ttgcttggtt ttgaaaacat atatttctga ttgaatgcct ggctggttag  41820
caagttttta atgagatttc tcaaagccac agacataccc cctcataatc atatcctcac  41880
tcacatctcc gtattttgtt agatttgttt tctcttagtt tataccaaac tgaaagcaga  41940
actgcagggt agtggggagc tctgagacat ttttcccctg tcaggagtca aagcattcaa  42000
atgtcctgat tagtgatatt tttaaaagcc ctaattatag actcgagaca gaggctttag  42060
tggggcttta gagagtttgt gagacttaat ctaggagctg gaacaggctg tgtttttaaa  42120
attttttgca tccataaaaa tacagttggc agtcattggt ggccgcggct cacataaatc  42180
ttgaactttt gacttaatta ccatgggaga gttcaaaggg caggctggag tggttgaagg  42240
aacactgctc agggagctgg agatgggcct ggcctcagcc cggcctctgg ctgtgtgacc  42300
ttgatcaaat cacttaacct ttctggatga cattgatatc atcagtcgtt gggccagatg  42360
gtcaccgagg tctcttttgg tacagcctgg taatatgatt ccatgtttct cctttaaatc  42420
attgggccgt gttctctgtt ttttggttcc agagagagag agagagagag agagagagag  42480
agagagagta gattataaac cttaggtgtc agcattgaga tgtgcaaggg ttttggtggg  42540
ggcaggccca gcagcctatg gtttctcact aagtttaaat tgcagggtca aaagaaatca  42600
cataatccta ccatttgttg acagaatcaa tacctgtcta gcacatagat acctggaaag  42660
tatgttcgaa ctggcgggga ccttaatcag tgcaactact tcattttata gctaaagctt  42720
ttaatagtca tccatccgtc catccatccg tccgtccatc catccatcca tccatccatc  42780
caataacgct tgagtgccta ctccataggc taaagacaac tccagctgta ccctccaggt  42840
gccctactgt tgttggtcag catcagaagg agtatttttc agtacagaga cactaatgtt  42900
ggaagcacac atctatcaca aagaaggggc cctgagaaag aataacttgg ctctagggtg  42960
ggaataataa aggctgtgtt ggagtccttt gaaggaagtt tctgtgggtt tataaatctc  43020
```

-continued

```
tctttaactc attgcatctt aaaagacttc tgttgtctta aagtaaaatt ctacttaata  43080
ttattactaa tgtgcaatga ctgttacagt gtagaaaatg ataatgagta ggtatgctat  43140
atgctggtga tgggatttaa ttgatgggat gggattgatt gattgtggct aggtctgact  43200
gttctttaac cagctcattc ttagtatttg atgattagga gaacatcatt cttgtggtac  43260
ctattacatc agaaggtcta agaatgtcag agccaaagga accatacctc tcatcgaggt  43320
taatttgttt cctttacagg tggattagtg tcattcattt tgaatgccat tggaagttta  43380
taccacacgt ctctattagc tgactttaag cccgctcttc atacacctct aaggtatata  43440
aagttcaggg aaactcatgt gtccttagct tgcagattca tttgattgat tgattgattg  43500
attgattgat tgagacagag ttttgctctt gtcgcccagg ctggagtgca atggcatgat  43560
ctcggctcac tgcaacctct gcctcctggg ttcaagcaat tctcctgcct caccctccct  43620
agtagctggg actacagcca tgcgtcacca tgtccagcta atttttgcat ttttagtgga  43680
gacggggttt caccatgttg gtcaggctgg tctcggactc ctgacctcag gtgatccgcc  43740
cacctcggcc tcccaaaggc tgggattaca ggcgtgagcc accgcgcctg gcctgcagat  43800
tcattttaga taagattgtt gagtaaacat ccctgttaag catctactat ggacaaggct  43860
gatctctgct tcagtagatc tttaatttgg tacatgagtt ccttctccaa atgagagttg  43920
ttaaagctgt tcacgagcct tggtataaaa ggggcttcct taggtagagg agcccgttct  43980
aagtgcctgg atggtgtttg tctccagctg ttttgcagtt cttgggaggc cctggcattt  44040
ccatgtgtgt cctttccaac tgcaaaaaca tacagaggac acaaggctgc tgatgaagga  44100
aacacagtag ggctatctta tagtattatt atttttctag atcttacaga ttcaaggttc  44160
acataaagct agtgtatttt aggaagagct attgtaaaat tataaaagag ttccagccgg  44220
gcgcggtagc tcacgcctgt aatcccagca ctttgggagg ctgaggcagg tggatcatga  44280
ggtcaggaga tccagaccat cctggctaaa acggtgaaac cctggctaaa acggtgaaac  44340
cctgtctcta ctaaaaatac aaaaaaaaaa aaaaaaaaat tagccgggca tggtggcggg  44400
cacctgtagt cccagctact cgggaggctg aggcaggaga atggcgtgaa cccgggaggc  44460
agagcttgca gtgagccaag atcgcgccac tgcactccag cctgggcaac agagcaagac  44520
gctgtctcaa aaaaaggaaa aaaaaaaaaa agacttcctc ccctcccgta tcaagttcat  44580
taaacatatt tgtgagcttg atatttaaag agaggctgtg tgctggtgtg atgttagcag  44640
tcaccagggt ggggctggtc acacatggga gcctgggtgg agggttgtgc ctggattttt  44700
tatggtggcc cccaaccttg gatctctgag acctagatga gcagcactgc acccgtaccc  44760
tgctgtatgg ctgtgtctgt gttttgcaga agcagatttt ataggtgtag ctttgatgat  44820
tgaaatatca cccgagggaa gtggctacct gccagaaatt ccagcaacat tatttcacct  44880
tagtccttaa atcactcccg aggcaccaag acaaaggtgc gggttgccca tgggctgttg  44940
ccacaggtca ggcctgcata ggtgcgcgtg gtctgggccg gtccctgggc tgttacagac  45000
tcacccatgg cttggcccag tgagggcaga aaagaacaac attcctagtt ccttcagcta  45060
aatcccactt ttttttagg gaacataaaa atcatgccta atggtatgta agcacatatc  45120
tgttgatttc ttttatgtaa aaaagaaaag acattccaca ggatcagctc agcagtaatt  45180
gatgttatct gaaagagtta ctgcattaat atttagctaa ttcatatgaa taggctattg  45240
tgtttactta aacaaatgac atgagtgcag acacctgaca gcatgaggta tgcttttcat  45300
ttaggttaga tttgtaaacg tctttgtgta gtgacaaagc tcattatttg ttttgtgctc  45360
```

-continued

```
tcaatggttt ctttttagtg gctgtggctg tggatggatt tttctaagta gaagctttta  45420
aaatgaaagt ttattgaaat tgtttcagta tatgccaggc cctgagagtc ttgggatgaa  45480
tgggaatcaa gtactccctg gtgaaccctc aaaagaatag gtgcgtttat gggcattcaa  45540
cacccagagc caaatgtcta cccaggttgc aaatgcaact ggattcaaag gaaggaattc  45600
agcccctgtt ccttctttct cctccttcct cttcttctct cctggcttcg atagttttgc  45660
ccctcttccc actgtttcag catcatatgg gtgcacctaa atcccatcac tttgacactt  45720
agataagcac agggataaag atacagcatg gccttgtaaa gaaatctcag ctctaccttt  45780
gacaacaggt ttcaagagca agcgtgaagg ctaattgggg taggtgtttg gatgcagcga  45840
tttcaattcc tgattgtacc ctgagtctgg ctgctaagtg aaggggatcc ttatccccca  45900
gggacgtgct ctacacccgt agaatagagg agacttctaa atatgcatca gagacaaagc  45960
ccctgcctag ggccattttg ccttgggttt gtgaactgtg tgtgctgttg ttcagtctag  46020
ccttcatcag aaataagcat agttatgaat tagccttcta caatgttcaa gtccctgttg  46080
gtggctgttt cagaggaata cagggatttt ggttactact ttgctaagac agaaacatat  46140
atgtgaatag ttaaattgct gtacagtaga ggttctggac aggaaaaaag gaggacgtgt  46200
gccttgaccc aggctggctt tcccggactt cagccttaaa catcagattg gtggaaggta  46260
cggattccaa cctcgtggag aagctgcatc ttcttagcag tggagagtag ggttgaagat  46320
agtgggctct ggcatcagac tgatgtggtt caaatcttgg ctgcacctct tccaagcttt  46380
gtggcttttg gcaggttact taactgctct gtgcctcagt ttccccactt ggaagccaag  46440
attatgatag tgcctttctt gttgaagcat tgtgaagatt aatgtgttga catgtaaaaa  46500
ctctttgagc agtgcttggc aaagtagaag ctttcagtcg gtagtagtca ttcgccatta  46560
ttagcagaca tgaagaattt acagtggtat tctggcttga tgttgtggct tttatttaga  46620
aaaaatatac tttactttgt gatttaaaac tttttttcttg actttaaaaa atcacttgta  46680
tttatgactt tcggggacat ctggagggca taactttaac atatcattta attggtagcc  46740
tcctcttaag ttatcattag gtggggtggt agggttatgg cattcataac caccattgga  46800
aagaaatttt ttttttaatt aaaaaagtta gtatgtattt agtgatacag tttttttttt  46860
tgtttgtttg tttgtatata agttctgaga aatgtacgaa tgactctctg ggttatttta  46920
ttatattaga atgacaattt atactattga ttgcccttaa agtaaggctc caatggataa  46980
gttgataggg cttttgagaa caacttgctt ttactagtgt gtatatgtga tcatttaata  47040
ggtgtggcaa tccaaaatga tctatttttg gaggactgag ctgtcgcagt tgtatatgtt  47100
gttcatatgt ttataaaata gcattttaaa acatgatttg gcatgaaatt attttctggc  47160
atcaagaaca agagagagaa ggggcctcaa acactttttt ttttttcttc ctgttggtag  47220
acatgaacca tccctctctg ggaccttctg ctcagccagc tggattagac ttctgaaaat  47280
attttccaaa tgtaaatatt acccaaagat ttaaaaaata gcctagcatt tacatgcaaa  47340
gcgaaatgat cttacctgtt tggagtttac tcatggaggg gaagctgtcc atcagtatac  47400
attctaatac tgttttccaa aacaggagca ccatactgga ccaacacaga aaagatggaa  47460
aagcggctcc atgctgtgcc tgcggccaac actgtcaagt ttcgctgccc agccgggggg  47520
aacccaatgc caaccatgcg gtggctgaaa aacgggaagg agtttaagca ggagcatcgc  47580
attggaggct acaaggtaga attaagcttt cagaacatca catttcttac atttttgttt  47640
atttatttat ttacattttt tttttgcgat ggagtctcgc tctgtcgccc aggctggagt  47700
gccgtggtgc gatctcggtt cactgcaacc tccatctccc aggttcaagc gattctcctg  47760
```

```
cctcagcctc ccgagtagct gggactacag gtgtgtgcca ccatgcctcg ctaatttttt  47820
gtatctgtag cagagacggg gtttcaccgt gttgtccagg atggtcttga tctcctgacc  47880
tcgtgatccg cctgcctcgg cctcccaaag tgttgggatt acaggtgtga gccacgatgc  47940
ccagccctac atttttgttt attttttgaa gtgctcaaaa gttagcagga attagaagga  48000
atactttaac aagaatcaat aattgtcaca attgcccatg tcagggtttg atattaaaaa  48060
aaaatattac cccggacttg cgtgtaattt taaagtacaa ttcccgtttg tgttgttctt  48120
catatgagga gagtttaata acagaagggt cgaaagttga gagtctgttt tctatatgct  48180
ttatagtgta taaaactaaa acgggtgtgg agtttgagaa gcgtcagtat agtttccctg  48240
tcagagcagg attgcatgaa tagtgagggg acttggatta gagactggag tatgaaatat  48300
gatgcattaa gggagagtgc gtggagatga cagtggcaat ctgctgtcct ccttgaagga  48360
ttcttgagag cacgtcacac aatgccatga aattttagtc tcatcactcc ctagggagtt  48420
tgaaattggc agctgtctcc ctgcagatgc ccgcgcatgc tcctctagcc tttgttcatc  48480
cacttagcag acattgattg agcaccctgt gtgccaggca cactcctggg ctctggggag  48540
atgagagggt gaggcatggc cccagctcca aggggctctt agtccagtcc agcaggagag  48600
gcagaggaga actctggcaa tgggagggac acaggtttgg ttgaagttgc aggagcatgt  48660
tgcatcccat ggatgtacat ggaaaggtga tattggattg gcgtttggaa gaataaggag  48720
aaaggaggtc aggaaaggat tcaggtctga gttggaagga aagatgtctc agaaagagag  48780
agatggaatt tccaaattat ttagtatgga aggagagaac tgtaataatt gagcatatga  48840
aaaggactga aggaaacctt atgatgaaat tctctgatgc atttggaaca taagtgggca  48900
tattagttac ctgttgctgc ataataaatt gccccaaggt atggtagctt taagcaacat  48960
ttattacctc attgttgcct ggatcaggaa tgaaggtgtg gcttagctgg gtcttccatc  49020
tccagctgtc tcacaggact gtaagcaagg aagggttgag gctgaggtct cattggaagg  49080
gttaattggg gaaggaactg ctcatgtggt tgctgttagg attcacttcc ttgcagaggg  49140
cctcagttcc tcactgactg ttggctgggg gctgcccact gttccatgcc acacgggcct  49200
cttcataggg cagctgctgt catcaggttg agcaaaggag gagccagaga gagagagagc  49260
aggatcgcag aagtcagagc cttttgtaac ctagtgttgg aagggacagc caccactttt  49320
gctttttttcc attattaagc aagacactag ggaggaggtt gcccaaggac ctgaatgcca  49380
ggagacaagg ggatcaccgg aacccatctg ggaaaactgc atggtgggag gaatagaaga  49440
cgctctttag ctcagacctc aggtccttta cagccaggta gggaggattc ctcagtagca  49500
gcagtggggt gtccaggact gtgtctcacg tgtctttaac acaccagcat cactttagct  49560
ccatcattgc tgtaggtaaa tgagcctcct ttccacctaa aaatgccctg caacccttttt  49620
ctgaaatttc ttagacagtt attcatcttt aaaggattat tttcttctgc aaaagttttt  49680
gcctttttgt tttaacactt agaaattaac atctagaggc caaaattcag aggaaaatgg  49740
ggacagccta tgagtaagtt tctaagaacg catggtgggc agtgaacatg tgaaacagtt  49800
atgaggcaga tctgctagca ggtgggtact gttgaagctt gaaagtagaa atactttggt  49860
tgttttccac aactcctact tggtggtgga agcaggaggc agggggtgat ttgtccttct  49920
gttcttagtt cagtccttag accagatacg atgagattca aaggttggcc cttttaaaag  49980
aaatcttttt gaaaaaaaaa agttaaggat ttcatggggg gatgctggtt agaaaggaag  50040
agttaagcca ctaaaatcac ggcccctggg attgttttta accaccaaat gctttctgaa  50100
```

-continued

```
actcacataa ttgatgcagt tccaatgatt tatttaaata caatctgagt gtgagaatgg  50160
tggtcaaaat cctggtggtt aactaatttt gtcaattaag acagccttgt aaataagtac  50220
aaagaggagc tgatgaggct ccagagaccc ctgggctcaa aataaatgga accgacatca  50280
ttattatggg gaaggagctt tttgcaaatc tgaattagtg attacaaata tgctaagaga  50340
ctaagagggc ctaatgagaa aatgctgcct gatttttaac aggtgcagtt cagtgttaat  50400
tattgattcc aacatttcgc tagatgaaga gcacctatgt tctaaaagca aaatgaggac  50460
tcccagcaga aagcctttag cctgcccctg tggagtgcag atgaccaaag tgattttgtt  50520
gtatcacgct gagccgtttc tggagggaaa aggaaatgga atttcagtgt gtgggacaaa  50580
aacctaaaat atattttgct ttaccaaaaa aaaaaaaaaa aaaaaaaaaa aaaaaaaaag  50640
gccaaaagcg gcagagggcc acacatttgg atgcagtgtg ctggcgtggt cctctccttt  50700
ctggttctct ggtggagaaa ggctatggct gtagggtggg gcggcctggg aggttggccc  50760
gctagttgca gaggtggtca gcctaggttg atcaagggct tttcacaaca gcagtggcat  50820
tgaacgttca ttttggagat gccagaaact cttagaaatt ccactgagtc ccaagggctt  50880
ccgggacttg aaaaggaaag acacatttct catctcctgg gaaggttcct tcagttacct  50940
aaggcatcat cttcgctaat gatgtgttaa gccaacccca ggtcctggag tcactggagc  51000
tcaaagaggc tcattcccac ctgtgggcct cccccatggg gagctccttg gctggctatg  51060
gcctgcgttt gcctcagaga gtccttgttg gggcctgacc aaggcagact ttggggagaa  51120
tggtccctgg tgttgggttt tctctctgat attttcttcg ttacctacgt agacttaaag  51180
aaatgtgcct ctgggttggg cacagtggca ctgtaatccc actgctttgg gaggctgagg  51240
caggaggatc atatgaggcc aggagcacaa gaccaactta ggcaacatag tgagaccccc  51300
atttctgcaa aaaatttaaa ccattagctg ggcgtagtag tgctcacctg tagtcccagc  51360
tactcaagca gctgaggtgg gaggatcgct tgagcccagg agtttggggc tgcagggagc  51420
tgtgattatg cctctgcagt ccagcctgga tgatagagga agactctgtc aaaaaaaaaa  51480
aaaagaaaaa aaaggtacct ttgcacattt gacttcaggg aactatattg ttattttcat  51540
tcctcggcac ttcctcaaaa gcaaagagac ctaattgaaa ctcagagggc ctgacatcta  51600
actgattcat tcctgactcc tgtccatttg ccactttgct ttattttatt tttattttt  51660
gagactgagt tttgctcttg ttgcccaggc tggagtgcaa tggcatgatc tcagcacact  51720
gtaacctctg cctcccgggt tcaagcgatt ttcctgtctc agcctcacaa gtagctggga  51780
ttacaggtgc ccgccaccac acccagctaa ctttgtattt ttagtggaga tggggtttca  51840
ccatgttggt catgctggtc tcgaactcct gacctcaagt ggtccaccct ccttggcctc  51900
tgcgagtgct gggattacag gcatgagcta ctgcacccgt cccatttgcc agtttattta  51960
atgaagaagc aaaatgtcaa gttttgtctt caccaatggg ccctccagga acgnnnnnnn  52020
nnnnnnnnnn nnnnnnnnnn nnnnnnnnnn nnnnnnnnnn nnnnnnnnnn nnnnnnnnnn  52080
nnnnnnnnnn nnnnnnnnnn nnnnnnnnnn nnntgaagac ggaggaggga agacaaaaaa  52140
agcaaaacaa agtcaaagag aattatgaaa tgtgacagaa agctcatttt cattcaaatg  52200
accaatagaa ctatttggaa ttcggcagtt cagtcttgtt tatcaaagaa cccatgctga  52260
gccatcctta ggtgattaag aatcaaatta ttatttttaa agtgcatgag caaagtcttg  52320
ctggatgtta ttaatatgtg attgatataa tagtaaagga cttgaatcat aactctatct  52380
ccctaatcat acttattcct gggcttttgc gtcagtcttg accatgggca agttttttca  52440
gctctctgtg ccccagaatc ccttgcctta aaatgggaag attggctgaa taatcctgat  52500
```

```
cccttcaggc tctgagaacc ataatttaat agtatcacca tcgtgtagca tcagccattt  52560
ctcttcttaa acaacagcac agattttttt tttttttttt taataaagag gttaccttca  52620
tggctagata tttcacaggg ctcaggacag ttattgcaat ttaatgcaga aaagcaagaa  52680
gctggctgag ataattaata gaccacctca attctcacct ccttcgtagg taattattta  52740
ggcatagggg gttcttaaaa accatctttt atgccacttc gaagtgcctg catagaccaa  52800
gagagatcgc aggacagagg gctcattcaa cgtgactgtg aaattggcac agaagccctc  52860
agcgttgggt attacagggg ttcaggttcc cctggagccc ctcagcagag agtaaagcat  52920
tattgagcat gaaccaagta tatttcagat ctaagaaaag atgattttta aaacttttgt  52980
tataatcact actaaactgg ttgttttgaa gcataggtta attagattta cattttctag  53040
gttagttact tagatgtcat tttaaagact ttttgatgaa atgttatgct taatccacaa  53100
gtatgtttag ggggagaaat catgactaat gtacttatca gcatgtttat actttatgga  53160
gatttttttt cagtgaagac atttcagctt taatcccaca tcaagcagtc tttgatgagg  53220
acacaggtat atgtttgtat tagccaacgt ttatggactg ctcccctgcg tcgtgactta  53280
ccaggtgcct cccatggagc aagttgctca gtccttccac agcccaaaga ggcagacact  53340
gttattttgc ccttttacat ttgagggctt gccctacccc tacctcatag gtggcacagc  53400
tgccatttgg acctacgtgg ttttgcacca gaatttatgc tcttgctaaa ctgcttgctt  53460
caaatgtagt tccgtgtttt gtaaaaacac tgttgctgtt gaatgagaaa cataatgaaa  53520
gtaatggctc cccaaaagca tgcaaagatc tagcccatgg tatacagttg agagcaaagt  53580
tggggatatg atgctgttct ttcaacttcc aagacctctg tgggttattt atttgtttgt  53640
ttttgagaca gagtccctct atattgcgca ggctggagtg cagtggtacg aacatggctc  53700
agtgcagtct tgacctcctg ggttcaagtg atcctcctgc ctcagcctcc tgtgtagcta  53760
ggaccacagg tgcatggcac cacatttggc taatttttaa attttttgta gagacggggt  53820
ctcacttggt tgcccagact ggcttcgaac acgtaagctc aagtgatcct cccacctcaa  53880
cctcccaaag tattggaatt acaggcttga gacactgtgc ccagctggtt atgaggtttt  53940
tacatttatt gtggtaatat atgcataaca taaaatctac catttaagtc attatcaagt  54000
ttagtaggca ttaattacat tcatggtgtt gtgcaaccat caccactatt ttcaaaactt  54060
tttcatctct ccaaacagaa actttgtacc cattaagtag taagtactca tttcccctcc  54120
cccactgcac ctggtaacct ctaacctact ttttgtgtct atgaatttgc ctattctgtg  54180
taccttatat aagtgaaatc aggatatttt tccttttgtg tctggcttat ttcacttaac  54240
aaaagtccat ccatattgta gcatgaatca aaactttatt ccttttttatg gctgaattat  54300
attccattgt atggatatac cacttttttt tttttttttt tttaagacgg agtttcactc  54360
tgttgcccag gctggagtgc agtggtgcaa ccttggctca ctgcaacctc cgcctcccag  54420
gttcgagcga ttttcctgcc tcagcctcct gagtatggga ttacaggtgc tcaccaccat  54480
gcccggctaa tttttgtatt tttagtagag acagggtttc accatgttgg tcaggctggt  54540
ctcgatctcc tgaacttgcc atccacccac ctcagcctcc caaagtgctg ggattacagg  54600
catgagccac tgtgcccggc cccacatttt gtttatccat tcatctgatg atgatcactt  54660
gggttgcttc taccttttgg ctattgtgaa tagccattgt agcaattggt gtacaagtat  54720
ctgtcccagt ccttgctata agtttctctg gtatatacct aggagtggaa ttgcaggacc  54780
atatggcatt tgtctgtttt gcaaaagcaa aaatggggaa gatcgtgaca tttttaaaga  54840
```

-continued

```
gctaagttca acaggcggtg gatgtcctgc cgcagccacc tttgtgagca ccgacaagca  54900
acgggcctct aagaaaacat ggcttgttgt aattcacttc ccacctcctc tggagagatc  54960
cagtggttgt ttaccgagca gagggaagag tttctgccac tggtcccgag gatcagattg  55020
cccggccctg ttctctggac acctcctgaa aagcaaactt cttgtatcaa tgttggagtt  55080
taagcattaa caggtgtttg cctccacatc tgcatggtgg tgagcaacag caggtacctc  55140
tgtccttgac atgcaaggtt agttggcaca aatgctttca gaaaggatgg cttcaagtcc  55200
cccaggcacc tgctgaaagt gggggactgg gatgggagaa taagatttta tgcatttttt  55260
gtttttgtt ttgttttgag acagagtctc actctgtcac ccaggctgga gtacagtggc  55320
atgatctcag ctcactgcag tctctgtctc ccgggttcaa gcgattctct tgcctcagcc  55380
tcctgagtag ctgggattac aggcacctgc taccatgcct gactaatttt tatattttta  55440
gtagagacag agtttcacca tgttggccag gctggcctcg aactcctgtc ctcaaatgat  55500
ctgcccgcct cggcctccca aagtgctggg attacaggcg tgagccactg cacctggcag  55560
attttttgca ttttaatggc aactcacctg ttgaatgaac tgatctgttc atggggtggg  55620
tgcctctgtg aaggccagga ttacaagaga ttgctgtctt cctgggaaaa ttgggtgctg  55680
atactggcgg gagaaaggct tgggaatatc tttctgatat cacatggaca cagcgttcta  55740
cctggcacag aataaaactt tgtatcacct tctgcatgtt tattctgctt gttatcgaac  55800
acctgagtat ttggaaatgt ctggattttt ttgcaatgtg gaaggtaaat atccaggtga  55860
cagcctgggt ctttaacctt tcacccttca cctttcactg cggtgttttg gtgtcaacaa  55920
actaaatcta cattcccagt tgtcacctga gggtagcctg ggatttaata ggcattttgg  55980
gggaatgaag gtaacagaag aattccgaaa aacctgtctg ggccaccttg tgtctttgtg  56040
tggatagggt gtggaatgtt catggaatcc gcttcttgta ttatacttgg gagtttaggc  56100
cattttgctt cagtctgctt tgtttcaata ttgaaatgtt attttaaaaa agtctttagt  56160
gaacatagtt ttgaagtcca tgctctcctg ttctgttact tggcagatga aaaataatga  56220
tgaattccac aaagatttgg ccatgagcag gaaagaaaaa gagtcgtgct tgtgttggtt  56280
ggtgcagaat ttcttctctc actggctttt gtgtttgttt tgccagatcc attggttctg  56340
cagggggtag ctactattga atgattatct aaggatctgt tttattatac ttttttgttg  56400
tgtgtgttga gatttctgtt tgtttgaaag gtagaaataa gaaaaaagta ggcaataccc  56460
ataatcccac tgcttaatta tataaagtac attgctaaca atttggtata ttttctttct  56520
gattttagct gtgtttatag tcaggcttat actttcagtt ttatatgcat ctttagggtg  56580
gtaaatgtgt ctgctttttt cttttttttta aataaattgg aatcatgaat taactgtttt  56640
tcatttatca ataactgttt aatgatacct taccaggtct gaacataata cttcattctt  56700
tttatgacta tagactacgc tgtttgaatg aactttccat cagttcatac aggatgaact  56760
atgcattctt aatgtctctc tccttgacag ttttttgctc ttacaagcag tgcttgaagc  56820
agcagttttg ttcatgtgcc ttgaagtaat tgtgctattt tctgtgggct agctttctag  56880
aagtagaatt aactagatca aaaaaaatgt gtgctgctaa ttttaatagg taccagcaag  56940
ttattttaca caaaggtttt tctcaattta tgttcccatt ctcaattgga atcttttatt  57000
tccctacaca ttcaccaagt actgaataac attgatcctt ctaatttttg ttaatcagct  57060
ggtgaataac agtgtctcat tattgtttta atttgcattt cccggatcgt taatgaggtt  57120
aagcatcttt tcatatgttt attgggtatt tacattccct cttctctgaa agcaaagacg  57180
gtgtatgtgc atttggccta actggcaaaa gaattgtagc actgaaaatc tgaggaattt  57240
```

```
agaaacacgc gttgtatata ttacgtcgga agagtggttt ctttaggttt attctgaatc  57300
tccatatgga aatagagtaa tgaaaaaaaa cccccaaact ttgtgctttt gtttgccatc  57360
tttataaagt taactattgt agtttcttag cttgctatta agcaaccact aatcaatggt  57420
aggatatccc ctacaaaagt gtccagcagt cccactgttg gtggatttaa gagcatccat  57480
ttggaaaatg ctacagctca taaaatttgg gtcaataaat caaatactgg agcaatggtg  57540
taagaaaata aatattaaca gcactgcatg gggcaatatt gatctagtac caagatttct  57600
ggatggacag aaacaccctg tttggtaatt gtgcttctca ttgtaaaaac atttttataa  57660
acgttaactt attaatattt gtagtgcatc tccaggaagt aaatattcag agagcacgtg  57720
ctcttgaaga gggatcttgt atggaatgcc atggccccag tgagagactt gagctgacca  57780
tatcccctgg ggttaaaaaa agggagcagt gagccaagct gcatatgcca agatttaatg  57840
tgtcagccga gtcaggcgat gtcccctccc tgtgcagttc aggttcagct ccatttggaa  57900
tactccatgt gccaaatctg gatccaggca caagaaagac attgacagtt tgaatggggt  57960
ccagagacag gcactagccg tgattaaggg cttatgggca tgacatttga gcgggggctc  58020
aaagaactga atatttacag cagggataaa tgctggatta catggcttgg tgacgtgggg  58080
acccgtggct acatccctaa gttacctgcc acatgactgg ttccccgtag gcaaagagag  58140
aatcatttct gttacccttg agagcttgag gtgaagggag ggtctccttt tgggtctgtg  58200
gacctcaagt aaaatcaagg agcttatacc tatgtgtccc atgctcttag cataacgatg  58260
ccgttgtagc acccagggat ccaggattta ggtagggaat tctcattgcg ctggaagatt  58320
tagcatccat atctcctcct ccttcagaag acacattctg catggaaggt gcttatctct  58380
cttaagggga gacgcgctag catgttgtct gggtcctgtt acaagtctac ggctcaacca  58440
agagcagaaa gcgagtcttt gtcatacagt aaagactctc cactgtcgat cagatgcccg  58500
tagattcatt tttctgccag acattttacc tgcgacagtg aggatcagtt tcccatcacc  58560
agctccaggc tgttagactc tgaaactacc ttcgtagttg tcgatgactg cagcagccca  58620
gcaaagtggc tgaccagaac tatcttaact cactgcttgt actctgttaa ggaggaagga  58680
ggccaacctt catccagtga tcctttctaa gactgtcagt gatgagcagc gacctcgttt  58740
tagaactcag cagcagtacc tccaccctgc agtcatggct tgcatagaac tgagtggctg  58800
acatgaaaac cgtggcactc cagtgtgctc ttcgcatctc ttaactctgt tggcaggcta  58860
atcactggcg ctgctttgca aagtggacag ctgctctgcc ctcctgtttt tatagtggag  58920
tggttacgag atgattttct ttattctcta gtttcttata tcactcatgt gcttgcagat  58980
gctctgcctg tatttgtttt ttacgtgatt aacccaaaaa cacttgcaat gcccagggca  59040
tggctcagaa ggtcagttga aattcctgaa atgatagcta aggttagtag gccttgactg  59100
tttatttttt catttcgttt cactggagtg ccttgtccaa aacacctgta gagaatgact  59160
tggattcaga tagaaatact aaagcctcaa accctgaaga tacaagatgt tgcattttgt  59220
ggtaaggaaa actctcgcaa gtttgaaaat ttgagtctat ggaaatattt gaaaagcagg  59280
gggagaacat aagaatggcg tctctttgtg tattgatggt accttgggta ggagtcacaa  59340
cagctgattt tcacatgtgc tgcttatctt tgaaaagtct caagaagttt gtgaacggac  59400
ggatatacaa cttgagtttt gtaaggattc attgccgcca tatttggaat tctgggtatt  59460
tctctgagga acatgtatat ctattcagcc acaaccagag atgggaaggg cagactgatg  59520
ttcccagctg aaacttcttg agacatccag acaacatctg agaactatga gccccttagg  59580
```

-continued

```
agaaatgaat tagctacggc agcacagagg gcttggagca gtgcctggca tatagtaaat  59640
gctcactata aatgttagtt ctacatggtt ctgtgatgcc atagaggctg aggcttccta  59700
gtggatgggc aaactggtag ctcgcctgcc cgtggccatt ggtaccaggc tggctggtgt  59760
tcaggctccc tggccagttg gcctctccta gaggagccct caaatccatt atggtaacag  59820
acccacgctg tacactgccg aatactcctg cagatctgaa tatgtcaata tttgcttcac  59880
aggtgttcac catgatgatg atgatggttt tcatttctca cgattcttaa tgacagttat  59940
caatttagaa tttaggtgat tcttccatac ctttcttgcc tccttcagct tctttttaaa  60000
tcaagaaagc acagtacttg gtattctgtg ctaggattgt taaataaccg cctttgcttt  60060
gatcttttca ggtacgaaac cagcactgga gcctcattat ggaaagtgtg gtcccatctg  60120
acaagggaaa ttatacctgt gtagtggaga atgaatacgg gtccatcaat cacacgtacc  60180
acctggatgt tgtgggtgag tttgcctctc ctcgtgtggc ggctgcatac cagcccattc  60240
ttgcttgact cgtttgaaag catgaacgtt aagtcctgtt tctcccataa gtttcaggag  60300
aattggttca ttcttattct ttctactatc attttacaag gctgcttctg tcatctgaca  60360
atattctgtt ttccaggcag ccagggttta tgagctttgc atgatcctca tggttcccaa  60420
gcgtcatctg tgtaaagtgg acgtggtatg aaatgtctga cattttggaa gctgagatta  60480
ctctgaaaat gttaattggg caggtgaaaa gggtacagat gtgctgtagc agacctttgg  60540
ttttaaaaga gaagcatcat ttccccaaca gggcaactgt agaaggccag ctgaagagta  60600
aaggaaaagg tctgaggact gagcctgtgg ctggctggaa aaaggtgaat gttgagggcc  60660
cttcacttcc atcacaagaa agtcattaga cggtaccaat tcagtgtctg ttcctggcat  60720
ctatttcctc tgtgcaaagg gaaccatgta tatgagctta taaatacatt tttgtcagag  60780
tgcacagata agtaggccat tttaattaaa cattgaagac cacctcgcct gttgtcttgg  60840
aaattcaagt ttcttcccag gttttgcctg tgatgatggg gctttgttgt aactaatgaa  60900
gaaaggaggt ttctgtgtct tggaggattg ctaacatatg gaactctacc caagacatac  60960
ttcattgttg caggatggca ggttaagatc ccttccatgt aggggccatc ttttctcttt  61020
cctgtcatgt gccttgactt tcaacctgcc accttgagcc ctttcttttg gtttgtcctc  61080
ccctaaatac aggttgctat cttctgctgt agactcaact cagttcacac tcacgttttg  61140
ccgtaatgtg actgttggta attccacaag cccacaccac ccactgtgcc tctgtaaacg  61200
aagtgtctcc tacatcatag cctgtgcgtg tgtgcctagt atcatctcat gtgtgggtct  61260
ccttcaataa aacatctttg aagagggaga ccccgttaca tattggaatt gcccaaaaag  61320
ccactaaaaa aataatccaa aagcttgatt aaccaaattg caaagatttg gttaattaaa  61380
attttaggtt aactgaaaag taaacaaaac tattttgatt ttctgtcaag ttaaatggaa  61440
ttggatctac gagacactct gccttagaaa gcatgatata accattactt ccatttgcat  61500
ataagcattc agggaaaata gtgtttattc gaagatttga gttttgttct tcagaagcct  61560
tcatgtgaaa tttgataggt ccttgaataa tgttgatcct atagatattc ataaaagagt  61620
gagttttaga gctctttccc catagagaaa acatgtggca tgtttcttag tgagaattac  61680
catgttcaga tattttacaa aacaaacaaa aagagaagta acactcaaat ttgagaagaa  61740
aatgattaac atttgtgttg gcattgatac actgtaaatc cattgatcaa agagcatatg  61800
acttggcctt tacctgggtt cctgtgtgta ccgaatgtga cgtaaaacta tttctattta  61860
gggaaagaga gattttgggc taaatgttct aaatacctaa ttttgaaatt aagtaattta  61920
ttgtgggaaa aaataattga gctatagcag tcttttggga ttatagcttt gcataggtct  61980
```

-continued acacatcatt cattaggctg ggctggggcc attctaggca tcgtggagtc agatggcggc 62040
cactccggtc tgggctcttg cttaaagcaa gttttaggtt gagttgttat gtaaaacatt 62100
caaaagcccc tcaccccacc tcccctttga gctttctggc ggctcatccc tgtgaagccc 62160
tgaaatctct cttagagttt agggttggga tttgaattgg gctgctgaat aatggaattg 62220
tgctgtctaa tgttaatccc ctggcaatca gtcttgttga aaagagcgta tgattcagtg 62280
gtgtaatgta gagagagcgt ggagtgtatg gagtaatgca gagagaggcc tgattatgtc 62340
acaaatttgg gagatcgccc agctaaacac gggccaataa tgacacaatg ctggttggga 62400
atatccatta aagctcaact ccaataattt tccaagcctt gaaccttctt tataaataga 62460
agccaaaagt cagtggagta aaaggcattt tcagtaaaga tggaagtgtg aaatactctc 62520
atctctgctc aaaaccctag taattgcttt gcgaagcact aataaaataa gaattgagtc 62580
agctaaagag gctcatatag acgtacaggg ttggcagtca ttctgaacat ctcagcaagt 62640
ggaaacaaaa aggattcaag cttaagcagt gaatttctgg tagcccacag gcccaaatgt 62700
gatacactgc tgtgtgataa cagcttttca gccacctctc tgtttcacag aaaatcagaa 62760
accctttccc agtgaaagcg aagtcccatt cttgcccaca ttctttgggg ttttattttt 62820
gtttctatga tacatagatt gtggttcaga tattatgaag catcaagatg ggtgagatct 62880
ttttattgaa attcttcctt ggaaaggcat tcccataagc actttaatgt aaaagccgtg 62940
taatttaagt gacattcttg tgttctagaa ttaaacggca agccattgtt gtgtgtaagg 63000
gaaatgcttt catttatggg agccctttta ggagcctggc ttgatcctca ttaaaattga 63060
caccattact tttcagctat ttactgcaag ggaaaattag tgtgatgctc cacgttttgg 63120
taattgtggc gataataaaa tgggctcccc taaagtagct gtggctccgg gaggtggcga 63180
gccttcacca tcgttcatca ttgagtggta ccagagccct ggattctgac tgaggtcctg 63240
tcactgtgaa gctacaatgc tgggatgact cattgcactt tccttgtgtc caaaaatgaa 63300
ggaactggaa ctcatgaatg ttagaacaaa aaaagcggct tatgccgtgg aatgaacagc 63360
aggtttgtcc gtggccatac ctggggcccc tagtgaattg ggacaaatta tttagctttt 63420
ctgaggctct gttttatcat cagtaaaatc ggaatgatga tacttacctc attcctatga 63480
tggttgtatt aggtttccta gggtacccct aacaaattac tataaactaa ttggcttaaa 63540
acaaaagaaa tctattctct tacagttctg gagcctaaaa attcaaaatt aaggtgttgg 63600
caagttccac gcccctctcc cagcttctgg tagctgtcct tggcttgtag aggcaccgct 63660
ccaatctctg cctccatctt catgtagtca tgttctcact gtgtgtctca aaatctcctt 63720
ctgtcttcct cttgtgagga cacctgtcac tggatttagg gcccaccgta aatccaggat 63780
gagctaacct tgatattttt aacttaagta cttttgcaaa gaccttttc ttcaaataag 63840
gtcacattcc tagtttccaa ggcttaggac gtggacgtac cttctcaaag gtcacccttc 63900
agctcactac attagttacg aggcatcagt tgggttagca gatgaaaaca tcaggctggc 63960
aggtaggtgg ccagcaacaa atgctggttt cctcccttcc aaaccaggat tcttttgagg 64020
gttagaatgg atctttaata gcttttatta gtctcaatca gaagtcttat taaacaaaca 64080
gaatgccatt ttggggctgg gcatggtggc tcacacctgt aacctagcac ttggggaggc 64140
cgaggcgggc agatcaccta aggtcagcag ttagagacca gcctggtcaa catggtgaaa 64200
cctcgtttct actaaaaata caaaaattag ccgggtgtgg tggtgggcgc ctgcaatccc 64260
agctactcgg gaagctgagg taggagaatt gctttaacct gggaggtgga ggtggtagtg 64320

-continued

```
agccaagatc atgccattgc actccagcct gggcagcaag agtgaaactc catctcaaaa  64380
aagaaaaaag aaagccgggc gcggtggctc acacctgtaa tcccagcagt ttgggaggcc  64440
gaggcaggca gatcatgagg tcaggagttc aagaccagcc tgaccaacat ggtgaaaccc  64500
cgtctctacc aaaaatacaa aaattaccca ggggtggtgg caggtacctg taatcccagc  64560
tactcaggag gctgaggcag gagaatcgct tgaacgcagg aggcagaggt tgcagtgagc  64620
tgagattgtg ccattgcact ccagcctggg cgacaaagtg agactccgtc tcaaaaaaaa  64680
aaaaaaaaaa aaaaaaagcc attttgggac ctacagacgt ggccagaggc tgacattgac  64740
atttcctgct gaggtttcca cctttgatta atgctgtcat caaggccatc ctgagactga  64800
tttggctgtt ggacttgcag gagaggggtg tggagtttga ggacttgaag ttcatggagt  64860
tggcttcttt acgcccaccc ctcccctccc ccactttgca gtggaggaag ttcaggttca  64920
gctggggtaa gtgatttgct aagtaagggc ttggagcagg cattctggag ctggggcctc  64980
catctgggtg ttctccacgc ctatctgtat gaatgctcct tgctctccaa gcggacttct  65040
tcatttgatg ttcactgtgg tgtgtttcag tagtgactgc cacagcccga ctctaaggag  65100
gtgctgctgt caccccaccc tgctttcagt tctttgctgc agaagacaga atgtgcggga  65160
gaaagatggg accttaaaag actagttgct cttcctcact catgtagacg atttggcttt  65220
gaatcgtgaa ttattgcttc ttttgggcat tccagttctg catttccaga gaccctcagg  65280
tatgtcaagc tttttgcctg gcatttgata ttttgggggc aaagtacagt ggaagtggaa  65340
atggtgcctc tggttttgtc aaggccagat atgtcttctc tccactcctt gtgtttttg  65400
agacagagtc ttgctttgtt gcccaggctg gagtacagtg gcatgatctt ggctcattga  65460
aacctctgcc tcccaggttc aagtgattct cctgcctctg tctcctgaat agttgggatt  65520
ataggcatgt gccaccatgc ccagctagtt tttgtagttt ttagtagaga tggggtttca  65580
ccatgttggc caggctggtc tcgaacacct ggcctggagt gatccgcccg cctcggcctc  65640
ccaaagtgcc aagattacag gcatgagcca ccgtgcccgg tcttttatca gtttaacttt  65700
ccagaaattt gttccccctg cctgtccgca tcccttcaaa tgaaagctgt aagcagcagg  65760
cagttgttgt ttgggggccc atcagaggcc gcatgtcact tctggatggg tcaggcatca  65820
ctaccagccc tgacttgatg gcggcagatc agcatggcac tgtcaactag cccttgacat  65880
aaatctgttg taactcagcc ccagacatga taggacacag cctgaaagcg cacaggaatc  65940
cgtaccagag cgaagtcccc cctcaggtgt gtgttcaaga atgaagcgtc ttttattcca  66000
agcactgact gataagctcg aatgtggagt tgacacctgg aagggagttt tgggagcttt  66060
tggcagccca tccccagtgg aagaaggagg aatggctgaa attgttgact gcttggggca  66120
gcctctgtcc caggaagaca aaggctccag tgtgatagct gagctggggc caggggacgg  66180
aggcacggcg gagtccctca aaccacagct ggagtgtgaa gtttggactg tctcctgggt  66240
tgggaacaaa gtagtggtta agtaaatgaa gaagcggtgg cctagttaat taattaacct  66300
gttaattcat tactgaagct gtcaagattc agtcattcct gctcacttgc tcgtgatgga  66360
aggctgcatc tcagtctcgg cttccatcac actgtggctt ctggatggaa tttttgtttc  66420
tgtgtgtgat aaggagtggc tgtggtggca tcatttaaat gacatgattc tgcacgtcca  66480
gagacgttag gatattgaaa gcctgaccat taccttttag gttgtcatgc ttgtacctgt  66540
tcctggcaca aggtctcggc tccgtagagc cctgtggggt tctgaacttg aagcctcttg  66600
acttagaggc ttcctggcca gggctcattt gattttccat actcctgact ttgctgccag  66660
tgaattcttt tccatttctt gctctgagtg taagacttgg tgtcctaccc tgacacgggc  66720
```

-continued

```
tctgcatgcc agctctagag ttgcgaaatc tcaccggagg ggggcagaaa gcccctctgt  66780
tgagaaggga ttggggtggc gtgccaggta atgggtcaca gcgacagcct ttctaagtgg  66840
gcttatttag ttgacagatc acggaaccgg agcggagttg aggaggaagc accttccttt  66900
tgccgctttc gtgtccccag cagccatctc atcctgttct tataaaccat cgctgtcaca  66960
gacaacccct aagggtctct actctgtgcc agatgccctc tctggaggtt caggtggaaa  67020
ttacgtggag aggggtgtca agttctgttt ccacccttgc taactctatg gccttagaaa  67080
aggcatggaa cctctgagcc tcagtttcct tgcctgtaaa atggggtgat gactgtttcc  67140
ttgtagcact atggggagga ggaggtggta ggagaggcag cgcttttaaa taatagtacc  67200
atgcaactgt tagtcgttat tgtgcgttgg tcccatactt cctcttgcat ctccagacag  67260
agccgtgcac cctgagccca tcctgatgaa aggaggggtc agtcctgtcc tttcctccag  67320
gatagagatt tcaaaacttc ctttggtagc tactgtttaa tgagcttttg attgctacaa  67380
agcagctttt cattcctgtt tcacaacagg gatcccgggg ggcaaaggct ggttagtggc  67440
agctagatca ctccaaacgt actgactggc aaatacagac tctcccgcag aactgacccc  67500
agcaagaagc ctttgggagc aggtggtatt ctgcgggtgc cagctccctg ggtgggagc  67560
aggcacacgc cagcctggat ggggcatggt agaactctgc gatgtcagct tttttgtcac  67620
attctctgca ggctacccgt tgtcctttgc ccccaccattg aggaaggaag ccttattgat  67680
tgctttcgat tcttgcaggg ggcctgggtg aggtggctgg agagagggct aatatttggt  67740
ctggcattta atcttggcat ttcatttatg gtgtgggcaa agaggatgta gaagtgttaa  67800
aatcaagtta atatcttaca gttttatgta agaagaggtt acctggagat tcaggtgagg  67860
atggggcaga gagaaagctg cttctgtcag agcttgggca aataaacttg ccatgaaatg  67920
tcaatttagt gatggcagta agagtgtgca gtaatgtgct ggaacttagc gaggtttcta  67980
tcagcgtgtg ctgaattgaa ataatcaaaa aacagtttaa taagttgctt atatttggag  68040
ttttgtggtt cttaacattg caaattctga agcaagaaat tagagtttct ctctaaactc  68100
atttactcat gtggctttat caacggctgc ctttgtaaac cgaaagacct cagttgggaa  68160
gttttatgag acggagtctt gttctgttgc acaggctgga gggcagtggc atgatcttgg  68220
cccactgcaa cctccgtctc ctgggttcaa gtgattctcc tgcctcagcc tcctggtagc  68280
tgggattata ggcggacatc atcatgcctg gctaattttt gtatttttag tagagatgga  68340
gtttcactat gttgcccagg ctagccttga actcctgacc tcagatgatc tgcccgcgca  68400
ggcctcccga agtgctggga ttacaggcat gagccaccgc acctggcctg ccaactcttg  68460
ttaagatgtg agtgtggaat gctgtgtgtt cttccccttt taaaagatgt gtctgttggt  68520
ttgctttcac ggattccctc tcccttagga gacccggctg ttgtattcat ggtcttcatg  68580
cttggtttgt tttcacagtc agagaaggta ggatgctgta gggttctacc tacaggtagg  68640
atgtgctcct tacttagaga tttggaaggg tggcatcaga gaaccactgt gcgtctttca  68700
tgatagctgg tcaaatgtgg gtgtctgtgg gaaatagatg gccaagggtg tcggtgttgc  68760
tgtggggagg ttgttctgtt tcctcttctg agaagagaca gatgaggcga tgaggcaatg  68820
ggagcctcat tgctttggct tggagggaga aaatagagca gagctctcta gctgggattt  68880
tgtgtatttg ctgagttgca gtggttaatt ctctatcctt gaagcacgtg gcacgctcac  68940
gcagccttta tgtggtcgag agggtgacag tcacttgaat gaggtataag gctttgccct  69000
catggagttc ctcaggtcac attttgaggt cgaagaccat aaattgggat ggaaatttct  69060
```

-continued

```
agatcttgat ggaactccaa ctttttctct ctttctcaaa gcctctggat tacaggattc  69120
tctcaaacaa ggctggcagg aattctgtcc atcccaaata agtatgcaaa tctacaggtc  69180
aaatggtgcc ccagacatat tccccactgg atcagggaga ttgtggtctt ttgagagaca  69240
aacattgaat attattctag taggatcttt tggaaattat gctctattag aaaaaggaac  69300
ttttcatttt actggttcag tgtacactct ggactgaaac tgaaaggtaa aggacttagc  69360
cctttaaatt ttacattttg gccgggtgtg ctggctcacg cctgaaatcc cagtactttg  69420
agaggctgag gcaggtggat catttgagat caggagtttg agaccagcct ggccaacatg  69480
gtaaaaaccc atctctacta aaaaatacaa aaattagcca ggcgtggtgt tgtgtgcctg  69540
taatcccagc tactcgggag gctgaggcag gagaatcact tgaacgtggg aggcggaggt  69600
tgcagtgagc tgagattgtg ccactgcact ccagactggg tgacagagtg agactccttc  69660
tcaaaaacaa acaaaaaaaa ttaaaatatt aaaaattagc caggcgtcat ggtgcacacc  69720
tgtagtccca gttattctag aggctgaggc aggagaattg cttgtacccg ggaggcagag  69780
gttccagtga gctgagattg tgccattgca ctccagcctg ggcaacagag cgagactcca  69840
tctcaaaata aataaataaa ttttacattt tggactgaaa aaacaaaacc attctgtatg  69900
tgagactctc accgagtgtt catagggagg gactggggct ggggcctgac ttgaggcttc  69960
ccatctggct tggacagtga gaagagcagt ggcgtttgga ttgaaggctt ttgtgatctg  70020
ggtgactatt ttgaagtttc tctttaggtc atgctgtact tagaagtatc tagaaccgtg  70080
attattttca gtttctgagt ttcatctcca agaaaacaaa tgggatttat tgttcagcct  70140
ctcatgttat tcctatcaaa gggaggcatt tcttgtttgc tcagatgggc tgaaagcttt  70200
tacttctgct cgaaccgccc taggagcaaa acaaggcatg tgagagagat gagcatgata  70260
gattttctag acttctctag aagaaaggct ttttagatgg tgaaggttga tgaaacctgc  70320
cagcattttt acaatggaca tccctctatg tctgcacatc tcaatctcct tcattcttac  70380
tagtggccaa tatgctcttc tttcacggat gtagtacaat tcgtttaatc atattaaaca  70440
atatgattgt tgtgcagatc ttttgttttc cagtaaaaaa aaccctacag cgacaagctt  70500
tgtccacact tatttagtgg gcatctgtgt gaatattttt ctaggacaga tttgtaaagg  70560
ttggttaact ggatcatttt tgatagattt cagtcaaaca ttttaaagct aaggggcctt  70620
acttacttgg agtggttgct gtctttgacg gagggctccc ctgtggtttg gtttttagct  70680
tctttgcaaa tcatttgaga gaagatactc taattgggag ttcacccatt gtaataagag  70740
ggtataccta attcctggac attaaaaaag aacaaacttt tccagctcga aggaaacatt  70800
ttcttcccct gaaggaaacc cagctatgca gacaccagct gataatcttg cattcctgaa  70860
agatgttgca cccctatggc aagtggcggc tgctgaggct ctgacgtgac tcccaggcat  70920
gaacgctctc agctgtgttt acctcagctc ctcgggaggg agcctgggag actgacgcct  70980
gagttttaca tcagtgtcaa aacccaagca caacctaggg agggacctcc tgcctagtgt  71040
gtgtgggtca ggagatagaa aagctctcac tgagtaaact ggacaaggtc aatatacctc  71100
gctgattgag aaggtaggtt ttccatgacc ctagaaattg atcttgttca ctctgagata  71160
ttgtcacctt tgttatgtct cctttttaaa aaaaaattgt ggtaaaatat acataacata  71220
aaatatacct ctgtaaccat ttttgaatgt gtaattcatt tacattaagt acattcaatt  71280
tgttttgcaa ttatcattat tgttcatctc caggactttt ccatcatccc caaaccatga  71340
ctccttttag caaaagagac caatttcgaa cgtaaatttg gcataataac tctctggtta  71400
ccaaagaatc ttcagttctg gtgaaacttt ttgaaggcag agagctcaga gtgtcttaaa  71460
```

-continued

```
cacttggggt gtaaataaca cacagcccta ctcctgtaat tcgcccaaga agacccaaat  71520
tgatacccag ctggtagaag ccactcaacc ccaagccaaa taatacagcc tgtaacatta  71580
attagggaag gtactaataa tacagcctgt aacattaatt agggaaggta ctttgcctcc  71640
acctgctttg gtcttcccag gccctgagcc cagccagcac tttactctct tcttcacttc  71700
atcgagcaag cacaaaggca ttagtggtgt tttgcttcta gcatttcaca gggtgcagcc  71760
tccataagtc actttgtgac tttagtgctg gagggaggac acttcatttt tacccaaaca  71820
agtttgttcc gcagacttca ctctctctgc aaagagacgt gtgtgtttta gaggaagtgg  71880
gagccccagc cgattctgca agacttccga gagtcagata tccagacaga agatgcggac  71940
acctgggtga ccagacagcg aagaggaaag aacaaaacga gcatgtgcca agcctgtgag  72000
ggagaaaggg caacaaacca gtgaccttcc acagaaatgt gtttaaacaa aacaaaacag  72060
gtgattctgg gtgcccagca tcccagccca ctcatctatt ctaggaggtg acaagccaag  72120
atactggctg tgggcacctg ggctctttct gaaggtggtc ttcctggccg tcatagcgtt  72180
cccttttttct gctaatcatt tttagttctg accttccttt gtgctgatct tcagaagctg  72240
gagaaagctt cgtatttctg ggaaaacaaa acaaaactca gaacccaacg agatttagcc  72300
tgtcaggctt gagtgcgtta ggtggagtct tgacaaggca atgaactcat tctactaatt  72360
gtaattagcg tggggccttt agcaagttct gggctcctca gacttcagag agctttgatc  72420
ggcctcctcc tcctcctaat aaccatgcct catgctaact ggtttagtgc gtttttatgc  72480
aacaaaagca accaccgcct actctttaga aaaaagctag gcaggcttta gaaaaagaat  72540
tctcagttgt tttcacttgt cctccaaatc gcagaatgtt ctttcccttt tcagctcttt  72600
ggcgttgcta agagactgcc attttggagg aaaggtaatt aaattttgat tttaatttaa  72660
agacagagca agcgaggtta tccacgctcc ttacatgaat gggggcctga gagcaggaga  72720
ctggctgttt ccagatcaat actgggaact ccgtgtgatt cgagtctctt ggtgtgtgac  72780
tgccggagag aggtggcttt gaaatggctc tttgtggcaa gtactgccta acttttgggg  72840
agaaatgctc aggagaccag tgtgagctgg gaaaccagcc actctgtgct tgattaattt  72900
ataggtgtaa tttaagagcc tggttctcct tctgatcccc gggatgcatg tttactgagc  72960
ctgtagacat gaggcctctc ggctcggtgg acatttttta tggcctttgc tatgtcagag  73020
caaaagttgt agatctctta tgagcaaaca tattactatg tccagaggag gactggcatg  73080
ttataaaatt tcaatggtca attaacaaag atttattctt tgtcactcag gtattttttt  73140
cctctctctc tctctctctc tctccctcaa taatgacctc ttggaaggaa gcaggctgtg  73200
ctttcctgct gcagtcttta ggtgggttat ggctcccagc tacagagcag ggcttgacag  73260
agcccatcct gatatttcaa ttcttagcag ctgggctttc tgctttagta gagtggacac  73320
ttgaagaaag gggcgagagac cgagagtgag agagagagaa cgctgggaga gaatgtattt  73380
tttaaagcac ttcagcctgt gtttactacg cgtttatttg gtggaacctc attccagcag  73440
tgcagccaac tgtcccggca gcagtggccg caccctttgg actgctttcc attccgtctt  73500
aatttggaat tcacacagcc accttccaat cactcttttg aaggttctca tcttgttcca  73560
ggtccatgca ctgtgcattt gcaacctgct gaacctcaga acgtctattc ttatatgtgt  73620
atatatgtaa ttaaaattac agtaaacaga ggagctactc atcagcctat tttccatgtg  73680
tttatctcac tccctttgta aaaaggaaaa tctgttttat ataatatctg agagttaaac  73740
atgctagaag agaatcttgc ctaaaactgt aaatccttcc tgtccttcct ggtggagaag  73800
```

-continued

```
atgtgatttt tgttatcaca tagaagaaga gatgaactag cactgggctt tagtctctcg  73860
cccagagata atacatcagg ggattctttt tatatcagtt tgttgcaaaa aagttgcaaa  73920
cttgaggggt ttggtttgcc cagggaccgg ggaggttcct ggtggggaga acacatgagc  73980
tctttgggtc atcgtcccct ttgtctctgc cgtagtgccc gctgggccag gccacgaagg  74040
gggcccccac tctgcccagc ctgcatcctc gtccaccatc tgcaccctgc catcacctcg  74100
gtttttcaga agttaggaaa ggagtccagg cgctgtcatc cacttactgt tcactgtttc  74160
tgaggttctt agggattccg aggggtggtg gatcgctgaa gggttcgaga ggaggagcgc  74220
agcgttcggc agatgctggc atcctgggcc cttttccaag acgtccaggc ctcctcctcc  74280
gacttgttta agggcagaga ataaggttgc aaaggaaatc aaagcctgat gtggagaaat  74340
gaaacatgag acctactgac tttttaaaaa cattttaaat aacattctct aaggtttcat  74400
tttatactga aggcagctgt aataagtttg gaagacagtg taaggtttct attacagaac  74460
aatcctgctt gcagtttttc taccagaagt gagaaagggc ggaggggggag tggaggtggt  74520
taagaggtta ttttgtataa ggtgagaaaa tttgaaaaga tgaattcaag actgcaagcg  74580
tgtaacattt ggtatgctgt aatttgcaaa tgcaataaca ttaaaccatt gcaaacttgg  74640
ggtgtgtgtg tgtgtgtgtg tgtgtgtgtg tgtgtgtgtg tgtgtgtata catagccggg  74700
atagcattgg aataacttaa taactggagc tcagcagcac tttgaccaca aggaaaacaa  74760
gactgcagct ctgtagtggg ccctgccagt gttgcctcag tgactaaatt ccctgccgaa  74820
gcctggcgca ggccagagat gtcaggcggg atgaaagcac tcattgttca cggggcatca  74880
tggtttggta ctgcatgcac aatgtttact tgtgaaacga tttattagaa acaaatatgt  74940
ttaagaaaga ggacttggtt tgaaactcag ttgatctggc ttatgacatt taagatttta  75000
tgacctttgt ttctaagaat agatgtgtag gcccactgta aatatttatc ttaaaacgca  75060
cccacactac acacacacat gcatgtacaa gtgcaaaact ggaaaacgga gccagggcat  75120
gaattgatac taaagttcac atttctgtgt gaaggaataa accttcttac tatttgctag  75180
gtgcatagga gcatagtttg tgaccttgtc tggcaggatc tagcccagag gacagcttcc  75240
cctcgtgctg tgaagtctct tggtaggagg cctggggagg agaggagcgt gtgtctgttc  75300
gtgcgcggac ttaactctgc ccttcccaca tggatgaggc cagctgggat taaatcagac  75360
ctcggtcact gcccgctgtg gacaggtccc tggggtgtcc agccagctgc taggcctgac  75420
caggaggctt gctggggccc atccctgggt cattgtatga gccagagagc aagggtttca  75480
cctgacgtct gaaggggccc agctttgaga ttttctgccc accaacacca gaagtcttaa  75540
cttcaggttc tttgctcagc ctacatgggc aatatagggg cagatgaatg atttctttgc  75600
ggctccagta tccttatctt tataatgtga aaacatagat gtctgtaaag tgatgggaga  75660
ttctggaatg aaatgtgcta agagtaacca ctagcacttt ttctttcttt ttaaagacca  75720
gcaacaggct tatgcagtaa agtcaatttg cacatggtct ggctcttgtc caacaaattc  75780
cactagatga tgttttaatc tgaaaggtcc aatgatgtag atatctattg ttctaatttg  75840
ctgtttccag cccagtgcat ggtgattctc aggtacagtg cagagacatc cttggtgtgc  75900
tgagctggct gagttctcct catttccctc agttgttttt taacactgga ggttagggta  75960
gtggtaccca cacctagggg aggaagagag ggaggaggct ggtaagtgca ggcctgttgg  76020
gatggagttg tattcatgta tggacacatg attgtgtttt gtgtggcttt tgacagatct  76080
gtgtaggaag gttccagtaa gtttgtacga caagatcagg tagcagtctg gtggtctggt  76140
ggttatttaa ttctttttat tttatttcat tttattgttg caagaatgct aagcatgaga  76200
```

-continued

```
actaccatct cacctaagtt ttttttcttt tctaagacgg ggtctcactc tgttgcccag  76260
gctggagtgc aatggcatga tcgtggctca ctgcagcctc aacttcctgg gctcaagcca  76320
ttctctcacc tcagtcccaa gtacctggga ctacaggcat gcaccaccat gtctggctaa  76380
cttttgtatt atttgtagag atagggatct tgctatgttg cccaggctgg tcccacactc  76440
ctggcctcaa gcaatcctcc tgcgtcagcc ttcaaagttc tgggattatg ctcaaaggca  76500
tgaaccactg cgcctggtct tcaactaagt tttcagtgta caatacgttg ttgttgacta  76560
taggcacgat gctgtgcagc aggtctctag agtttgctca tcttgcttta ctgaaacttt  76620
atgcctcttg attgcaactc accatttcct tccctgtccc agcccctggc aaccaccgtt  76680
ccgctctttg attttatgaa tgcgatgaat ttagatacct catatcagtg gagtcaggca  76740
gtgtctgtct ttctgtgact atcctgtttc acttagcatc atggcttcca cgttgtcaca  76800
tattgcacca tttcctcctt cttcatggct gaatagtatt ccgttgtgta tatagccaca  76860
ttgtaaaaat taatcctttg gcagacactt agattgattc catttcttgg ctattgttaa  76920
tggtgctgca attaatatag gagtgcagat cctgattgca gttcttttag ataaatagag  76980
aagtgggatt gcaggatctt agggtagttc tgtttttaat tttttgagga acctccatat  77040
tgttttccat ggtggctgca tcattttata ttcccaccaa cagtgcgcag gggttccagt  77100
gtctccacat ccttgccgac acttgtcttt tttttttttt cttcccatcc tgacaggtgt  77160
catgtgatag ctccttgtgg ttttgatttg gaacgcgccc gatctcgtct gatttgcatt  77220
tctctaatga ttagtgacat tgagaaactt ttcatacacc tagtggccat ttgtgtcttg  77280
gagaaatgca tagttaagtc cttagcccat ttttccatgg gtattactta acacttgagg  77340
agtctcatgt gtggttgcta gcacaccttg gcttgattgt ctccacaaaa gttttgcaga  77400
gaccgcctct tagctggaga gaagcctttc caggcataag atgagagggt gtattctttg  77460
ttgagaacgt gttctcgaag gagagagagg caagacaagt gaagctagga agtaattttg  77520
ggataccatc tctgcccttt tatagggcag tctaaaacat agccaggagt tggaaaccag  77580
catctcctta tgtttcattc agtgccatat tggaataagc taagaaacat ctacttgtgc  77640
atttagtaac tggcatagag taacacctga tattcatcaa agagctaaat gggtgaataa  77700
agaatgaatg aatggagtga attccacaat aaagaggtga atcccattat taatcaaatc  77760
tgttcataac tttgggcttt aggctttagt ttaattttta aaacaaaggt tggaagtctt  77820
ctcagagcat cttagaaatg tactggagcc gagcgtggtg gctcacgtct gtaatcccag  77880
caatttggga ggccaaggca ggtggatcgc ttgagcatag gagtttgaga ccagcccagg  77940
caacatgatg aaatcctctt tctataaaac atttgaaagt cagctgggcg tggtggcggt  78000
tgcctgtagt cccagctact caggaggctg aggttggaga atcacctgag cctgggaggc  78060
tgaggctgca gtgagccgtg atcatgccac tgcactccag cctgggcaat gaagtgagac  78120
cccgtctgag aaaagaaaaa aaaatgtatt gggagacatg tgcctattga aaccattttt  78180
ggtattcaga gtgtctttaa agttagtctt gtcatttgcc tgtgatgtta agcttgtggt  78240
tgaggtgagt ttttgagatt atctcaaata ggataagtga agaagcttcc ctcccctacc  78300
atttgtcact tagattgtca gagtagaatt tcttcccgta ttcatcaggt ggcagtggac  78360
agccaataac ctgggatgta ataagttctt ttctcaattt tctaagtaag tgttcttttt  78420
acaagggtcg cgctccggca gtctcctttg aagtcgtttc tgttattcat ggggccacag  78480
tgttatttca aaggtgtcag ccagcaggct tgaggctttt ctggcatgag gtcactgaca  78540
```

-continued

```
gccctctgga caacacagct tatttattgg tctctcattc tcccatcccc actcctcctt  78600
tcttccctct ctccaccaga gcgatcgcct caccggccca tcctccaagc cggactgccg  78660
gcaaatgcct ccacagtggt cggaggagac gtagagtttg tctgcaaggt ttacagtgat  78720
gcccagcccc acatccagtg gatcaagcac gtggaaaaga acggcagtaa atacgggccc  78780
gacgggctgc cctacctcaa ggttctcaag gtgaggactt tctgaatcta aaggtaccca  78840
caactggggt ctccttcatg ggtttggcca caggttcttt gatttcctgt tggagttgag  78900
agaggatgat tctctttttt gactagccag cagagagtgt tctaaggaat taacagatca  78960
ttacacttgc tagtagaatt tcagaaggga actatggagt aggggaagaa ctactaaact  79020
tggggaagaa ctactaaact tggagagaga atagttcagc tatttatcag ccctgagatc  79080
gcagacattt aggcttagct gcgcctctat aaaagtagag atcgtgatac tctgtccccc  79140
atagggcggt tgtgcagaat aaatgggatg gagtggatgg aaagagcttt gtaggctcaa  79200
ggcattgtgc cagtgttgat tgttactctg atgttgtttt ctattaatag gacattagga  79260
tccaatttta gtagccacgt tttagaaaca atttggattt ttttttaac aaaaacaaaa  79320
caaaacaaaa ccctgacctt tgaaatccat tcagaggtga tttagacaat aaactctagg  79380
tcatatttct gcaccagtga aatgttgaac aaggaaaata tctttccctc cttatttctt  79440
atttgcaagc ccccattttc atagcatctg cctctttttt agatctaggt ttgctcttca  79500
ggagactgag gacaggggca gctaagtctg tacagctggc tcttaactcc ttgcctacca  79560
cgcctcccat gtctagttgc tcatggagaa tgaatgtcct taagaagaac attcttccag  79620
tagaaccata ggtgacccag ctaagaactt tcagccaatg aagtgttctc accagctaat  79680
aattccaagg atcaaaggca ttgggaaaag atgaccaacc tggggaccca cccgacctat  79740
ccagttagct atcgctcaca ccctcctgcc cttctctcca ccaggtcttt ccgttgtcca  79800
ccactggact gattttgttc tttaaaatcc gcagcccttt aatgccgctg tttagacgta  79860
atggagtttg ttttcttgcg gtgtgttggt ggtgggacca tagacaatgc taagaccttc  79920
ctggttggcc gttatattgt tctcctgtgt ctgttctagc actcggggat aaatagttcc  79980
aatgcagaag tgctggctct gttcaatgtg accgaggcgg atgctgggga atatatatgt  80040
aaggtctcca attatatagg gcaggccaac cagtctgcct ggctcactgt cctgccaaaa  80100
cagcaaggta acaatgcttt catttttgtc tttttttaaa aagaaagctg gatatagaag  80160
ctgaaaagac ttggtgcttt gggagactgc aggcagctta taggataact cttgtggcct  80220
tggtatattt ataataatct ttcttcggtg atgcagctgg tatgatgcca gtagccatgg  80280
aaaaatgccc acaacgttca aagtgcttgc tccaatttct tctagagatt agcctccacc  80340
cccacccagt ttttaagttg ttccttctgg ttgatcttgt ttaggctgca catttcccat  80400
cattactgca cattaacacc atttaaaaca cacgcttcca tgcctgttta atacggggca  80460
tttgagtatc agcagagttt gtctccttct acttcaagtt tttagggaaa tattggcaag  80520
atgcaatttg ttcaacaaag catcatttct ttggttgcat ggttgatcct tatgagttgc  80580
tgttcttgac cttgttgcac caaatttgag gggagctcat cttaatgaat gtactactgg  80640
acgctactaa aggcaaaagg ttgacttttt aggtttgtca tgactcacat ccaaatgttt  80700
attaatgaaa agagaaaaag cccagttttt ttggttacca agatgatgct tgcttccatt  80760
tctttttgtc aatgctatgt agggcaagat ggtatcgcag aagtaaaaat aaccagagcc  80820
tggtaaccaa gacaaccttc caccccaatt ggttcccaca gggccaggag gatgggtgag  80880
gtgtccatct gggcttatgt gcagtgtgtt gtcttaaaac acagcaattt agatagaact  80940
```

```
accctttcct cttggtggga gtctgcagcc aacaggacca gaaccagctt ggccttctgg  81000
gcaccatact tttggaaaac cacccctaaa tgcaaaccaa agcacaggcc aagagaacgg  81060
acctctgtgg gttgattttt tccatgcgtt tgattgcgtg catgtgtagg aggtgaagcc  81120
ggtgtggtga cgggcctgtg gaggtgagct ggtcagtgtt gctccgtgtc tctcggttgt  81180
gggctttgtg gatgggctgc agtcggaatc tcccagtggc cagcaccccc tgaagccccc  81240
ggtgcgacgc cttgtggttc cacagccccc tccacaatca ttcctgtgtc gtctagcctt  81300
ttcttttgct tcccttgttt tctaggccgc cggtgttaac accacggaca aagagattga  81360
ggttctctat attcggaatg taacttttga ggacgctggg gaatatacgt gcttggcggg  81420
taattctatt gggatatcct ttcactctgc atggttgaca gttctgccag gtatatactg  81480
ttctttctct ctgggttttt ttccctttc ttggctgact gctattaaaa ttaacacagc  81540
ttctgttatc agaaatggcc ccttttatcg ttgcataaag atataaaaaa tgttaaaaat  81600
gatccctcag ggataagaaa actgccttgg aaattcacac acagtgagat cccacactca  81660
catttatgat caagggaaat ttcaccctta aaacctgaag ggatctcata tttttagtga  81720
gtcattgagc caatgtataa attagcccat ccccctttct cttaaggaac aagttgccat  81780
tactttggta aaattcaaag taatttattc tcatttcaaa ttccattttg ctaaaatcct  81840
gtatgtgttt ttattgcttt catcccactt tgtattttta acgagatgta aatagaggga  81900
tgtgtatgga ggagcctggg gagcggcacc tctgaatgtc agatgcacag aagcagtgtg  81960
ttgcctacct tggggatcgg tggcttgctg catgttgcga taggatggac tttcggtttg  82020
ctttcattgc aaagcatgct cctgccatct tgggcttgat gttatttctg cctcacagag  82080
aaataaacat cattgcagcc ctgttgccta aacattgctg ctgtctgaat ctttaaccga  82140
catctctatt ctagtgaaac tttcttgaaa ttaaacactg tcctctctga tgcatctgcc  82200
tctttgtcat ttcctttgtg aaactgcaga gactgtggtt tgctagctta tgatgttcca  82260
ctccagttat taattccttg tttttagagt acagtgctta cctgcatgct tattttacat  82320
ctagtaaaaa taaaatagat cgtttcattt ttgtgctgtt gctgctgaga gttttgacta  82380
tcttgcaagt atttttctga ttaaaatgta taagctttca ataataccat tgcatccgtt  82440
tttccttttg ttgcgaatct gctctgtgaa tatttgcttt gaaacaaaga gatgtctctt  82500
atgttgaagc ttgcttttat ttgcagtact gcattctgtg gtgcctaact ggcacttctt  82560
aaccagtttg cctgacagtg ctagcactta actaagaatg cagtttgaga aaaacactat  82620
ttggaaatac actgcttgta gatggatcat cgaggactaa gaagaagtca gacattggaa  82680
gttgatataa aaatgtgcta aattaagtaa ttatatgtat actcacacat aataccttta  82740
tgttttttct ttaagagaaa agctgtagtg acataacaat ataaccggat atgtataaac  82800
ttaaaaggtt attaaagaat attataatct ttatgtatta tggatctaat ggttctatat  82860
tataagcaat tcaatctgtg tatttaatgc attggtttgt ttatggacta gatggtatta  82920
aggaattcac caaaactttt tcagaccagc ctactagatg aacatcagtt tcatatggaa  82980
ttgtgttcat ccgggttaaa ttatcctgtg gagtcttcct ttggaagagc ctacccatgt  83040
aagactgaag cattgtcact gtctccttag aaacaaaagt gggcatcgtt gatatttcag  83100
aatttttat ttggtttgca ttcacagacg atcatgaaag ataatccttt cattgtgggt  83160
acagttggtc gtcctccact gaaatgtcta acaaaatgtg gcctcatagc ctgccctgtg  83220
caactgggtg tcaaccactc actggattgc aggtgcccac tgaggctagt gacagtgact  83280
```

-continued

```
acctgggtcc tggtggtcaa atgatggacc cctggttatt cattttcatt tgggagtttt  83340
tgggaagccc accttgcctt gagaatggtc gtcgcctttt ggttcctttg gttgtgctat  83400
gatgcgtcag tctggtgtgc taactctatg gcctgcttat ctgttcctcc tcctgtgatc  83460
tgcaatctag cgcctggaag agaaaaggag attacagctt ccccagacta cctggagata  83520
gccatttact gcataggggt cttcttaatc gcctgtatgg tggtaacagt catcctgtgc  83580
cgaatgaaga acacgaccaa gaagccagac ttcagcagcc agccggctgt gcacaagctg  83640
accaaacgta tccccctgcg gagacaggta acagaaagta gataaagagt ttaaagaaat  83700
ttactcctcc cccatgaccc agccagcttg tggatcttgt cctctgcttt gatgccatcg  83760
acttctgtga gcttccatgt gcgagtgatt ctggtgtgat gcttggcggt cacccagtta  83820
gtgtttggag cttggagagt ctagtcatgg tggcgttgct tggatcaatg gggtccagtt  83880
ccaagggcaa gaaaggtcaa tactgtcaga atcagacaac taatcagcag gactggaaat  83940
aactggaggc aaatccccct gtgtgtgttt gatcagactc aagtacagcg gtctcttcga  84000
agctttagcc acattcgtgt cctgtgatct aataccttt ttaagataag catgaacatt  84060
cgcttgggac ttatgccact agtacgaaag agactctaag ttctctgact tattttttaa  84120
agtcaagatc agtatcttat gccctggggg tgcatctgaa ctgtttgatt taaactgttg  84180
cacaataact ttctacacag aattttaggc ttaacctctt tgcaatttac aatagaattg  84240
tatgcatcta ttatgtctca ttgttagtag ttcacaggtg tggctgtgga tttattagta  84300
gaatatttgt atggaaccag caacagattg tttttaacca ccaacttggt ctttggtggt  84360
tgctttttgc ttgtgtgtgc ctcctgattg gtttaatttt gctttggggg agatggggca  84420
agatggagcc tctggtgtaa accaaagccc tgcataggta ggtgggacag gaaatgcctc  84480
agctcttttc tgcttattca cagagatgga agcggaaggc agatgtagat gcagaacgtt  84540
tacaaaagca tttgaaactt ggttctgata aaggtttctt ttgaaatagc aagtaaaaca  84600
gcaaactcat tggctctatt tcagtgtgta ttttagtaaa atgtacgggg tgcttgttaa  84660
aatttcagat tcctttgtct cagccccaga gattcttgtt cagtcatctt ggatagggcc  84720
aggaatctgc attttacaca agccctatgg tgattttaga atgcactttg agaaactcca  84780
ggttaattcc aggcatgcct ctcccgggac ttcaggtagg aatgacattt tctggacaag  84840
gcattaggaa ggattaggaa ccagttggtc agcagtggtt ttggaatggg tctggttgtt  84900
cacaacccag cttcaaactc ctggctgaat gggtccttgt taacttctct aaagccatgt  84960
ttcaagcagg tctttctttg tggagacgga ggatagaatt taaagtgtgt gtcaagcgta  85020
ggcgaatgac caaattgtgt taacagcatg gaaaagaggg gcctgttggg tcacgtctgc  85080
caccaagaat gctgttgtca ttttgagtga catgattatc tttcttgggg ccaggaaagc  85140
aaagatgagg ccagttggcc aaccagtttc tagaagagtc cagtcctgag ataactctta  85200
catggtttct attattttt ttctaatagg gaaaaatggt aacttctgga ggcaacttgt  85260
aatttggcat agctaggcca ctgcccctta attatctcat catctttttt tctgcaactg  85320
ttaaaatgct tttcttttta cttaatatag aagggtaaga tgcccttaaa atccccctga  85380
ctcagccaca gtcatcgtgt tttctttccc cagtgccagc tggcttttct tcactgtcca  85440
tctaagaata cagtttgaga aaaatagtat ttggaaatat actgcttgtg gatggatcct  85500
tgaggactaa gaagagggca gacattggaa gttgacataa gaatgttcta aattaagtaa  85560
ttatatgtat actcacatgc aataccattt atattttttc tttaagagaa ttcagcctgg  85620
ccgggcgtgg tggctcacgc ctgtaatccc agcactttgg gaggctgagg cgcgtggatc  85680
```

-continued acccgaggtc aggagttcga gaccatccag cctgactaac atgttgaaac ctcgtctcta 85740
ctaaaagtac aaaaattagc tgggtgtggt ggtgcatgcc tgtagtccca gctgcttggg 85800
aggctgaggc aggagaatca cttgaacctg ggaggtggag gttgcaatga gccaagatca 85860
caccattgcg ctccagcctg ggcaacaaga gtaaaactcc gtctttaaaa aaaaagagag 85920
agaattcagc ctaagttggt cctttttcct ctcttccctg tgttaccaga gggaacatca 85980
gagttccttc ctctttttct tccctccttc ctttatttat tcatcataat ttactaagtg 86040
cggggtataa atcaggttac atgtaagaca cagcctgtca cattcaccag tggttccaag 86100
gttatttgat ggtaaatgcc tgtaatccta gctccacagg aggctgaagc gggaggatcc 86160
tttgaaccca ggagttcaag accagcctga ccaacacagc gagactccaa ctcaaaaaac 86220
aaaacaaaac aaaacaaaac aaaaacccaa agtgggaaaa aaaagaaaat gtaattggct 86280
tgtgttcagt agggccgagg agtataacag aagcagagga aagggggcaa ataccagttc 86340
cctggaaaag tacatctctg cgagattaat ttatttgggg ggaatgttga cacacctcag 86400
ctccttctac atgtccaagt ggggtacatt attggatctt cacaaagaat gtttcatcag 86460
tacgcatggc ccctttggta gagaaagaga tgcttatcgg gtatctggat aaaagagggt 86520
tattggactg gagctggaat gaaaagcccc agaaaggcct gcagatacgt tgatgacaga 86580
gcaaatacca cagggatgcc aagcatgcct ttacctgagc ctctaatcag atgtgtcaag 86640
gatgggttgt ttctaggcat ttatgaggcc actttttatt ctgtgttggc cagtctcctc 86700
taggacacag ggatcactca gtgtctccat ggccctgact ctttccctct ccaacaccca 86760
tacacacaca gcgtctcact caggtccctc agtccatcct tgttctcttt tcaggacaag 86820
aaaagttggg ttttcgttcc tcctgtgagt ttttccttct tggcatttat taatttgcac 86880
tagacttact ggtgtaacac agacgtttca gtttatgtta ttttttgag caaaaatatt 86940
tttttccagt accaaagaag aaattccttg caatcatttc ctagtaagcg tgaatttttt 87000
gagactttgt atgcacatgg ttgaagaagg agaagcaact tttgggtggt gggaggcaga 87060
tggcaggtgg catctccctg tgtcctttga tggaggctca tgtcacattc agtgtcaggg 87120
cttgggcacc gtgccagaca ctgctcaccc actcccactc ctttggtgcc cagcgagtta 87180
aatgagacca acaacagcca gcccagagag gggcatcttt gtgagcgtgt tggttctggt 87240
acaggtatgc tggacagcca gtgaccagtg tgaagcagcc tttgtgagtt aaagggggca 87300
gcattacttt ctgtgttttc cacacatcaa ttgggtggtg ggggaaggtg taggggtggg 87360
tggaggatgg agtgcagagg aaactgagga tgcctgttta ggagacgtgc ggtgttgctg 87420
ggtttgctga atcagtttta catcgagcac atcagtttct ttctctgggg cttgaagctt 87480
ccatagggta ggatggagat ttaactgtct tatggttggc tccgtccaga taaattcatc 87540
tcctgtgcag cttacaccct ctctcactgc cgtcagcatg gtacaagagg ctgcagggtg 87600
gttttttttt tgttttttc agactttagt ttcaccttct cagctgctga tataggtagg 87660
ctgaaaacca gagaaaaatc aagagcagac tgggtgccgt ggctcatgcc tgtaatccca 87720
gcactttggg agaccaagac aggcagatca cctgcagtca ggagttctag accagcctgg 87780
ccaacatata gtgaaacccc atctccacta aaaaatacaa aaattagctg ggtgtggtga 87840
tgcatgcctg tagtctcagc tacttgggaa actaaggcag gagaatcact agaacccagg 87900
aggtagaggt tgcagtgagc tgagatcgcg ccactgcact ccagccttgg tgacagagtg 87960
atactccgtc tcacacaaat aaaataaaat aaaataaaat aaaataaaat aaatcaaggg 88020

-continued

```
cagtgaaggc taccttttgt agcaatactt ttgaggcaaa tggcatattc ctggggacgt  88080
taggaatagg accaagatga agggggagga gcggagcggg tgcctcgggg gaggaatgtg  88140
tgactcagta gccagttctc aggtccagtg ttagtgatcc tcaaacatat gccaaattcc  88200
gggaaggggg atggatgttc tactcccaga agctcgttta ctgcctggca gctgaacatc  88260
atgatctggg aatattctct gtattttggt caatcaggtg gtctaaacct taccggctcc  88320
agaaaacatt tgggtaatta gagtggtcac ggatgactta actggaatct gccctttcat  88380
gtgggcacct catcctccct gcccctattt cgctgctccc ttttctcctc tctcagcctc  88440
caaaggacat gacagtttgc ccaagatctg acctggacct tggctgatgc gatctctcga  88500
gcagagccag cgcatctggg gctggtgcgt catggctctg ataggtttac tcacagagtc  88560
ccagggaaag gcctgcggga ggcagagact cgctatggga gaaaagtgag tgtctgatga  88620
actgccttgc ctaattacct aaattttgtt atggaggaat taaaaatgca acttcagaag  88680
cctttgaagg tttatctcag gcacccagct tgcggtggtg aaagcatttt gtttggccat  88740
aggggagtgg tgggcaaggc ttatattaga gcagaagtat gttaatgcca gcctcgtgtt  88800
cttgtggggg aaggtggttt gcagcctaag agtcacaggg cctgtttggc aggctgtggt  88860
ccaagtgtgt ttgtcagtcc tggggagtaa acacacaaat attaattcgt ctcttctccc  88920
tggaacatct ttgcttctgc ttgctctgtt ctctgagaaa tcccctctag atggtaaatt  88980
taattcagta taaagagata acactgttag accgggcgca gtggcccaca cctgtaatcc  89040
cagcactttg ggaggccgac gtaggtggat cacctgaggt caggagttcg agaccagcct  89100
gaccagcgtg atgaaaccat gtgtctacta aaaatacaaa attagctggg cgtggtggta  89160
catgcctgta atcccagcta cttgggaggc tgaggcagga gaatcacttg aacccggtag  89220
gcgggggttg cagtgagcca agatcgtgcc tggataatga gagtgaaact ctgtctcaaa  89280
ccaaaaaaaa aaaaaaaaaa aaaaaaaaag aaaagaaaca gataacactg tttcttggtg  89340
gccctttaaa aagaaaggaa aaaaaaaaaa cacttcctca cttaatctcc catatgtact  89400
atggaaatgt acgaaaagca catttactta aaagcttgac ttatggcaca tgctggagag  89460
attccggaaa gtgaggaaat ggaattggag tctgtgaaaa tacatgctta aaaaaaaatg  89520
cctgccaaga ttcgggagtg ggaaaacagt ttactagagt gttcgtgttg attgtttata  89580
agtaactcac ttatcactaa caagagaata tgttaaaatt ggttaggaat gaaactctgg  89640
aattgaagtt tctaggtagg aattgaagaa taaggaagat tatgattttg tgcaaaagaa  89700
aagagaattt aatagtgcta aagaagtaga aggatttcag agatgagcag tgggagttat  89760
ttgaggttcc tgattcagag gaaagatgcc cagtaaaaca tggagtccca caggggaatg  89820
gcctgcccag gaccgggcca agcccccaac acaggctcgc tcttggagtg gaagggaatg  89880
aagagaaagc cagccgtatt ttatagcccc agaggggatt ttaaaagcat agtaaaaatg  89940
catggaggta aaattaagat atacctcagt agacagagca atcaaattct atagtttctt  90000
agactttgca cgttttctta cccttttccc ccgtttcgtg ttcttataaa agtattttcc  90060
aggtttgtac atttaatctg aatctccgta cttcatctga acaaaattcc cgtaagtcat  90120
ccttcttgta gacctcattt ttaaaattct aataataatg acaataaagt tgataaaggc  90180
tttcttattt atttattttt aggctttcca tttgaaaagc tgtcacatga aaatcttctc  90240
gagacagtct gtttggggga tggtgtagat acatgtgaac ttttgccagg ggtttgtgga  90300
tgcagattcc tttggggtca tgggtgagcc atagaggggt gaacttcaga ctgaatgtta  90360
aatttttctc ttctgaggta acccctaagc catatttgtc attaggaccc tcttactgtc  90420
```

-continued

```
cagttttcct cctgccctga gatgattccc tgactcctgg attcttcatc tcctgcttac  90480
tagaacccca gcccatcctt ggcagtgagc agagggcctc atctagcaaa tcagacatgc  90540
ccactaaggc atatcttctg cagtcagcct ttaatgtcac tgggttatct tcctggttgc  90600
acacagtttg acagtacaat cgtcgcttgg tatgcgttgg ggattggttc taacaacccc  90660
gaatatacca aaatctgtgg atgcccaaga cctttattta aaatggtgta gtatttgcat  90720
atgaactgtg tacatcctct catatactta gtcatttcta gtgatacctg taataactaa  90780
cgcgttgtaa atgctatgta aatagttgtt atactgtatt gttttttatt tgtattttaa  90840
aattgttgta ttgttatttt ttattaatta gctttcaaat atttttgatc tgtgattggt  90900
tgaaaccatg aatgcggaac ccacagatat ggaggactga ctgtatctta cacacagaac  90960
caccctaggc tccaaacgct ccaagttacc cagagagaag tgtctttgtc tgttctctca  91020
gatctgggca gcaaatgatt ctaaagggac taagagaaaa tattgcagtg ttggtagcag  91080
acattaactg agctcttagt gccaggccta gcactaagca cttcatcagt ttttttttcc  91140
ctcattttat catcacatta atgctgtgca gttggacctg ttcctgtctc ctcttttctt  91200
ttttgagatg gagtcttgct ctgtcgccca gactgcagtg cagtggcacc atctcggctc  91260
accgcaacct ctgcctccca ggttcaagca attctcctgc ctcagcctcc ccagtagctg  91320
gggttacagg cactcaccac catgcccggc taacttttct atctttagta gagacagggt  91380
ttcaccatgt tggtcaggct ggtctcgaac tcctgacctc agaagatctg cccaccttgg  91440
cttcccaaag tgctaggatt acaggtgtga gccactctgc ctggcccctg tcttgttttt  91500
aacagatgag gaaacccagg tctagaaagg ttaagtgatt tcccaaagct cacacagtga  91560
gtgagtgctc aaactgggac agggaccctg acaatctgac cgcacagtcc catgttattg  91620
cagttggtca ggatgcagcc tgcctaatgc ggggcctcat gttgtgaatg atgagcacag  91680
gaagggcagc aacgggattg gctgttgccc acatcgaagg atgcagagat gccacaaaac  91740
ctagcctggt agcagaagga agggccgaaa gcagtgatct tgtaagtttt cactcatttt  91800
agaagtcagc atatttcaag catatgccct tcgttttctt ttccgttgtt catgcctcag  91860
ctcagatcct tattattcta aaaaatattt ttgttaaata aagtacttct tctagaacat  91920
aaaagaatta catacacatg gtcataaaat ccaaatggtc tagaaagttc tgaaataaaa  91980
tgtattttct accccctctc tcaactccta atctctctgc ccacaggtga tcactgctaa  92040
gtctcttata tatccttcca gaaacgttta agtgcccttg ttctcacacc tcgctgtggg  92100
acagctgcct tccccacatc ctattctgtg agcctcgctg atgagagcgg tgattttcag  92160
ggaggaggca cagaagccca gccatgcctc tgcctctgct gggtgttaac gtcatccagg  92220
actgcggtcc caagcaattg cttaatcggt tcccactcct ctattgattg cagcttccta  92280
tgcaccccat agtggaatcc tggaaactgg tatccagtga tgaggggcta cgctgcaggc  92340
catgcagaga gtgttctggc tgtacaacct gccagaccct ggccatttgc ggaagtcgtc  92400
ccattgctag gcctcttttt tttttttttt ttttgagacg gagtcttgct ctgttgccca  92460
ggctggagtg ctgtggtgca atctcagctc actgcaacct ctgcctcctg ggtttaagcg  92520
attctcctgc ctcagcctcc caagtagctg ggattacagg cgcctaccac cacaaccgac  92580
tcattttttt tatttttagt agagataggg tttcaccatg ttggccaggc tggtctcaaa  92640
ctcctgacct caagtgatct gcccacttcc tcctcccaaa gtgctgagat tacggcgtga  92700
gccaccgcgc ctggccggcc ggttcttact agtttggctg gagcttcttg cccatgatat  92760
```

-continued

```
cctcaagcat aaggtccccc tgcaatgagt ggtgattttt gcctgttcat ggggaagaac  92820
tttcagaaga ccttcttagt cttgaaaaca cctgcgtact taagcatcca cagcacacgg  92880
ccctgatgca gaatgaatta ggaggacaga aagatttggg gaagcatcat tggccgttaa  92940
acccgctcct gaatctttct gagctctgta ggtggagctt gagatgttcc tgtggaccaa  93000
tgcaaactgg aagtcttgat gttctctgaa agttcctggc ttctgatgtg tcccgcagac  93060
gaggttagct cactacagtg aggttggata ccacatggcg gggactttaa agttgtctgt  93120
ttcatccagg gtggggctta tgcctagtct gtgacctcag tggggagcag gacggattcc  93180
ccaggagcac ccacatttac cttctcgtct tttcccgctt gcttctgcca tttgcttgtg  93240
caacccagac acttgggtgt gaggatctca gctccacaat taatgattct ttagttcccg  93300
cttttaaaac attttgacca tacaatgaat aaatgttgct catactatct gcataatgaa  93360
gtttaggaat aactgccccc tgccaaaaga ttgaatggaa ggctcaggaa gtgctcatgt  93420
acgttttaaa agataatagg aattctatgt gaaaaatggc ccacttcttt attttaatac  93480
tgaaaacaac ttcctaatcc taaaatgatt ttcttcccct aatctattct tgggcatctt  93540
cttgaatttc cagcctgctt tgagggaagt ctgggtttac aaaggcgaga ttcaaagctt  93600
ttcaaacagg acaggtcctc tggttccctg tgagaagagc ccaggaccca ccctgtgaaa  93660
gttcatccca cctaaatttg ttcatctgga ctcagtcttt gccagtgtga ttgaaggcgt  93720
ttgtaagcac atccaggagt actatccacc tgggcagtca cgcaggagac agagcccagg  93780
gtgggctagt tgcctgcttg gagatggatc gtggttaact tcacattctt gttctcttgg  93840
gccaaagtct tgttcatggt ttagaataag acagtgttca agcagcctgt ggtcagacta  93900
agattgcgta gtcatcctca aaagtggcct tccagtgtgc tctgtgtgag tctttttttt  93960
tccatagaaa ccagccaaag gacagtgata tatttaagaa ataatcattt tatcagacac  94020
actgaaatgg atcaggataa acaagaaagt aactcggtgg agccctgtgt actgccaggt  94080
gggagaggag ttctcttgtg tggttatggg aaaaggtgta ttttctttcc attgatgctt  94140
catcccacgt gtttagtgca ctggtttctg aaaccgaaga caagaggcag cccatttcca  94200
ctgaatagcc tggccatcaa taagtttcca gaaggactgg ggagaaacaa agaatggccc  94260
ccaatgctgg ggtctggggt tattttgagt taaagggact cggagctact gaatgtcttc  94320
cacattcaag tcctagaact ctttccttga gatattccac tttacatttc caaagacaga  94380
ggaaatatgg tagagccaat ttcctaaaag ttttcgtaga atttcataag cacagcattg  94440
atccatgatc cgggtggtct gagaggggat ccattatcca gggctccagt acaggtgcag  94500
gtacaaccat aaaggcacta atgaagccag agaggactgt ctgcatgtcc tcaagtgact  94560
ctctggagga attaggacag aaagaaaatt tacattgtga tcagatggta tagaaaaatt  94620
tcatagaaaa acctgaacat aggaacataa aatttggatg aaatctggta ctgcatggac  94680
tggagggcag aggagttaga ttccagtggt tttctaattt ggtttctgac ttctgccagc  94740
ccccaaccca ttcctttcta agattcgata ctctggctgg gctctggctg acttccagcc  94800
ttctcagatg gagccaggat tacatctgtg tctttgcatt ttgtatccag gtttcggctg  94860
agtccagctc ctccatgaac tccaacaccc cgctggtgag gataacaaca cgcctctctt  94920
caacggcaga cacccccatg ctggcagggg tctccgagta tgaacttcca gaggacccaa  94980
aatgggagtt tccaagagat aagtgagtac ttctcttggc catgtcccag gatggagact  95040
cagctataaa tggggatatt ggattaacat tttcttttta tgacccttag ccacaaaggt  95100
cttggtgtga tgatgtcagc aggagtaaga ttgtatttct aaataaccaa ctcctggaaa  95160
```

-continued

```
agaaaaaaat ggatttaaaa aaaaaaataa ctccttgaaa gcagagctac ttgcccctgg  95220
ctggtcccca aagaagatgg catctggtta tcatttttta agtgtctggg caattcagac  95280
tccgtcaaat ggaataaaag tagaattatc caatttataa aacagatctg acattctagc  95340
ttttggttac tagaacaaga ctgttctctg ttcacttctg tggagaaatt agatgcagaa  95400
tataaatggc cttaaggacc gctacccagt gttgctgttc tcattggtta ttaatgtcat  95460
attgggctga aaagcttcaa atatggtacc tgacatctaa tttctgtgat ccataatatt  95520
ttccttgttg gatgatacag aggtgtgcca atcagatgtt tagtcaaaat atggccacct  95580
gggtggtgtt ggggctacgt atctcttggt ctcgcttgaa ctccacgtac tggagctccg  95640
ttgggctgca tttgaatcct ggctttgcca gacagtggct gggcaacctc gggtgaggca  95700
cctgattctc tgaaattcat tctcataaaa tgagggtggt ggttcagacc tcccaggact  95760
gagcagagtt cttggcttgt gcgagttttc ctttcatttc ccttcacgtg gtggtaacct  95820
gggagctctg aactgcaaac ctcagcagga tcatcgtgtg gggcatggag tcagtgggca  95880
gaatttgagc tcctagccct cgtcctctag gcagggaccg acccctagat cctccttatg  95940
aaaggaagtg cagtggtcat tgtagggctg tccactcact tctggggtac tttttgtcgt  96000
cacagcttga gagtacggga aggtggaaat gctgactact tctgcatcac atacactgga  96060
ataagctctt gacttgctta taagcagcta ccctgtttgc cttgacattt tcagtagctc  96120
ctcagattat atacacttct catgtgtacc tatacacatt tggaaatgca aagataagct  96180
cttccagaga ctgatctgat gagctctatt tggaagggag aggtagctta tgtggctggc  96240
acttctgatt ttgattcacg tgatgtcaca tcagttttgt ttcccaagtg ccaatttaga  96300
gatgtgtacc gttagctagg actgaataat tgtatggata ttatttggtt agagtgttaa  96360
tggaagtaat ttccagttga tttgtatact gtagtgaaaa gaccactcac tcattcactt  96420
attcattcac tcaaggcatg ttaattggac atttactggt ggggcaccag agaaaacaca  96480
aagaatggtt tctttacctg taggatgtgg agaaatggat gtttcttgtg aactccgcca  96540
gccctagttt gtgtgtgatt atatacacag ataggttcat gtgcacattc ctatatatat  96600
aactgaactg gggagttgtg atcatatttt aagaaattgc agctttcggg tttagtccat  96660
agtttttgcc acctgtgaca ccacagtcaa cagtggaagt ctgtatgtgc ccaactgtta  96720
cctcccaccc ggggtaccct gagtgtggaa aatctgagtg ctaaacattt caaaacagtg  96780
tttagcgcaa acgtaggtgg aacagatttc caatgaatga aggctattta gaagcagttt  96840
attagatcgg aggcagaagt tatacaaaga aaggattgtt atgcttgtag tagcaaggcg  96900
gtgggacata aattagccat ttttccaatg caaatattta ttttctgcca agatgttaaa  96960
tttaattttc gttctgggta gaaacaaaat gacctcagca tagcacatgc tgcccttagt  97020
ctttatgctg cacttttgca aactattgtg tacttacctt aaatactgtt tactaatggc  97080
agctccatgc tttgctgtgt tatgcttaag ttagaaagag ccgtattcat aagtattcca  97140
aagacttttg cgttttgttg gtttctggaa tgcacaagga caatatatgg ctattcgtcc  97200
gatgtgcata gaccttgtaa tcttagaaat ttaatttgtg gtgttcactt tggattttct  97260
tcattgttaa ttttatgtag tcataaggac ttttaaactt atgtcaaaaa aaaagtcccc  97320
aattttttag aattttcttt ttagtaaaaa attagagatt ccttgaaatg cttttaagag  97380
gcatatcctg taacttggca aggaatgtga ccataaaatc cattggtatt tgaataataa  97440
ttttaaagcc accattttac agggacaaaa aaataagaac agtcttaacg ttttttcttt  97500
```

-continued

```
gagccattct aaattacaaa tatttaattg gctcaagatc aaaagctctt ctctggcact  97560
taggaaagct gaccaccgca ctagcaagga taccttccct aaagaaaata aaccgagaat  97620
accaatgtga aatttaatag ccgttccacc agtaattgac attctctaaa acgtcactag  97680
gaaaatactc aggcgcgtgt gtaccctaag tctcattagt tccatatgat aagcactcca  97740
tgctttagta agccgctgaa agatttttat atttagttct ggaatttccc tcactacacc  97800
ccatcaccag atgctatgtg ctaatcccct atttacacat ttaggctgac actgggcaag  97860
cccctgggag aaggttgctt tggGcaagtg gtcatggcgg aagcagtggg aattgacaaa  97920
gacaagccca aggaggcggt caccgtggcc gtgaagatgt tgaaaggtga gcggggaggc  97980
gggaggctcg gggaggggct gggtggagag tcttatcaag aaagttcctt ttgtggcatg  98040
tgaactctat catggcacgg ggtcagagag cacatagttg acctaggggt tgagaagttt  98100
tcggtataaa tcagcatctc ggacagacta tttatcttga gctgtgtgta cttataaaga  98160
aaagccagtt ttgttagaaa gcggtagcct cctacataga gttattcttt gactccttct  98220
tcgtgaccac aattcttcat tctctctgta tttttatgtg cttagaaatt atcaactcac  98280
atataattga atttattagc taggagttgg tgtgttagat ttgggactta aaccttaact  98340
ttacaagtac aagaaaattt gtgtttttgg agggaacgaa gagacgtaag ggagcagaaa  98400
gccttctctt ttgcgtgagg aacaaagcag aaatgacact ggtctgggag agtcacttag  98460
aagctgagaa ggagtgaaca ggatcagggc tggtgcagag cctcctggga cacataaaca  98520
attaccctga gatgtaaatg tcgtgttgtg tttgtgggac tgtgaacact tctacgttaa  98580
ccttccaacc ctgcttcatg cccatgtcca aagaacttaa agaactttta accattaact  98640
tattcgtcct gcagtattct tttatgagaa gagttatagg gaactgtcac attataaatc  98700
ctcttgtagg gatctcggaa agaagatccc atgccgagtg tttcccacgt ttccaggcag  98760
agaggcccat ccttgggata tggtgctggg catgtcgcag gcgctctgga gttaggcttt  98820
gtctttcttt tgtgggttct catgggatag tcatcacatc cctcccaagg ggaagtagca  98880
ggctggactt tgtcaacaag atgtgcattt tgtttttttgg gtttttttaaa aggctgttta  98940
tctgagtgac tcccaaggaa aactagagtg ctttgagatg ttccccacct tggagcctga  99000
tgccggggag gaacactgtg ctgtcttgcc ccaggtgtca tggcaccact gactgaggca  99060
gcccctggct gcgtaccagg gccaggtgtg gggaggaccc aggcttctca tctcttttgg  99120
cggaacttct ggttttgcta atggagctca gagttacatg ggatattgca aaaagggagg  99180
tctgggagtt ctctttctct tgtgatgccc aggctggcag ccttccctgt aaggacacag  99240
aaggatatta gtccccaagc cattgtggcg tgtcctttct tacagcccac ggctgtgtct  99300
ccctccctcc tcatggcccg tggctccctc cttcacatac atcagtgtaa attttgcaca  99360
cacagtcact tgtattgatc ttccttttgt gaagctaaaa aactgtttgc aacatggttg  99420
cttatccatg cccatatttc attttttttt taaaggaaac ccagattttt ccatactgaa  99480
ttagcttgag gtggagggca catgggaaag tcttgccact taggagaatc taagagaagc  99540
taactgcgag cccgcgtatg tggaacctgt gccattcttg cttgaaatta cagagcggaa  99600
gtttatgtaa cttttcttag gatgggaact gcagtgccct ctgagaagcc actagaagtc  99660
gcagcccttt acctgctcag aatgcacatg cacacacgtt tatggccctg tttatgggga  99720
accgtctgaa cccacctcgg aacgctctaa gggcctcgag ggctgggtt aagaatgctt  99780
ggtcgggagc aagtctgtag tgatttgaaa tggccctacc ctcggtctcc tcgctggttt  99840
caggcaccat gaagtttggt gtggttttct gagacgcctt agatatggca gaggatgaga  99900
```

-continued

```
ttatctcatg gtctaggaaa gaattggcat tagtgtcaga agcccctgct ctcgtcctga  99960
ctcttggccc cattggcccc ccagtgagct ctttgacaca gagtgaggca gttccctgtg 100020
taggcctttg tcccttcctc gataaaatga gggagatgat ttggaaaatc ttttctgatt 100080
ctgaaattca atttcatgct gtttcaacta agtctttggc aactaacagt agctgcccat 100140
gagttagagg aaatgaactg atttgtgaat atgcctactg ttcatagatg atgccacaga 100200
gaaagacctt tctgatctgg tgtcagagat ggagatgatg aagatgattg ggaaacacaa 100260
gaatatcata aatcttcttg gagcctgcac acaggatggt gagtaggagg aaaaactgca 100320
ttcgcccaaa tactctgcag tttgattgaa tcattttaga aatggctggg cttccagatc 100380
ctgctcccag agcaccctgt gtgcatgttt aaagttcttt ttaaaatccc cattggaaga 100440
tgttcctagc catgaacaca aagaagggtc tgtgcccgta cctgggggcc agtggaaagg 100500
agggtgcagg tgactttgga tttgagggcc tagagggcgc tgctgtttct aggtcataac 100560
ctggaggggg ttttggaaaa ggcagcctcc ttatgttttt gttttgtaag tgctaagaga 100620
gatttgtcag aataagatcc tatgttttgg ttgagaagtt cttcccttaa aacagggatt 100680
gaagaatcca catcttgctg tgggtcacag atggctgagc tcccaagaat agcttaaaag 100740
aggagaaagc ggtatgaagg aatacgttat tttccctggg ggagagagac cctggcttct 100800
tccattgaat gtttactggc actttgaaat caatttgcta agtaattagt aaacttgaaa 100860
acgcctatct ttgacttagc aatttctctt gtaggtctat atagtaattg gtgaactttt 100920
tctgtaaagg gaggtcgtag atattttaga cttttgtggg ccgtatggtc tttgtcgcaa 100980
cttctcgtgt ctgccatagt agtgagaaag cagtgctaga agtacagaaa tgaatggacc 101040
tggctgcatg ccaataaaat ttaattaccc aaacaggcgg taggcaggat ttggcttgca 101100
ggctgtagtc tgccaacccc gagcctatac catggagaaa ttattgcaca cgtgtgtaag 101160
ggaacatgta cagagatgtt cattgcctac tgtttgttat ggctgaaacc tggaagcaaa 101220
tgcctatgca tataagggaa tggataaata aagtgtggtg tgtttatacg atacagtata 101280
tgcagctgtg aaaaggaatg atctggtttt gtttttataa gcccaacagg ttccaaaagg 101340
ataatgtatg ggtaaaaaat gttgcaaaga tctaagagct ttattattca tttatgtgat 101400
taaaaataat atattactta ttgaatagtt aaaatgaacc aaaaggatag agtggaggga 101460
tccattgctt tccaagaggg cgcaggtgac agcatgagag tgacagggaa gagcacgtca 101520
actgtgtctc tgtgcctttt gaggctatca tgaccaaggg cttatttatc attttggaga 101580
gattataatc atatttttat gtgtgctttt ctgtatgtta aaactttttc tttttttcttc 101640
ttcttttttt tttttttttt ttgagacaaa gtctcgctct gttgcctagg ctgcagtgca 101700
gtggtgtgat ctcggctcac tacagcctcc acctcctggg ttcaagcgat tctcctgtct 101760
cagcctctca agtagctggg actataggtg tgtgtcacca tgcccagcta atttttgtat 101820
ttttagtaga gacgaggttt cgctatgctg gccaggctgg tcttgaactc ctggcctcat 101880
gtgatccacc tgcctcggcc tctgtaaggg ctgggattac agatatgagg caccacgccc 101940
agccgctgta tgttaaactt taaaaaaaaa aaaaaaagca tgggttgtaa taactaaaaa 102000
tgttttgctg aattgcccaa ggggagaccc tggattctct ctttagggag cttctcttct 102060
tcctcaacag ggcctctcta tgtcatagtt gagtatgcct ctaaaggcaa cctccgagaa 102120
tacctccgag cccggaggcc acccgggatg gagtactcct atgacattaa ccgtgttcct 102180
gaggagcaga tgaccttcaa ggacttggtg tcatgcacct accagctggc cagaggcatg 102240
```

-continued gagtacttgg cttcccaaaa agtgagtctt tcacattcta cttggctggg tggaatccaa 102300
ctaaaaatgt ctttaaagaa aacaggcaat ttggacatgc tcatttgcta gatcaagccc 102360
tcgcatgtct tgtacaacct ggaaaatatt tattgcgtta ttcccatttg agtttaatga 102420
actgtttaaa accaaagcag cctcataaac ctatagcatc gctgcagaga tgagcagaaa 102480
agatacctct tctttgagac aggaccatgt gtgatttccc tcggaattca gctctccagg 102540
tgggaaatgg atggttttaa aggccccctt taattcggat gattttcttt ctttcttttt 102600
ttttttcttt aagcttcatt tattttgtgg ttactgagtt tttgaacata gactttaggt 102660
gtttagtgtt ttgggtttga tatggcatta aatattctaa gagtaaaggt caaacaaagg 102720
ggtattttag taaccttgcg tcctggagct ctgcgtttat tttgcctcgt ttggcgggtg 102780
accctctgtg gttagaagtt ggccaggtcc cctgaggtgg actgcctgca ttccaggcgt 102840
gccacttacc gtggaacttg aaacatttca gttattctga gagtagttag acaggtgccc 102900
agatgtcctc ggaggcattt tggatgaccc aaaactccct tgtcagcccc acacataggg 102960
aagcggaggg gcggagctgc ctcctgtgca gaggtgggcc ttgctcctac ctgcattgca 103020
gtttattgca gtgccaggaa ttccttgggt ccccaaagag gtgagatcct ctggtcggcg 103080
tgcaccctct gtcactgggg gtctgggttg cctgaagagt cacaaactca agtctccatg 103140
gggccatgcc agtcacacca ccaaggcctg cggatcactc agagtgcaga gattcgaggg 103200
atggctgcac ctcagctcta ctctctggcc acataggaac atggcccaga gctaccccat 103260
gttctggatg gttttttctt tctttcaaac aggctggagt gccgtggcat aatcacagct 103320
cactgcagcc ttgacctcct gggttcaggt gagcctccca cctcaacctc ctgagtagct 103380
gggagtacga ggatgtgcca ccatgcctgg ctaagttttg tgttttttgt tttttgtttt 103440
ggtagagacg gggttttgcc ttttttcttt ttaatttaag aaaaacttta aaaacatttt 103500
ttcaggagag tttagagttt aagacttttt cagatctttt tcgtataaaa atctcccaat 103560
atataggttt tgggaaacta attaaacaca gttttgactt ctgtgattgt gtttacgtac 103620
acgtgcgtgt gtgtgcgtgt atgtagggta gtttgccaat ctatttggca tccagagaca 103680
accagacaga tccagaacat gggacatttg acaagatatc gcttccaaat gtcagtgtct 103740
cgaaagacaa aaactgctgg ggagacggtt ccagataaaa gggggccgat gagacaattc 103800
ctaagtgtaa aagtgggatc ctggactgga tcctgtgggt cggggagggt ggccagttct 103860
tagaaaggac atttgtgagt gtcctttgaa tatggactgt ataatattac tggttatatt 103920
tctgtatcag tgttgaattt gccgggggtg gtgacagtgg tatctgttgt aggagaaata 103980
cgctgaagaa ttgagatttg tgaagtatca gtgatgcctg cagctcagtt ttaagtggtc 104040
cagccataaa atataatcaa tccattcact atcccaagtg tgtatgtgtg tgggggcagg 104100
tggggcagga catggagaca gcaagtgatt gagtaggtgt aacaagcaaa cccagcagtg 104160
gtggatactc actgtgccat ccctcctttt ctgcagctgt gaactcttcc taaataagcc 104220
tggggagggt agcccatctg taggctgcct attttgatat tctggtcttg atcactccct 104280
gccctacctg tgtgggagat aggggaagca gttttgcacc cagcagggtg gtgctactag 104340
gggaaatgtg gtaggagggc tggctcagtc attttattaa atccttcaac atctactcct 104400
agagcacccc cgatgtctca tgcccttggt caggctctcc agcgaagtgg ccagaagaga 104460
catagtcctt gacctcctgg ggcaagaacc atgggtgaca gtaagagaaa ttgactgtaa 104520
atgtgggaat gaaaataagg ttgtaaaaaa atattgaaaa aggtgccatg gaggaaacag 104580
ggggataagg ccttactcat gccaggacgc tgcactttgc tgtcactgcc atggaagcct 104640

-continued

```
ctgaggggga ggaagaggat cagttagtgc ttcaaaaatg cctctcactg ctgcttgtgt 104700
ggtgaatggg aaggctgagc ccctgtcaaa ggtgatgatg gtttgggcta gggtctgttg 104760
ggtccaaaga caccgagaaa agctggtggg ctgatgttgg acatattttg ctcttgggat 104820
aatgaatgga ttgattagat aggagggaga gaaagagaga tcaagggtga cttctggatt 104880
tccagcttga aaaactggat ggtggtgcag cttccaagtc tgggaggact tgggaatcag 104940
ggctggggca gggggcatag atttgggtgg aaaatccgag ctcgtcttga gcgtatctga 105000
gtcatccaag gggagataat gaagaagctg caggcagcag ctcagctctg agggtgggct 105060
aacagctggg aggcagcaaa gggagctgtg agttcaagcc atgggcgtgg acaaactcat 105120
ctgcggagaa gcttggaaga ggagaataga agcctgaagt caggtcctga gaaaattctc 105180
aaatctagag attgactgaa agcaccagaa acagcagcgg aggccgagca ggcacagcct 105240
gagcagtagg aaaatcagga cacggagcac agaggcccca catgggagct tcaggaagga 105300
gggggcaggt agtagagcct cggcgctcag actggtgaga agcacgggtg ttgagtcctg 105360
gtcctagagg cagtggtggt acccctgccc accctagccc tgaggaccca gagctccttc 105420
ctgttttgga gctggcagag agaaaactaa gagacgaact ttgctaagca gggcaaatgc 105480
atccatttaa tcgtggaaga acggaagtac ccatattaaa gtgttgtgat aatagtaact 105540
atcgttatta ttaattactg acccctccgg gagaagctaa ccatcttcca ggcaccgtgg 105600
cagagcattt gacataaagc atcttacgta gccctcagaa caacccggaa ataggtggga 105660
tttggatccc ccattgtatg gggggaggacg atgaggaagc agcatgaatg gtttgagacc 105720
agatgtgtca ggaggactca gatgtcctca cttctgagaa gcggacttgt aggtctgaag 105780
agtggagtgg caggtcccag acctaggtct cctggtcccc cactcagctg tctcctgctc 105840
tcatgaggcc cctaactctc tctaaactga ggcaagacca atgagattcc acgtgggggg 105900
cgggtgaggg gttgtttagt gccccagtgt ggcctcattg tctctacatt gaataacagc 105960
ccaaggtaaa agggatattg tatgggcctt taagacatgg catggttcca aagccactta 106020
ctggaggcca cctgcagtta aggacccaga ataggtttga aaatggaggt agatgaagat 106080
gttaagcatg gtccccttgc gagggctctg cttccaaaaa tggagggctt attcttgaaa 106140
gtggagaatg aagaaccagg caaagggtcc ggccctggct ttcccacacc catcccctca 106200
caatggggag ccatgggctt gtgagagacc tgcttgcctg aaggaagggg caaaagagaa 106260
ctgttgatta catcgttact gatgtactgg gttcatctgt gctcagcgct gggccgattg 106320
agatgaacac acagtgcctg gcctccagca gctttcagtt gtgtgtgtac atgtgtgtgt 106380
gtgcgtgagt gtgtgagtgt tggggtaggg gttggggatt ggagacagag aagtgaaaaa 106440
acaccatggt gtatatagca atgcaattag gtaatagggt atttgagcct tacacaattt 106500
ataaaatcct tactattttt agctcaaatc acactaattt tactttttta accaaatccc 106560
aaacccagtt aaccctcaaa gtgttaaacc tgagcagttt gtttttcgtt tttgtttttg 106620
agacagggtc tcactctgtc acctggctgg agtgcagtgg cgtgatcttg gctcactgca 106680
gccttggcct cctgggttca agtgattctc ccacctcagc ctcctgagtt gctgggacta 106740
caggcatgta ccaccacacc tggctatttt ttggtagaga cggggtttta ccataccatg 106800
ttggccaggc tggtcttgaa ctcctgacct caagtgatct gcccacctca gcctcccaaa 106860
gtgctgggat tacaggcatg agccactgcg cctggccctg agcagttttt tttttttttt 106920
ggttgagaca gagtctagct cttttgccga ggctggagtt cagtggcgct atctcggctc 106980
```

-continued

```
actgcagcct ctgcctccca ggttctagcg attctcctgc ctcagcctcc caagtagctg 107040
ggactacagg cgcttgccac cacgcccggc taattttttg tgtttttagt agagatgggg 107100
tttcgctgtg ttagccaggg tggtctccat ctcctgacct cgggatccgc ctgccttggc 107160
ctcccaaagt gctgggataa caggtgtgag ccaccacgct cagcctgagc agttttttta 107220
gtgaagcccc agcttcccca cctgtaaaat gggtataaca ctatccatgt cataggttgc 107280
cgcaggaatt cgatgtcatc agccatactg ggcacagggc atactgtcta catcataggg 107340
atgttggtct tccttccctt agtgacccac tgaccttcac ctatggaaca ccaaactgtc 107400
ccagggccct aattgtataa aatggtcagc tccctgtgct ggagaacggc tgacattcct 107460
gtggatgacg gggatttggc ttgcctttga ttactttctt tttctcgggt gtgggttcca 107520
agtctcctct tattcaaccc agaggctggg gtttgatgtt tcctagcccc tgggatgagg 107580
gatggccacg ctagactctg gctttcgctg agaagatggt ggagggagcc gtcagcagtg 107640
tctctgtgca agctgagccc taatgcatag ttggagccca gtgcgtggga agcacattct 107700
tctgaccaca cagcttgcca gacacacaga gcgcgtgtcg gcaggagcac accaccggga 107760
gagtttggcc cggggcttgg aagttcaatt tgaacaggcc tccaaaactg ggaacagggc 107820
tgcagcccca gacgaatctc caggcagctt ctgtgagctc tcatgtttcc tgcttccaac 107880
ctggccaggg attgcaagct tgcgtggctt tcttgctttc ccgcttctgg gcttaggcta 107940
cccgggaggc ccagaagtgt gtgaacacaa ggaatagcta ggggtcgggg tggaatcaaa 108000
taattcctta tttatatttc agggatcacg tagcttgccc ctttttaat tgtccatttc 108060
gtggagtgcc taagatcgcc cccatttcag ccttgttgaa tggactgata agactttctg 108120
cttcgtatga tagttaacct ttgccaataa ccagtgtaaa aggcttcggt ggtgatattt 108180
gcttctttgt gtcttatctc ttcccaaaat agaaggtgat gattggagac cctaattacc 108240
ttgtatcttg tggaaatctt gctatatgaa agtgtaacaa aaatgcagca gctcacagta 108300
gcgtatcatt tgtagaaagg aaaaatcata ggccgggcgt ggtggctcac gcctataatc 108360
ccagtacttt gggaggccga ggcgggtgga tcacttgagg tcaggagttt gagaccagcc 108420
tgaccaacat ggtgaaaccc tatctctacc aaaaatacaa aattagcctg atgtggtggt 108480
gggcacctgc aatcccagct acttgggagg ctgagggcag gagaatcact tgaacctggg 108540
aggcagaggt tgcattgagc caagatcgtg ccactgcact ctagcctggg aaacaagagt 108600
gaaactccgt ctcaaaaaaa aaaaaaaaaa aaaaaaaaag aaggaaaagt cgtaatagct 108660
agatctttct gagacccaag agttagtgtc aagacaataa attagctgtt ctgcagcaag 108720
tatttaatat ttcagtgttt agaatcagtg tatgtggcac attcaggctg aggccaggtg 108780
ttaggagaaa ctggactgag aacgtggata gacgggcatt ggccatggta gagaccaaga 108840
aaggacatga ctagtcattt caggaacctt agtcatggga catggaggag gtacaacagg 108900
gctaagtttg gaagcgtaga gacccgctag acgggcagtg tggaagtctc agggggaggg 108960
gcagacagtg aagatggcct ggactaaggc attagcagtg ggaaaggcat ggtgtggaca 109020
catgggaagg cattttggag ttgaaatcaa caggacttgg gaggaatgtg taaagaatac 109080
cggtgtatag ctctccgatt aagagagaca aagcattgga ggagttgaaa ccttgaattt 109140
gagacgtcaa gggaatgtca gtggggaagt gtcccataga cagttgaaaa tgagaacatg 109200
ggtctcagga gggaggtcat gatggagata cgaacttgcg catattttgt atgtgtttag 109260
aattaatgcc ttgaggatat atggaaatac ataaacttaa tggaacaatt cctctatttg 109320
aagggacaga aaaagagaag agccagccag agattctaag agggcaggga gagacagaga 109380
```

-continued ggcagctgag ggaaggggac gggataaaac taaacagagg ggctgggtgt ggtggcttac 109440
acctgtaatc ctagcacttt gggaggccga ggcggatggc tcacctgagg tcaggagttc 109500
gagaccagcc tgaccgacat ggtgaaaccc cgtctctact aaaaatacaa aatattagcc 109560
gggtgtggtg gcaggcacct gtagtctcag ctactcggga ggctgaggca ggagaatcgc 109620
ttgaacccag gaggcggagg ttgcggtgag ccaagatcgc accattgcac tccagcctgg 109680
gcgacaagga caagactcca tgttaaaaca aaaaaaacaa aaacaagaaa acctaaacag 109740
agggaccatt ttaaaaaaca agcaagaaat caatagcatc tgaagccaca gaggaggaac 109800
aactgaggag ttggaggacg tcatttgcgt ctaacaattc agaggttctt cataagcttc 109860
aggagaggca agagtggaac acagattaga atgtttgaga agtgaccagg aatgaagaag 109920
acacaatgtt ggattttaac caacgcttct gaaaattcag gtttaaaggg caggagagca 109980
agtgttgaga gaaaagattt taggatgatc agatacagat ctataagcag ctgaaagaaa 110040
gacactggtg tggctggaca actggaggta gaagagaata tggttattta gtctaccttc 110100
gctcttcaaa atgatcattc tatttattta taattccaaa acaaatacat gtcgtgatcc 110160
aggctctccg atgatcccag ttgacctgtc ttcttaatct tagagccaca ctgcgttttc 110220
ttttcttttc tttcttttt tttttttttt tttgagacag agtctcactc tgtcacccag 110280
gctggagtgc aatggcgtga tctcagctca ctgcaacctc tgtctcccag gttcaagtga 110340
ttcttgtgcc tcagcctcct gagtagctgg gactacaggt gcacaccacc acgctcggct 110400
aatttttgta gttttagcag agatgggatt ttgccgtgtt ggccaggctg gtctcgaact 110460
actgacctca agtgatccgc ccaccttgac ctcccaaagt gctggtatta caggcatgag 110520
ccaccgcacc cggcccacac tgtatttctt atagtatacc gcaactggtt tttaacatca 110580
gctatatttt ctatctgcat tttaagaaat gaacatattt cctttttgtt ctggcggtgt 110640
tttgaaatta gttatttctc ttgcttcttt cttgatttca gtgtattcat cgagatttag 110700
cagccagaaa tgttttggta acagaaaaca atgtgatgaa aatagcagac tttggactcg 110760
ccagagatat caacaatata gactattaca aaaagaccac caatgtaagt cgatggcagt 110820
aacacagtgg gcaggggcgg gggtgaggct cagaatgttc caggaagaaa ggccgtcaat 110880
gttgagagct gggtgggatg gctggggacc cattcccctg ccccgattcc cgttcttttg 110940
acttactatt cacaaactct caatatgcaa atttagcctc tattatgtca attttagtaa 111000
atgtgaaaca cttatataca gaataatcag caaccgctag gattttctta tggttctcat 111060
caagaacttt catagcaaaa actacagctt ggaagttact ggtttaattt ttgcctaata 111120
actggtcaag gagcatctgt gtgctaggga gataaaggat agaatccaag gagatggcat 111180
tttattaacg gcccagacct gtgcatctca cacattgttc atggtcctca ttgggactga 111240
tttctgctct attgactgac tagtaaaaac cgagaatatc agctcttaaa cagggcatag 111300
ccctattgag cctgctaaga taaattcttt taaatatatt tagtttttgc attttcctct 111360
acatttgcag gggcggcttc cagtcaagtg gatggctcca gaagccctgt ttgatagagt 111420
atacactcat cagagtgatg tgtgagtaac tctcttttct ctggcttttt cctgggcttg 111480
agctgcaaaa atactgtacg tacttcacct ttcttccttc tttagtggct gctgcatttc 111540
acacattcgt agaaggtgca ggagctggcc ttagaaagga cagattttat ggtaggctga 111600
taaccaatgc tctgttacta atctgcctgg cttcaaagag cacagaaggt ggaactgctg 111660
acctccccct gccagagcgg aagtccttcc cttgaacata ttcatggatg tgcaactaca 111720

-continued aagcggttat ctaattcgcc aagctcttgg catgttcttc actccattaa aggagtaatc 111780
ctggagcttt tcccacttac gagtagtttg tcatatttcc ctctaaccca gatttgtcct 111840
taaagagtgg agctgagtga gatgtggtcc aggctgggga cctccacagg gtctactctc 111900
tatgtttatc cctcaacaaa aaggtctgat cttgctttgg catccttgat agcattctag 111960
aaacacagta gaatatttct attatgatat actgacaaaa ccagtggggt caggctccaa 112020
ctgatatttt agatttgaaa attcagttga aggctgtgtg cagtgactca tacctgtaat 112080
caatcccagc actttgggag ggcaaggcgg gtggatcacg aggtcaggag atcaaggcca 112140
tcctggccaa catggtgaaa ccccgtctct actaaaacta caaaaattag ctgggcgtag 112200
ttatgcgtgt ctgtaatctc cactacttgg gaggctgagg caggagaatc gcttgaacct 112260
gggagtcaga ggttgcagtg agctgagatt gtgccactgc actccagcct ggcaacagag 112320
cgagactctg tctggggaaa aaaaaatcac ttgaactatt ttttatttgt atgagcagga 112380
ggagttctgg gtaggcatta attctgtgct accatagttg gtcctctcaa caatcctaaa 112440
aaaaagacat gactatccca tttttgctgt gagcaactga ggcacagagg ctgttctgcc 112500
tgtcctgtgc tgctgctttt gctctgtaga aaactgcgga gtgaaacacc accatcgagt 112560
acagaaggtt gagtttccag aacgaccatg atgtagctaa acctggctct ctcagcttgc 112620
tcctcccaga gattgagcct cctgaacttg gcacaggaag tccaaatctc tgaagagtca 112680
agtgtaaata aattatggcc tgtgagatgt gttcagtttt gttgtgtgca actcatctgg 112740
ggcatgtgat tcctcatcct aaccccagcc cagtgctgat tgcctttgcg atcttagtaa 112800
gttccagagc ctctgtgcag cagatgttcc gccagccaca cagggcagct gtgatcctgc 112860
ggagttggct tgctggcctt attctgtcaa ctgcccatcc tggtagatca caacccttgg 112920
gtcaggcaca taaggagttg gaaaggagcg taaaggcttt gaaactgaga aactgagatc 112980
cttgcattgc taacaccaca tttaagacaa gcagctctat tccagagtga tggcagtttg 113040
ccttttttgtc tattgatgga aaattccatc agcacatccc cgtgtcatca tcattcgggg 113100
atgctcttgc agggcaggaa agagcacata ggaggaactg caggagggcc catttgtctt 113160
tgaacttcag aagtgaggag gtgtttatgt ctcagctggg cgtgtttagg ttttggcaac 113220
gtggatgggt tagtaatgcc gtgctttctc cttttgttgc agctggtcct tcggggtgtt 113280
aatgtgggag atcttcactt tagggggctc gccctaccca gggattcccg tggaggaact 113340
ttttaagctg ctgaaggaag gacacagaat ggataagcca gccaactgca ccaacgaact 113400
gtaagggctg ttgtctttcc tgccggtgcc ccagtggact tgccacacca gtaatacctc 113460
tcctgatgta tctcgttttt gaaggcccct ggtttcctaa acatgctcta agaagaatgg 113520
ctgaagctct ctgggctcaa tccagagctg ggatacatag cgacaccgac aaccattact 113580
tgtctgagag aaagaacatt attctgagta tggagagggc tttggatcag agggtgtctg 113640
gctgcctggc tgagggctcc tgactttgca gagccagcag gagtggtctt cctgggccac 113700
tgtgctgcac cttctgcggt ctcccgtgga gtgacaggaa gacccacggg tcaggaaaca 113760
agctagaaag ccgcggggcc gccctgcagg gtgtaggatt aaggaaccaa cacagccttt 113820
ccctggtggt tgtgcctggc ccccgcctgg ccccatcgtg gccagtagag aatcggtgtt 113880
tccagaactt ctcgaaccat tgaaaattgc cattacagat tgacgccaac cacatttcct 113940
cagagcgaag gaactcgtgt ttggttacct aggtctcact tgtgttttag tgcagagaat 114000
taaacatgtg tccaggcgcc ctccttactg taccagatct gcctgtaaaa ccatgaactg 114060
gtttgtagca aaacctgcct cacactttaa gtggagttat gttgtgtttg tgacgtgtgc 114120
ctggtgcaat agaatcagtg ctttgaaagg agtctctctg cctcctgcct caacccctcc 114180
aggattaact aagaagagtg attgtcccag aaactgcggt ctattgtgta tcatttcatg 114240
gggattttat atcagtaatc ccgtgagtgc ttttcggtgt accgtggatg tctgatgaat 114300
ggccacattt tatagcatat tatataaagg catttattgt gctctttgtc attcctattg 114360 tttttttttct tttgtaacgt agaggatctg tcgaaaccca aaatcaagat aagacctggg 114420
aagctaagcc tatctaagag ttaatcagga agttagtgtg cagcccagtg gtggcagatt 114480
aattcatcaa aaacttgaag ttgtagtttt caaattttat ttaatttttt tttaactcag 114540
gaagctgtgt caactagaat cattaagacc caaagcaccg ggcagataaa tagtggagct 114600
gctttggtgc tgggcagggt gtcaggggag ggaagactgg agaccagccc atggaaatac 114660
gcattttcct tcagcctcca aagcatcttt agggtgtgac gccattgtga gatgtcactg 114720
tggcccaggg ttaccaggga aaacacatag ctgtgtcttt cttgatggct tcgatgcctt 114780
tctaacatgt ttttgtaagt caaagtgcct ttcggaggaa ctggcaggga agcttttggg 114840
aaagtgattc atgacccccct aatctagttg cttggaaggt tctgatgcat tttcctaatt 114900
tacaccacgt ccccatattg cctattaaaa ctgactataa ccacgtaccc agtgcatatg 114960
aaattaattc aaggaaatcc atttttccca ggtacatgat gatgagggac tgttggcatg 115020
cagtgccctc ccagagacca acgttcaagc agttggtaga agacttggat cgaattctca 115080
ctctcacaac caatgaggta agaacttcct tctagaagcc ccttgtcctt ggttgtcttg 115140
tgagacatgc gtagtgtttt acacacacac tcccctgttg gctgttggtt ggagtctgtg 115200
gtcttgttta ttctttttcc atagggtcag atagttcaac tatgggttcc tctcaaatca 115260
tgatttttct cagaacttca ttttgtgagt tctgactcat gaaaccaaag acagagggac 115320
atccccgagg ctgccttcag tgtagctgct ggtggagcag tccggggtat gtgggagagt 115380
gggaaagggg aagcagtatt cacttgcatt ttggtgtgca tgggaaaaag cttggattcc 115440
tgtgcaagtt tgattctgtg ctttggtcat tagtgggtaa actgataatg ttcgtcatca 115500
tttgcttgat ggaatacaat gaagttttct aacaccagct tctgttacca cagtactatc 115560
ctatgtgatc ctgttggtaa tgctatatgc cttgcagcct ctttctaggt gtatataaac 115620
atacactgtt ttctacaatg agcaacttac atgattttta cataaaaaca tgtacctttt 115680
gttaaaatat ttattttccc taaaatattt atgctctcgc ctgtaatccc agcattttgg 115740
gaagccgagg agggcagatc acctgaggcc aggagttcga gagcagcctg gccaacatgg 115800
cgaaaccctg tctctactaa aaatacaaaa attagttgga tgtggtggta tgtgcctgta 115860
atcccagcta cttaggaggc gaggtagggg aatcgcttga acccaggagg tgaagtttgc 115920
agtgactgag attgcgccac tgcactccag tctgggagac agagcaagac ttcatctcaa 115980
aaagaaaata ataataattt atgatccttg ccaacaaaat aaacactcgt ctgtcactca 116040
ctgtgcaaat ttagccatgt cagtggctcc ttcaatatgc agatagagtg ccttttataa 116100
ttatggaaag catatgctct gagcaggaaa gatgataaac ccatcaagtc tagtcaaatc 116160
ttaagataga gaaattgtta atgaatgtat tttgagatat ttaatgagga tgcacaatag 116220
tgttctttta cacaggaaac taactccaaa ccatgcaatt gtctcaacaa gaaaaaagtt 116280
aaagtccccc aagtatttta gaaggaaaat aatacactta atttctgatt taggaaatag 116340
ttttagagtg attttttaaa aagtaataat caaatgtagt gatatgaagt cttagctcag 116400
cagctttatc ttatgcgtct gactgtggcc tgtgctggat aaaggaagag attgcactta 116460

-continued aatgaataca gctgaccttc agaagttgaa aggaaaggaa cggttcaagg gggggaagaa 116520
accaactttc ttcttctgcc aaaattgttg tttctagtat aagttccttt aactgtagac 116580
ttggaatcta ctgatatccc tgttttttttc ctatcagatc tgaaagttta tggcttcatt 116640
gagaaactgg gaaaagttgg tcaggcgcag tggctcatgc ctgtaatccc agcactttgg 116700
gaggccgagg caggcggatc atgaggtcag gagttccaga ccagcctggc caacatggtg 116760
aaaccctgtc tctactaaag atacaaaaaa ttagccgggc gtgttggtgt gcacctgtaa 116820
tcccagctac tccgggaggc tgaggcagga gagtcacttg aaccggggag gcggaggttg 116880
cagtgagccg agatcatgcc attgcattcc agccttggcg acagagcgag actccgtctc 116940
aaaaaaaaaa aaaataaaaa taaaaaagaa agaaaccggg aaaagcacta aagttctatt 117000
ttaatgatct catgtctatg ctcaaagtga tttatttata tatttacatg tagagtgggt 117060
ccgttgatac tgaaatttgt atctagtacc ctaaaataaa aaagcagaat gccatattgt 117120
ctggtggata taaaaatcga agtttctttc cttctgaaaa tcattaccat atgctcaaga 117180
aaaacggttc catttaggac aaaatttcgt ttttatcatt gtaagcaaaa agttctcttt 117240
tgatgtggtg ggcgtgtttg tttccagttg tgtggttaat gctgatgttg ttggaactga 117300
tacattcccc ttctgggatg ctgggatggg gactctttct cttgccaacc ctggtgatga 117360
attagagggt tttgtgtgtg tgtgtgtgtg tgtgtgtgtg tgtgtcttta aaaatgtcta 117420
gttgccaaca ttccatgggc tcttttctga taacactgag gctgtttgtg ctgtggtctg 117480
cactttttgc cccctctcag caaaaccaca tgtcatagaa tagttgttgg cttctggatg 117540
tgtgagcaga actgccccac tgtgccagcc cagtggaggc agagagaccc acaagttccc 117600
aatttagaaa gcttttcata gcttcagaac aggggtcggc aactgctttc tgtaaagggc 117660
cagggagtaa atattttcag ctttgccggc cctgtggtct ctgttgcaac ttcgccactg 117720
tagcctcaaa gtagccacag acaatatgta aatagatgtg ttctagtctg tcttctagta 117780
aaattttatg gatcctgaaa ttggaatttt atataattgt atataaattt tattcatttt 117840
aatcctataa gatattcttc ttcttttgat tttttttttc aaccgcttac caatgttaaa 117900
gaccatcttt agccctcagg ccatacaaag tcgtctgtgg gcacccaagt cggaggaagt 117960
gtcaccctgg ggtgatccag agggcttttt gcagcaccag cactggatgc cttggggagc 118020
aaaggacact ttctgaatct cgaaccttca aaactttgaa acttaaccga tattttcctg 118080
aagtttcctt taacagtgca ttatggattt aacatacatg agtatgtcta agcctttttt 118140
gaacctgttt acattttcaa ctcggagagc ttctgagagt aatcagttac atctgttaaa 118200
ttacccactg aatgaagaag tattcccctt caattatccc cgaaactaca atagtaaaat 118260
gtaattcaga aaataaatat tcatagtctc aactacttaa aggggtctg gggacccaca 118320
acatgttacc ggttttcatt ttgctggggc tcgcatttga agcaagggct ctagtgagga 118380
ggtggtgtag actcagcggg ttatttaggt ccgtgtgaag ccgagttgcc tgcccagcac 118440
ctatagctca actaggtttt attgttctct acctgtcaat agttgattta tgatggattc 118500
caagagaaaa gctaaggaca gcctggggta catcagacgt ggtctcaggg aggtcttcgt 118560
ggaagtcagg tgggctgggt ctctgttcac cttctagggg tctcctgtcc tgtcccacgt 118620
ccaataccca catctcaaga gtttgtgttt gaaataaaac tcttctcttc ccttctttca 118680
ggaatacttg gacctcagtc agcctctcga accgtattca ccttgttatc ctgacccaag 118740
atgaaataaa acgtctctct tcccttcttt caggaatact tggacctcag ccaacctctc 118800
gaacagtatt cacctagtta ccctgacaca agaagttctt gttcttcagg agatgattct 118860

-continued

```
gttttttctc cagaccccat gccttacgaa ccatgccttc ctcagtatcc acacataaac 118920
ggcagtgtta aaacatgaat gactgtgtct gcctgtcccc aaacaggaca gcactgggaa 118980
cctagctaca ctgagcaggg agaccatgcc tcccagagct tgttgtctcc acttgtatat 119040
atggatcaga ggagtaaata attggaaaag taatcagcat atgtgtaaag atttatacag 119100
ttgaaaactt gtaatcttcc ccaggaggag aagaaggttt ctggagcagt ggactgccac 119160
aagccaccat gtaacccctc tcacctgccg tgcgtactgg ctgtggacca gtaggactca 119220
aggtggacgt gcgttctgcc ttccttgtta attttgtaat aattggagaa gatttatgtc 119280
agcacacact tacagagcac aaatgcagta tataggtgct ggatgtatgt aaatatattc 119340
aaattatgta taaatatata ttatatattt acaaggagtt attttttgta ttgattttaa 119400
atggatgtcc caatgcacct agaaaattgg tctctctttt tttaatagct atttgctaaa 119460
tgctgttctt acacataatt tcttaatttt caccgagcag aggtggaaaa atacttttgc 119520
tttcagggaa aatggtataa cgttaattta ttaataaatt ggtaatatac aaaacaatta 119580
atcatttata gttttttttg taatttaagt ggcatttcta tgcaggcagc acagcagact 119640
agttaatcta ttgcttggac ttaactagtt atcagatcct ttgaaaagag aatatttaca 119700
atatatgact aatttgggga aaatgaagtt ttgatttatt tgtgtttaaa tgctgctgtc 119760
agacgattgt tcttagacct cctaaatgcc ccatattaaa agaactcatt cataggaagg 119820
tgtttcattt tggtgtgcaa ccctgtcatt acgtcaacgc aacgtctaac tggacttccc 119880
aagataaatg gtaccagcgt cctcttaaaa gatgccttaa tccattcctt gaggacagac 119940
cttagttgaa atgatagcag aatgtgcttc tctctggcag ctggccttct gcttctgagt 120000
tgcacattaa tcagattagc ctgtattctc ttcagtgaat tttgataatg gcttccagac 120060
tctttggcgt tggagacgcc tgttaggatc ttcaagtccc atcatagaaa attgaaacac 120120
agagttgttc tgctgatagt tttggggata cgtccatctt tttaagggat tgctttcatc 120180
taattctggc aggacctcac caaaagatcc agcctcatac ctacatcaga caaaatatcg 120240
ccgttgttcc ttctgtacta aagtattgtg ttttgctttg gaaacaccca ctcactttgc 120300
aatagccgtg caagatgaat gcagattaca ctgatcttat gtgttacaaa attggagaaa 120360
gtatttaata aaacctgtta atttttatac tgacaataaa aatgtttcta cagatattaa 120420
tgttaacaag acaaaataaa tgtcacgcaa cttatttttt taatactcgt gtcttaccaa 120480
atggtttgcc tgtgcttgga ggtgctgact gagtgctgtt gtgaatgcag gaagggcagg 120540
gctgccaagg gtcttatgtg ctacacacgg gggtgacttg ccagaggggt tgactgagac 120600
cagcagtacc tgtgacaggt tgaggttgat ccagtggaaa atctgaatca gttggttgga 120660
gccctggctc ggttgcttac tggcacctca atggaatcat cgttcctttc tgagccctac 120720
cagttcccca gaggagcaaa caaagagcca catggtagag agctttgcaa actggaaggt 120780
gacctaagga tgacaggtat tgagtaggga agacgttcag aacatctgaa tcctggggac 120840
ttaaaaacct tttaggctgt tttcttcatg atgtatggag agaaggattt gcttcaaatt 120900
ttccaaaaga aaacttggac aaatgttcga ataattattt attttcatac caccaacgat 120960
ctgaagaggg aaatggagtt ttgcctgtca gttaacaaat gtgaatctgt gactcttaag 121020
ggtctgttgt atctacttgc cagcctcatc agcagcagga aagggaattg aacataggcc 121080
aacttctcct gcacttcagc caggctctta gaaccttaca gggccattgg taaagagtgc 121140
tgtctttggg gtcttctttc tgtttgaggc cattcatggt ggagcaaggt gtcaccagcc 121200
```

-continued atcaggggag tggcctaggg tcctggttct gtatttccca aacctctgtc cttctgtttc 121260
ttacaggata acagggctct tgggaatgtg attttaaaaa taaggtgcat gaaagccacc 121320
taagaaaatt gtcacctgtt agacacaagt gtacagggtg atgttctgta cccctgggga 121380
catttctacc gtgagatgtc cttggcaagg gtgaggatgg acttgctggg gtctacgctg 121440
gttcctccgt gcagctctct ggtgcatatg ctgtacttta gacactgaag ggcagtttat 121500
agccttgaca gtgtagatta taatggcagt aagaactgct gtatttctgg cccatttcat 121560
ggagatgggt gggcaagaat cctaaatggt cttttggcca ttttgatttt agaattattt 121620
tgaaagagac acttgtcatg aagggcaaga aggcagtgtg gtccatgaga atgataggta 121680
atacagtacc tttttttttt tgagacctgt cccaaatgag catacacagg taggattcga 121740
taagaatcct ggagcttatg gctctcctcc cccaagaacc taaggagagc gttggaaatt 121800
agttgcaact acatgtgatg gtcacctaac catcatgaga tgagttcatt tgtgaagaac 121860
caaaagattg caggcatctt ggatgtgtag tgcccggcct gctgttccta actgggaaag 121920
gcatatccaa gaggctgcct caaaacgtct agctgatggt agcctctggc aggatgggga 121980
gccagagaaa gcgggtggaa aagtagcatc ttcacggggg ttctgtgcat tcccagggga 122040
cagggtaccc tgcatccacc acacagcctc tccatccctc ctcagggagc ttctctgcat 122100
ctgatcttgt ggggagttcc ttaaccccac acataggaac ataggaaatt aaaacatgca 122160
tttatagtaa aacgtctgaa caacttgagc tgctatgaac tgaggactcc acctccagtt 122220
ttgaaaacaa gaaatggggc tgctacctta tactgcatca ctgaagattg cttgcagggc 122280
tgggtccaga gggctcagct aggacagaag aggaagctga ggctccgctt gaggtccctg 122340
agggtcacat ggctgggatg tggtctaagg aacaagactg cagccttgtt cagtgcagga 122400
gaaagacagt ggacttgtgg gcttggacag aattgattgg tttgtttctt acagctgggt 122460
gatggtgcgc aaatcccagc ttctgtctgg atgtttgtct ctaggtgaac ctggtcctca 122520
ccagcctctc gacttgccat gaggatttgc tgtagggctt agctgtggca gacaggactc 122580
aataagtgtt cgttttctac ttcctgagaa tttttttcta catttcagtg attttagtat 122640
atccacgttg tgtaaccatc accactatct aattccaaaa cgttttcatc actccataaa 122700
gccaacaaat tcccattgtt agccacttgc atttccccct cccccagtcc ttggcaaccc 122760
ccaatctgct ctctgtctat ggatttgcct actctagaca tttcatgtaa atggaatcat 122820
atgctatgtg accttttttg tccaacttct tcacttaatg ttttcaagat ttgttcatac 122880
ggtagcctgt aacagcactt catttttatt gccaaatcct attccatgat ataaatttac 122940
tacattttgt ttatccattt gtccattgat ggacatttag attgtacttt ccagttatga 123000
atagtgctgt tatgaacatt catgtactgg gtttttgtgt ggtcaggttt tcatttctct 123060
tgggcatata tgtaggagtg gaattgcggg atcatatggt aactgctaga ctgttttcca 123120
aggtggctgc actattttac attcccacca gcagtgcatg agcattccag tttttccaca 123180
tccttgtcaa cacttgttat tatccatatt ttttattata gccatcctag tggatatgaa 123240
gtatcttcat aagaatttcg tagctgagga gataggatgc agatcattga ataaagatac 123300
ataatgcttt cctggttttt ccagaaaaag atacttcaat taatcagctt ggtttctaca 123360
ctgatgaaat ggccaaggta gctaagatgc ctcagtggat cttcatgaaa tggagaagct 123420
gagaaaccaa tcaattccct gtcttccctc ttggctgaga gaggaaggaa gcactgctaa 123480
gtggtgcaag gatgcaggat ctttctggct ggaatgcttg agtgtatctg tcctcacatc 123540
cccagtttta taccaagtaa agtcacgcaa gcttgagcag tccatgcgga ctaatgaatg 123600

-continued caccattact tatgtatgtg ggtccattag gttcctcctt accaagcctg cattttgatg 123660
ttatttattt tttcatggtt ttaaagatga aagcaaagtt tatcttctct cacatttcat 123720
ccccaggagc cttgaaatga cttggctgtc gaccctgggc agggacagca gaagccgtcc 123780
atgtctcaag tgacattctg gagtagggcc cttcttgtgc ccttttttta tgccgggtgt 123840
ctgggatttt tgaatgggct cctccaaatt gccttgaagt cctgtttcag aaggtcacat 123900
gaggtgctgt agaagtcagt ggatgggagg gcattcaatg tccggcactg gggaaccatc 123960
cgctccggac ctttgaaata caatttacaa agggatacct cagcacatga agctgttcag 124020
tgactgaatt cagcttaccg tgcacatatg ggtaggtgat tttttccttc tgcagctcag 124080
aacactgcct ccttttgggc tgcactcctt ttaggtttct tttcctcttc taattctttt 124140
ttaggctgga gtgcaatggc atgatctagg ctcactgcaa cttccgcctc ctgggttcaa 124200
gccattccac tgctcccagc ctctaattct cttttgagga cacttaactg atgcttgctg 124260
gtgtctctta ctagttaaaa tccatagcat gaggtgcttt gaaagggaca gaggacactt 124320
aactgacgct tgctggtgtc tcttactagt taaaatccat agcatgaggt tctttgaaag 124380
ggacagagga cacttacaga tttataaatt aagaatcaag cagctgggcg cggtggctca 124440
tgcctataat cccagcactt taggaggccg ctgtaggcag atcacctgag gtcaggagtt 124500
cgagaccagc ctgactaaca tggtgaaatc ctgtctctac taaaaataca aaaattagcc 124560
aggtgtggtg gctaatgcct gtaatcccgg ctactcagga ggctgaggca ggagaattgc 124620
ttgaacccgg gaagtggagg ttgcagttag ccaagatcac gccgttgcac tccagcctgg 124680
gtgagaagag ctaaactccg tctcaaaaaa aaaaaaaaaa aaaaaagaag caaagaacgc 124740
tttcttggtc tgtaagtggg atgacaaatg attctatgtc aaaggattgt tgagttaaat 124800
gagattgtac ctgggaagca tgaaacagtg cctgctgcat attagccact atcaacactc 124860
aggtattagc tgctatttcc atctgtctat ctacagctat ttgacataga tgtacttact 124920
gaaacaaata tgaagataaa atatgtgtat gtgtatagat ataaaattgt cattgcggaa 124980
gaaatttgtt tgtgaaattg ctaatctatt acaaacacaa gtgtccattg tacacacaat 125040
ttttaacaaa aaacatttaa taagtttttg gtttgttttt tttttaattt tttgagacag 125100
ggtcttgctc tgttgcccag gctagagagc agtggcacaa tcatgaccca ctgcagactt 125160
gtccttctgg gctcaagcca tcctcccacc tcagcttccc gagtagctgg gactacaggc 125220
atgcaccacc atgcctagct aatttctgta tgttttttgt agacctgggg ttatgccatg 125280
ttgcccaggc tggtcttgaa ctcccgagct caagcgatcc acctgcctgg gcctcccaaa 125340
gtgctgcaat tacaggcgtg agccactgcg cccaggttaa taagttttaa atcaatgaaa 125400
ataatgatca aaattttcaa aaacttatga agttgtattg ataacattca acctgttatg 125460
gttccctttt taaacaagca ttcactttac gaatactaaa taggcaatga atgcctaata 125520
tgatttttaa gggacaatta aacactttta gaagtgcaca gaccaggcca ggcacggtgg 125580
tacacacctc taatcccagc actttgggag gccgaagcgg gtgtatcacc tgaggtcagg 125640
agtttgagac cagcctggcc aacgtagtga aaccccatct ctactaaaaa tacaaaaatt 125700
agcctggcat ggtggcggca tgcctgtaat cccagctact cgggaggctg aggcaggaga 125760
atcgcttgag cctgggaggc ggaggttgca gtgagccaag attgcaccac tgcactccag 125820
cctgggcaac agagcaagag tccatctcca aaaaaaaaaa aagacatgcg cagaccaagc 125880
tggtgaatgg tgaagtacca cgatctcaaa ggcagaccgg aacaggagca gctcaggatg 125940

-continued

```
gtttctgcac ggcaaggtct ctccggctcc aggtttggtg ttgttacaag caaattgaaa 126000
tgggtggtgt tacaaaggga aatatcacat gggaaaaacg gaggaagcct ggggctctcg 126060
aagtttagga ttgtgtatgg ttcaggggct gcggaatttc tgggaattgt aaaattagcg 126120
ccgttcacct gacagggttg gagagtgaaa taaactttcc gttgtgtggg gaagtccatt 126180
agatgttctt aatcacttct acagcgtgta ctgcagaggt ttaagtggga gaagatggct 126240
ggaacatgaa cacgggctca aggctgccct ttcagattgt tctgtgactt gacttgctgc 126300
ctcttctgga aggaggctgt gtatatcttt gtacacatga tcacagcagg agaggaaatc 126360
ggaagcctcc tcttcttcct ggcctggtct tgactcccca tgagactggc cctttcgttg 126420
cctcttgccg gatttaggtt tcaccaaaat gcagaaattc cttgttgatg gctggctctc 126480
acccagtagc agccagagct gtgaatgaaa aaggcaaagt ccaaacttca aacctgggct 126540
gaggggtgca gggagtggga gggcttgttc tgctgttgct tatttcagag cctgacaaat 126600
ggaggcccac agaccaaacc cagctcacta cccgcctttg tactgcttat gagctaagaa 126660
atatttttaa atggttgaaa gtattatttt aaatatatat tttggctcac gcctgtaatc 126720
ccagcacttt gggaggctga ggtgggtgga tcacgaggtc aggagatcga gaccatcctg 126780
gctaacatgg tgaaaccccg tctctactaa aaatacaaaa aattagttgg gcatggtggt 126840
gggcgcctgt agtcccagct actggggagg ctgaggcagg agaatggcat gaacctggga 126900
ggcagagctt gcagtgagcc gagatcatac cactgcactc cagcctgggc aacagagtga 126960
ctccgtctca aaaaaagaaa aaaaaaaaaa aaaaaaatat atatatatat atatatatat 127020
atatatatat atatatatat atgtgcaaat tatataaagc cccagtttca gtgtccgtaa 127080
atatttactg ggacacagcc acattcattc atgtacataa tgtctatggc tgctttccca 127140
caacagcagc agagtggaat ggtggcgaca gggattaccc acaaaactga agacatttac 127200
tacccatggc tctttatgaa aaaatttgat gacccctggc ttagatctac aatgtgctag 127260
ttggttgcca gacctaggca ggtggaatcc ttcccatgcc ttgtggggaa agacaatagc 127320
agataacaag ggcctgaaac tgggagttgc tttcaaaaat aggggtccaa actgggtgtg 127380
gtggtccagg cctgtagtcc cagctaccga agaggctgat gagggagtat tgcttgagcc 127440
caggaatttg aggccaccct gggcaacata gtgaaatctc atctcaaaaa aaaaagaaaa 127500
aaagaaaaaa gaaaaaaaaa aaaaaagaaa gaggccgggt gcagtagctc atgcctgtaa 127560
ttctagcact ttgggaaact gagacgggtg gatcacgagg tcaagagatc gagacaatcc 127620
tggccaacat ggtgaaatcc cgtctgtact aaaaatacaa aaattagcca ggtgtggtgg 127680
cacgcacctg tagtctcacc tactcgggag gctgaggcgg gagaatttct tgaacctggg 127740
aggcagaggt tgcagtgagc tgagatcgtg ccactgtact ccagcctggt gaaacagcaa 127800
gactctttct aaaaaaaaaa aaaaaaaaaa aaaaaaaagc caggcgcggt ggctcacacc 127860
tgtaatccca gcactttggg aggctgaggt gggcggaaca cggggtcagg agatcaagac 127920
catcctggcc aacatggtga aaccccatct ctactaaaat acaaaaattt agccgggcat 127980
ggtggcacac acctgtagtc ccagctactt gggaggctga ggcaggggaa tcacttgaac 128040
ctgggaagcg gaggttgcag tgagccgaga tggcaccact gcactccagc ctggtgacag 128100
agcaagactc cgtctaaaaa acaaaaacaa aaaacagaat tggggtccat ttgagagatc 128160
tccactaagg gtggggatga aagtcatgaa aactgccctt tgaccaagtg ggatgttcta 128220
agattgtctg gagacagtaa gtggccaacg cgctgtgtct aaaccagcct tctgggcacc 128280
gttttgcccc tgcagcaaca tgcccactgc tcttcctaac aagcttgcca cagagatcca 128340
```

-continued

```
caaaccaaag gctaaataaa caatgcggtt cttccggaag gaagggaggt gagaggctga 128400
cattcggatt tgaacgctgc ttgtttggta ggaagtaaac ctggtctctt ccagcgaggg 128460
agcacctctg taccgtaaca ctgtattcct tgctcaggct ggaacaccaa gttcaggggg 128520
cagggtggcc ctctacacaa ccttgttgcc cgggttttct ttcccatcac cccggtgtcc 128580
ttgcacgcat taagctttcc atggatgcaa tgacaggcac gcacccttgt cagactctga 128640
acacaaaggc aatcccagga cagactagtg ttggaaccgc cttagtttgc ctggacacaa 128700
cgtaactgaa acttcttttt cttcccatta gctggagttt aaaaagcgtc tccacagctg 128760
tgatggctga aggcttgaaa tgacagagcc acttgcccca taaatcagca tgcaacaccc 128820
cccacgtaaa cagatccggg aaaaaaaatc tacatacgca ataaatgtgt acaggtactg 128880
gagactggta ataaaaatgc ttggatctgc tttcagtttt tcccttgtct tctaaatgaa 128940
gctgaaagca aatcaagcac taagccctta tttttctgat ctgaaagcag gtgaatgtgg 129000
tcaagagcag gagatatgca gatgaagggg ggacccctaa tagtggaaac ctgggtgttc 129060
atagcctctt tggggaagca aagccttggg cagatcccca gggtgaaagc gtagactctt 129120
tttaaagact gggcaggagg gagggagcag gcgaggctgg agcccgcatt gttgggctgc 129180
tctgacttac atggcacctg tagacccagg gagaacctga gaaggggctc ctgggccagg 129240
ggccaggcag gtatttgtgg ttgtgtgtgt gtgtgcatgc ctatgcactg tcgtagacca 129300
gggtttcaca gcttttaaga acaataaaaa cattcagaat tcttctagtg gccccacgac 129360
gtagggcctt ctggttattt aagatctcca acatgcgtca aaagcagctt aggaggggag 129420
tccagatcat ccctacagct gcagaagagc acagcagcca gtaagaaaga agggtagtgg 129480
gggagcgggg tgtgggggaa catggatggt tccagaattt cttcagagaa ttagtcaagg 129540
gtctgaagtt ggcatgaaac ggggtttgag gaactgggga gttgactggg agctggtttt 129600
gcagagcaaa catactgctt taatgtaaat caagtagttt tgttcatttg atttaggagg 129660
ctggagtatg atacggtttg gctctgtatc cccacccaaa tctcatcacg aattgtgatc 129720
cccacatgtt gagggaggta cctgtaatcc ctacgtgttg aggggaggag gtgattggat 129780
catgggggtg gtttcccccca tgctgttctt atgatggtga gtgagttctc ctgacatctg 129840
atggttttat aagtgtttga cagttcctcc tacacacatt ctctctcgca cctgccacgg 129900
tgtaagatgt gccttcttca actttggccg tgactgtaag ttccctgaga cctccccccgc 129960
catgtggaac tgtgaatcaa tgaagcctct tttctttata aattacccag tcacgggtat 130020
atctttatag caatgtgaaa acagactaat gtagagttta aaaatctccc caagctacct 130080
caccctggcc tgccacttcc aaaaggtcta gttagcccga atagtttcat ttctaagccc 130140
ttctctcaat cttccagacc aaagttgtag ccacccccagg ggtgcctgct ccccatcctt 130200
gcaggtaaga agggacatgc gtattttcct gctcccccac actcctttaa gcagtcatgc 130260
ctcgcctgtt ggctgcttgt tgtgcctggc tgatggatgc agctccaaag ctgaaacacc 130320
gtcagagttt gtgtgaaggg agttggggtg gagtggttaa cttatctccc atgaggcagg 130380
tgctttgacc caaggggcat ggtacattct agaaatgtgt agccaccccc cgtttccagg 130440
ggagaatagg ctgtttgggt agagctggca tcacgagggg agaaacgagg ctggcacctt 130500
cagagctggc tctttaagcc tggcccaaag caagtgtgtg aagttgctgt ctggggagac 130560
ctctggaaca atttctggcc tcattctgcc ttccccagca agccagcaag tcacaggtac 130620
tatgggccca gcactgcact ggagatggga agtcatatta gttattaatc atccttgaaa 130680
```

-continued

```
tagccctaag ggtgttctgt tagttttcta aggctgcttt aagaaactac cacagacttg 130740

gtggcttaac acaacagaaa tttattctgt cacagttctg gaggccagaa gtgtgagatc 130800

aaggtgtcgg cagggccatg ctccttctga aggctctggg ggggatttct ttacctcttc 130860

tggcttctgg tggcgccaag tgttccttgg tttgtgactg catcacccca gtctgtttct 130920

gtcttcacat gaccgtctcc tcttggtgtt tgtctgtcct ctgtgtgtct cttaggatgc 130980

ttgtcattgg atttagggca cacccacgta acacacgatg atctcatctt gaaatcctta 131040

acttatttat atctgcaaag accctgtttt caaaaaaggc catgtttaaa agttccggtg 131100

gttaggacat gggcatatct tttgggggcc actatttaac ccattgcaga agtggagggt 131160

tggagatttg aggtttggtg gccctctcca agaattttac aatcaggtta gtggagaaca 131220

gggttggtac tcgtgaaaga atttgctagg taacatattt tatccaaggg gctgctgtgg 131280

tggcagagac tgtgtagaga ggccaggccc attccctgcc tcaccctgcc gagaaggaaa 131340

cttgcttggg gtgcgtcttc ccagcgtttt ttctcatttc atcctcgtaa cagtggcgtg 131400

agataggcac tgagaggtca gttaacacct acacaatcat gtggttgcca catgggagag 131460

ctgggatgca aatctgtgtg agctgattct ggatctgggg atctaaatac tggtaaccct 131520

gacagctgcc cagcaggccc tctctgatgg gggagcttca agggaggtgg ggacccacac 131580

ttgaccttcc tggaggctag aacaggagac agaaagtgag tgagcttacc taggccagag 131640

gaaggcttga gggtcattct tgggtggaca acagctatag gaataagccc tgcacaggag 131700

gggaacaata agagaagact cttaaaaaag actctttagg ctgggtgcgg tggctcacgc 131760

tggtaatccc agcactttgg gaggccaagg cggacagatc acctaaggtc gggagttcga 131820

gaccagcctg gccaacatgg tggaacccca tctctcctaa aattacaaaa caattagcca 131880

ggtgtgttgg tgctcgccta taatcccagc tactcgggat gctgaggtgg gaggatcact 131940

tgaacccagg aggcaggggc tgcggtgagc tgagatcatg ccactgcact ctagcctggg 132000

ctacagagca gattctgttt caaaaaaaaa aagactccat aaagacttcc cttcccttca 132060

catctgccca cgtgaaggga actctttaaa gaaaaaatga ttgtctgagc tcactggggc 132120

aggcctcaac ccacgtctcc atggaatgga aatagtatcc cttgtggctt cctgaggagg 132180

aaaaagattt taggggggatg gtgttaggca gagaaactgg gggggtggga tggcatgatg 132240

ccccctgggt ggtagctggc cgctgtgagg tgggtccatg ctttctccct cttcttctga 132300

gtttgtcctt gacttagctc tggctgccat aacaaaatac cacagactgg gtgccttaaa 132360

caacacgttt attcgcgtac agttctggag gctggaagtt cgagatcagg gtaccagcat 132420

ggttgggttc ttaccgaagg ccctcttcct ggcttgcaga tggccaccct ctcgctctgt 132480

gcccacctgg cattttcttg gtgcaagggc atggagagat taagcgatat ctcccactct 132540

cttcctcttc ttatcaggcc accgatccta ttagaccagg accccattct tataacctcc 132600

tgtaatcttc attacctcct aactccatct cttagtcaca ttagggggtt aggacttcaa 132660

catatgaatt ttggggtggg gggcacaatt cagtccatag tagccctcct ccttccttcc 132720

ttccctgcct gcctccatta gtcccttctg tcttgactgc ct                   132762
```

<210> SEQ ID NO 18
<211> LENGTH: 2941
<212> TYPE: DNA
<213> ORGANISM: Homo sapiens
<220> FEATURE:
<221> NAME/KEY: CDS
<222> LOCATION: (419)...(2878)

<400> SEQUENCE: 18

```
cccgcgagca aagtttggtg gaggcaacgc aagcctgagt cctttcttcc tctcgttccc      60

caaatccgag ggcagcccgc gggcgtcatg gcgctcctcc gcagcctggg gtacgcgtga     120

agcccgggag gcttggcgcc ggcgaagacc caaggaccac tcttctgcgt ttggagttgc     180

tccccgcaac cccgggctcg tcgctttctc catcccgacc cacgcggggc cggggacaac     240

acaggtcgcg gaggagcgtt gccattcaag tgactgcagc agcagcgcag cgcctcggtt     300

cctgagccca ccgcagctga aggcattgcg cgtagtccat gcccgtagag gaagtgtgca     360

gatgggatta acgtccacat ggagatatgg aagaggaccg ggattggta ccgtaacc        418

atg gtc agc tgg ggt cgt ttc atc tgc ctg gtc gtg gtc acc atg gca       466
Met Val Ser Trp Gly Arg Phe Ile Cys Leu Val Val Val Thr Met Ala
  1               5                  10                  15

acc ttg tcc ctg gcc cgg ccc tcc ttc agt tta gtt gag gat acc aca       514
Thr Leu Ser Leu Ala Arg Pro Ser Phe Ser Leu Val Glu Asp Thr Thr
             20                  25                  30

tta gag cca gaa gag cca cca acc aaa tac caa atc tct caa cca gaa       562
Leu Glu Pro Glu Glu Pro Pro Thr Lys Tyr Gln Ile Ser Gln Pro Glu
         35                  40                  45

gtg tac gtg gct gcg cca ggg gag tcg cta gag gtg cgc tgc ctg ttg       610
Val Tyr Val Ala Ala Pro Gly Glu Ser Leu Glu Val Arg Cys Leu Leu
     50                  55                  60

aaa gat gcc gcc gtg atc agt tgg act aag gat ggg gtg cac ttg ggg       658
Lys Asp Ala Ala Val Ile Ser Trp Thr Lys Asp Gly Val His Leu Gly
 65                  70                  75                  80

ccc aac aat agg aca gtg ctt att ggg gag tac ttg cag ata aag ggc       706
Pro Asn Asn Arg Thr Val Leu Ile Gly Glu Tyr Leu Gln Ile Lys Gly
                 85                  90                  95

gcc aca cct aga gac tcc ggc ctc tat gct tgt act gcc agt agg act       754
Ala Thr Pro Arg Asp Ser Gly Leu Tyr Ala Cys Thr Ala Ser Arg Thr
            100                 105                 110

gta gac agt gaa act tgg tac ttc atg gtg aat gtc aca gat gcc atc       802
Val Asp Ser Glu Thr Trp Tyr Phe Met Val Asn Val Thr Asp Ala Ile
        115                 120                 125

tca tcc gga gat gat gag gat gac acc gat ggt gcg gaa gat ttt gtc       850
Ser Ser Gly Asp Asp Glu Asp Asp Thr Asp Gly Ala Glu Asp Phe Val
    130                 135                 140

agt gag aac agt aac aac aag aga gca cca tac tgg acc aac aca gaa       898
Ser Glu Asn Ser Asn Asn Lys Arg Ala Pro Tyr Trp Thr Asn Thr Glu
145                 150                 155                 160

aag atg gaa aag cgg ctc cat gct gtg cct gcg gcc aac act gtc aag       946
Lys Met Glu Lys Arg Leu His Ala Val Pro Ala Ala Asn Thr Val Lys
                165                 170                 175

ttt cgc tgc cca gcc ggg ggg aac cca atg cca acc atg cgg tgg ctg       994
Phe Arg Cys Pro Ala Gly Gly Asn Pro Met Pro Thr Met Arg Trp Leu
            180                 185                 190

aaa aac ggg aag gag ttt aag cag gag cat cgc att gga ggc tac aag      1042
Lys Asn Gly Lys Glu Phe Lys Gln Glu His Arg Ile Gly Gly Tyr Lys
        195                 200                 205

gta cga aac cag cac tgg agc ctc att atg gaa agt gtg gtc cca tct      1090
Val Arg Asn Gln His Trp Ser Leu Ile Met Glu Ser Val Val Pro Ser
    210                 215                 220

gac aag gga aat tat acc tgt gta gtg gag aat gaa tac ggg tcc atc      1138
Asp Lys Gly Asn Tyr Thr Cys Val Val Glu Asn Glu Tyr Gly Ser Ile
225                 230                 235                 240

aat cac acg tac cac ctg gat gtt gtg gag cga tcg cct cac cgg ccc      1186
Asn His Thr Tyr His Leu Asp Val Val Glu Arg Ser Pro His Arg Pro
                245                 250                 255
```

-continued

```
atc ctc caa gcc gga ctg ccg gca aat gcc tcc aca gtg gtc gga gga      1234
Ile Leu Gln Ala Gly Leu Pro Ala Asn Ala Ser Thr Val Val Gly Gly
            260                 265                 270

gac gta gag ttt gtc tgc aag gtt tac agt gat gcc cag ccc cac atc      1282
Asp Val Glu Phe Val Cys Lys Val Tyr Ser Asp Ala Gln Pro His Ile
        275                 280                 285

cag tgg atc aag cac gtg gaa aag aac ggc agt aaa tac ggg ccc gac      1330
Gln Trp Ile Lys His Val Glu Lys Asn Gly Ser Lys Tyr Gly Pro Asp
    290                 295                 300

ggg ctg ccc tac ctc aag gtt ctc aag cac tcg ggg ata aat agt tcc      1378
Gly Leu Pro Tyr Leu Lys Val Leu Lys His Ser Gly Ile Asn Ser Ser
305                 310                 315                 320

aat gca gaa gtg ctg gct ctg ttc aat gtg acc gag gcg gat gct ggg      1426
Asn Ala Glu Val Leu Ala Leu Phe Asn Val Thr Glu Ala Asp Ala Gly
                325                 330                 335

gaa tat ata tgt aag gtc tcc aat tat ata ggg cag gcc aac cag tct      1474
Glu Tyr Ile Cys Lys Val Ser Asn Tyr Ile Gly Gln Ala Asn Gln Ser
            340                 345                 350

gcc tgg ctc act gtc ctg cca aaa cag caa gcg cct gga aga gaa aag      1522
Ala Trp Leu Thr Val Leu Pro Lys Gln Gln Ala Pro Gly Arg Glu Lys
        355                 360                 365

gag att aca gct tcc cca gac tac ctg gag ata gcc att tac tgc ata      1570
Glu Ile Thr Ala Ser Pro Asp Tyr Leu Glu Ile Ala Ile Tyr Cys Ile
    370                 375                 380

ggg gtc ttc tta atc gcc tgt atg gtg gta aca gtc atc ctg tgc cga      1618
Gly Val Phe Leu Ile Ala Cys Met Val Val Thr Val Ile Leu Cys Arg
385                 390                 395                 400

atg aag aac acg acc aag aag cca gac ttc agc agc cag ccg gct gtg      1666
Met Lys Asn Thr Thr Lys Lys Pro Asp Phe Ser Ser Gln Pro Ala Val
                405                 410                 415

cac aag ctg acc aaa cgt atc ccc ctg cgg aga cag gta aca gtt tcg      1714
His Lys Leu Thr Lys Arg Ile Pro Leu Arg Arg Gln Val Thr Val Ser
            420                 425                 430

gct gag tcc agc tcc tcc atg aac tcc aac acc ccg ctg gtg agg ata      1762
Ala Glu Ser Ser Ser Ser Met Asn Ser Asn Thr Pro Leu Val Arg Ile
        435                 440                 445

aca aca cgc ctc tct tca acg gca gac acc ccc atg ctg gca ggg gtc      1810
Thr Thr Arg Leu Ser Ser Thr Ala Asp Thr Pro Met Leu Ala Gly Val
    450                 455                 460

tcc gag tat gaa ctt cca gag gac cca aaa tgg gag ttt cca aga gat      1858
Ser Glu Tyr Glu Leu Pro Glu Asp Pro Lys Trp Glu Phe Pro Arg Asp
465                 470                 475                 480

aag ctg aca ctg ggc aag ccc ctg gga gaa ggt tgc ttt ggg caa gtg      1906
Lys Leu Thr Leu Gly Lys Pro Leu Gly Glu Gly Cys Phe Gly Gln Val
                485                 490                 495

gtc atg gcg gaa gca gtg gga att gac aaa gac aag ccc aag gag gcg      1954
Val Met Ala Glu Ala Val Gly Ile Asp Lys Asp Lys Pro Lys Glu Ala
            500                 505                 510

gtc acc gtg gcc gtg aag atg ttg aaa gat gat gcc aca gag aaa gac      2002
Val Thr Val Ala Val Lys Met Leu Lys Asp Asp Ala Thr Glu Lys Asp
        515                 520                 525

ctt tct gat ctg gtg tca gag atg gag atg atg aag atg att ggg aaa      2050
Leu Ser Asp Leu Val Ser Glu Met Glu Met Met Lys Met Ile Gly Lys
    530                 535                 540

cac aag aat atc ata aat ctt ctt gga gcc tgc aca cag gat ggg cct      2098
His Lys Asn Ile Ile Asn Leu Leu Gly Ala Cys Thr Gln Asp Gly Pro
545                 550                 555                 560

ctc tat gtc ata gtt gag tat gcc tct aaa ggc aac ctc cga gaa tac      2146
Leu Tyr Val Ile Val Glu Tyr Ala Ser Lys Gly Asn Leu Arg Glu Tyr
```

-continued

```
                565                 570                 575

ctc cga gcc cgg agg cca ccc ggg atg gag tac tcc tat gac att aac     2194
Leu Arg Ala Arg Arg Pro Pro Gly Met Glu Tyr Ser Tyr Asp Ile Asn
            580                 585                 590

cgt gtt cct gag gag cag atg acc ttc aag gac ttg gtg tca tgc acc     2242
Arg Val Pro Glu Glu Gln Met Thr Phe Lys Asp Leu Val Ser Cys Thr
        595                 600                 605

tac cag ctg gcc aga cgg atg gag tac ttg gct tcc caa aaa tgt att     2290
Tyr Gln Leu Ala Arg Arg Met Glu Tyr Leu Ala Ser Gln Lys Cys Ile
    610                 615                 620

cat cga gat tta gca gcc aga aat gtt ttg gta aca gaa aac aat gtg     2338
His Arg Asp Leu Ala Ala Arg Asn Val Leu Val Thr Glu Asn Asn Val
625                 630                 635                 640

atg aaa ata gca gac ttt gga ctc gcc aga gat atc aac aat ata gac     2386
Met Lys Ile Ala Asp Phe Gly Leu Ala Arg Asp Ile Asn Asn Ile Asp
                645                 650                 655

tat tac aaa aag acc acc aat ggg cgg ctt cca gtc aag tgg atg gct     2434
Tyr Tyr Lys Lys Thr Thr Asn Gly Arg Leu Pro Val Lys Trp Met Ala
            660                 665                 670

cca gaa gcc ctg ttt gat aga gta tac act cat cag agt gat gtc tgg     2482
Pro Glu Ala Leu Phe Asp Arg Val Tyr Thr His Gln Ser Asp Val Trp
        675                 680                 685

tcc ttc ggg gtg tta atg tgg gag atc ttc act tta ggg ggc tcg ccc     2530
Ser Phe Gly Val Leu Met Trp Glu Ile Phe Thr Leu Gly Gly Ser Pro
    690                 695                 700

tac cca ggg att ccc gtg gag gaa ctt ttt aag ctg ctg aag gaa gga     2578
Tyr Pro Gly Ile Pro Val Glu Glu Leu Phe Lys Leu Leu Lys Glu Gly
705                 710                 715                 720

cac aga atg gat aag cca gcc aac tgc acc aac gaa ctg tac atg atg     2626
His Arg Met Asp Lys Pro Ala Asn Cys Thr Asn Glu Leu Tyr Met Met
                725                 730                 735

atg agg gac tgt tgg cat gca gtg ccc tcc cag aga cca acg ttc aag     2674
Met Arg Asp Cys Trp His Ala Val Pro Ser Gln Arg Pro Thr Phe Lys
            740                 745                 750

cag ttg gta gaa gac ttg gat cga att ctc act ctc aca acc aat gag     2722
Gln Leu Val Glu Asp Leu Asp Arg Ile Leu Thr Leu Thr Thr Asn Glu
        755                 760                 765

cga att ctc act ctc aca acc aat gag aac ttc cag agc acc tca gga     2770
Arg Ile Leu Thr Leu Thr Thr Asn Glu Asn Phe Gln Ser Thr Ser Gly
    770                 775                 780

aga gag ggc acg gag att cat gct ctt caa tgc ctc aga tcg gaa gta     2818
Arg Glu Gly Thr Glu Ile His Ala Leu Gln Cys Leu Arg Ser Glu Val
785                 790                 795                 800

aca cct gcc att tcc tgt gag agc cca ttg gct gac act ggt tcc aag     2866
Thr Pro Ala Ile Ser Cys Glu Ser Pro Leu Ala Asp Thr Gly Ser Lys
                805                 810                 815

gtc cca aac taa ctacatggga agcaggaagc accaagaagc tgatggagaa         2918
Val Pro Asn

tcgggttttg gaagcaatag tga                                           2941


<210> SEQ ID NO 19
<211> LENGTH: 2868
<212> TYPE: DNA
<213> ORGANISM: Homo sapiens
<220> FEATURE:
<221> NAME/KEY: CDS
<222> LOCATION: (419)...(2734)

<400> SEQUENCE: 19

cccgcgagca aagtttggtg gaggcaacgc aagcctgagt cctttcttcc tctcgttccc     60
```

-continued

```
caaatccgag ggcagcccgc gggcgtcatg gcgctcctcc gcagcctggg gtacgcgtga    120

agcccgggag gcttggcgcc ggcgaagacc caaggaccac tcttctgcgt ttggagttgc    180

tccccgcaac cccgggctcg tcgctttctc catcccgacc cacgcggggc cggggacaac    240

acaggtcgcg gaggagcgtt gccattcaag tgactgcagc agcagcgcag cgcctcggtt    300

cctgagccca ccgcagctga aggcattgcg cgtagtccat gcccgtagag gaagtgtgca    360

gatgggatta acgtccacat ggagatatgg aagaggaccg gggattggta ccgtaacc      418

atg gtc agc tgg ggt cgt ttc atc tgc ctg gtc gtg gtc acc atg gca      466
Met Val Ser Trp Gly Arg Phe Ile Cys Leu Val Val Val Thr Met Ala
  1               5                  10                  15

acc ttg tcc ctg gcc cgg ccc tcc ttc agt tta gtt gag gat acc aca      514
Thr Leu Ser Leu Ala Arg Pro Ser Phe Ser Leu Val Glu Asp Thr Thr
             20                  25                  30

tta gag cca gaa gag cca cca acc aaa tac caa atc tct caa cca gaa      562
Leu Glu Pro Glu Glu Pro Pro Thr Lys Tyr Gln Ile Ser Gln Pro Glu
         35                  40                  45

gtg tac gtg gct gcg cca ggg gag tcg cta gag gtg cgc tgc ctg ttg      610
Val Tyr Val Ala Ala Pro Gly Glu Ser Leu Glu Val Arg Cys Leu Leu
     50                  55                  60

aaa gat gcc gcc gtg atc agt tgg act aag gat ggg gtg cac ttg ggg      658
Lys Asp Ala Ala Val Ile Ser Trp Thr Lys Asp Gly Val His Leu Gly
 65                  70                  75                  80

ccc aac aat agg aca gtg ctt att ggg gag tac ttg cag ata aag ggc      706
Pro Asn Asn Arg Thr Val Leu Ile Gly Glu Tyr Leu Gln Ile Lys Gly
                 85                  90                  95

gcc aca cct aga gac tcc ggc ctc tat gct tgt act gcc agt agg act      754
Ala Thr Pro Arg Asp Ser Gly Leu Tyr Ala Cys Thr Ala Ser Arg Thr
            100                 105                 110

gta gac agt gaa act tgg tac ttc atg gtg aat gtc aca gat gcc atc      802
Val Asp Ser Glu Thr Trp Tyr Phe Met Val Asn Val Thr Asp Ala Ile
        115                 120                 125

tca tcc gga gat gat gag gat gac acc gat ggt gcg gaa gat ttt gtc      850
Ser Ser Gly Asp Asp Glu Asp Asp Thr Asp Gly Ala Glu Asp Phe Val
    130                 135                 140

agt gag aac agt aac aac aag aga gca cca tac tgg acc aac aca gaa      898
Ser Glu Asn Ser Asn Asn Lys Arg Ala Pro Tyr Trp Thr Asn Thr Glu
145                 150                 155                 160

aag atg gaa aag cgg ctc cat gct gtg cct gcg gcc aac act gtc aag      946
Lys Met Glu Lys Arg Leu His Ala Val Pro Ala Ala Asn Thr Val Lys
                165                 170                 175

ttt cgc tgc cca gcc ggg ggg aac cca atg cca acc atg cgg tgg ctg      994
Phe Arg Cys Pro Ala Gly Gly Asn Pro Met Pro Thr Met Arg Trp Leu
            180                 185                 190

aaa aac ggg aag gag ttt aag cag gag cat cgc att gga ggc tac aag     1042
Lys Asn Gly Lys Glu Phe Lys Gln Glu His Arg Ile Gly Gly Tyr Lys
        195                 200                 205

gta cga aac cag cac tgg agc ctc att atg gaa agt gtg gtc cca tct     1090
Val Arg Asn Gln His Trp Ser Leu Ile Met Glu Ser Val Val Pro Ser
    210                 215                 220

gac aag gga aat tat acc tgt gta gtg gag aat gaa tac ggg tcc atc     1138
Asp Lys Gly Asn Tyr Thr Cys Val Val Glu Asn Glu Tyr Gly Ser Ile
225                 230                 235                 240

aat cac acg tac cac ctg gat gtt gtg gag cga tcg cct cac cgg ccc     1186
Asn His Thr Tyr His Leu Asp Val Val Glu Arg Ser Pro His Arg Pro
                245                 250                 255

atc ctc caa gcc gga ctg ccg gca aat gcc tcc aca gtg gtc gga gga     1234
Ile Leu Gln Ala Gly Leu Pro Ala Asn Ala Ser Thr Val Val Gly Gly
```

```
            260                 265                 270

gac gta gag ttt gtc tgc aag gtt tac agt gat gcc cag ccc cac atc      1282
Asp Val Glu Phe Val Cys Lys Val Tyr Ser Asp Ala Gln Pro His Ile
        275                 280                 285

cag tgg atc aag cac gtg gaa aag aac ggc agt aaa tac ggg ccc gac      1330
Gln Trp Ile Lys His Val Glu Lys Asn Gly Ser Lys Tyr Gly Pro Asp
    290                 295                 300

ggg ctg ccc tac ctc aag gtt ctc aag cac tcg ggg ata aat agt tcc      1378
Gly Leu Pro Tyr Leu Lys Val Leu Lys His Ser Gly Ile Asn Ser Ser
305                 310                 315                 320

aat gca gaa gtg ctg gct ctg ttc aat gtg acc gag gcg gat gct ggg      1426
Asn Ala Glu Val Leu Ala Leu Phe Asn Val Thr Glu Ala Asp Ala Gly
                325                 330                 335

gaa tat ata tgt aag gtc tcc aat tat ata ggg cag gcc aac cag tct      1474
Glu Tyr Ile Cys Lys Val Ser Asn Tyr Ile Gly Gln Ala Asn Gln Ser
            340                 345                 350

gcc tgg ctc act gtc ctg cca aaa cag caa gcg cct gga aga gaa aag      1522
Ala Trp Leu Thr Val Leu Pro Lys Gln Gln Ala Pro Gly Arg Glu Lys
        355                 360                 365

gag att aca gct tcc cca gac tac ctg gag ata gcc att tac tgc ata      1570
Glu Ile Thr Ala Ser Pro Asp Tyr Leu Glu Ile Ala Ile Tyr Cys Ile
    370                 375                 380

ggg gtc ttc tta atc gcc tgt atg gtg gta aca gtc atc ctg tgc cga      1618
Gly Val Phe Leu Ile Ala Cys Met Val Val Thr Val Ile Leu Cys Arg
385                 390                 395                 400

atg aag aac acg acc aag aag cca gac ttc agc agc cag ccg gct gtg      1666
Met Lys Asn Thr Thr Lys Lys Pro Asp Phe Ser Ser Gln Pro Ala Val
                405                 410                 415

cac aag ctg acc aaa cgt atc ccc ctg cgg aga cag gta aca gtt tcg      1714
His Lys Leu Thr Lys Arg Ile Pro Leu Arg Arg Gln Val Thr Val Ser
            420                 425                 430

gct gag tcc agc tcc tcc atg aac tcc aac acc ccg ctg gtg agg ata      1762
Ala Glu Ser Ser Ser Ser Met Asn Ser Asn Thr Pro Leu Val Arg Ile
        435                 440                 445

aca aca cgc ctc tct tca acg gca gac acc ccc atg ctg gca ggg gtc      1810
Thr Thr Arg Leu Ser Ser Thr Ala Asp Thr Pro Met Leu Ala Gly Val
    450                 455                 460

tcc gag tat gaa ctt cca gag gac cca aaa tgg gag ttt cca aga gat      1858
Ser Glu Tyr Glu Leu Pro Glu Asp Pro Lys Trp Glu Phe Pro Arg Asp
465                 470                 475                 480

aag ctg aca ctg ggc aag ccc ctg gga gaa ggt tgc ttt ggg caa gtg      1906
Lys Leu Thr Leu Gly Lys Pro Leu Gly Glu Gly Cys Phe Gly Gln Val
                485                 490                 495

gtc atg gcg gaa gca gtg gga att gac aaa gac aag ccc aag gag gcg      1954
Val Met Ala Glu Ala Val Gly Ile Asp Lys Asp Lys Pro Lys Glu Ala
            500                 505                 510

gtc acc gtg gcc gtg aag atg ttg aaa gat gat gcc aca gag aaa gac      2002
Val Thr Val Ala Val Lys Met Leu Lys Asp Asp Ala Thr Glu Lys Asp
        515                 520                 525

ctt tct gat ctg gtg tca gag atg gag atg atg aag atg att ggg aaa      2050
Leu Ser Asp Leu Val Ser Glu Met Glu Met Met Lys Met Ile Gly Lys
    530                 535                 540

cac aag aat atc ata aat ctt ctt gga gcc tgc aca cag gat ggg cct      2098
His Lys Asn Ile Ile Asn Leu Leu Gly Ala Cys Thr Gln Asp Gly Pro
545                 550                 555                 560

ctc tat gtc ata gtt gag tat gcc tct aaa ggc aac ctc cga gaa tac      2146
Leu Tyr Val Ile Val Glu Tyr Ala Ser Lys Gly Asn Leu Arg Glu Tyr
                565                 570                 575

ctc cga gcc cgg agg cca ccc ggg atg gag tac tcc tat gac att aac      2194
```

-continued

```
Leu Arg Ala Arg Arg Pro Pro Gly Met Glu Tyr Ser Tyr Asp Ile Asn
            580                 585                 590

cgt gtt cct gag gag cag atg acc ttc aag gac ttg gtg tca tgc acc     2242
Arg Val Pro Glu Glu Gln Met Thr Phe Lys Asp Leu Val Ser Cys Thr
        595                 600                 605

tac cag ctg gcc aga cgg atg gag tac ttg gct tcc caa aaa tgt att     2290
Tyr Gln Leu Ala Arg Arg Met Glu Tyr Leu Ala Ser Gln Lys Cys Ile
    610                 615                 620

cat cga gat tta gca gcc aga aat gtt ttg gta aca gaa aac aat gtg     2338
His Arg Asp Leu Ala Ala Arg Asn Val Leu Val Thr Glu Asn Asn Val
625                 630                 635                 640

atg aaa ata gca gac ttt gga ctc gcc aga gat atc aac aat ata gac     2386
Met Lys Ile Ala Asp Phe Gly Leu Ala Arg Asp Ile Asn Asn Ile Asp
                645                 650                 655

tat tac aaa aag acc acc aat ggg cgg ctt cca gtc aag tgg atg gct     2434
Tyr Tyr Lys Lys Thr Thr Asn Gly Arg Leu Pro Val Lys Trp Met Ala
            660                 665                 670

cca gaa gcc ctg ttt gat aga gta tac act cat cag agt gat gtc tgg     2482
Pro Glu Ala Leu Phe Asp Arg Val Tyr Thr His Gln Ser Asp Val Trp
        675                 680                 685

tcc ttc ggg gtg tta atg tgg gag atc ttc act tta ggg ggc tcg ccc     2530
Ser Phe Gly Val Leu Met Trp Glu Ile Phe Thr Leu Gly Gly Ser Pro
    690                 695                 700

tac cca ggg att ccc gtg gag gaa ctt ttt aag ctg ctg aag gaa gga     2578
Tyr Pro Gly Ile Pro Val Glu Glu Leu Phe Lys Leu Leu Lys Glu Gly
705                 710                 715                 720

cac aga atg gat aag cca gcc aac tgc acc aac gaa ctg tac atg atg     2626
His Arg Met Asp Lys Pro Ala Asn Cys Thr Asn Glu Leu Tyr Met Met
                725                 730                 735

atg agg gac tgt tgg cat gca gtg ccc tcc cag aga cca acg ttc aag     2674
Met Arg Asp Cys Trp His Ala Val Pro Ser Gln Arg Pro Thr Phe Lys
            740                 745                 750

cag ttg gta gaa gac ttg gat cga att ctc act ctc aca acc aat gag     2722
Gln Leu Val Glu Asp Leu Asp Arg Ile Leu Thr Leu Thr Thr Asn Glu
        755                 760                 765

cct cta tcc tga agagcgttgg accctggagc tgctggccac atcttgatct         2774
Pro Leu Ser
    770

gccatatgtg gtccaagaat gaagtcaaca cgaaggagaa tgaaggtgct gagggataaa   2834

gttattgaca ttctaggagc tcctggatca aacc                               2868


<210> SEQ ID NO 20
<211> LENGTH: 2923
<212> TYPE: DNA
<213> ORGANISM: Homo sapiens
<220> FEATURE:
<221> NAME/KEY: CDS
<222> LOCATION: (419)...(2872)

<400> SEQUENCE: 20

cccgcgagca aagtttggtg gaggcaacgc aagcctgagt cctttcttcc tctcgttccc     60

caaatccgag ggcagcccgc gggcgtcatg gcgctcctcc gcagcctggg gtacgcgtga    120

agcccgggag gcttggcgcc ggcgaagacc caaggaccac tcttctgcgt ttggagttgc    180

tccccgcaac ccccgggctcg tcgctttctc catcccgacc cacgcggggc cggggacaac    240

acaggtcgcg gaggagcgtt gccattcaag tgactgcagc agcagcgcag cgcctcggtt    300

cctgagccca ccgcagctga aggcattgcg cgtagtccat gcccgtagag gaagtgtgca    360

gatgggatta acgtccacat ggagatatgg aagaggaccg ggattggta ccgtaacc       418
```

-continued

```
atg gtc agc tgg ggt cgt ttc atc tgc ctg gtc gtg gtc acc atg gca      466
Met Val Ser Trp Gly Arg Phe Ile Cys Leu Val Val Val Thr Met Ala
  1               5                  10                  15

acc ttg tcc ctg gcc cgg ccc tcc ttc agt tta gtt gag gat acc aca      514
Thr Leu Ser Leu Ala Arg Pro Ser Phe Ser Leu Val Glu Asp Thr Thr
             20                  25                  30

tta gag cca gaa gag cca cca acc aaa tac caa atc tct caa cca gaa      562
Leu Glu Pro Glu Glu Pro Pro Thr Lys Tyr Gln Ile Ser Gln Pro Glu
         35                  40                  45

gtg tac gtg gct gcg cca ggg gag tcg cta gag gtg cgc tgc ctg ttg      610
Val Tyr Val Ala Ala Pro Gly Glu Ser Leu Glu Val Arg Cys Leu Leu
     50                  55                  60

aaa gat gcc gcc gtg atc agt tgg act aag gat ggg gtg cac ttg ggg      658
Lys Asp Ala Ala Val Ile Ser Trp Thr Lys Asp Gly Val His Leu Gly
 65                  70                  75                  80

ccc aac aat agg aca gtg ctt att ggg gag tac ttg cag ata aag ggc      706
Pro Asn Asn Arg Thr Val Leu Ile Gly Glu Tyr Leu Gln Ile Lys Gly
                 85                  90                  95

gcc aca cct aga gac tcc ggc ctc tat gct tgt act gcc agt agg act      754
Ala Thr Pro Arg Asp Ser Gly Leu Tyr Ala Cys Thr Ala Ser Arg Thr
            100                 105                 110

gta gac agt gaa act tgg tac ttc atg gtg aat gtc aca gat gcc atc      802
Val Asp Ser Glu Thr Trp Tyr Phe Met Val Asn Val Thr Asp Ala Ile
        115                 120                 125

tca tcc gga gat gat gag gat gac acc gat ggt gcg gaa gat ttt gtc      850
Ser Ser Gly Asp Asp Glu Asp Asp Thr Asp Gly Ala Glu Asp Phe Val
    130                 135                 140

agt gag aac agt aac aac aag aga gca cca tac tgg acc aac aca gaa      898
Ser Glu Asn Ser Asn Asn Lys Arg Ala Pro Tyr Trp Thr Asn Thr Glu
145                 150                 155                 160

aag atg gaa aag cgg ctc cat gct gtg cct gcg gcc aac act gtc aag      946
Lys Met Glu Lys Arg Leu His Ala Val Pro Ala Ala Asn Thr Val Lys
                165                 170                 175

ttt cgc tgc cca gcc ggg ggg aac cca atg cca acc atg cgg tgg ctg      994
Phe Arg Cys Pro Ala Gly Gly Asn Pro Met Pro Thr Met Arg Trp Leu
            180                 185                 190

aaa aac ggg aag gag ttt aag cag gag cat cgc att gga ggc tac aag     1042
Lys Asn Gly Lys Glu Phe Lys Gln Glu His Arg Ile Gly Gly Tyr Lys
        195                 200                 205

gta cga aac cag cac tgg agc ctc att atg gaa agt gtg gtc cca tct     1090
Val Arg Asn Gln His Trp Ser Leu Ile Met Glu Ser Val Val Pro Ser
    210                 215                 220

gac aag gga aat tat acc tgt gta gtg gag aat gaa tac ggg tcc atc     1138
Asp Lys Gly Asn Tyr Thr Cys Val Val Glu Asn Glu Tyr Gly Ser Ile
225                 230                 235                 240

aat cac acg tac cac ctg gat gtt gtg gag cga tcg cct cac cgg ccc     1186
Asn His Thr Tyr His Leu Asp Val Val Glu Arg Ser Pro His Arg Pro
                245                 250                 255

atc ctc caa gcc gga ctg ccg gca aat gcc tcc aca gtg gtc gga gga     1234
Ile Leu Gln Ala Gly Leu Pro Ala Asn Ala Ser Thr Val Val Gly Gly
            260                 265                 270

gac gta gag ttt gtc tgc aag gtt tac agt gat gcc cag ccc cac atc     1282
Asp Val Glu Phe Val Cys Lys Val Tyr Ser Asp Ala Gln Pro His Ile
        275                 280                 285

cag tgg atc aag cac gtg gaa aag aac ggc agt aaa tac ggg ccc gac     1330
Gln Trp Ile Lys His Val Glu Lys Asn Gly Ser Lys Tyr Gly Pro Asp
    290                 295                 300

ggg ctg ccc tac ctc aag gtt ctc aag cac tcg ggg ata aat agt tcc     1378
Gly Leu Pro Tyr Leu Lys Val Leu Lys His Ser Gly Ile Asn Ser Ser
```

-continued

```
305                 310                 315                 320

aat gca gaa gtg ctg gct ctg ttc aat gtg acc gag gcg gat gct ggg     1426
Asn Ala Glu Val Leu Ala Leu Phe Asn Val Thr Glu Ala Asp Ala Gly
                325                 330                 335

gaa tat ata tgt aag gtc tcc aat tat ata ggg cag gcc aac cag tct     1474
Glu Tyr Ile Cys Lys Val Ser Asn Tyr Ile Gly Gln Ala Asn Gln Ser
            340                 345                 350

gcc tgg ctc act gtc ctg cca aaa cag caa gcg cct gga aga gaa aag     1522
Ala Trp Leu Thr Val Leu Pro Lys Gln Gln Ala Pro Gly Arg Glu Lys
        355                 360                 365

gag att aca gct tcc cca gac tac ctg gag ata gcc att tac tgc ata     1570
Glu Ile Thr Ala Ser Pro Asp Tyr Leu Glu Ile Ala Ile Tyr Cys Ile
    370                 375                 380

ggg gtc ttc tta atc gcc tgt atg gtg gta aca gtc atc ctg tgc cga     1618
Gly Val Phe Leu Ile Ala Cys Met Val Val Thr Val Ile Leu Cys Arg
385                 390                 395                 400

atg aag aac acg acc aag aag cca gac ttc agc agc cag ccg gct gtg     1666
Met Lys Asn Thr Thr Lys Lys Pro Asp Phe Ser Ser Gln Pro Ala Val
                405                 410                 415

cac aag ctg acc aaa cgt atc ccc ctg cgg aga cag gta aca gtt tcg     1714
His Lys Leu Thr Lys Arg Ile Pro Leu Arg Arg Gln Val Thr Val Ser
            420                 425                 430

gct gag tcc agc tcc tcc atg aac tcc aac acc ccg ctg gtg agg ata     1762
Ala Glu Ser Ser Ser Ser Met Asn Ser Asn Thr Pro Leu Val Arg Ile
        435                 440                 445

aca aca cgc ctc tct tca acg gca gac acc ccc atg ctg gca ggg gtc     1810
Thr Thr Arg Leu Ser Ser Thr Ala Asp Thr Pro Met Leu Ala Gly Val
    450                 455                 460

tcc gag tat gaa ctt cca gag gac cca aaa tgg gag ttt cca aga gat     1858
Ser Glu Tyr Glu Leu Pro Glu Asp Pro Lys Trp Glu Phe Pro Arg Asp
465                 470                 475                 480

aag ctg aca ctg ggc aag ccc ctg gga gaa ggt tgc ttt ggg caa gtg     1906
Lys Leu Thr Leu Gly Lys Pro Leu Gly Glu Gly Cys Phe Gly Gln Val
                485                 490                 495

gtc atg gcg gaa gca gtg gga att gac aaa gac aag ccc aag gag gcg     1954
Val Met Ala Glu Ala Val Gly Ile Asp Lys Asp Lys Pro Lys Glu Ala
            500                 505                 510

gtc acc gtg gcc gtg aag atg ttg aaa gat gat gcc aca gag aaa gac     2002
Val Thr Val Ala Val Lys Met Leu Lys Asp Asp Ala Thr Glu Lys Asp
        515                 520                 525

ctt tct gat ctg gtg tca gag atg gag atg atg aag atg att ggg aaa     2050
Leu Ser Asp Leu Val Ser Glu Met Glu Met Met Lys Met Ile Gly Lys
    530                 535                 540

cac aag aat atc ata aat ctt ctt gga gcc tgc aca cag gat ggg cct     2098
His Lys Asn Ile Ile Asn Leu Leu Gly Ala Cys Thr Gln Asp Gly Pro
545                 550                 555                 560

ctc tat gtc ata gtt gag tat gcc tct aaa ggc aac ctc cga gaa tac     2146
Leu Tyr Val Ile Val Glu Tyr Ala Ser Lys Gly Asn Leu Arg Glu Tyr
                565                 570                 575

ctc cga gcc cgg agg cca ccc ggg atg gag tac tcc tat gac att aac     2194
Leu Arg Ala Arg Arg Pro Pro Gly Met Glu Tyr Ser Tyr Asp Ile Asn
            580                 585                 590

cgt gtt cct gag gag cag atg acc ttc aag gac ttg gtg tca tgc acc     2242
Arg Val Pro Glu Glu Gln Met Thr Phe Lys Asp Leu Val Ser Cys Thr
        595                 600                 605

tac cag ctg gcc aga cgg atg gag tac ttg gct tcc caa aaa tgt att     2290
Tyr Gln Leu Ala Arg Arg Met Glu Tyr Leu Ala Ser Gln Lys Cys Ile
    610                 615                 620

cat cga gat tta gca gcc aga aat gtt ttg gta aca gaa aac aat gtg     2338
```

-continued

```
His Arg Asp Leu Ala Ala Arg Asn Val Leu Val Thr Glu Asn Asn Val
625                 630                 635                 640

atg aaa ata gca gac ttt gga ctc gcc aga gat atc aac aat ata gac     2386
Met Lys Ile Ala Asp Phe Gly Leu Ala Arg Asp Ile Asn Asn Ile Asp
                645                 650                 655

tat tac aaa aag acc acc aat ggg cgg ctt cca gtc aag tgg atg gct     2434
Tyr Tyr Lys Lys Thr Thr Asn Gly Arg Leu Pro Val Lys Trp Met Ala
            660                 665                 670

cca gaa gcc ctg ttt gat aga gta tac act cat cag agt gat gtc tgg     2482
Pro Glu Ala Leu Phe Asp Arg Val Tyr Thr His Gln Ser Asp Val Trp
        675                 680                 685

tcc ttc ggg gtg tta atg tgg gag atc ttc act tta ggg ggc tcg ccc     2530
Ser Phe Gly Val Leu Met Trp Glu Ile Phe Thr Leu Gly Gly Ser Pro
    690                 695                 700

tac cca ggg att ccc gtg gag gaa ctt ttt aag ctg ctg aag gaa gga     2578
Tyr Pro Gly Ile Pro Val Glu Glu Leu Phe Lys Leu Leu Lys Glu Gly
705                 710                 715                 720

cac aga atg gat aag cca gcc aac tgc acc aac gaa ctg tac atg atg     2626
His Arg Met Asp Lys Pro Ala Asn Cys Thr Asn Glu Leu Tyr Met Met
                725                 730                 735

atg agg gac tgt tgg cat gca gtg ccc tcc cag aga cca acg ttc aag     2674
Met Arg Asp Cys Trp His Ala Val Pro Ser Gln Arg Pro Thr Phe Lys
            740                 745                 750

cag ttg gta gaa gac ttg gat cga att ctc act ctc aca acc aat gag     2722
Gln Leu Val Glu Asp Leu Asp Arg Ile Leu Thr Leu Thr Thr Asn Glu
        755                 760                 765

cgg tac aag ctg ctt ccc tgt cct gac aag cac aat aaa agg tgc aaa     2770
Arg Tyr Lys Leu Leu Pro Cys Pro Asp Lys His Asn Lys Arg Cys Lys
    770                 775                 780

cct gag gaa cgt ggg gac ctc aca gag gca ggc gca gcc ggc tca tcg     2818
Pro Glu Glu Arg Gly Asp Leu Thr Glu Ala Gly Ala Ala Gly Ser Ser
785                 790                 795                 800

aga tgt gtg gac agc aga aag cga gtg agg caa gag aaa atc agc aca     2866
Arg Cys Val Asp Ser Arg Lys Arg Val Arg Gln Glu Lys Ile Ser Thr
                805                 810                 815

ggg taa acatcagaga tcaaagggca gcagctggag tcactgggtg gagaagcagt      2922
Gly

g                                                                   2923


<210> SEQ ID NO 21
<211> LENGTH: 2826
<212> TYPE: DNA
<213> ORGANISM: Homo sapiens
<220> FEATURE:
<221> NAME/KEY: CDS
<222> LOCATION: (419)...(2725)

<400> SEQUENCE: 21

cccgcgagca aagtttggtg gaggcaacgc aagcctgagt cctttcttcc tctcgttccc     60

caaatccgag ggcagcccgc gggcgtcatg gcgctcctcc gcagcctggg gtacgcgtga    120

agcccgggag gcttggcgcc ggcgaagacc caaggaccac tcttctgcgt ttggagttgc    180

tccccgcaac ccccggctcg tcgctttctc catcccgacc cacgcggggc cggggacaac    240

acaggtcgcg gaggagcgtt gccattcaag tgactgcagc agcagcgcag cgcctcggtt    300

cctgagccca ccgcagctga aggcattgcg cgtagtccat gcccgtagag gaagtgtgca    360

gatgggatta acgtccacat ggagatatgg aagaggaccg gggattggta ccgtaacc      418

atg gtc agc tgg ggt cgt ttc atc tgc ctg gtc gtg gtc acc atg gca      466
Met Val Ser Trp Gly Arg Phe Ile Cys Leu Val Val Val Thr Met Ala
```

-continued

```
 1               5                   10                  15

acc ttg tcc ctg gcc cgg ccc tcc ttc agt tta gtt gag gat acc aca      514
Thr Leu Ser Leu Ala Arg Pro Ser Phe Ser Leu Val Glu Asp Thr Thr
             20                  25                  30

tta gag cca gaa gag cca cca acc aaa tac caa atc tct caa cca gaa      562
Leu Glu Pro Glu Glu Pro Pro Thr Lys Tyr Gln Ile Ser Gln Pro Glu
         35                  40                  45

gtg tac gtg gct gcg cca ggg gag tcg cta gag gtg cgc tgc ctg ttg      610
Val Tyr Val Ala Ala Pro Gly Glu Ser Leu Glu Val Arg Cys Leu Leu
     50                  55                  60

aaa gat gcc gcc gtg atc agt tgg act aag gat ggg gtg cac ttg ggg      658
Lys Asp Ala Ala Val Ile Ser Trp Thr Lys Asp Gly Val His Leu Gly
 65                  70                  75                  80

ccc aac aat agg aca gtg ctt att ggg gag tac ttg cag ata aag ggc      706
Pro Asn Asn Arg Thr Val Leu Ile Gly Glu Tyr Leu Gln Ile Lys Gly
                 85                  90                  95

gcc aca cct aga gac tcc ggc ctc tat gct tgt act gcc agt agg act      754
Ala Thr Pro Arg Asp Ser Gly Leu Tyr Ala Cys Thr Ala Ser Arg Thr
            100                 105                 110

gta gac agt gaa act tgg tac ttc atg gtg aat gtc aca gat gcc atc      802
Val Asp Ser Glu Thr Trp Tyr Phe Met Val Asn Val Thr Asp Ala Ile
        115                 120                 125

tca tcc gga gat gat gag gat gac acc gat ggt gcg gaa gat ttt gtc      850
Ser Ser Gly Asp Asp Glu Asp Asp Thr Asp Gly Ala Glu Asp Phe Val
    130                 135                 140

agt gag aac agt aac aac aag aga gca cca tac tgg acc aac aca gaa      898
Ser Glu Asn Ser Asn Asn Lys Arg Ala Pro Tyr Trp Thr Asn Thr Glu
145                 150                 155                 160

aag atg gaa aag cgg ctc cat gct gtg cct gcg gcc aac act gtc aag      946
Lys Met Glu Lys Arg Leu His Ala Val Pro Ala Ala Asn Thr Val Lys
                165                 170                 175

ttt cgc tgc cca gcc ggg ggg aac cca atg cca acc atg cgg tgg ctg      994
Phe Arg Cys Pro Ala Gly Gly Asn Pro Met Pro Thr Met Arg Trp Leu
            180                 185                 190

aaa aac ggg aag gag ttt aag cag gag cat cgc att gga ggc tac aag     1042
Lys Asn Gly Lys Glu Phe Lys Gln Glu His Arg Ile Gly Gly Tyr Lys
        195                 200                 205

gta cga aac cag cac tgg agc ctc att atg gaa agt gtg gtc cca tct     1090
Val Arg Asn Gln His Trp Ser Leu Ile Met Glu Ser Val Val Pro Ser
    210                 215                 220

gac aag gga aat tat acc tgt gta gtg gag aat gaa tac ggg tcc atc     1138
Asp Lys Gly Asn Tyr Thr Cys Val Val Glu Asn Glu Tyr Gly Ser Ile
225                 230                 235                 240

aat cac acg tac cac ctg gat gtt gtg gag cga tcg cct cac cgg ccc     1186
Asn His Thr Tyr His Leu Asp Val Val Glu Arg Ser Pro His Arg Pro
                245                 250                 255

atc ctc caa gcc gga ctg ccg gca aat gcc tcc aca gtg gtc gga gga     1234
Ile Leu Gln Ala Gly Leu Pro Ala Asn Ala Ser Thr Val Val Gly Gly
            260                 265                 270

gac gta gag ttt gtc tgc aag gtt tac agt gat gcc cag ccc cac atc     1282
Asp Val Glu Phe Val Cys Lys Val Tyr Ser Asp Ala Gln Pro His Ile
        275                 280                 285

cag tgg atc aag cac gtg gaa aag aac ggc agt aaa tac ggg ccc gac     1330
Gln Trp Ile Lys His Val Glu Lys Asn Gly Ser Lys Tyr Gly Pro Asp
    290                 295                 300

ggg ctg ccc tac ctc aag gtt ctc aag cac tcg ggg ata aat agt tcc     1378
Gly Leu Pro Tyr Leu Lys Val Leu Lys His Ser Gly Ile Asn Ser Ser
305                 310                 315                 320

aat gca gaa gtg ctg gct ctg ttc aat gtg acc gag gcg gat gct ggg     1426
```

-continued

```
Asn Ala Glu Val Leu Ala Leu Phe Asn Val Thr Glu Ala Asp Ala Gly
                325                 330                 335

gaa tat ata tgt aag gtc tcc aat tat ata ggg cag gcc aac cag tct      1474
Glu Tyr Ile Cys Lys Val Ser Asn Tyr Ile Gly Gln Ala Asn Gln Ser
            340                 345                 350

gcc tgg ctc act gtc ctg cca aaa cag caa gcg cct gga aga gaa aag      1522
Ala Trp Leu Thr Val Leu Pro Lys Gln Gln Ala Pro Gly Arg Glu Lys
        355                 360                 365

gag att aca gct tcc cca gac tac ctg gag ata gcc att tac tgc ata      1570
Glu Ile Thr Ala Ser Pro Asp Tyr Leu Glu Ile Ala Ile Tyr Cys Ile
    370                 375                 380

ggg gtc ttc tta atc gcc tgt atg gtg gta aca gtc atc ctg tgc cga      1618
Gly Val Phe Leu Ile Ala Cys Met Val Val Thr Val Ile Leu Cys Arg
385                 390                 395                 400

atg aag aac acg acc aag aag cca gac ttc agc agc cag ccg gct gtg      1666
Met Lys Asn Thr Thr Lys Lys Pro Asp Phe Ser Ser Gln Pro Ala Val
                405                 410                 415

cac aag ctg acc aaa cgt atc ccc ctg cgg aga cag gta aca gtt tcg      1714
His Lys Leu Thr Lys Arg Ile Pro Leu Arg Arg Gln Val Thr Val Ser
            420                 425                 430

gct gag tcc agc tcc tcc atg aac tcc aac acc ccg ctg gtg agg ata      1762
Ala Glu Ser Ser Ser Ser Met Asn Ser Asn Thr Pro Leu Val Arg Ile
        435                 440                 445

aca aca cgc ctc tct tca acg gca gac acc ccc atg ctg gca ggg gtc      1810
Thr Thr Arg Leu Ser Ser Thr Ala Asp Thr Pro Met Leu Ala Gly Val
    450                 455                 460

tcc gag tat gaa ctt cca gag gac cca aaa tgg gag ttt cca aga gat      1858
Ser Glu Tyr Glu Leu Pro Glu Asp Pro Lys Trp Glu Phe Pro Arg Asp
465                 470                 475                 480

aag ctg aca ctg ggc aag ccc ctg gga gaa ggt tgc ttt ggg caa gtg      1906
Lys Leu Thr Leu Gly Lys Pro Leu Gly Glu Gly Cys Phe Gly Gln Val
                485                 490                 495

gtc atg gcg gaa gca gtg gga att gac aaa gac aag ccc aag gag gcg      1954
Val Met Ala Glu Ala Val Gly Ile Asp Lys Asp Lys Pro Lys Glu Ala
            500                 505                 510

gtc acc gtg gcc gtg aag atg ttg aaa gat gat gcc aca gag aaa gac      2002
Val Thr Val Ala Val Lys Met Leu Lys Asp Asp Ala Thr Glu Lys Asp
        515                 520                 525

ctt tct gat ctg gtg tca gag atg gag atg atg aag atg att ggg aaa      2050
Leu Ser Asp Leu Val Ser Glu Met Glu Met Met Lys Met Ile Gly Lys
    530                 535                 540

cac aag aat atc ata aat ctt ctt gga gcc tgc aca cag gat ggg cct      2098
His Lys Asn Ile Ile Asn Leu Leu Gly Ala Cys Thr Gln Asp Gly Pro
545                 550                 555                 560

ctc tat gtc ata gtt gag tat gcc tct aaa ggc aac ctc cga gaa tac      2146
Leu Tyr Val Ile Val Glu Tyr Ala Ser Lys Gly Asn Leu Arg Glu Tyr
                565                 570                 575

ctc cga gcc cgg agg cca ccc ggg atg gag tac tcc tat gac att aac      2194
Leu Arg Ala Arg Arg Pro Pro Gly Met Glu Tyr Ser Tyr Asp Ile Asn
            580                 585                 590

cgt gtt cct gag gag cag atg acc ttc aag gac ttg gtg tca tgc acc      2242
Arg Val Pro Glu Glu Gln Met Thr Phe Lys Asp Leu Val Ser Cys Thr
        595                 600                 605

tac cag ctg gcc aga cgg atg gag tac ttg gct tcc caa aaa tgt att      2290
Tyr Gln Leu Ala Arg Arg Met Glu Tyr Leu Ala Ser Gln Lys Cys Ile
    610                 615                 620

cat cga gat tta gca gcc aga aat gtt ttg gta aca gaa aac aat gtg      2338
His Arg Asp Leu Ala Ala Arg Asn Val Leu Val Thr Glu Asn Asn Val
625                 630                 635                 640
```

-continued

```
atg aaa ata gca gac ttt gga ctc gcc aga gat atc aac aat ata gac     2386
Met Lys Ile Ala Asp Phe Gly Leu Ala Arg Asp Ile Asn Asn Ile Asp
                645                 650                 655

tat tac aaa aag acc acc aat ggg cgg ctt cca gtc aag tgg atg gct     2434
Tyr Tyr Lys Lys Thr Thr Asn Gly Arg Leu Pro Val Lys Trp Met Ala
            660                 665                 670

cca gaa gcc ctg ttt gat aga gta tac act cat cag agt gat gtc tgg     2482
Pro Glu Ala Leu Phe Asp Arg Val Tyr Thr His Gln Ser Asp Val Trp
        675                 680                 685

tcc ttc ggg gtg tta atg tgg gag atc ttc act tta ggg ggc tcg ccc     2530
Ser Phe Gly Val Leu Met Trp Glu Ile Phe Thr Leu Gly Gly Ser Pro
    690                 695                 700

tac cca ggg att ccc gtg gag gaa ctt ttt aag ctg ctg aag gaa gga     2578
Tyr Pro Gly Ile Pro Val Glu Glu Leu Phe Lys Leu Leu Lys Glu Gly
705                 710                 715                 720

cac aga atg gat aag cca gcc aac tgc acc aac gaa ctg tac atg atg     2626
His Arg Met Asp Lys Pro Ala Asn Cys Thr Asn Glu Leu Tyr Met Met
                725                 730                 735

atg agg gac tgt tgg cat gca gtg ccc tcc cag aga cca acg ttc aag     2674
Met Arg Asp Cys Trp His Ala Val Pro Ser Gln Arg Pro Thr Phe Lys
            740                 745                 750

cag ttg gta gaa gac ttg gat cga att ctc act ctc aca acc aat gag     2722
Gln Leu Val Glu Asp Leu Asp Arg Ile Leu Thr Leu Thr Thr Asn Glu
        755                 760                 765

taa agccaaggat atgggaggga aaaaaagggg aaagagtcat ggaaagccag         2775

cttcttgctg aaactccact aggtgccctg ctggaatctc ccttgaaaga g            2826


<210> SEQ ID NO 22
<211> LENGTH: 310
<212> TYPE: DNA
<213> ORGANISM: Homo sapiens
<220> FEATURE:
<221> NAME/KEY: CDS
<222> LOCATION: (1)...(99)

<400> SEQUENCE: 22

gac ttg gat cga att ctc act ctc aca acc aat gag gaa tac ttg gac       48
Asp Leu Asp Arg Ile Leu Thr Leu Thr Thr Asn Glu Glu Tyr Leu Asp
  1               5                  10                  15

ctc agt cag cct ctc gaa ccg tat tca cct tgt tat cct gac cca aga       96
Leu Ser Gln Pro Leu Glu Pro Tyr Ser Pro Cys Tyr Pro Asp Pro Arg
             20                  25                  30

tga aataaaacgt ctctcttccc ttctttcagg aatacttgga cctcagccaa          149

cctctcgaac agtattcacc tagttaccct gacacaagaa gttcttgttc ttcaggagat    209

gattctgttt tttctccaga ccccatgcct tacgaaccat gccttcctca gtatccacac    269

ataaacggca gtgttaaaac atgaatgact gtgtctgcct g                        310


<210> SEQ ID NO 23
<211> LENGTH: 3025
<212> TYPE: DNA
<213> ORGANISM: Homo sapiens
<220> FEATURE:
<221> NAME/KEY: CDS
<222> LOCATION: (595)...(2643)

<400> SEQUENCE: 23

cgcggacggc gagggagcgc gcgcggccgc cacaaagctc gggcgccgcg gggctgcatg     60

cggcgtacct ggcccggcgc ggcgactgct ctccgggctg gcgggggccg gccgcgagcc    120

ccgggggccc cgaggccgca gcttgcctgc gcgctctgag ccttcgcaac tcgcgagcaa    180
```

```
agtttggtgg aggcaacgcc aagcctgagt cctttcttcc tctcgttccc caaatccgag    240

ggcagcccgc gggcgtcatg cccgcgctcc tccgcagcct ggggtacgcg tgaagcccgg    300

gaggcttggc gccggcgaag acccaaggac cactcttctg cgtttggagt tgctccccac    360

aaccccgggc tcgtcgcttt ctccatcccg acccacgcgg ggcgcgggga caacacaggt    420

cgcggaggag cgttgccatt caagtgactg cagcagcagc ggcagcgcct cggttcctga    480

gcccaccgca ggctgaaggc attgcgcgta gtccatgccc gtagaggaag tgtgcagatg    540

ggattaacgt ccacatggag atatggaaga ggaccgggga ttggtaccgt aacc atg      597
                                                            Met
                                                              1

gtc agc tgg ggt cgt ttc atc tgc ctg gtc gtg gtc acc atg gca acc      645
Val Ser Trp Gly Arg Phe Ile Cys Leu Val Val Val Thr Met Ala Thr
                5                  10                  15

ttg tcc ctg gcc cgg ccc tcc ttc agt tta gtt gag gat acc aca tta      693
Leu Ser Leu Ala Arg Pro Ser Phe Ser Leu Val Glu Asp Thr Thr Leu
        20                  25                  30

gag cca gaa gat gcc atc tca tcc gga gat gat gag gat gac acc gat      741
Glu Pro Glu Asp Ala Ile Ser Ser Gly Asp Asp Glu Asp Asp Thr Asp
    35                  40                  45

ggt gcg gaa gat ttt gtc agt gag aac agt aac aac aag aga gca cca      789
Gly Ala Glu Asp Phe Val Ser Glu Asn Ser Asn Asn Lys Arg Ala Pro
 50                  55                  60                  65

tac tgg acc aac aca gaa aag atg gaa aag cgg ctc cat gct gtg cct      837
Tyr Trp Thr Asn Thr Glu Lys Met Glu Lys Arg Leu His Ala Val Pro
                70                  75                  80

gcg gcc aac act gtc aag ttt cgc tgc cca gcc ggg ggg aac cca atg      885
Ala Ala Asn Thr Val Lys Phe Arg Cys Pro Ala Gly Gly Asn Pro Met
            85                  90                  95

cca acc atg cgg tgg ctg aaa aac ggg aag gag ttt aag cag gag cat      933
Pro Thr Met Arg Trp Leu Lys Asn Gly Lys Glu Phe Lys Gln Glu His
        100                 105                 110

cgc att gga ggc tac aag gta cga aac cag cac tgg agc ctc att atg      981
Arg Ile Gly Gly Tyr Lys Val Arg Asn Gln His Trp Ser Leu Ile Met
    115                 120                 125

gaa agt gtg gtc cca tct gac aag gga aat tat acc tgt gtg gtg gag     1029
Glu Ser Val Val Pro Ser Asp Lys Gly Asn Tyr Thr Cys Val Val Glu
130                 135                 140                 145

aat gaa tac ggg tcc atc aat cac acg tac cac ctg gat gtt gtg gag     1077
Asn Glu Tyr Gly Ser Ile Asn His Thr Tyr His Leu Asp Val Val Glu
                150                 155                 160

cga tcg cct cac cgg ccc atc ctc caa gcc gga ctg ccg gca aat gcc     1125
Arg Ser Pro His Arg Pro Ile Leu Gln Ala Gly Leu Pro Ala Asn Ala
            165                 170                 175

tcc aca gtg gtc gga gga gac gta gag ttt gtc tgc aag gtt tac agt     1173
Ser Thr Val Val Gly Gly Asp Val Glu Phe Val Cys Lys Val Tyr Ser
        180                 185                 190

gat gcc cag ccc cac atc cag tgg atc aag cac gtg gaa aag aac ggc     1221
Asp Ala Gln Pro His Ile Gln Trp Ile Lys His Val Glu Lys Asn Gly
    195                 200                 205

agt aaa tac ggg ccc gac ggg ctg ccc tac ctc aag gtt ctc aag cac     1269
Ser Lys Tyr Gly Pro Asp Gly Leu Pro Tyr Leu Lys Val Leu Lys His
210                 215                 220                 225

tcg ggg ata aat agt tcc aat gca gaa gtg ctg gct ctg ttc aat gtg     1317
Ser Gly Ile Asn Ser Ser Asn Ala Glu Val Leu Ala Leu Phe Asn Val
                230                 235                 240

acc gag gcg gat gct ggg gaa tat ata tgt aag gtc tcc aat tat ata     1365
Thr Glu Ala Asp Ala Gly Glu Tyr Ile Cys Lys Val Ser Asn Tyr Ile
```

```
            245                 250                 255

ggg cag gcc aac cag tct gcc tgg ctc act gtc ctg cca aaa cag caa     1413
Gly Gln Ala Asn Gln Ser Ala Trp Leu Thr Val Leu Pro Lys Gln Gln
        260                 265                 270

gcg cct gga aga gaa aag gag att aca gct tcc cca gac tac ctg gag     1461
Ala Pro Gly Arg Glu Lys Glu Ile Thr Ala Ser Pro Asp Tyr Leu Glu
    275                 280                 285

ata gcc att tac tgc ata ggg gtc ttc tta atc gcc tgt atg gtg gta     1509
Ile Ala Ile Tyr Cys Ile Gly Val Phe Leu Ile Ala Cys Met Val Val
290                 295                 300                 305

aca gtc atc ctg tgc cga atg aag aac acg acc aag aag cca gac ttc     1557
Thr Val Ile Leu Cys Arg Met Lys Asn Thr Thr Lys Lys Pro Asp Phe
                310                 315                 320

agc agc cag ccg gct gtg cac aag ctg acc aaa cgt atc ccc ctg cgg     1605
Ser Ser Gln Pro Ala Val His Lys Leu Thr Lys Arg Ile Pro Leu Arg
            325                 330                 335

aga cag gtt tcg gct gag tcc agc tcc tcc atg aac tcc aac acc ccg     1653
Arg Gln Val Ser Ala Glu Ser Ser Ser Ser Met Asn Ser Asn Thr Pro
        340                 345                 350

ctg gtg agg ata aca aca cgc ctc tct tca acg gca gac acc ccc atg     1701
Leu Val Arg Ile Thr Thr Arg Leu Ser Ser Thr Ala Asp Thr Pro Met
    355                 360                 365

ctg gca ggg gtc tcc gag tat gaa ctt cca gag gac cca aaa tgg gag     1749
Leu Ala Gly Val Ser Glu Tyr Glu Leu Pro Glu Asp Pro Lys Trp Glu
370                 375                 380                 385

ttt cca aga gat aag ctg aca ctg ggc aag ccc ctg gga gaa ggt tgc     1797
Phe Pro Arg Asp Lys Leu Thr Leu Gly Lys Pro Leu Gly Glu Gly Cys
                390                 395                 400

ttt ggg caa gtg gtc atg gcg gaa gca gtg gga att gac aaa gac aag     1845
Phe Gly Gln Val Val Met Ala Glu Ala Val Gly Ile Asp Lys Asp Lys
            405                 410                 415

ccc aag gag gcg gtc acc gtg gcc gtg aag atg ttg aaa gat gat gcc     1893
Pro Lys Glu Ala Val Thr Val Ala Val Lys Met Leu Lys Asp Asp Ala
        420                 425                 430

aca gag aaa gac ctt tct gat ctg gtg tca gag atg gag atg atg aag     1941
Thr Glu Lys Asp Leu Ser Asp Leu Val Ser Glu Met Glu Met Met Lys
    435                 440                 445

atg att ggg aaa cac aag aat atc ata aat ctt ctt gga gcc tgc aca     1989
Met Ile Gly Lys His Lys Asn Ile Ile Asn Leu Leu Gly Ala Cys Thr
450                 455                 460                 465

cag gat ggg cct ctc tat gtc ata gtt gag tat gcc tct aaa ggc aac     2037
Gln Asp Gly Pro Leu Tyr Val Ile Val Glu Tyr Ala Ser Lys Gly Asn
                470                 475                 480

ctc cga gaa tac ctc cga gcc cgg agg cca ccc ggg atg gag tac tcc     2085
Leu Arg Glu Tyr Leu Arg Ala Arg Arg Pro Pro Gly Met Glu Tyr Ser
            485                 490                 495

tat gac att aac cgt gtt cct gag gag cag atg acc ttc aag gac ttg     2133
Tyr Asp Ile Asn Arg Val Pro Glu Glu Gln Met Thr Phe Lys Asp Leu
        500                 505                 510

gtg tca tgc acc tac cag ctg gcc aga ggc atg gag tac ttg gct tcc     2181
Val Ser Cys Thr Tyr Gln Leu Ala Arg Gly Met Glu Tyr Leu Ala Ser
    515                 520                 525

caa aaa tgt att cat cga gat tta gca gcc aga aat gtt ttg gta aca     2229
Gln Lys Cys Ile His Arg Asp Leu Ala Ala Arg Asn Val Leu Val Thr
530                 535                 540                 545

gaa aac aat gtg atg aaa ata gca gac ttt gga ctc gcc aga gat atc     2277
Glu Asn Asn Val Met Lys Ile Ala Asp Phe Gly Leu Ala Arg Asp Ile
                550                 555                 560

aac aat ata gac tat tac aaa aag acc acc aat ggg cgg ctt cca gtc     2325
```

```
Asn Asn Ile Asp Tyr Tyr Lys Lys Thr Thr Asn Gly Arg Leu Pro Val
            565                 570                 575

aag tgg atg gct cca gaa gcc ctg ttt gat aga gta tac act cat cag     2373
Lys Trp Met Ala Pro Glu Ala Leu Phe Asp Arg Val Tyr Thr His Gln
        580                 585                 590

agt gat gtc tgg tcc ttc ggg gtg tta atg tgg gag atc ttc act tta     2421
Ser Asp Val Trp Ser Phe Gly Val Leu Met Trp Glu Ile Phe Thr Leu
    595                 600                 605

ggg ggc tcg ccc tac cca ggg att ccc gtg gag gaa ctt ttt aag ctg     2469
Gly Gly Ser Pro Tyr Pro Gly Ile Pro Val Glu Glu Leu Phe Lys Leu
610                 615                 620                 625

ctg aag gaa gga cac aga atg gat aag cca gcc aac tgc acc aac gaa     2517
Leu Lys Glu Gly His Arg Met Asp Lys Pro Ala Asn Cys Thr Asn Glu
                630                 635                 640

ctg tac atg atg atg agg gac tgt tgg cat gca gtg ccc tcc cag aga     2565
Leu Tyr Met Met Met Arg Asp Cys Trp His Ala Val Pro Ser Gln Arg
            645                 650                 655

cca acg ttc aag cag ttg gta gaa gac ttg gat cga att ccc ccc aac     2613
Pro Thr Phe Lys Gln Leu Val Glu Asp Leu Asp Arg Ile Pro Pro Asn
        660                 665                 670

cct tcc ctt atg agc att ttt aga aaa tag tcttagccaa tgttctaaaa       2663
Pro Ser Leu Met Ser Ile Phe Arg Lys
    675                 680

tgctcataag gaagggttgg ggaattaccc tttagacaca agctctaaga actctggata   2723

caacgggaac ttggatggat acagtctggg cctgctgggc cagatgttcc gagggcggcc   2783

cggcaagcag cctgtcttgc acattgcaac tgactggctt aatctacggc aagagtcctt   2843

cagctccgtc acagagtact ctccaatgtg ttatagttat ccttaaagct cttcaattca   2903

aggaagtgct tggcacgttt actcttctga ctggagggga ggtatgtcac ctggatggtt   2963

gttggggaga cctcagggga ctgagttagg tctttggctg ctgactggtg atgtcgctga   3023

gg                                                                  3025
```

<210> SEQ ID NO 24
<211> LENGTH: 3244
<212> TYPE: DNA
<213> ORGANISM: Homo sapiens
<220> FEATURE:
<221> NAME/KEY: CDS
<222> LOCATION: (488)...(2605)

<400> SEQUENCE: 24

```
ccggccgcga gccccggggg ccccgaggcc gcagcttgcc tgcgcgctct gagccttcgc     60

aactcgcgag caaagtttgg tggaggcaac gccaagcctg agtcctttct tcctctcgtt    120

ccccaaatcc gagggcagcc cgcgggcgtc atgcccgcgc tcctccgcag cctggggtac    180

gcgtgaagcc cgggaggctt ggcgccggcg aagacccaag gaccactctt ctgcgtttgg    240

agttgctccc cccaaccccg ggctcgtcgc tttctccatc ccgacccacg cggggcgcgg    300

ggacaacaca ggtcgcggag gagcgttgcc attcaagtga ctgcagcagc agcggcagcg    360

cctcggttcc tgagcccacc gcaggctgaa ggcattgcgc gtagtccatg cccgtagagg    420

aagtgtgcag atgggattaa cgtccacatg gagatatgga agaggaccgg ggattggtac    480

cgtaacc atg gtc agc tgg ggt cgt ttc atc tgc ctg gtc gtg gtc acc      529
        Met Val Ser Trp Gly Arg Phe Ile Cys Leu Val Val Val Thr
          1               5                  10

atg gca acc ttg tcc ctg gcc cgg ccc tcc ttc agt tta gtt gag gat      577
Met Ala Thr Leu Ser Leu Ala Arg Pro Ser Phe Ser Leu Val Glu Asp
 15                  20                  25                  30
```

-continued

```
acc aca tta gag cca gaa gag cca cca acc aaa tac caa atc tct caa      625
Thr Thr Leu Glu Pro Glu Glu Pro Pro Thr Lys Tyr Gln Ile Ser Gln
                 35                  40                  45

cca gaa gtg tac gtg gct gcg cca ggg gag tcg cta gag gtg cgc tgc      673
Pro Glu Val Tyr Val Ala Ala Pro Gly Glu Ser Leu Glu Val Arg Cys
             50                  55                  60

ctg ttg aaa gat gcc gcc gtg atc agt tgg act aag gat ggg gtg cac      721
Leu Leu Lys Asp Ala Ala Val Ile Ser Trp Thr Lys Asp Gly Val His
         65                  70                  75

ttg ggg ccc aac aat agg aca gtg ctt att ggg gag tac ttg cag ata      769
Leu Gly Pro Asn Asn Arg Thr Val Leu Ile Gly Glu Tyr Leu Gln Ile
     80                  85                  90

aag ggc gcc acg cct aga gac tcc ggc ctc tat gct tgt act gcc agt      817
Lys Gly Ala Thr Pro Arg Asp Ser Gly Leu Tyr Ala Cys Thr Ala Ser
 95                 100                 105                 110

agg act gta gac agt gaa act tgg tac ttc atg gtg aat gtc aca gat      865
Arg Thr Val Asp Ser Glu Thr Trp Tyr Phe Met Val Asn Val Thr Asp
                115                 120                 125

gcc atc tca tcc gga gat gat gag gat gac acc gat ggt gcg gaa gat      913
Ala Ile Ser Ser Gly Asp Asp Glu Asp Asp Thr Asp Gly Ala Glu Asp
            130                 135                 140

ttt gtc agt gag aac agt aac aac aag aga gca cca tac tgg acc aac      961
Phe Val Ser Glu Asn Ser Asn Asn Lys Arg Ala Pro Tyr Trp Thr Asn
        145                 150                 155

aca gaa aag atg gaa aag cgg ctc cat gct gtg cct gcg gcc aac act     1009
Thr Glu Lys Met Glu Lys Arg Leu His Ala Val Pro Ala Ala Asn Thr
    160                 165                 170

gtc aag ttt cgc tgc cca gcc ggg ggg aac cca atg cca acc atg cgg     1057
Val Lys Phe Arg Cys Pro Ala Gly Gly Asn Pro Met Pro Thr Met Arg
175                 180                 185                 190

tgg ctg aaa aac ggg aag gag ttt aag cag gag cat cgc att gga ggc     1105
Trp Leu Lys Asn Gly Lys Glu Phe Lys Gln Glu His Arg Ile Gly Gly
                195                 200                 205

tac aag gta cga aac cag cac tgg agc ctc att atg gaa agt gtg gtc     1153
Tyr Lys Val Arg Asn Gln His Trp Ser Leu Ile Met Glu Ser Val Val
            210                 215                 220

cca tct gac aag gga aat tat acc tgt gtg gtg gag aat gaa tac ggg     1201
Pro Ser Asp Lys Gly Asn Tyr Thr Cys Val Val Glu Asn Glu Tyr Gly
        225                 230                 235

tcc atc aat cac acg tac cac ctg gat gtt gtg gag cga tcg cct cac     1249
Ser Ile Asn His Thr Tyr His Leu Asp Val Val Glu Arg Ser Pro His
    240                 245                 250

cgg ccc atc ctc caa gcc gga ctg ccg gca aat gcc tcc aca gtg gtc     1297
Arg Pro Ile Leu Gln Ala Gly Leu Pro Ala Asn Ala Ser Thr Val Val
255                 260                 265                 270

gga gga gac gta gag ttt gtc tgc aag gtt tac agt gat gcc cag ccc     1345
Gly Gly Asp Val Glu Phe Val Cys Lys Val Tyr Ser Asp Ala Gln Pro
                275                 280                 285

cac atc cag tgg atc aag cac gtg gaa aag aac ggc agt aaa tac ggg     1393
His Ile Gln Trp Ile Lys His Val Glu Lys Asn Gly Ser Lys Tyr Gly
            290                 295                 300

ccc gac ggg ctg ccc tac ctc aag gtt ctc aag gtt tcg gct gag tcc     1441
Pro Asp Gly Leu Pro Tyr Leu Lys Val Leu Lys Val Ser Ala Glu Ser
        305                 310                 315

agc tcc tcc atg aac tcc aac acc ccg ctg gtg agg ata aca aca cgc     1489
Ser Ser Ser Met Asn Ser Asn Thr Pro Leu Val Arg Ile Thr Thr Arg
    320                 325                 330

ctc tct tca acg gca gac acc ccc atg ctg gca ggg gtc tcc gag tat     1537
Leu Ser Ser Thr Ala Asp Thr Pro Met Leu Ala Gly Val Ser Glu Tyr
```

-continued

```
335                 340                 345                 350

gaa ctt cca gag gac cca aaa tgg gag ttt cca aga gat aag ctg aca     1585
Glu Leu Pro Glu Asp Pro Lys Trp Glu Phe Pro Arg Asp Lys Leu Thr
                355                 360                 365

ctg ggc aag ccc ctg gga gaa ggt tgc ttt ggg caa gtg gtc atg gcg     1633
Leu Gly Lys Pro Leu Gly Glu Gly Cys Phe Gly Gln Val Val Met Ala
            370                 375                 380

gaa gca gtg gga att gac aaa gac aag ccc aag gag gcg gtc acc gtg     1681
Glu Ala Val Gly Ile Asp Lys Asp Lys Pro Lys Glu Ala Val Thr Val
        385                 390                 395

gcc gtg aag atg ttg aaa gat gat gcc aca gag aaa gac ctt tct gat     1729
Ala Val Lys Met Leu Lys Asp Asp Ala Thr Glu Lys Asp Leu Ser Asp
    400                 405                 410

ctg gtg tca gag atg gag atg atg aag atg att ggg aaa cac aag aat     1777
Leu Val Ser Glu Met Glu Met Met Lys Met Ile Gly Lys His Lys Asn
415                 420                 425                 430

atc ata aat ctt ctt gga gcc tgc aca cag gat ggg cct ctc tat gtc     1825
Ile Ile Asn Leu Leu Gly Ala Cys Thr Gln Asp Gly Pro Leu Tyr Val
                435                 440                 445

ata gtt gag tat gcc tct aaa ggc aac ctc cga gaa tac ctc cga gcc     1873
Ile Val Glu Tyr Ala Ser Lys Gly Asn Leu Arg Glu Tyr Leu Arg Ala
            450                 455                 460

cgg agg cca ccc ggg atg gag tac tcc tat gac att aac cgt gtt cct     1921
Arg Arg Pro Pro Gly Met Glu Tyr Ser Tyr Asp Ile Asn Arg Val Pro
        465                 470                 475

gag gag cag atg acc ttc aag gac ttg gtg tca tgc acc tac cag ctg     1969
Glu Glu Gln Met Thr Phe Lys Asp Leu Val Ser Cys Thr Tyr Gln Leu
    480                 485                 490

gcc aga ggc atg gag tac ttg gct tcc caa aaa tgt att cat cga gat     2017
Ala Arg Gly Met Glu Tyr Leu Ala Ser Gln Lys Cys Ile His Arg Asp
495                 500                 505                 510

tta gca gcc aga aat gtt ttg gta aca gaa aac aat gtg atg aaa ata     2065
Leu Ala Ala Arg Asn Val Leu Val Thr Glu Asn Asn Val Met Lys Ile
                515                 520                 525

gca gac ttt gga ctc gcc aga gat atc aac aat ata gac tat tac aaa     2113
Ala Asp Phe Gly Leu Ala Arg Asp Ile Asn Asn Ile Asp Tyr Tyr Lys
            530                 535                 540

aag acc acc aat ggg cgg ctt cca gtc aag tgg atg gct cca gaa gcc     2161
Lys Thr Thr Asn Gly Arg Leu Pro Val Lys Trp Met Ala Pro Glu Ala
        545                 550                 555

ctg ttt gat aga gta tac act cat cag agt gat gtc tgg tcc ttc ggg     2209
Leu Phe Asp Arg Val Tyr Thr His Gln Ser Asp Val Trp Ser Phe Gly
    560                 565                 570

gtg tta atg tgg gag atc ttc act tta ggg ggc tcg ccc tac cca ggg     2257
Val Leu Met Trp Glu Ile Phe Thr Leu Gly Gly Ser Pro Tyr Pro Gly
575                 580                 585                 590

att ccc gtg gag gaa ctt ttt aag ctg ctg aag gaa gga cac aga atg     2305
Ile Pro Val Glu Glu Leu Phe Lys Leu Leu Lys Glu Gly His Arg Met
                595                 600                 605

gat aag cca gcc aac tgc acc aac gaa ctg tac atg atg atg agg gac     2353
Asp Lys Pro Ala Asn Cys Thr Asn Glu Leu Tyr Met Met Met Arg Asp
            610                 615                 620

tgt tgg cat gca gtg ccc tcc cag aga cca acg ttc aag cag ttg gta     2401
Cys Trp His Ala Val Pro Ser Gln Arg Pro Thr Phe Lys Gln Leu Val
        625                 630                 635

gaa gac ttg gat cga att ctc act ctc aca acc aat gag gaa tac ttg     2449
Glu Asp Leu Asp Arg Ile Leu Thr Leu Thr Thr Asn Glu Glu Tyr Leu
    640                 645                 650

gac ctc agc caa cct ctc gaa cag tat tca cct agt tac cct gac aca     2497
```

```
Asp Leu Ser Gln Pro Leu Glu Gln Tyr Ser Pro Ser Tyr Pro Asp Thr
655                 660                 665                 670

aga agt tct tgt tct tca gga gat gat tct gtt ttt tct cca gac ccc      2545
Arg Ser Ser Cys Ser Ser Gly Asp Asp Ser Val Phe Ser Pro Asp Pro
                675                 680                 685

atg cct tac gaa cca tgc ctt cct cag tat cca cac ata aac ggc agt      2593
Met Pro Tyr Glu Pro Cys Leu Pro Gln Tyr Pro His Ile Asn Gly Ser
            690                 695                 700

gtt aaa aca tga atgactgtgt ctgcctgtcc ccaaacagga cagcactggg        2645
Val Lys Thr
        705

aacctagcta cactgagcag ggagaccatg cctcccagag cttgttgtct ccacttgtat   2705

atatggatca gaggagtaaa taattggaaa agtaatcagc atatgtgtaa agatttatac   2765

agttgaaaac ttgtaatctt ccccaggagg agaagaaggt ttctggagca gtggactgcc   2825

acaagccacc atgtaacccc tctcacctgc cgtgcgttct ggctgtggac cagtaggact   2885

caaggtggac gtgcgttctg ccttccttgt taattttgta ataattggag aagatttatg   2945

tcagcacaca cttacagagc acaaatgcag tatataggtg ctggatgtat gtaaatatat   3005

tcaaattatg tataaatata tattatatat ttacaaggag ttattttttg tattgatttt   3065

aaatggatgt cccaatgcac ctagaaaatt ggtctctctt tttttaatag ctatttgcta   3125

aatgctgttc ttacacataa tttcttaatt ttcaccgagc agaggtggaa aaatactttt   3185

gctttcaggg aaaatggtat aacgttaatt tattaataaa ttggtaatat acaaaacaa    3244


<210> SEQ ID NO 25
<211> LENGTH: 3080
<212> TYPE: DNA
<213> ORGANISM: Homo sapiens
<220> FEATURE:
<221> NAME/KEY: CDS
<222> LOCATION: (612)...(3080)

<400> SEQUENCE: 25

catctgtgga ctgctaccga gcgggcgagg gagcgcgcgc ggccgccaca aagctcgggc     60

gccgcggggc tgcatgcggc gtacctggcc cggcgcggcg actgctctcc gggctggcgg    120

gggccggccg cgagccccgg gggccccgag gccgcagctt gcctgcgcgc tctgagcctt    180

cgcaactcgc gagcaaagtt tggtggaggc aacgccaagc ctgagtcctt tcttcctctc    240

gttccccaaa tccgagggca gcccgcgggc gtcatgcccg cgctcctccg cagcctgggg    300

tacgcgctga agcccgggag gcttggcgcc ggcgaagacc caaggaccac tcttctgcgt    360

ttggagttgc tccccacaac cccgggctcg tcgctttctc catcccgacc cagccggggc    420

gcggggacaa cacaggtcgc ggaggagcgt tgccattcaa gtgactgcag cagcagcggc    480

agcgcctcgg ttcctgagcc caccgcaggc tgaaggcatt gcgcgtagtc catgcccgta    540

gaggaagtgt gcagatggga ttaacgtcca catggagata tggaagagga ccggggattg    600

gtaccgtaac c atg gtc agc tgg ggt cgt ttc atc tgc ctg gtc gtg gtc     650
             Met Val Ser Trp Gly Arg Phe Ile Cys Leu Val Val Val
               1               5                  10

acc atg gca acc ttg tcc ctg gcc cgg ccc tcc ttc agt tta gtt gag      698
Thr Met Ala Thr Leu Ser Leu Ala Arg Pro Ser Phe Ser Leu Val Glu
     15                  20                  25

gat acc aca tta gag cca gaa gag cca cca acc aaa tac caa atc tct      746
Asp Thr Thr Leu Glu Pro Glu Glu Pro Pro Thr Lys Tyr Gln Ile Ser
 30                  35                  40                  45

caa cca gaa gtg tac gtg gct gcg cca ggg gag tcg cta gag gtg cgc      794
```

-continued

```
Gln Pro Glu Val Tyr Val Ala Ala Pro Gly Glu Ser Leu Glu Val Arg
                 50                  55                  60

tgc ctg ttg aaa gat gcc gcc gtg atc agt tgg act aag gat ggg gtg      842
Cys Leu Leu Lys Asp Ala Ala Val Ile Ser Trp Thr Lys Asp Gly Val
             65                  70                  75

cac ttg ggg ccc aac aat agg aca gtg ctt att ggg gag tac ttg cag      890
His Leu Gly Pro Asn Asn Arg Thr Val Leu Ile Gly Glu Tyr Leu Gln
         80                  85                  90

ata aag ggc gcc acg cct aga gac tcc ggc ctc tat gct tgt act gcc      938
Ile Lys Gly Ala Thr Pro Arg Asp Ser Gly Leu Tyr Ala Cys Thr Ala
     95                 100                 105

agt agg act gta gac agt gaa act tgg tac ttc atg gtg aat gtc aca      986
Ser Arg Thr Val Asp Ser Glu Thr Trp Tyr Phe Met Val Asn Val Thr
110                 115                 120                 125

gat gcc atc tca tcc gga gat gat gag gat gac acc gat ggt gcg gaa     1034
Asp Ala Ile Ser Ser Gly Asp Asp Glu Asp Asp Thr Asp Gly Ala Glu
                130                 135                 140

gat ttt gtc agt gag aac agt aac aac aag aga gca cca tac tgg acc     1082
Asp Phe Val Ser Glu Asn Ser Asn Asn Lys Arg Ala Pro Tyr Trp Thr
            145                 150                 155

aac aca gaa aag atg gaa aag cgg ctc cat gct gtg cct gcg gcc aac     1130
Asn Thr Glu Lys Met Glu Lys Arg Leu His Ala Val Pro Ala Ala Asn
        160                 165                 170

act gtc aag ttt cgc tgc cca gcc ggg ggg aac cca atg cca acc atg     1178
Thr Val Lys Phe Arg Cys Pro Ala Gly Gly Asn Pro Met Pro Thr Met
    175                 180                 185

cgg tgg ctg aaa aac ggg aag gag ttt aag cag gag cat cgc att gga     1226
Arg Trp Leu Lys Asn Gly Lys Glu Phe Lys Gln Glu His Arg Ile Gly
190                 195                 200                 205

ggc tac aag gta cga aac cag cac tgg agc ctc att atg gaa agt gtg     1274
Gly Tyr Lys Val Arg Asn Gln His Trp Ser Leu Ile Met Glu Ser Val
                210                 215                 220

gtc cca tct gac aag gga aat tat acc tgt gtg gtg gag aat gaa tac     1322
Val Pro Ser Asp Lys Gly Asn Tyr Thr Cys Val Val Glu Asn Glu Tyr
            225                 230                 235

ggg tcc atc aat cac acg tac cac ctg gat gtt gtg gag cga tcg cct     1370
Gly Ser Ile Asn His Thr Tyr His Leu Asp Val Val Glu Arg Ser Pro
        240                 245                 250

cac cgg ccc atc ctc caa gcc gga ctg ccg gca aat gcc tcc aca gtg     1418
His Arg Pro Ile Leu Gln Ala Gly Leu Pro Ala Asn Ala Ser Thr Val
    255                 260                 265

gtc gga gga gac gta gag ttt gtc tgc aag gtt tac agt gat gcc cag     1466
Val Gly Gly Asp Val Glu Phe Val Cys Lys Val Tyr Ser Asp Ala Gln
270                 275                 280                 285

ccc cac atc cag tgg atc aag cac gtg gaa aag aac ggc agt aaa tac     1514
Pro His Ile Gln Trp Ile Lys His Val Glu Lys Asn Gly Ser Lys Tyr
                290                 295                 300

ggg ccc gac ggg ctg ccc tac ctc aag gtt ctc aag cac tcg ggg ata     1562
Gly Pro Asp Gly Leu Pro Tyr Leu Lys Val Leu Lys His Ser Gly Ile
            305                 310                 315

aat agt tcc aat gca gaa gtg ctg gct ctg ttc aat gtg acc gag gcg     1610
Asn Ser Ser Asn Ala Glu Val Leu Ala Leu Phe Asn Val Thr Glu Ala
        320                 325                 330

gat gct ggg gaa tat ata tgt aag gtc tcc aat tat ata ggg cag gcc     1658
Asp Ala Gly Glu Tyr Ile Cys Lys Val Ser Asn Tyr Ile Gly Gln Ala
    335                 340                 345

aac cag tct gcc tgg ctc act gtc ctg cca aaa cag caa gcg cct gga     1706
Asn Gln Ser Ala Trp Leu Thr Val Leu Pro Lys Gln Gln Ala Pro Gly
350                 355                 360                 365
```

-continued

```
aga gaa aag gag att aca gct tcc cca gac tac ctg gag ata gcc att      1754
Arg Glu Lys Glu Ile Thr Ala Ser Pro Asp Tyr Leu Glu Ile Ala Ile
                370                 375                 380

tac tgc ata ggg gtc ttc tta atc gcc tgt atg gtg gta aca gtc atc      1802
Tyr Cys Ile Gly Val Phe Leu Ile Ala Cys Met Val Val Thr Val Ile
            385                 390                 395

ctg tgc cga atg aag aac acg acc aag aag cca gac ttc agc agc cag      1850
Leu Cys Arg Met Lys Asn Thr Thr Lys Lys Pro Asp Phe Ser Ser Gln
        400                 405                 410

ccg gct gtg cac aag ctg acc aaa cgt atc ccc ctg cgg aga cag gta      1898
Pro Ala Val His Lys Leu Thr Lys Arg Ile Pro Leu Arg Arg Gln Val
    415                 420                 425

aca gtt tcg gct gag tcc agc tcc tcc atg aac tcc aac acc ccg ctg      1946
Thr Val Ser Ala Glu Ser Ser Ser Ser Met Asn Ser Asn Thr Pro Leu
430                 435                 440                 445

gtg agg ata aca aca cgc ctc tct tca acg gca gac acc ccc atg ctg      1994
Val Arg Ile Thr Thr Arg Leu Ser Ser Thr Ala Asp Thr Pro Met Leu
                450                 455                 460

gca ggg gtc tcc gag tat gaa ctt cca gag gac cca aaa tgg gag ttt      2042
Ala Gly Val Ser Glu Tyr Glu Leu Pro Glu Asp Pro Lys Trp Glu Phe
            465                 470                 475

cca aga gat aag ctg aca ctg ggc aag ccc ctg gga gaa ggt tgc ttt      2090
Pro Arg Asp Lys Leu Thr Leu Gly Lys Pro Leu Gly Glu Gly Cys Phe
        480                 485                 490

ggg caa gtg gtc atg gcg gaa gca gtg gga att gac aaa gac aag ccc      2138
Gly Gln Val Val Met Ala Glu Ala Val Gly Ile Asp Lys Asp Lys Pro
    495                 500                 505

aag gag gcg gtc acc gtg gcc gtg aag atg ttg aaa gat gat gcc aca      2186
Lys Glu Ala Val Thr Val Ala Val Lys Met Leu Lys Asp Asp Ala Thr
510                 515                 520                 525

gag aaa gac ctt tct gat ctg gtg tca gag atg gag atg atg aag atg      2234
Glu Lys Asp Leu Ser Asp Leu Val Ser Glu Met Glu Met Met Lys Met
                530                 535                 540

att ggg aaa cac aag aat atc ata aat ctt ctt gga gcc tgc aca cag      2282
Ile Gly Lys His Lys Asn Ile Ile Asn Leu Leu Gly Ala Cys Thr Gln
            545                 550                 555

gat ggg cct ctc tat gtc ata gtt gag tat gcc tct aaa ggc aac ctc      2330
Asp Gly Pro Leu Tyr Val Ile Val Glu Tyr Ala Ser Lys Gly Asn Leu
        560                 565                 570

cga gaa tac ctc cga gcc cgg agg cca ccc ggg atg gag tac tcc tat      2378
Arg Glu Tyr Leu Arg Ala Arg Arg Pro Pro Gly Met Glu Tyr Ser Tyr
    575                 580                 585

gac att aac cgt gtt cct gag gag cag atg acc ttc aag gac ttg gtg      2426
Asp Ile Asn Arg Val Pro Glu Glu Gln Met Thr Phe Lys Asp Leu Val
590                 595                 600                 605

tca tgc acc tac cag ctg gcc aga ggc atg gag tac ttg gct tcc caa      2474
Ser Cys Thr Tyr Gln Leu Ala Arg Gly Met Glu Tyr Leu Ala Ser Gln
                610                 615                 620

aaa tgt att cat cga gat tta gca gcc aga aat gtt ttg gta aca gaa      2522
Lys Cys Ile His Arg Asp Leu Ala Ala Arg Asn Val Leu Val Thr Glu
            625                 630                 635

aac aat gtg atg aaa ata gca gac ttt gga ctc gcc aga gat atc aac      2570
Asn Asn Val Met Lys Ile Ala Asp Phe Gly Leu Ala Arg Asp Ile Asn
        640                 645                 650

aat ata gac tat tac aaa aag acc acc aat ggg cgg ctt cca gtc aag      2618
Asn Ile Asp Tyr Tyr Lys Lys Thr Thr Asn Gly Arg Leu Pro Val Lys
    655                 660                 665

tgg atg gct cca gaa gcc ctg ttt gat aga gta tac act cat cag agt      2666
Trp Met Ala Pro Glu Ala Leu Phe Asp Arg Val Tyr Thr His Gln Ser
670                 675                 680                 685
```

```
gat gtc tgg tcc ttc ggg gtg tta atg tgg gag atc ttc act tta ggg     2714
Asp Val Trp Ser Phe Gly Val Leu Met Trp Glu Ile Phe Thr Leu Gly
                690                 695                 700

ggc tcg ccc tac cca ggg att ccc gtg gag gaa ctt ttt aag ctg ctg     2762
Gly Ser Pro Tyr Pro Gly Ile Pro Val Glu Glu Leu Phe Lys Leu Leu
            705                 710                 715

aag gaa gga cac aga atg gat aag cca gcc aac tgc acc aac gaa ctg     2810
Lys Glu Gly His Arg Met Asp Lys Pro Ala Asn Cys Thr Asn Glu Leu
        720                 725                 730

tac atg atg atg agg gac tgt tgg cat gca gtg ccc tcc cag aga cca     2858
Tyr Met Met Met Arg Asp Cys Trp His Ala Val Pro Ser Gln Arg Pro
    735                 740                 745

acg ttc aag cag ttg gta gaa gac ttg gat cga att ctc act ctc aca     2906
Thr Phe Lys Gln Leu Val Glu Asp Leu Asp Arg Ile Leu Thr Leu Thr
750                 755                 760                 765

acc aat gag gaa tac ttg gac ctc agc caa cct ctc gaa cag tat tca     2954
Thr Asn Glu Glu Tyr Leu Asp Leu Ser Gln Pro Leu Glu Gln Tyr Ser
                770                 775                 780

cct agt tac cct gac aca aga agt tct tgt tct tca gga gat gat tct     3002
Pro Ser Tyr Pro Asp Thr Arg Ser Ser Cys Ser Ser Gly Asp Asp Ser
            785                 790                 795

gtt ttt tct cca gac ccc atg cct tac gaa cca tgc ctt cct cag tat     3050
Val Phe Ser Pro Asp Pro Met Pro Tyr Glu Pro Cys Leu Pro Gln Tyr
        800                 805                 810

cca cac ata aac ggc agt gtt aaa aca tga                             3080
Pro His Ile Asn Gly Ser Val Lys Thr
    815                 820


<210> SEQ ID NO 26
<211> LENGTH: 1541
<212> TYPE: DNA
<213> ORGANISM: Homo sapiens
<220> FEATURE:
<221> NAME/KEY: CDS
<222> LOCATION: (276)...(1040)

<400> SEQUENCE: 26

gacccaagga ccactcttct gcgtttggag ttgctcccca caaccccggg ctcgtcgctt      60

tctccatccc gacccacgcg gggcgcgggg acaacacagg tcgcggagga gcgttgccat     120

tcaagtgact gcagcagcag cggcagcgcc tcggttcctg agcccaccgc aggctgaagg     180

cattgcgcgt agtccatgcc cgtagaggaa gtgtgcagat gggattaacg tccacatgga     240

gatatggaag aggaccgggg attggtaccg taacc atg gtc agc tgg ggt cgt       293
                                       Met Val Ser Trp Gly Arg
                                         1               5

ttc atc tgc ctg gtc gtg gtc acc atg gca acc ttg tcc ctg gcc cgg     341
Phe Ile Cys Leu Val Val Val Thr Met Ala Thr Leu Ser Leu Ala Arg
            10                  15                  20

ccc tcc ttc agt tta gtt gag gat acc aca tta gag cca gaa gag cca     389
Pro Ser Phe Ser Leu Val Glu Asp Thr Thr Leu Glu Pro Glu Glu Pro
        25                  30                  35

cca acc aaa tac caa atc tct caa cca gaa gtg tac gtg gct gcg cca     437
Pro Thr Lys Tyr Gln Ile Ser Gln Pro Glu Val Tyr Val Ala Ala Pro
     40                  45                  50

ggg gag tcg cta gag gtg cgc tgc ctg ttg aaa gat gcc gcc gtg atc     485
Gly Glu Ser Leu Glu Val Arg Cys Leu Leu Lys Asp Ala Ala Val Ile
 55                  60                  65                  70

agt tgg act aag gat ggg gtg cac ttg ggg ccc aac aat agg aca gtg     533
Ser Trp Thr Lys Asp Gly Val His Leu Gly Pro Asn Asn Arg Thr Val
                75                  80                  85
```

-continued

```
ctt att ggg gag tac ttg cag ata aag ggc gcc acg cct aga gac tcc      581
Leu Ile Gly Glu Tyr Leu Gln Ile Lys Gly Ala Thr Pro Arg Asp Ser
             90                  95                 100

ggc ctc tat gct tgt act gcc agt agg act gta gac agt gaa act tgg      629
Gly Leu Tyr Ala Cys Thr Ala Ser Arg Thr Val Asp Ser Glu Thr Trp
        105                 110                 115

tac ttc atg gtg aat gtc aca gat gcc atc tca tcc gga gat gat gag      677
Tyr Phe Met Val Asn Val Thr Asp Ala Ile Ser Ser Gly Asp Asp Glu
    120                 125                 130

gat gac acc gat ggt gcg gaa gat ttt gtc agt gag aac agt aac aac      725
Asp Asp Thr Asp Gly Ala Glu Asp Phe Val Ser Glu Asn Ser Asn Asn
135                 140                 145                 150

aag aga gca cca tac tgg acc aac aca gaa aag atg gaa aag cgg ctc      773
Lys Arg Ala Pro Tyr Trp Thr Asn Thr Glu Lys Met Glu Lys Arg Leu
                155                 160                 165

cat gct gtg cct gcg gcc aac act gtc aag ttt cgc tgc cca gcc ggg      821
His Ala Val Pro Ala Ala Asn Thr Val Lys Phe Arg Cys Pro Ala Gly
            170                 175                 180

ggg aac cca atg cca acc atg cgg tgg ctg aaa aac ggg aag gag ttt      869
Gly Asn Pro Met Pro Thr Met Arg Trp Leu Lys Asn Gly Lys Glu Phe
        185                 190                 195

aag cag gag cat cgc att gga ggc tac aag gta cga aac cag cac tgg      917
Lys Gln Glu His Arg Ile Gly Gly Tyr Lys Val Arg Asn Gln His Trp
    200                 205                 210

agc ctc att atg gaa agt gtg gtc cca tct gac aag gga aat tat acc      965
Ser Leu Ile Met Glu Ser Val Val Pro Ser Asp Lys Gly Asn Tyr Thr
215                 220                 225                 230

tgt gtg gtg gag aat gaa tac ggg tcc atc aat cac acg tac cac ctg     1013
Cys Val Val Glu Asn Glu Tyr Gly Ser Ile Asn His Thr Tyr His Leu
                235                 240                 245

gat gtt gtg ggc agc cag ggt tta tga gctttgcatg atcctcatgg           1060
Asp Val Val Gly Ser Gln Gly Leu
            250

ttcccaagcg tcatctgtgt aaagtggacg tggtatgaaa tgtctgacat tttggaagct   1120

gagattactc tgaaaatgtt aattggcag gtgaaaaggg tacagatgtg ctgtagcaga    1180

cctttggttt taaaagagaa gcatcatttc cccaacaggg caactgtaga aggccagctg   1240

aagagtaaag gaaaaggtct gaggactgag cctgtggctg gctggaaaaa ggtgaatgtt   1300

gagggccctt cacttccatc acaagaaagt cattagacgg taccaattca gtgtctgttc   1360

ctggcatcta tttcctctgt gcaaagggaa ccatgtatat gagcttataa atacattttt   1420

gtcagagtgc acagataagt aggccatttt aattaaacat tgaagaccct gtctcaaaaa   1480

aaaaaaaaaa aaaagaaaag aaaagaataa agaaaaaacc cattactcca agacgtttag   1540

c                                                                   1541
```

<210> SEQ ID NO 27
<211> LENGTH: 1475
<212> TYPE: DNA
<213> ORGANISM: Homo sapiens

<400> SEQUENCE: 27

```
tcttctgcgt ttggagttgc tccccgcaac cccgggctcg tcgctttctc catcccgacc     60

cacgcggggc cggggacaac acaggtcgcg gaggagcgtt gccattcaag tgactgcagc    120

agcagcgcag cgcctcggtt cctgagccca ccgcagctga aggcattgcg cgtagtccat    180

gcccgtagag gaagtgtgca gatgggatta acgtccacat ggagatatgg aagaggaccg    240
```

-continued

```
gggattggta ccgtaaccat ggtcagctgg ggtcgtttca tctgcctggt cgtggtcacc     300

atggcaacct tgtccctggc ccggccctcc ttcagtttag ttgaggatac cacattagag     360

ccagaagagc caccaaccaa ataccaaatc tctcaaccag aagtgtacgt ggctgcgcca     420

ggggagtcgc tagaggtgcg ctgcctgttg aaagatgccg ccgtgatcag ttggactaag     480

gatggggtgc acttggggcc caacaatagg acagtgctta ttggggagta cttgcagata     540

aagggcgcca cacctagaga ctccggcctc tatgcttgta ctgccagtag gactgtagac     600

agtgaaactt ggtacttcat ggtgaatgtc acagatgcca tctcatccgg agatgatgag     660

gatgacaccg atggtgcgga agattttgtc agtgagaaca gtaacaacaa gagagcacca     720

tactggacca acacagaaaa gatggaaaag cggctccatg ctgtgcctgc ggccaacact     780

gtcaagtttc gctgcccagc cggggggaac ccaatgccaa ccatgcggtg gctgaaaaac     840

gggaaggagt ttaagcagga gcatcgcatt ggaggctaca aggtacgaaa ccagcactgg     900

agcctcatta tggaaagtgt ggtcccatct gacaagggaa attatacctg tgtagtggag     960

aatgaatacg ggtccatcaa tcacacgtac cacctggatg ttgtggagcg atcgcctcac    1020

cggcccatcc tccaagccgg actgccggca aatgcctcca cagtggtcgg aggagacgta    1080

gagtttgtct gcaaggttta cagtgatgcc cagccccaca tccagtggat caagcacgtg    1140

gaaaagaacg gcagtaaata cgggcccgac gggctgccct acctcaaggt tctcaagcac    1200

tcggggataa atagttccaa tgcagaagtg ctggctctgt tcaatgtgac cgaggcggat    1260

gctggggaat atatatgtaa ggtctccaat tatatagggc aggccaacca gtctgcctgg    1320

ctcactgtcc tgccaaaaca gcaaggccgc cggtgttaac accacggaca aagagattga    1380

ggttctctat attcggaatg taacttttga ggacgctggg gaatatacgt gcttggcggg    1440

taattctatt gggatatcct ttcactctgc atggt                               1475
```

<210> SEQ ID NO 28
<211> LENGTH: 2650
<212> TYPE: DNA
<213> ORGANISM: Homo sapiens

<400> SEQUENCE: 28

```
ggaccgggga ttggtaccgt aaccatggtc agctggggtc gtttcatctg cctggtcgtg      60

gtcaccatgg caaccttgtc cctggcccgg ccctccttca gtttagttga ggataccaca     120

ttagagccag aagagccacc aaccaaatac caaatctctc aaccagaagt gtacgtggct     180

gcgccagggg agtcgctaga ggtgcgctgc ctgttgaaag atgccgccgt gatcagttgg     240

actaaggatg gggtgcactt ggggcccaac aataggacag tgcttattgg ggagtacttg     300

cagataaagg gcgccacgcc tagagactcc ggcctctatg cttgtactgc cagtaggact     360

gtagacagtg aaacttggta cttcatggtg aatgtcacag atgccatctc atccggagat     420

gatgaggatg acaccgatgg tgcggaagat tttgtcagtg agaacagtaa caacaagaga     480

gcaccatact ggaccaacac agaaaagatg gaaaagcggc tccatgctgt gcctgcggcc     540

aacactgtca agtttcgctg cccagccggg gggaacccaa tgccaaccat gcggtggctg     600

aaaaacggga aggagtttaa gcaggagcat cgcattggag gctacaaggt acgaaaccag     660

cactggagcc tcattatgga aagtgtggtc ccatctgaca agggaaatta tacctgtgtg     720

gtggagaatg aatacgggtc catcaatcac acgtaccacc tggatgttgt ggagcgatcg     780

cctcaccggc ccatcctcca agccggactg ccggcaaatg cctccacagt ggtcggagga     840

gacgtagagt ttgtctgcaa ggtttacagt gatgcccagc cccacatcca gtggatcaag     900
```

```
cacgtggaaa agaacggcag taaatacggg cccgacgggc tgccctacct caaggttctc     960

aagcactcgg ggataaatag ttccaatgca gaagtgctgg ctctgttcaa tgtgaccgag    1020

gcggatgcgg gggaatatat atgtaaggtc tccaattata tagggcaggc caaccagtct    1080

gcctggctca ctgtcctgcc aaaacagcaa gcgcctggaa gagaaaagga gattacagct    1140

tccccagact acctggagat agccatttac tgcatagggg tcttcttaat cgcctgtatg    1200

gtggtaacag tcatcctgtg ccgaatgaag aacacgacca agaagccaga cttcagcagc    1260

cagccggctg tgcacaagct gaccaaacgt atccccctgc ggagacaggt aacagtttcg    1320

gctgagtcca gctcctccat gaactccaac accccgctgg tgaggataac aacacgcctc    1380

tcttcaacgg cagacacccc catgctggca ggggtctccg agtatgaact tccagaggac    1440

ccaaaatggg agtttccaag agataagctg acactgggca agcccctggg agaaggttgc    1500

tttgggcaag tggtcatggc ggaagcagtg ggaattgaca aagacaagcc caaggaggcg    1560

gtcaccgtgg ccgtgaagat gttgaaagat gatgccacag agaaagacct ttctgatctg    1620

gtgtcagaga tggagatgat gaagatgatt gggaaacaca agaatatcat aaatcttctt    1680

ggagcctgca cacaggatgg gcctctctat gtcatagttg agtatgcctc taaaggcaac    1740

ctccgagaat acctccgagc ccggaggcca cccgggatgg agtactccta tgacattaac    1800

cgtgttcctg aggagcagat gaccttcaag gacttggtgt catgcaccta ccagctggcc    1860

agaggcatgg agtacttggc ttcccaaaaa tgtattcatc gagatttagc agccagaaat    1920

gttttggtaa cagaaaacaa tgtgatgaaa atagcagact ttggactcgc cagagatatc    1980

aacaatatag actattacaa aaagaccacc aatgggcggc ttccagtcaa gtggatggct    2040

ccagaagccc tgtttgatag agtatacact catcagagtg atgtctggtc cttcggggtg    2100

ttaatgtggg agatcttcac tttagggggc tcgccctacc cagggattcc cgtggaggaa    2160

ctttttaagc tgctgaagga aggacacaga atggataagc cagccaactg caccaacgaa    2220

ctgtacatga tgatgaggga ctgttggcat gcagtgccct cccagagacc aacgttcaag    2280

cagttggtag aagacttgga tcgaattctc actctcacaa ccaatgagat ctgaaagttt    2340

atggcttcat tgagaaactg ggaaaagttg gtcaggcgca gtggctcatg cctgtaatcc    2400

cagcactttg ggaggccgag gcaggcggat catgaggtca ggagttccag accagcctgg    2460

ccaacatggt gaaaccctgt ctctactaaa gatacaaaaa attagccggg cgtgttggtg    2520

tgcgcctgta atcccagcta ctccgggagg ctgaggcagg agagtcactt gaaccgggga    2580

ggcggaggtt acagtgagcc gagatcatgc cattgcattc cagccttggc gacagagcga    2640

gactccatct                                                           2650
```

```
<210> SEQ ID NO 29
<211> LENGTH: 36221
<212> TYPE: DNA
<213> ORGANISM: Homo sapiens
<220> FEATURE:
<221> NAME/KEY: misc_feature
<222> LOCATION: (1)...(36221)
<223> OTHER INFORMATION: n = A,T,C or G

<400> SEQUENCE: 29

acccccagac tattacagga ggagaaggtt aaggtctgtg caaatggtcc gaatctaata      60

gggatgggat cggggttgtc atatcggggt gttatgagag acaaaagatg gtttttgttc     120

caccgttgtt aggggggag gtcatccgcg ggggaatcgg ttttccagaa tgatgaagtc     180
```

-continued

```
accaggcctt caaagcccct tttgaagggt aaccaagcca ggtttttctt ctcctaaggg    240
ttcggaaagt taccttggct cttcggaggg gagaaacgag tatgtacccc gaaattgagg    300
acacttactg caagcctgcc gaacagagca agccccatt tctttagtta caacccaaag     360
gggaatcaaa aagcaaataa tctacaaaaa acgcctcagg gggaaaagac tgaaagctct    420
acatcagaat gctgaaaagg tctgtgagaa gctaaaagta gcttgtaggg tcaggaacac    480
tgcctctggc atcagccacc tgagaactgc ttgatcttgg gaaaatcaca ttgctttctt    540
ttttgtcttt atgaaatttt ctaaactaag gatggattgt ttttagaatg agaaaaaaac    600
taataaaaaa actacaaata gtaaaagagg aagtgacaga gaagcaaaag aagacacaat    660
ggggcaataa aggagtttaa atggcaacat ttcctaccca aagtgactgg aggagaaaag    720
agaagtcatt gacttgcaca gccaaaacta ctagagggct ggcccgaggc tcagcttggg    780
gcagggctcc aatggtgagc ctcatgcccc attccctctg tctctcagat cactatctgg    840
atttccccct gcagtagccc aggcctcact cacgtccttc ccgcttcaca agctgtgaga    900
gtttgccaga attcccccca gtgaaaattt catctcatct cattggttct agttgagtca    960
catgctcatg tctcaaccaa tcaaagtggc cagagaaaat gcaacttgtt gagtggttta   1020
agcctggatc cctcaacctt cagaatcaag gatgaaatca gcttccccag aaccacgtgg   1080
agtgacatta agtaaaagag tgattcccta atgggaacta ctgggtggca attaacaaaa   1140
gatgctcttt gtccctgaag ggaggtggct ccacagctct gccagacgtt ttgggtgaat   1200
ctctgcagca cccatgtcac tcctgaagta gttttagggg tatttgtttt cacgcccaca   1260
gtagaggtgg ctgtattggt ttgtgctgaa ccaagacctg accaggcagc aaatgactgg   1320
tcctcaggac actgggacca caggcttatt gttaacatct ttcagtttgt gctttcagca   1380
tttcacatca aaaggatttt ataaaatgcc ctttttaaac tttctgagac tattagtctg   1440
agtattggga ggcacagaga cggcatccct gaggcagggg ttaggggatg ggagatcttc   1500
ttttctgtgt aactgaagtg cagtgatgtc ttttatgacc tccccaaaga caaaagatga   1560
gtataacaat actcttgcca atttgctgga aagtttatcg tttttagttt cacagctgga   1620
gatcctcagc ccatttcatt atccttgggc taaacagagt cctcatttta tggctgttgt   1680
gaaactgtat tcttggaaca atgacaacct ctgactcctc taaagtcatg gccagttgaa   1740
ctcccttgtg tcattgggat tggcaataaa aacaggttgg atactaagca gatacacctg   1800
ccgctcaggc atctctcagg tgccaaaaga tagactgatt gtgtggacca agctccatgc   1860
tctgggacga agggaataga attgaattcc cttgggaggt tgaagcttca gggagtatag   1920
atcaaataaa cctcccttct gtgtaggctg tccttccatc tgacagtgaa atgatccagt   1980
tttcttgggc tatgaatatg gacagacctt tagccccacc ttagccaaca catgaaaaag   2040
tatataatcc tggcaggaac ccatatagaa gaagacacta gaccaggcca tctgcacctt   2100
gtcatttctt taataaaatg ggatttcatt acctcggccc tgtcagtatt tttatcttgc   2160
ctctgcctct ttacacttgg agggggttgc tgggttacct gaaaagagac tgtttttcaa   2220
agcaaaatac tgcattacta ttactaatat cactattagt aatagtaatg tgtccggaat   2280
tggtgggttc ttggtctcac tgacttcaag aatgaagccg cggaccctcg ccgtgactgt   2340
tacagctctt aaggtggcac gtcttgagtc tgtcccttct gatgttcaga tgtgttcgga   2400
gtttcttcct tctggtgggt tcgtggtctc gctgggctca ggaatgaaac tgcagacctt   2460
cgcagtgagt gttacagctc ttaaggcagc gcatctggag ttgttcgttc ctcccagtgg   2520
gctcgtggtc tcgctgggct caggagtgaa gctgcagatc tttgcagtga gtgttatagt   2580
```

-continued

```
tcacaaaagc agcgtggacc caaagagtga gcagtagcaa gatttattgc aaagagcgaa   2640
agaacaaagc ctccactgtg tgcaagggga cccgagctga ttgccaatgc tgacctgggc   2700
agcctgcttt tattctctta tctggcccca cccacatcct gctgattggt agagcccagt   2760
ggcctgtttt gtcagggcgc tgactggtgc gtttacaatc cctgagctag atacaaaggt   2820
tctccaagtc cccatcagat tagttagata cagagttttg acacacaggt tctccaaggc   2880
cccaccagag cagctagata cagagtgtcg attggtgcat tcacaaacct tgagctaaac   2940
acagggtgct gattggtgtg tttacaaacc ttgagctaga tacagagtgc cgattggtgt   3000
atttacaatc cctgagctag acataaaggt tctccacgtc cccaccagag cagctagata   3060
cagagtgtcg attggtgcac tcacaaacct tgagctaaac acagggtgct gattggtgta   3120
tttacaatcc ctgagctaga cataaaggtt ttccaaggcc ccaccagagc agctagatac   3180
agtgtcgatt ggtgcactca caaaccttga gctaaacaca gggtgctgat tggtgtgttt   3240
acaaaccttg agctagatac agagtgccga ttggtgtatt tacaatccct gagctagaca   3300
taaaggttct ccacatcccc accagagcag ctagatacag agtgtggatt ggtgcattca   3360
caaaccttga gctaaacaca gggtgctgat tggtgtattt acaatccctg agctagatat   3420
aaagactctc cacgtcccca ccagactcag gagcccagct ggcttcacct agtggatccc   3480
acactggggc tgcaggtaga gctgcctgcc agtcctgtgc cgtgcactcg cattcctcag   3540
cccttgggtg atcgatggga ctgagcacca tggagcaggg ggtggtgctc gttggggagg   3600
ctcgggctgc acaggagccc atggaggggg tgggagactc aggcatggcg ggctgcaggt   3660
cccgagccct gccccgcggg aaggcagcta aggctcggtg agaaatcgag ctcagcgccg   3720
atgggctggc actgctgggg gacccagtac accctccgca gccgctggcc cgggtgctaa   3780
gtccctcatt gcccggggcc agcagggctg gccggctgct ccgagtgcgg ggcctgccaa   3840
gcccacgccc acccggaact ccagctggcc cgcaagtgcc gcaggcagcc cccgttcccg   3900
ctcacgcctc tccctccaca cctccctgca agctgaggga gtgggctcca gccttggcca   3960
gcccagaaaa aggctcccac agtgcagtgg gggggggggg gggctgaagg gctcctcaaa   4020
tgccaccaaa gtgggagccc aggcagggga ggtgccgaga gcaagcgagg gctctgagga   4080
ctgccagcac gctgtcacct ctcagtaata gcacagcccc atccttgctg tacattgtgg   4140
acattatctt gactcctcac aataactctc caaggtaggt ctcatagtca ccattttaaa   4200
tgggaggaaa ttaaggctat gtcttgttag gtaatttacc cagttcatac agttctatgt   4260
gatagaactg gagtttggaa actaagcctg acaatgccaa atactttgtt tcttctcctc   4320
attatcaata gctgactaaa atgtaatttt gtcaacctga tcttgaaaaa atttagcctg   4380
attttatttt tatctgttat tcctaaatta agcagcctca gtggcattac aagccgaatc   4440
cttgaggtga ctggtcacca gaaggaatcc agccttctcc atgcataatc actctacagc   4500
agccttccag acccatccat gggaatcctt ttcttgaggt ctgggcaaaa ccactccaag   4560
aacaaacccc ccaatctcca tcagagcttc tctgccccgt atttgtctga cccctcagtt   4620
cagcagtgat gatgaccagg gcaagtcaaa tctatgtctg agcctgtggc ctgaccccat   4680
tgtttgtact tatccgatgt gaaatgctag tacttgcttt gcaattttac attttgatgc   4740
aagtgaaagg tttgaaccag ctgtttaaaa aaacaaatag ctttaaaccc cattgtaaag   4800
tgatgacctc atgtaggaaa actggttggg ctcctgccct aggaggggct gggggtaggt   4860
tccccataga caagctgctc cttgtgaacc actcagaagc tggctcttgc tcagcggctg   4920
```

-continued

```
tggatgagcc atgagagcca catctgtttt taaatcttca agatgaatgg agttgaattt   4980
tctattcttt aaatgtggag aagaaaagaa caaaacgctt cctgtcagtg aagtcctgtg   5040
tttctaagtg gggtaacttc ttttttattg aacgaaagct tttcaagaag cattccaaag   5100
aggatatacc agaatctgga actggcatat gaaaatatca cctctaggga acaattcata   5160
aaaccaccaa ttactccgtg gactcctttt ggctctgtcc ttgctttaga tgataggtac   5220
attctcacac ccctgagctc ctcagaaaag caggagggat ccctttgtgc cctcgtttat   5280
accctgctag aggttaagca tagatgatac actgtcacct cactggaaca ttttaaactt   5340
gaaaaaaaaa aaaaagagaa agaaaaccta ttaaaattgt caacattccc acagtaattg   5400
agttttctaa attcattcaa tagctagttt attcatttaa tcaaccattt tttgagtccc   5460
tactatatgc caaatgctgc tgtagggtga agagttgaag atataagatc cattacaatc   5520
atccccctca tcctcaggaa tacatgccaa gacccccggt ggatgcctga aatcacagac   5580
agcaccgaat cttatatata caccacattc ttcctctaca ttcatactca tgatagctta   5640
atttataaat taggcaaagt aagaaactgg caacaataat aagaataatt gtaagtacac   5700
tttaataaat gctctgtgaa tgtagtctct ctccctctca gagtatctta ttgtaatgta   5760
cctactgctc ttgtgagatg ataaaaagcc tacatgataa gataaagtga tagggctggg   5820
cgtggtggct catgcctgta atcccagcac tttgggaggc cgaggtgggt ggatcacctg   5880
agatcaggag tttgagacca gcctggccaa catggtgaaa ccccatctct tctgaaaata   5940
gaaaaattag ccaagcgtgg tggctggtgc ctgtaattgc agctacttgg gatgctgaga   6000
cagaagaatc actggaaccc aggaggtgga ggttgcagtg agccgagtca gaacagcatg   6060
cactttaaag cttatgaatt gcttatttct ggaattttcc acttagtatt ttcagaccat   6120
ggttgactgc aggtaactga aaccatggaa agcaaaacca cagatagagg gactactata   6180
cctgtactca agtcgacagt ctagcagaag aggaagagaa atagataact tgaagtccat   6240
gtggtcagct atgctcagga cactggggga taggcctggg ggtaaggaag gaagtgatga   6300
ccaaagatgg cttcctgtaa gaagaaaccc caatctgagc tttgaaggac acgatggggt   6360
tagcaaaacg tttaagacag aagaagcagc ctgtacaaag gtggaggagt gagacaggag   6420
ataggagatg tattgcaggg gctgtggggg ccagggcacg atgctggttt atgatagtgt   6480
tatccctgtg ataagtccca cacctttggt ccatgggagc atctcagcac tgggaggcat   6540
ctgtgcatgt gtctcctcat agctgtagac tctctgaaga tgtctctatg gatgtggaca   6600
ctcttcccct gcatgttatg actgtctgtt tcacactttc caaagcacat gcacacacat   6660
gcaggcttcc acacagaaat ttcaaacaga ttgttattta atgactacag tcattcatcc   6720
aaacctacac tactggttgg gtgtttggtc tgtcttatct ccatttatag cacagagaaa   6780
ggtatcatca accagccttc aagatgtcat ctcagaggcc ttccctctac tggtagggaa   6840
ccccccgccc caacacctct ctacactttc tcccctccag aacttctgcc tgtttaactc   6900
ttttcctcta acaatgtccc cacatccctt cttattctgg ctactctcac cctcaggcaa   6960
aagtcagcaa gtggcttgtc cttttggcac tcacagcctc cctggatcag tgttgagtga   7020
agaaagccct tccctcctca gccaggtgaa ggaagggaga gctttgggtc aggaagctgt   7080
gtgtggctgg tgaagatgat catttactcc tggttgtgct tttcctgatt tttcctttgg   7140
tgcctcttac tatctctgga aaataaaaaa acacacaact tacgccagga gcatgagatc   7200
tctgccaaga agccctgttg aatcctttga gagtcacaat ctctccgagt aattctgaac   7260
ttattggtcc agacatggat ttatccctct actcatcttc atcttctttg tgaagccccc   7320
```

-continued

```
ttccattcat gccaccctaa tggaagtgtc cagtcattct ttcttaattc tccctgattg   7380
gagggaagaa gcgttgtcca atcacacacc aaacaaaatt agtaatctta aggggttcca   7440
tgcatgaata cctgctaggt gctaaccaca gggttcaatt ttgttcatta ctcagtggct   7500
agcacggtgt cgggcacaca caagttcttc actaaagcga agttcttcaa taaagaaatg   7560
attcccaaca ctcacaatga acctggaagt taggtatgat tatttccaat ttataaatga   7620
gaaggctaag gctcagaaag attaccatag tcatttagct gataaatggt agtttggttc   7680
ctaacaaagg tctttctggc cccaaagctc atgctttttc cagaaaacca tgaagtcatc   7740
cacctgccaa ctcactaaat atagttcatt atgtcaataa agattaaccc tttacatgga   7800
cacttaactg caatggtctt ggtgctgcat aacgaagctg tggacttggg caactcttca   7860
tgacccaact tgctacttct gagttgcctc cctctctaga gtttgtctcc ttcagcctat   7920
tcaatgcagc acctattcat tcattcattc attcattcat tcattccaca aattttctgg   7980
aagtatctac catatgctag atgctagaga tacaaaaatg agtccaacag ctcctgcctt   8040
caaggacact agaattcatc acagtatatt agtcgcctat gtgactacct taaggacaga   8100
gagagttgta tgatttttgt ggttgtttcc agctcccaac agaagacctg gctgatgaga   8160
ggccctcagt aagtgttggc tgtattggat tgatatggtg tctaatgtaa tgatgagtgt   8220
tatatataaa gctatgttcc atgagccaca ggcattcttt tggggacatg catattaatt   8280
atttttttca gatcattgag ctgtcattca ataaatgaca caactgcctt aatatagaaa   8340
attgctagag gagctagatt tattttcttt cctcacacta agaagcaatt gtagtaattc   8400
cttatgcaat aaaccagtaa gaactaattt aatttaaaaa aattttttaa actggattac   8460
acacaaatat ggtagaaagt tttaaaaact tacaaaagga tataacatta aaaataagtc   8520
tcccacttct ggccctaggc acccagcttt catccttaga atgcacggct attaccagat   8580
ttcttgaata ttattccaga gatcttctgt aggcacacaa gaataaatat gtgtacttct   8640
atgcatgtct gcacacactg ccccccacac aagttggtat acttcgcaca atgttctaga   8700
ctttgctttg ttcatttaat gctgtgccct aaagaccttt tcatgttatg acatagatat   8760
tattctcatt tttaaatgac tgttatacgg attgtaccat cttatccatt ccttcattaa   8820
ggtacattca ggttgtttcc aaatgtttgt tttattacta acaaagccac agtaaatttc   8880
cttatccata tatcattttg cactctaaca gctgtgagat aaattcccag atgcaaaatg   8940
taaataaatt tatttcactt ttaaaattta aatttaaaat gtattattat aataaataaa   9000
attgaataca ttcccagaag tgctggccaa aggatatatg cattttaaga taaataagat   9060
gcatttaacg taaatgacat agcctaattg ctctacacag cagttgtgct aatttgcact   9120
cctatagcaa tgcatgacag aaattttctc ctatggtcaa gacgactgac ttaccaaatt   9180
tttttgatct atgctaatct cattgcaatt ttcatgttcc tttatcttat tatgagatct   9240
tatttacttc ttaatagtcc agtttaatgt taagaaacca taattcctgt catgtcaaag   9300
gaactgcgat cataaatttt gagtttatct gaactactgt tcaccagaag ttaaaaataa   9360
cagtgttatt agttacattt ttatatcact gccaatctca aagtgaactt gagataactt   9420
aataaacaca caaaacaatg agagagatag aaacaacatt tttaaaatca agacaacaga   9480
aagtagaggc aaaatggtaa aatgaagtaa gagggaagtt tagtgaaaca aaatgcatat   9540
cttcaggtcc aaaaatctac taattttggt ccactgtttt ggccttaagc ttcttagagg   9600
tcaaagcaaa aaggaaaatg taatcaattt taaaatgtac attgttaaag aaaagaaaat   9660
```

-continued

```
caaaagattt ttggctttta aatctaaggg aaattcataa ggtttattgc agaagggact   9720
ccagatagta tctcaacaag attcctaaaa tgaaagaaaa agtaggggtt ttggagaaca   9780
aagctctgac gctgtctatg tagaatgctt tcctagggcc ctttgtctgg taagagctcc   9840
ccttttcctc cgaggaccaa ctctctgact cttcatagtc ctggtaggga tatcaatgac   9900
catgccctat tccttccacc ttgaatactg ctgtacaaca aaccacacca aaatgcagag   9960
gctacagggc agtcctttag ctcgtgcatc tacaggtaga tcattctgtc tgagcttggc  10020
ctcacagttc tattcttggc tgggttctct cccaatccag ggctgtctg gccattgcag  10080
gggcatttgg gtatcttggt cctgtcccac aggtccctca gcctttagta tgctggcctg  10140
gcatgttgtc atggtatggc acagctccgg gagtagaagc agaggtatga agatgccttt  10200
ttcaacctcg gtttgtgtca tatctattaa tgtctgatgg accagatgaa tcacatagcc  10260
acactcagaa tgaaaaggtg gagaggtgaa tttgtgggag gattgcaaaa tcacatggaa  10320
aaggctgtgg gtaagggaag tgtgagtgcc acaactcatc acaggggaca gtgatctagg  10380
cttagaaagt ggggaggaag tgcactttcc actgggttgc ccaactgaga cttcggggag  10440
ccatgttttt cactacttgc tgcaggaggg aatgggtatt caaaaagaag aggagagggg  10500
tggatcagac acatgcagaa agaaagagcc cggtgctata aagtccctga agctcttcca  10560
gtgtgtctgc aggtcactcc agtacccaaa ccagcccctg agctagtact ttttcctgtt  10620
tgctatatca ggcggtactc aagagtgaat gctgcagcca gtctacctgg gtacaaattc  10680
cagctgtggc tgaataactg tgtggcttgg aggcaagttg cctcatttct ttgtgcctca  10740
gttttttcat ctataagatg gggataatga taatcttacc tctcagagct gttgtgaaga  10800
tcgaatatat tgatattggg aaggacttag aacagtgcct ggcatatatt aataaatgtg  10860
tggtaattat tttttgctga cattagtttg aattgtgtcc ctgtcaatag attggatttc  10920
gtgggtggca tctcaggtgg atttgatgga aagacaaagc tgtctctcat gggagctggg  10980
ctcctacttt cacccaaagg cactgaactg catcccaatt gccaaatcta ccaaccaaga  11040
aaaaataaac ccaatacctt ccacgggaat taccctaatc tgtgactggc ctggtgagtg  11100
tgtcatttat agagtcacca taaccacaga acgtggtaca tgcccgcaat cttcggggac  11160
cttagtgctc cccttccaga tatagagcga ggtttgcctg agtccaggac ctggccgagt  11220
gggccagatt gctgtgtggg tttatggaac agagtgtgat gataatgggc ttctagattc  11280
tttcggtgca gactccacct ccctgcctgc agccaatacg gagccctgac aggaaataca  11340
aagccgctga cagccccaga cttgtccgca ccaccatcag ggctctgagc agccgagctg  11400
gagccccctc tccctccagg tcggccatcc ggctgggtcg gctcagtcaa cagcagttta  11460
cagtttggct gactacagcc tgactccaca aggggaataa agcccagcat tgtgctgggc  11520
ttgcaacatc tttccccgtc cagagttcct gatgtgtttg ttacacagga tctggtctga  11580
atgtttcctt tgtcgcagac cttcacgtgc tgaggtgggt ctgccttctc cgcggcagtc  11640
ctgggttaaa taaatacatt aaggcaacat acacggcttg acactggagc cagcctcaat  11700
aactcaaata attcatgtgg caaaagatgg agcctctgtg gttttgaatt catttaaaga  11760
tggatttctt tgttcacttc ctttgctcga ggagaacaca aactgggaag gggccgccat  11820
gctccaactc agctggccat tttctccag caagtctgtt tgagagtttc taaatcccgt  11880
gcagatgaac acagaacatg accttcagcc agttatagga taccatgctg acatcaccac  11940
ataaatatac actcccgaga aagctgtgat taagctccgc gcagattttt atcacttttc  12000
cagtgcaccg gcaggctgct tgttcgccat gcacctttac aaaactcata atatttagaa  12060
```

-continued

```
atgtgctgtg ttagccccag aggcttaaat aaactaaagc ctgtgaaggt tttaatgtaa 12120
caagttacct tcacatgtga aattacgagt ctacatgata ctcaataagg ccaacattgt 12180
acacactctg ttcttttggg atcttatgta catttatcct gacatatctg tttcagtttt 12240
ttaagaacgg aaaatatttc tatttcaata ccaccataca tgttcatgac actaaagaat 12300
gagtgagatt gtatatttaa agaaattcag agtctccgcc gggtgctatg gctcatgcct 12360
ataatcccag cactttggga ggctgaggtg ggcgcatcac aaggtcagga gtttaagacc 12420
agcctggcca acatggtgaa acctcgtctc tactaaaaat accaaaatta gctgggcatg 12480
gtgatgggtg cctataatcc cagctacttg ggaggctgag gcaggagaat tgcttgaact 12540
cgggaggccg agattgcagt gagccgagat cgtgccatgc actccagcct gagtgacaga 12600
gcaagagtac atctcggaaa acaaaacaaa acgaaatatt cagaatctct actcaaggag 12660
tttgtgcttt aaggccaaca caaggatggg tgggagggtg ctgtcattgt aatctcctat 12720
aaaatcacca agttttcatt ttcttttctt ttcttttttt tgagacagag tctctctgtc 12780
gcccaggctg gagtgcagtg gcacaatctc agctcactgc tcactgcaac ctcggcttcc 12840
cgggttcaag cgattctccc acctcagcct cctgaatagc tgggattata ggcatgtgcc 12900
accatgcccc gctaattttt gtacttttag tagagacagg gtttcaccat gttggtcagg 12960
ctggtctcaa actcctgacc tcttgatcca cccgcctcgg cctcccaaag tgctgggatt 13020
acaggtgtga gccatcatgc ccggccttca tttactttta aaagtgcaga taaaagattt 13080
gttttatgag tatagcagag attctcaact gagacaattt tgccccccag gggacactta 13140
gcaatgccta gagatatttt ttggttgtta caactggaga agcagggtac tattggcatc 13200
tagagggtag aaatcatgat gccaatatct atgtatgtat ccttccatac acaggacagc 13260
ccccctcaac aaagaattgc tcattccaaa atgccaacag taccatgctt cagaaaccct 13320
aaggtacagt acatttggga ggaggggttg ggacagcata tgttctaaca ggctggatga 13380
ctgtaaactt tttaaggtgc tatgcaaaca ctaaccttgc cttctagtca atttactggc 13440
tgctaaacat tgtttcaaaa ttctgactct ccatttatcc taagcacatt gctataaaat 13500
gccttattga tgaggcttgc ctggcccaaa atctaaacag ggctgctcaa gttttctctt 13560
tttaaaagag aaaaataaaa aacttttctt ttttactttg aaatgatgtt aaactaaaca 13620
tgtagtttct aacatagtag acagtacctt caccctgctt tcccccagtg acagcatctt 13680
acataactat agtataatat caaaaccaga aaactgatat tggtatgata ctattaaact 13740
acaatctgat ttggacttta ctactttgct caagttttaa ataataaaac attttaaatt 13800
ttatttctcc caaaatattc aactttattc ttgtagaaat gcttaccatg aaaaacaaaa 13860
caatgatgat ctttctgctt ctaaatgatc ctcattgcca aggtgctacc cgttgcgaga 13920
aaagaaagtg accggtggaa ataattggct tctagtttta ttaatcagtc tctaccctct 13980
tcaaaacaaa gactcccatg atattttctg gctgtcagtg ccttcttgtt gttgttgttg 14040
ttttgatcgg tttacatgtc cttcaaaggc tcaagtattg aacattagga ccaaaggtaa 14100
caaatttctc aaccttcacc cccacacccc tcaccccgac actacagcct cctggaagca 14160
ctctgcagaa cttccctgcc aatatatata tatatgtgtg tgtgtgtgtg tgtttactgg 14220
gtttacaccg tcggtgcccc tgtttttcag gccttcagat tcagactagt actattgtat 14280
tatagtacca agagcagaag ataaatgaga tgtcctagcc atatgtgtat gtgtgtgtat 14340
atatatacat atatatacaa aaactatata tatacacaca cacatatata tacaaaaact 14400
```

-continued

```
gtatatatat atatacacac acaaaaatat atatatatat ataaactata tatatagttt  14460
ttggatgttt ttaagggaat cttttacaaa tacaaatgga gtgccctgct gcagacccac  14520
ccgagggaag gtgggaaggt gttgtcttta ctgccgcaca gctattaaga ccttcaggtg  14580
taatgatcgg gataagatac atgctgcttc taccttcagc atccttcaag agcataggag  14640
aggaggcatt gtgaggacct gggccccaag tgggattcct tatgttgttc taacctcaga  14700
aagaaaaata cactcaaaga cagccagaaa aagccctagc agaggggctt tagcgtggac  14760
ttttagagca ccatctgaga aggtcggcat tcagtggaag agaaagcctc agaccatgga  14820
gaactgagtt caagggttgg tcctgccact ttctggctat gaagccttgg agaaggcact  14880
gaactaagct tggtttctct atcaataaaa cagtgacact ggtatcaatc ccggtaaata  14940
cagaaggtgg tgtgacggtc gctgacctgc ttcattggaa ggtgtctttt ataataggag  15000
aaatgaaaaa aatagggtgt cctcatatag tgaaagtaaa tagagctaca gccacacaca  15060
tcaacatgaa gaaaccctgc aaatacaaat aatacaatgt attaatcaga tttctccatg  15120
gaaacaagga aagagaacca atgtgttata tacatatata atatatggat gtaatattac  15180
atatatgtat ataatatata tgtatgtaat attacatatg tgtattatat atgtaatatt  15240
acatatatat aacatattgt tctctttatt aatacatata ttgtattata tatatgctat  15300
gtaatatata attacataat tatataatat atacatgtat aattacatac ctacataata  15360
catatatgca ttacatacat atatattaca tagcatatac acacatacat ataatataca  15420
tgtattacat atgtatattc atatagtgtg tgtgtgtgta tgtgtgtgtc tgtgtgtgtg  15480
tgtataaaat gtattatgag aaattgactc acacaattat ggaggctgag aagtcccatg  15540
aaccactgat atgtttggct gtgtcctcac ccaaatctca tcttgaattg tagctaccat  15600
aattcccatg tgctgtgggt gagacccagt gggagataac tgaatcatgg gggtggtttc  15660
accaatactg ttctcatagt agtgaataag tctcatgaga tctgatggtt ttataaggcg  15720
tttcccottt cacttggctc tcattctctc ttgcctgcca ccatgtaaga tgtgactttt  15780
gccttctgtc atgattgtga ggcctcccca gccaggtgga actgtgagtc cagtaaactc  15840
gtttttcttt ataaataccc agtcttgggt atgtcttcat cagcagcatg agaacagact  15900
aatacagcta ccatctgcaa gctggagacc caggggggaaa aaaaagagtg gtataatatc  15960
agtctgaatc tgaaggcctg agaactgggg gagctgatgg tgtaaacccc actcccagag  16020
cagaagatga gatgagatgt cctagcttaa gcagtgaggc aggggaaaaa aggaggagca  16080
aatttctctt tcctccttct tttgttctat ccaggctctc aacagattag atgatgacca  16140
ccagctctgg ggagggcagt ctgttttact gagtccccca atgtaaatgc tcatctcatc  16200
tggaaacatc ctcacagaca cactcagaaa taatgtttaa ccagccatct gggcatcctt  16260
catccagtca agttgacaca taaaattaac tatcacatac aacgttgggc aaaaaaagtt  16320
gtaaaagaac acataaggta tgatatacca ttcatacaaa catataaaac catactatat  16380
gtatagcgta aggatataca ttgatgtagt gaaagtagaa agcaatgcat gagaatgata  16440
agaatccagt tcaggttaag agttacctct ggaaaagggg gagggcaggg aaggagattg  16500
aggaaggtat acatgatgga tttaactgtg ctggcaatat ttatttctta accttggagg  16560
gtgcctatgt gagatgcctt ccattattct tgatagattc tttaaatgtc tttaatattt  16620
ctaaatgctc aagttttttt ttaattgcta tcattgttga cagaggcctt gagtgtggaa  16680
tacagtgtgt gggttgagaa catggggctg gcctgaatga gaactccatc acatttttac  16740
cctgggcaat tgcttaaaac tggcctatgc cttaggttcc tcatttgtca agagcaccta  16800
```

-continued

```
cttcataata tgacttggga ggcttaaaca agataatgtt taaagctcac tcaccaccat  16860
gcttgatgca taatcacctc tcaagaaacg ttagatttta gctactgcac agtacatgag  16920
attacctgat catcatgata actcatcgat tgacaatgga gtaacactgt gtacaaataa  16980
tatagatgct tccatcttct gctaattgta acgtaatatt tagggcatag aataatgtta  17040
ttattccaac ctcagattta tgagccagaa ccttacttga ctaacttagg tcactccgct  17100
gaaatatctt gtggggagat agttgaatct ttgtttggat tcttgccagt ggccataaaa  17160
attctttgcc actcagtaag gttatgtgtt atagccatgt aggaactctg gatatcagaa  17220
ctttcacttt ttggctgtgc caggtaaacc taaatttaag ataccttcag tggttttaag  17280
atttatggca tcaaattcta acctcctggc cccaggccca tgcaagctat gtttcttacc  17340
tctatataat gttaccctcg gtagccaact cacaaagcaa ggtgcctgga atgatgttag  17400
cttcaatgcc aaaatatcag tgaaatggaa aagaccttaa taactgtaag ccacatatat  17460
gtctctatat tctccagcat ttgagccaat gtggagatat ttccctttgc cctgttaccc  17520
tcaagtaatc ttgttaaaat ctgagagagc cttgctatct taaaacagcc ctgtcctctg  17580
gagttgaccc accaattgct gggctttctc cttaacaaac agagcagagc agagtggatt  17640
acaacatgaa gcctcaagtg accaaagaaa ggtaaatgtc acctacccct gccatctgca  17700
aggctagaca tcccccattt aatctgtttt aagaatgaaa gcgtctgtct attcttaaac  17760
agcacagtcc tcccagcctt ttcttgggcc tataaatgta ctttttacat gtaggtctgt  17820
gaagtagggc cttgttgatt caacatctgg aactactcag gtggtttgtc tctgctgact  17880
ttatgaacaa taaaagcaaa ccactggatg attcctggat atttaaactc ggggtatagg  17940
catccttgcc tcattgctga caaacacaag attttaattt ttcctactag agccaaatgc  18000
aacaaatgtg gttatgaata gaaggctaag tgttctcctt aaaaataggc tacttgtctg  18060
aggtataatt ttatttattt atttttcttt aatcagctga atttaagatt catctaaggt  18120
atggtttttt aactgtgggg cacataactc agaatttcca aagtccttgc aaatctcgag  18180
tctgttctca aacccaacta cagtcccact tcaaagaaat agactcaagt tgatcacttt  18240
ctaactatag tttctgcaaa gactgagaag aaacctatca tactactatg gagacaccac  18300
agtcaacccc actcctggaa ctacttaatc aacaccattt tttgttatgt ggggaaagac  18360
ttctctaaag tgatcctagg ctgttttcag ctaagattca attttatgac tatccttaga  18420
aatgtcacca aaaccaagaa gaatgagtca ttgaggccaa gtatgggaaa ggaaaaacca  18480
actgcataga ctggattgga aaatatagaa aaatatgtga ctgtgctgtg aaaatatcac  18540
ctggtagtca tagtatatta taagctgata taaataatac aatgtcataa tgttataaag  18600
tgctaaaata catggttcat taagagtctt aagatgaggt atcaacagaa cttttaacat  18660
ggacctctgg gaacaatgct aacctactat actctaagac tctctaggat aagaatcacc  18720
tttctttgtc tctgtctttc tttgtctctc ctccaagcac cacgtctggt ccacagtagg  18780
tacttactgc atgtttcatt ctggattgca agtgctagaa atggctttat gactttatta  18840
agtaaaatgt tagcaaaact acaatgtttc gaagaagtac cttgacacct gcctactcca  18900
tggaaatttc aaaatgcaga cccaaagaaa gatattgtga tcctcctcac aatttactaa  18960
caagaaataa tccctcatgt atacaccgat catgttcagg aaggtgactt gggaaaatag  19020
ttgtttggaa ctggagtccc ctctgtttca ctctgcccag cagccaagat ggtcttttct  19080
aaatgtggat tatgtcatct cactgtccca ctttcaaggg ctcaccattg tcctttcctt  19140
```

-continued

```
aaggctaaaa atctcctcca gaacctgcct cctgcctaat ctgcagctcc tattcttaat  19200
atactccagg agcactggtc tccatcatgt ccatataaaa agaccagact ctgtcttctc  19260
acatggcctc tgcatttgag cttccatctg cctatttatg ttctttaccc acttctgcat  19320
gttgttagct cccaaacatc tcaatacaaa tgctacctcc tcaaagaggt ctcttctgag  19380
cactcagccc agagaagttc ccaccaggcc attggatgtt cctcaatatc acatcctctt  19440
gtttgtttac ttctcatgtt gcagagggca gcaccagcaa aagagtagaa atggtgggaa  19500
acatggttaa caaagtattt ggtttgggcc aaatttcata aggccttcag cgtcagtgat  19560
ggagttcaga tggtatatgg ggagaaatct ggcatcagct ggggcagttt taggactgga  19620
tcatattgca gtgtggacaa gaggtcatgc tgaagagact ggaggcagga agctcctcta  19680
gaagccactg taatagtcca gttagaggta gtgattaccc atattaaggc aattgagaca  19740
agataacgaa taggagatac ggttgagtta aacaattcct gatcttaagg aacctatcta  19800
tcagggagtg aagttaaggt tgaaataact gaactgcaaa gccctgtaag ggaagaactc  19860
caagagagac acctcaaagg agaatggttc cccatgaatg gtcctactaa attgacatca  19920
tttcctccct ctcattatta aagcaacgac aatctcattc agtttctctt tgagcctcat  19980
gacttgtctc tgcaatttca gtaaagtttg acttgacttt ttttttcctg ttttcctttt  20040
gaaattagat cactcttcca gattgttcca acaagatttc aaagtaaagc tatggagggt  20100
taattgtcaa cccttttaga ttttagcaca actctgaaaa agattaaatt tttccaaaag  20160
aggttatttt caagtgttag tgttgatgta aaagttgaaa ggaaaaccaa tagtatcata  20220
aggggctttc ctcttgttag gtaaaataat ggccccactt tgttctcaga tgaagttaac  20280
acattcccag aggccaaagg gaaaactgga aagggcacca gaaaaaatat cactgaaaat  20340
aatgatgggt aatgtacaag acgaaaatgg ccaattagtg ctattatagc acgattaaat  20400
atttgcaaaa tttttttgat ttcagcactt aacttttaat atntgtgatg tagcttgaga  20460
acggttatga aagctaatca ctgaagaatt gaataattca aactcaatta gataaaattg  20520
ctaattgctt tgaatccagt gacaattata ccgttaataa tattattaaa ttgagaccat  20580
tgtaaataac ttctggctac caaaggaaga aggaagagat aagacccgca gtaatagagc  20640
agagtcaggc aggtctgagc tctaatctct gatttattac ttatcagcca tgtgactctg  20700
gacaaactgt ttactctcta tgaagctcag tttccttatc tgtaagatgg gtttaatact  20760
actacttgct tcctagggct gttgtaagga ttaaattata tatttgtgca atgtgccttg  20820
cacataaaac tcctcaacaa ataagagttt tccttctctt tgggacctga acaagacaat  20880
gacacttggt gcctcagttt ctcgctgtgc aagatgactg actgcaggca ctgaattact  20940
tggtgagggg gatgccatga tatttggtaa aatgagcacc agcttatagt gaatattgta  21000
attgccaaaa attttgctgg ctgtcattct aaagaccatg tagtttctat cttttccaaa  21060
aactaaggct aagtctatta aataagttca tgaggcttta aaagtattac ttattacttc  21120
tgcaaaagat gagaaaacaa gagataatgc aataactaac tcaaaatttg ggtttgatta  21180
agatgacctg gaatgtacag agacaactgt gagaccaaag aaatttttcc tatggtcatt  21240
aaaccaaaga ggttttggct atacaaatca tttatactta acacttgttt aataggttgg  21300
cgatgccttt taataagtat caagtatgaa atgtaatggg agagttttta gaaaatgtgt  21360
gatttcatac acctaccaag gaatgcctcg cattttataa agtcctctgt aggttctaaa  21420
acactttcac tggcatgacc tcattgaatc cctgttatgc ccctttaagc ctctttaact  21480
gatgagaaaa cagagattca agagattcaa ccacttgccc agctggtgtg tagtggaact  21540
```

-continued

```
ttggcccaaa atcaggtctt ccaaggccaa gtctgacgat cttctcagta ctgcagagtt  21600
acttctacat gattgatatc taataccgaa gttagaaaag aaaaaaaaaa gtataatatg  21660
ggctgaattg tgtccctcca acatttgtgt gttgaagctc taatccccta gtactttaga  21720
atatgactgt atttggacag ggcccttaaa gatgtgatta agttaaaatg aggctgaaac  21780
agtcgccctc aatctgattg gtgtccttat aaaagaaaac ttgaatacac agaaagactc  21840
caggcatgtg tgcacacaga gaaggtcatg tgaggacaca tcaagaaggc agacatctgc  21900
aagccaagga aaggggcctc aggagacact caacctcctg acaccttaac cttggacttc  21960
tagcttccag aactgtgaga gaataaattt ctgttgttta agtcccccta ctcacccccct  22020
actcccgccc ttcagcctgt ggtctattgt tatggcagcc ctagaaaact aactgacagt  22080
aatacaagat gaagagagct tacaccaaaa ctaaccaccc aacattaaaa aatgaacaat  22140
taatttaact atatttgtta tgatttaaaa tatttctctc tttcaatctt cccataaata  22200
caagtcaatt ttcaccttgg gatgtttatt ggtcagggtc caatcaggaa acagaaacca  22260
cacagtaatt taaataggaa aagtttaaca taggatttat taactataaa atcagattag  22320
ggtcatgggg gatgggctac tactggataa acagaactct aagaaatata ggaatggcag  22380
gtgtaaggag cagttaccac acctaaggct tatggagaga gcctgaggta gagcctccgc  22440
cccatccacc tcagtctcgg ggctgaattg cagaccttgt tggagaaggc atggccatgg  22500
ctcactggat ggcagggaag ctgctgtggt gctgtacaag aagaacctgc tggaaacctg  22560
cccttgagag tgccagggaa agctgttcac agagcgttgt ctctatgaca caaggcacta  22620
gactatgaga ttgccctgtg gggagacaag gcaaagctcc tggccactgg gtactgctga  22680
ccatgtaccc tgaggggatt ggggctggga aagtcaccat tactgcaggt gctggacact  22740
gctgaagccc ttggggccac cagaaacctg gtgctaaaga agccctgcca ggtgcacaag  22800
acaagtgagc tcccagaacc ggtaagaaaa accccctcct cctgcagcat ctctccagca  22860
ccttccacta acacagcctg gtattatacc agctggaaag ggcaacatat ttaaagggct  22920
ctctccattc tccaagggca ggcaacgaag ggtgaatctg gagctgagag gcatgaataa  22980
ctggcacagg atgacacaca gttgtactta atgtgtgagt ctcatggtac tcaggtaact  23040
aaagaatctg tatcaatatt ccaaatcctg ttgaaagcgg taccaaggga cttgttgata  23100
tttggggaag cttctccaaa gataggtata gaattttcaa agtgcaaagg aaggaaaaat  23160
aatgaagggc aatctgaaga aacaggctac cacaatccaa agccgtgcat tcttaactgg  23220
aatcttttgt cccaaacaat gaatatgagt tcacgaggtt gcacaatgca taacgtgacc  23280
caactgcagc atggtgttcc tggattttaa tctcctaaac ttccttgtta ataaagttat  23340
gtttatctgc atcactatat ttacaagtta aatatttaaa acctcagtca tcttggaatt  23400
agcaaatatt tagtgccgat atgttttttt cttaattaac tctaaactag ctcaatttat  23460
ttcaaatcat aattatctct aaagattttt atttatgagg ggaagagata taccaaagac  23520
tactccaaac ttacaggaat tagatcagaa gtcttacaat tttctccaaa ttttcttcat  23580
ggctgcctca aagagaaatc atgctatact ctatattttc tgcagtaaag ccaaggatat  23640
gggagggaaa aaaaggggaa agagtcatgg aaagccagct tcttgctgaa actccactag  23700
gtgccctgct ggaatctccc ttgaaagagg taagttggag ggaaaccatt tttcccattc  23760
tcattcttcc ccaatgtctg gagtgatcaa atgcaaaaca ctaggaatgt ctggtttttt  23820
aaaggaaaca gctgaaggca tactcttgtt taaggatgat gtaagaagca agaatttcag  23880
```

-continued

```
ttctatttcc ctcttgtttt gctttcttgt ttttgtttgt ttcttttctt atatttggtt  23940
gctttggttt gtgttggaaa tttagagggt tgaactgttt ggataactta gtcactcaca  24000
cctaggagag agtgtactaa tggtgcaaat tgtaaactag caatacgaat agaattttct  24060
catttctccg actaacccaa gaatttggat gcaatcagga tgcccattag gcatttatat  24120
tttcaatgga ttataaattt ttttttggaa taatgaattt tgcattagcc ctataaaggg  24180
aaattaaagt ctacaattta taaatacagg tgtgctagca cattagggta ttttataaac  24240
atggacttta actttgtaat aaaatttttt ttcatcaatt tctagactag gagatttgta  24300
gaagggggag attgtaattt ttgagatgat ctgttgtagc tgatgagatg atccctttat  24360
tagtaaggaa atgaagatcc agtccggatc acctgactta tgtggttgga gtttatattc  24420
ttcttcttct tttttttttc tttttttgag acagtgtctc actctgtggg ccaggctgga  24480
gtgcagtggc acgatctcag ctcactgcaa cctccacttc ccggactcaa gcaattctcc  24540
tgcctcagcc tcccaagtag ctgggattat aggtgtgtgc caccacgccc ggctaatttt  24600
tgtattttta gtagagacag ggtttcaccc tgttggccag actggtcttg aactcctgac  24660
ctcaggtaat ccgcccacct cggcctccca cagtgctggg attacaggcg tgagccactg  24720
tgcccggcct gtattcttca ttttctaacc atatcttctc tcctcctcac tttgcctttt  24780
ggacttgaga taatagcata gataatctgg gttttcacaa aggacctttc ccctggtgcc  24840
tggtggcatc tacattttct gtgttgctga aataaatgtg tgtctcactg catcaggctg  24900
tcaaaacatg ctgggcactg atgaactgca gaatcttttc ctctcatact gtggaaccgg  24960
gcataggacc cagcaagaaa atgaacccaa gaacccgctc catccagcag ccatgccaga  25020
agcaccaact aaatctaaaa accacagatc caattaactc cctttcctgg aagcaccaaa  25080
aagacataat cttgtcagca ccccccttgtc atgagcccag atccaatgtt caatattctt  25140
tttattttcc tagagccttc caaaataaaa attatttcaa ggccactccc tgtcaccgtt  25200
ttccacattc ttaacagagg tatgttgtcc atgctccaca acaactcttc actgatagga  25260
cagtatttgt ttttaatttc tgtatagtat tatgattggt tcttgtgtgt ttcataatta  25320
attgaacata catagccaga ttcattatag agagcaatgt gagtaaagac atcccaggaa  25380
ttttttttcct gctggaaata tgaaagattc atcttcccaa ttttttcctg atcacctgag  25440
agcctacgca gcagagatat taaattccat cttgtgacat aacaccaaaa gcatttagcg  25500
acatcctccc ctgaacaatg ctcaacgaga ctgcacttca tgacaaactt tattccccaa  25560
tcatatgagc cagatcacag ctcaaaaaaa catgtcctca aacagatggg ctcttgcaaa  25620
gtgttttcct atagatcatt ttcacttttc tctgttttct tttcactttc ctgtcacata  25680
aaaattggat catagctgga tttatctcag ggcaatagg gcacaacttg tgttatgtct  25740
aagatggttt cgtgcgactt ttatcaacaa cagccaagga cagaagaaag tttcttgtta  25800
ctaaattacc ctgaaagtga tgaagagttt tattgattac aaaaatttaa gtgtgaaaat  25860
tgtaccacga tgttactaca aacacatttt cttttcagaa gtttcagagt attaaatgga  25920
cgtagtgcca actaaaacag agctgactat ttgatttggg gcatgatttt ctcagtgaaa  25980
atattactta tttggagagt ggtccaggcc aactttgaag aagtctaaca gaaggagaaa  26040
agctgcaagg atgaggtgaa tcaggccctg aagtttatct ggctgtacaa ctcagatcaa  26100
atcaagagct ggcccactgc ttattgaccg ctgacctctg gactgagact tccagaatgt  26160
tccccagcat ggtggtcatg gtggcagttt ttgtttacct tcaagcagga tgttttgaga  26220
gccggttgag aaatgatgct aatttgtatg gcaaactttc aagtcgaaat tgtctgtggg  26280
```

-continued

```
ttttctgctg cttattgaaa tctgaactaa aagcaaaacc tatgatttct gccactcggg  26340
tttaataaca gaaaacaaag caatcacata aacagacccc ttttattgac tagaggcccc  26400
aacttctccc ttcttgaaac atgagtcatt gggaaataga acttatacca taagcagaaa  26460
ccggataccc ttagaatcag aagtatctcc aacactaatt ggattaaaaa tcactaagcg  26520
ctctcacaga ctggagcatt caaatcaaat tagccaccat cttattttgt gaaaataaag  26580
aattagtgcc ttgtgtgtac attttcatca caagttaatg agggacgtag catgactgaa  26640
actgctcacg ttaccggaat tcagatatca ccaaatgccc ttttcttttt tctttttctt  26700
tttcttttct tttttttttt tttttttttt tttgagacag agtatttctc tgtcatccag  26760
gctggagaac agtgacatga tctcagctca ttgcaacctc tgcctcctgg gttcaagtgg  26820
ttctcctgcc tcagcctcct gagtagctgg gactacaggc ttgcaccact acccccagct  26880
aatttttgta tttttagtag agacagggtt tcgccatgtt ggccaggctg gtctcaaact  26940
cctgacctca agtgatctgt ctgccttggc ctcccaaagt gctgagatta caggcgtgag  27000
ccactgtgcc cggccccttt tcattttttt tcatgcaaaa gctgaactgg aatcctaaag  27060
ttctccagct gaattctttc ctaaggtagc aaggcagaac tcctcacttt gcaaatgaga  27120
acatggaagt ctaaagagtc tgtgatgagc tctagacctt gcagtggttt gacagcaaca  27180
catacaggta agacccagct gtcctcacct gcaatgctgt atgtgctctg gtgattccac  27240
tagtgtttcc ttgagataaa gggagatgca gtgatcattc caagtgggag tgacccatcg  27300
agcagcccag ctactggctt tgggtaaacc agagccctgt gatcttcctg gctcataata  27360
taatatgatc cacatcagct cctcacagca atccactgat gcaggaggaa agagagcaaa  27420
ggccaggcaa gcaggcagag gacctctgct tctggttaga acgtaagaga acgggaaaga  27480
cctttgtttc tgagagaact acaagaaaag ctgggacaaa ataaaaagtg tgcttctcta  27540
ccaggctagt taagagcagt gggatgcaag aaatcttgga tgacctgaac tccagagaga  27600
agtgagacct ttatggtgag cagcttccac acctgcggga gggagtcaga tccctgaatt  27660
acaagatgga ggagggtcct gctggagcca gggagactct gcagggatgg ggagaactca  27720
gctgagcctg actgtgccag ctggcagggt ggatggcatc tggaggagcc ccaaacaaag  27780
cactcagccc agtaattcag cctgcctaga ccacacccag tcccaaattt tgttgaggag  27840
gtggcagtgg aagagaaact ggaaaacatg ccccgtggtg cttggattca gaagcccaga  27900
gtttacctca cgaggaacca agggcatctg gaatcgcagc ttaacccctt cttacctgaa  27960
atactgacaa gatcagcaag gtatctccac tgatactgaa atgcagagca cccaaaaggg  28020
caaatatgcg agtcactatg aaaggctgct tttcatcatt gctttaaaag gtaattgttc  28080
aaggcacaaa taatagcaat atgctatggg atttatgggg tttataacat atgtagaagt  28140
aaaatatatg gcatcatagc accaaagatg gagaagcagg taaatgtgaa tataccatta  28200
aaaccttgta tctgggccag atgcagtggc tcatgcctgt aatcccagca ttttgggagg  28260
ccaaggtggg tggatcatga ggtcaggaga ttgagaccat cctggctaac acggtgaaac  28320
cccatctcta ctaaaaataa aaaaaaaaaa aattagctgg gcgcggtggt agatgcctgt  28380
attcccagct actcgggagg ctgaggcagg tgaatggcat gaacccagga ggcagagctt  28440
gcagtgagcc aagatcatgc cactgcaccg cagcctgggt gacagagcga gactccgtct  28500
caaaaacaac atcatcatca acaacaacaa caacaacaaa cctcgtatct gacgtggtag  28560
aaggttaatt cagtgcattt tatattaagg ttgcaaatta taatcacaag agcaatcatt  28620
```

-continued

```
tcaaatataa aacaaagggg ctatttttatt tttaatctct tttcttctct ctcattggag  28680
agaaaaagtg aagggacatg ctgcccagat gtgccatcag gatgggagca ctacttcccc  28740
tagctgctgc aagatgtaga tattgtagcc tcttgctgag cccctctcca gaattaccat  28800
tggtcctaag aagcagtctc acccaaagat acatccctta cctggaggca gcctgcatcc  28860
tattactcac tgatgaaggg gcacagggtt ccagccgtct tgcctcaact ggaaagagtc  28920
cagttccaga gctccccaca ggattggctg agtctgctgt tgcaactgga tcatagttta  28980
ttccccctgc ccacttctgc ttccctcacc cctcgcaggg gctggtcctg agaccactca  29040
taggaaacct cctgcacaca gtctgttttc tggggaactt gacctatgaa cgttggtccc  29100
agcagcatgt tggagctgtc atctgctagc tgcttcagtg aagacctcat cactggtggt  29160
aggcacttgc agttatgatt cacttgttaa aattttcact ggtggtgaac taggacatga  29220
tacttgggaa gaaactgctc tggcagatgc gagatctcag gtgtttaaga gttttggggg  29280
aaatagtaat tataagaact atggaatcag atggttgttg ctagaagctg ttaattcatt  29340
ggagaaattt aataaaagac taagtgatta aacaccaata taaggcaagg tacacatacc  29400
agaggacctc ttggctttta tatgaagcct atgaaaagac tattatcctc tgcaactgca  29460
gggcagatac agctgagaag caggccccag gtttaattat aagagtagaa atgctgaaag  29520
caacactgaa gtttagtcct ggcaggtcgg ctaggccaaa gtcagttcta tgattaggaa  29580
agagtgggat ggggacattt gggttcatat attaaaacat ctcaagttct caagttccca  29640
gatcctctgg aattctctag gcctggaata gtatcctact cttctcctta aaggctaatg  29700
cctgcttttg catgaagatg atgatgaggt tctgctttgc aagacaatgc atgacaactc  29760
cctccttctc ccctcaaaaa tctactcttg gccaccagac ccataggtaa ggtcaagcca  29820
caacatattc tagccagaaa agtgtaaacg tgctaaggga agaaacgaac tatagcccag  29880
agagctgtgg gacccagcca atatgtccta caagtgccac aagcacatgt gcaggaggga  29940
atagagagac tgctggacaa agtgggatga aatgcaaagc tggatgggga aaatgtattg  30000
ctatggaagc actctccttt gatgcaacat ttaacatcct ggtaaggacc ccaggagttg  30060
gacgcttaga aaatgtgatg ccaagtcaaa tggagatgtc agatcatgga ggatggggaa  30120
ggaagggatg aaaggctcag aaaataggca agctagagtg gatataccat acaaggccag  30180
agaaccgaac agctgatagg ttttttttc acaagagggc ctagaagaat gctgtatttg  30240
ccaaagcaag aagaatacgc cggtgagagg gcaagtgtca tgaagaagct cagtgggtgc  30300
tcttctctga aggtcaagac tattacagga tatccaaagg tagatgatat aggcctgggc  30360
tccctagtaa caatgggact gatagaggta gcacttactg tccaatgcaa ggtgtttgta  30420
gtcatcataa tgtaattatc ataaggggca gcaaagtggg tgtgacagct agtgggatct  30480
aacccacaaa gagctacgga aatggtaaaa agaaatttgc attcgagggg aaaaacaggc  30540
agccaacaaa gtattattgc tcaacctcta caactaaaat aaaccaagga tggctcatca  30600
ggaagctgag ggcaagacgg actgaagaag aagctaatct cccagacctt cctccaaagg  30660
gacctgcagc catttccttg ggtaactgga ctctggggag ggtaaatgcc caaacatttt  30720
gaagatgttg gacacggatt gttgttgaca ttgatacctg gggacctgaa acaagaatga  30780
acactccatt agagggggtg aacataagac ccagataata aataaagtcc tgaacaaaat  30840
tcagttcaca gtcagctcag atatgtcttc tgagtaggta taccgggctg gcaaaggcag  30900
tctaatgaag gcaatcatgg gttctagatt taggatggca aacctcacca tacaaatggc  30960
aggattacac ctgctgggca tgaaatagta ggtaatagct gcttccccta actgctacaa  31020
```

-continued

```
gaggtaaata ctgtagcctc tgctgagcgc ctctccagag ttacccttgg tcccaagaag  31080
cagtctcacc caaatataca gcttatatta gagcatgagc tttgaaacca gacagaggtg  31140
tattcacatc ccagttctgc cactcagtaa ctaggattct tgacaaggta acctctctga  31200
gcctcagttt tttgatcttt aaaatgggaa tattactaac atcttcataa ggttattttc  31260
acatgtagaa gagacaataa gtggttaacc ctcagcccaa tgctgggcac tacagagatg  31320
gcagctgtta tgatgagagt tactgtgaaa agggtttgga aatttgcagc aatgcgttcc  31380
gaccatgaag tcttggacac accaatttgg atggtggttg cagaagtgtg tgctgctgcc  31440
caggggtgtt gctgtggaag gaccttgaca ggcaatggga ggcaggagct ccgcaaacat  31500
gaaaatgtca caggaacctc tgagatgtgt cacctggagc cacaacagat gacagagatg  31560
gcaaaacatc tgctttagtt ttgttcagag caaagagctc aagaaaagtg aggatcaaat  31620
tctacagaac tgttcccatt cccttcttgt ctctcttttc ctggctcaga atgatcttga  31680
caatgaagag gcagtaggag acttactacc tctgtagcca gaacaagctg aaaacagaag  31740
caggcctcgg ggcattgggt tcacttagag gatgattgat gctgagatgc ttcagttatt  31800
cagaatccag caatctggta acctcgtgta tccgggatgt tatagaaaat gtggaagtaa  31860
gtctgcaaaa catctcaggt gtcaaaagag aaatatcaaa gtatactcac aatatgcaag  31920
gagagaagag gagaggccct ttccctgagc cctcagtaag gcttatctgt ttctattttc  31980
cccacagcgg tacaagctgc ttccctgtcc tgacaagcac aataaaaggt gcaaacctga  32040
ggaacgtggg gacctcacag aggcaggcgc agccggctca tcgagatgtg tggacagcag  32100
aaagcgagtg aggcaagaga aaatcagcac agggtaaaca tcagagatca aagggcagca  32160
gctggagtca ctgggtggag aagcagtgca actgtggctt acccaggcag ccagggttcc  32220
aggagattct tctaggccag agctctgaca tattcaccaa acagctgaca actttgcctt  32280
ttgcatggga aataagtgga aatgaatctt ggccatccac cactggtttc gaaaagatcc  32340
aggcaaggtc tgtgtgcacc tgccacacaa aaatgaattt catgtgattg caacaaacag  32400
aacaatagtg caagcaaaat tcctaggaaa acttttgtcc agaggtaatg ccagctggtt  32460
gtagcattgc aactaaagtt cagagaggga ctcactcatt cccacagggct ccagtggggt  32520
tttggactta caactggatg tcatcacctc tgcgggtgcc tgaataatga ctctcataga  32580
ttttcagggt tatactctgg aacaacttgt agttgttatt aataccttac attacaaaac  32640
gggttttgca gatgtgatta aggtaaggat tttgagatgg ggagattatc ttggattatc  32700
taggtgggct ctaaatgtaa tcacaaggat ccttataaga tacttataaa tatgaggagg  32760
gggaagagag atgactatag aagaagaaaa ggcaatatgg tggcagaatt ctgggacaga  32820
tggtgggagg ttggaagatg cttttctact ggctttgaag atggaggaag gagtcatgtg  32880
ccaaggaata caggtggctg ctagaagctg aaaaaggcaa gaaacagttc tccctgggag  32940
cctcctgaag taaccaacca aacattgaaa gggtagaggg aagtgttcag tgttggtcag  33000
acatgtgaaa aaataattca tgatccattc agaaactgat caccatacac ttatcagtta  33060
gagggctaaa gctagtgtag caacatttag agaatgtata atatctgttt tttttttttt  33120
ttaagacaaa gtcactctgt tgcccaggct ggagtgcagt ggcatgatct tggctcattg  33180
caacctccac ctcccgagtt caagtgattc ccctgcctca gcctcctgag tagttgggat  33240
tacaggcaag cgctaccatg cccagttaat ttttgtattt ctaatagaga cagggtttca  33300
tcctgttggc cagacgggtc tcgaactcct gacctcaggt gatctgcccg cctcagactc  33360
```

-continued

```
ccaaagtgct ggaattacag gcatgaggca ctgcacccag tgtataatac catttttaat  33420
gtaatatcat tttgtatcga gaaaaaagga acaacagaaa aattctgact ggcctccata  33480
tctcttggtg gcccacattt tcaacttcct cagttaattt tttccacctt tttcttcaat  33540
ggcttgattg agatctattt cacatacctt ataattcaca tactttaaag tatacaatgc  33600
agtagtgttc agtatattta caaaattttg caaccatccc cattatctaa ctccagaaca  33660
ttttcatcac cctaaaaaga aagctcatgt gcattggtag tcactcccca tgttaccaca  33720
gccctcatcc ctaggcaatc attaatctac ttcctgtctc tatagactaa cccattctag  33780
acattttatg taaatggaat catacaatat gtggcctttg ggtctggctt ctttcagtta  33840
gcataaagtt tttaaggttc atccatgttt atcagtatca gtacttcatt ccttgttaag  33900
gctactattc cattgtatgg atataccatg ctttatccat tcatcagctg atagactttt  33960
gggctattat atataatatt gacatgtatg aattttcata tggacatata ttttcaacta  34020
tcatgggcat actgtacctg gcataaaatt gctggatcat atggtaactc tatgtttaac  34080
tttttaagga attgccagac aactttccaa gatcatgaca ccctattaca ttcccatcag  34140
caatctatga gttgtccagt tcctccacat ctttgtcaat acttgttact gtctgccttt  34200
ttgattatag ctattctaat gggtgtgaag tgatatttca ttgtggtttt gacttgcact  34260
tccctaatga ccaatgatgt tgaatatcct ttcatgtgtt aatcatttat ttgaatatct  34320
tcatcagaga aatgtctatt cagaccgttt gcctattttt aaattggttt gtctgtcttt  34380
ttgttgttga gttgtaagag ttctttatat attctggata taatttcctt atcagatata  34440
tgattggcaa atattttctc ccattgggtg ggttgtcttt ttactttcgt aatagcatac  34500
tttgaagcac aaacgtttta aattttgatt aaatttgatt atctggatat tttttgttcc  34560
ttgtgcttta ggtgtcatat ctaagaagtc attgcctaac ctaaagtcat caagatttac  34620
acatatttcc ttctaaaaga tttgttgttt tagttctata tttaggtcta tgatctattt  34680
taaattaatt tttgtatact gtgtggggca gggatccaac ttcatttgtt tgcatgtgaa  34740
tatatagttg tttcagtata atttgttgaa aagactgttc tttcccccat tgaatggtct  34800
tggcactttt cttgaaaatc aactgactac agatatatgg gtgtattatt ggactcacaa  34860
ttctgttcca ttaatctata tgtctatctt tatgccagta ccacacagtc ttggttactg  34920
tagttttata gtagtttttg aaatctttgc atgaatcctc caactttatt ctttttattt  34980
ttcaagattg ttttggctat tctgggtcct ttgaatttcc ataaatactt tggaatcact  35040
tgtcaattta cacatgcaca tacatataca aaggcagctg gagttttgat agaacttgta  35100
ttgaatattg aattcataga ccatttgggg aagtattgcc atcttaacac tattaagtct  35160
tccaattcat aaattcttta tatttaatct tttgaaattc ttcaacaatg ttttatagtt  35220
ttcagtgtgt atatcttata cgactttgtt taaatcgatt cccaagcatt ttattctttt  35280
ttatactatt gtaaatggaa ttgttttctc aatttcattt tcagatcatt ctttgctatt  35340
gtatagaaat ataattgatt ttatatactt atcttgtgtt ctgcaacctt gctgaactga  35400
tttagtagtt ctaatatatt ttagtggatt ccttaggatt ttctacaaga ttatacagtc  35460
tacaatatta tgtcatctgc aaatggaggt agttttgtgt cttcatttct agtcaggatg  35520
atttttattt ctttttcctg gctaattttc ctggctaaaa cctccagtgc aatattgatt  35580
agaagtgcca aaaatgaaca tttttttctt gtacctgatt tttaggggga aagcattcag  35640
tcttttacct ctttttggct atgggcttat tatagatacc ctttgtgtta gttcattcag  35700
gctgctgtaa caaaatataa taaacggggt ggcttatgaa caatagacat gtatttttca  35760
```

```
caattctgga aactgggagg tccaagatca aggtgctggc ggattcagtg tctggtgagg  35820

gccaaccttc tgattgatct tttctctgtg tcctcacatg gtgaaatgag taagggagat  35880

ctctcgagcc tcttccataa gggcactaat cccattcatg agggcttcac cctcacagcc  35940

taatcatccc ccaaatgtcc accttctaac accatcccct tgcaggttag gatttcaaca  36000

tatgaatttc ggggggacac attcagacca cagcaccctt tctcaggttg aggaagttcc  36060

ctcctattcc tactttctga gtgttccctg tttctttaaa aaacaaaaat tatgcccagc  36120

ttagggcata attatgtccc cctccattat cttatttcca tatcattcaa ttccagctcc  36180

ctcntgtgtc ttcacgacgg gtataaaagg ggccgctcaa t                      36221
```

<210> SEQ ID NO 30
<211> LENGTH: 2397
<212> TYPE: DNA
<213> ORGANISM: Homo sapiens
<220> FEATURE:

<400> SEQUENCE: 30

```
gagctaaagc gggttcatag aagagtacgg gggcacatgc catcgcggaa gggctcttcg     60

aaaaaaaaaa aatgttaaag taagatcgtc agaggagtcc tgccccggtg ccaggagtct    120

gcgggcgctc tcttcctccc agtcagtgaa tcacacatcc tttatccccg atagggaacc    180

agtccctctc aagcctgcca cgggttatct tccagtcgcg aagttcttct tcctttatcc    240

ccactaattg caagtctccc tccattatct tcttatttcc acattgttca attccagtgg    300

aatacaggaa ttggcccatg ggaagagca gaaaaacgaa aggaatgaaa atgcttcagt     360

gtttcaggag atttgaagat gtttcaggag atttcagtgt ttcaggagat tgaagctgca    420

gtgaggatga gcctccctga tcccttctc ctcccgtgtc cctgctggac taaaggagtt     480

cccatgaggg aggctggcag ctgacaggat cacccaggac taggacttgt ggcccccaga    540

ccactcctgg atgtgcccca tagcggcccc tgaaggcgct gcctccttct ttgctgggcc    600

tcagcctctt tgctgggcct tgggtctcgg gacctccaag gcatgtcatc ttctttctct    660

gtgtcctcca ctgctcagat tgtggccgcc tcagccatgg caaatggcaa ggaccccagt    720

ttcacttccc ggcccaccca gacaccaggc agaaactcta ataaccactt ttctgggttt    780

ctacatcctg tgtctctgga tgactaatca tctccagagc atgaacaatt gagtcatctc    840

aagccccagg cttgaattgg tgcacaaggc aaccagcttc tcctcggcag gctctgggag    900

cactggctga agtaggtgtg gccctcctaa gtcaccatcc tggcctggaa ctcttggagc    960

acaataggct cctccgggtt tgttgaagag cctttgctca actgaacctc tttattgtag   1020

gcttttgctc ctttctgaac aggctcttac aagtagagca tgcaagatcg cattatgttt   1080

agagtcccca tgaggccatg ctctgcaggc ggccttggga caccagcgca tcctcttctg   1140

ggaacagaac tccaagctcc tttgaataac aactactccc cttctctctg agctgactca   1200

ggccggccaa ttgacataat tccaatctct ggtgacagtt attgcttcag ggattggcac   1260

ataacccaag tttgtcctac tagaataaat cctgggactt atttataagc tgacagaagg   1320

agatgtattc ttttttccac agcctctatc ctgaagagcg ttggaccctg gagctgctgg   1380

ccacatcttg atctgccata tgtggtccaa gaatgaagtc aacacgaagg agaatgaagg   1440

tgctgaggga taaagttatt gacattctag gagctcctgg atcaaaccat gcctgaactc   1500

aatttatccc ttgaactttt caattacatg aataaatcct ccttttgcct gagtcaatgt   1560

ggattagtat cattggcatt cagaagattc ctaaagtctc aggtcttctg cacatctata   1620
```

-continued

```
accgtggcaa ttgcggtcct gctctccttt cccctcccct gagcaggcaa gctttccttc   1680

tctatcatgt aaaacctcct gggtcattca gagtatttct caaatgttac ctggagtttc   1740

ccaagacttc agttctcact gaccatttac ttcttaaact gctaggatga taacctataa   1800

ctttgcatct aaccaatccc ttagcacttt ccttagagac ttcttagaga tctttttgat   1860

gcctaagggt aggaatcagg gcttctctat cttgtatatg cactgccccc cacccacagg   1920

tccatagaat aacagctgag gacctgtagc tctgcaaggg cagggactgt caaacatgcc   1980

agactgcaca tggtagttac cactagaggg ctctgggtat gggcaataag caggacttct   2040

gcattttaca tctatgttat cattcgagtc ttgtatgagc atttatttta caaatctcta   2100

tcttgcaaag caaaccctta gtgtgaataa ctgaggagtg gtggatcggc cagctcttcc   2160

gtgcagtgtt ctaaagcctc ttgctcctgt ctctcctgtg ggaaacccat agttacggct   2220

tcaagcagag acccaagcac cacctcaggg tcttgacctt gtttgggaat aatctatcac   2280

caagatgcag acagagacaa actgcttcac agagcatttt atcccctaga aaatccccaa   2340

ccccagcatc gtcttcacca cggggctgtc aagatacccg cggttggtcg caacagg      2397
```

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31

```
tgcggtgggc tcaggaaccg                                                 20
```

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32

```
ttccatatct ccatgtggac                                                 20
```

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33

```
ccagctgacc atggttacgg                                                 20
```

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34

```
caaggttgcc atggtgacca                                                 20
```

<210> SEQ ID NO 35
<211> LENGTH: 20
<212> TYPE: DNA

<213> ORGANISM: Artificial Sequence
<220> FEATURE:
<223> OTHER INFORMATION: Antisense Oligonucleotide

<400> SEQUENCE: 35
agggacaagg ttgccatggt 20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
ctaaactgaa ggagggccgg 20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
ggtatttggt tggtggctct 20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
cacggcggca tctttcaaca 20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
tccaactgat cacggcggca 20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
ccatccttag tccaactgat 20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
gggccccaag tgcaccccat 20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
ttgttgggcc ccaagtgcac 20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
cactgtccta ttgttgggcc 20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
ccccaataag cactgtccta 20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
ctgtgacatt caccatgaag 20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
ggcatctgtg acattcacca 20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
gagatggcat ctgtgacatt 20

<210> SEQ ID NO 48
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 48
tgcttaaact ccttcccgtt 20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
gctcctgctt aaactccttc 20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
gcgatgctcc tgcttaaact 20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
cagtgctggt ttcgtacctt 20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
ggctccagtg ctggtttcgt 20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
acccgtattc attctccacc 20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
gatggacccg tattcattct 20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
accttgaggt agggcagccc 20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
accggcggcc ttgagaacct 20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
tccgtggtgt taacaccggc 20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
cgaatataga gaacctcaat 20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
cattccgaat atagagaacc 20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
tcaaaagtta cattccgaat 20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
cagagtgaaa ggatatccca 20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
gcagagtgaa aggatatccc 20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
aagaccccta tgcagtaaat 20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
ggcgattaag aagaccccta 20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
agtctggctt cttggtcgtg 20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
gctgaagtct ggcttcttgg 20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
tggctgctga agtctggctt 20

<210> SEQ ID NO 68
<211> LENGTH: 20

<212> TYPE: DNA
<213> ORGANISM: Artificial Sequence
<220> FEATURE:
<223> OTHER INFORMATION: Antisense Oligonucleotide

<400> SEQUENCE: 68 atgtcataggagtactccat 20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69 ggttaatgtcataggagtac 20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70 acacggttaatgtcatagga 20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71 ttcctccacgggaatccctg 20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72 agaattcgatccaagtcttc 20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73 tcctcattggttgtgagagt 20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74

-continued

```
agtattcctcattggttgtg                                                 20


<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75

tttatgtgtggatactgagg                                                 20


<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76

cacagtcattcatgttttaa                                                 20


<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77

ccagaacgcacggcaggtga                                                 20


<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78

accttgagtcctactggtcc                                                 20


<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79

actgcatttgtgctctgtaa                                                 20


<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80

caatcgtctgacagcagcat                                                 20


<210> SEQ ID NO 81
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 81

cagagagaagcacattctgc                                                20


<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82

tttctatgatgggacttgaa                                                20


<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83

ctggatcttttggtgaggtc                                                20


<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84

tagtacagaaggaacaacgg                                                20


<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85

tgcattcatcttgcacggct                                                20


<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86

gcagttacttactcttgttg                                                20


<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87

ccccgagtgctagaacagac                                                20
```

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88 accggcggcctagaaaacaa 20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89 ccactcttgcctctcctgaa 20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90 ctttcagatctgataggaaa 20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91 caagtattcctgaaagaagg 20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92 cacaggaaatggcaggtgtt 20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93 acttcattcttggaccacat 20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94 tgcctctgtgaggtccccac 20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95 ggcacctagtggagtttcag 20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96 atactgttcgagaggttggc 20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97 gagatggcatcttctggctc 20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98 cagtccctcatcatcatgta 20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99 agccgaaaccttgagaacct 20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
gcgcttgctg ttttggcagg 20

<210> SEQ ID NO 101

-continued

<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
gtcctcagac cttttccttt 20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
ccccgagtgc ttgagaacct 20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
accggcggcc ttgctgtttt 20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
tggcatgatc tcggctcact 20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
ttggctttac tgcagaaaat 20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
gcagcttgta ccgctgtggg 20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107

-continued

```
ggatagaggc tgtggaaaaa                                                  20


<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108

gcgctagatt gcagatcaca                                                  20
```